(12) United States Patent
Iwakuma et al.

(10) Patent No.: US 9,991,447 B2
(45) Date of Patent: Jun. 5, 2018

(54) MATERIAL FOR ORGANIC ELECTROLUMINESCENT ELEMENT, AND ORGANIC ELECTROLUMINESCENT ELEMENT PRODUCED USING SAME

(71) Applicants: Toshihiro Iwakuma, Sodegaura (JP); Kei Yoshida, Sodegaura (JP)

(72) Inventors: Toshihiro Iwakuma, Sodegaura (JP); Kei Yoshida, Sodegaura (JP)

(73) Assignee: IDEMITSU KOREA CO., LTD., Tokyo (JP)

( * ) Notice: Subject to any disclaimer, the term of this patent is extended or adjusted under 35 U.S.C. 154(b) by 462 days.

(21) Appl. No.: 14/347,937

(22) PCT Filed: Sep. 25, 2012

(86) PCT No.: PCT/JP2012/006074
§ 371 (c)(1),
(2) Date: Mar. 27, 2014

(87) PCT Pub. No.: WO2013/046635
PCT Pub. Date: Apr. 4, 2013

(65) Prior Publication Data
US 2014/0231794 A1 Aug. 21, 2014

(30) Foreign Application Priority Data
Sep. 28, 2011 (JP) .................. 2011-213330

(51) Int. Cl.
*H01L 51/00* (2006.01)
*C07D 405/14* (2006.01)
(Continued)

(52) U.S. Cl.
CPC ........ *H01L 51/0071* (2013.01); *C07D 209/86* (2013.01); *C07D 401/14* (2013.01);
(Continued)

(58) Field of Classification Search
None
See application file for complete search history.

(56) References Cited

U.S. PATENT DOCUMENTS

2012/0223276 A1   9/2012   Parham et al.

FOREIGN PATENT DOCUMENTS

JP   2004-079265   3/2004
JP   2006-352046   12/2006
(Continued)

OTHER PUBLICATIONS

Machine English translation of Igarashi (JP 2006-352046 A). Jul. 20, 2016.*
(Continued)

*Primary Examiner* — J. L. Yang
(74) *Attorney, Agent, or Firm* — Foley & Lardner LLP

(57) ABSTRACT

A compound represented by the following formula (1):

wherein in the formula (1), $Ar_1$ and $Ar_2$ are independently a substituted or unsubstituted aryl group, a substituted or unsubstituted heteroaryl group, or a substituted or unsubstituted alkyl group; $X_1$ to $X_4$ and $X_{13}$ to $X_{16}$ are independently $CR_1$, CH or N; one of $X_5$ to $X_8$ is a carbon atom bonding to one of $X_9$ to $X_{12}$, and at least one of $X_5$ to $X_8$ that is adjacent to the carbon atom bonding to one of $X_9$ to $X_{12}$ is $CR_2$; one of $X_9$ to $X_{12}$ is a carbon atom bonding to one of $X_5$ to $X_8$, and $X_9$ to $X_{12}$ that is adjacent to the carbon atom bonding to one of $X_5$ to $X_8$ is CH or N; and the remaining $X_5$ to $X_8$ and the remaining $X_9$ to $X_{12}$ are $CR_1$, CH or N.

(Continued)

1: Organic EL device

| 60: Cathode |
| 50: Electron-transporting region |
| 40: Phosphorescent layer |
| 30: Hole-transporting region |
| 20: Anode |
| 10: Substrate |

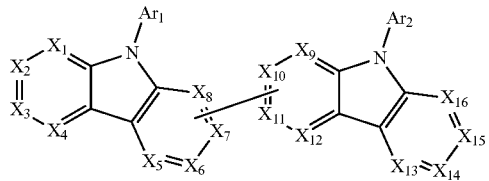

(1)

43 Claims, 1 Drawing Sheet

(51) Int. Cl.
| | |
|---|---|
| C07D 403/14 | (2006.01) |
| C07D 409/14 | (2006.01) |
| C07D 471/04 | (2006.01) |
| C07D 491/048 | (2006.01) |
| C09K 11/06 | (2006.01) |
| C07D 401/14 | (2006.01) |
| C07D 495/04 | (2006.01) |
| C07D 519/00 | (2006.01) |
| C07D 209/86 | (2006.01) |
| C09B 57/00 | (2006.01) |
| H01L 51/50 | (2006.01) |

(52) U.S. Cl.
CPC ......... *C07D 403/14* (2013.01); *C07D 405/14* (2013.01); *C07D 409/14* (2013.01); *C07D 471/04* (2013.01); *C07D 491/048* (2013.01); *C07D 495/04* (2013.01); *C07D 519/00* (2013.01); *C09B 57/00* (2013.01); *C09K 11/06* (2013.01); *H01L 51/0067* (2013.01); *H01L 51/0072* (2013.01); *H01L 51/0073* (2013.01); *H01L 51/0074* (2013.01); *C09K 2211/1007* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/0085* (2013.01); *H01L 51/50* (2013.01)

(56) References Cited

FOREIGN PATENT DOCUMENTS

| | | |
|---|---|---|
| JP | 2012-089777 | 5/2012 |
| WO | WO-2006/061759 A2 | 6/2006 |
| WO | WO-2010/044342 A1 | 4/2010 |
| WO | WO 2011/044342 A1 | 4/2010 |
| WO | WO 2011/057706 A2 | 5/2011 |

OTHER PUBLICATIONS

Notification of Transmittal of Translation of the International Preliminary Report on Patentability dated Apr. 10, 2014, including Translation of Written Opinion of the International Searching Authority and International Search Report.
International Search Report issued in related International Patent Application No. PCT/JP2012/006074, completed Oct. 30, 2012.

\* cited by examiner

MATERIAL FOR ORGANIC ELECTROLUMINESCENT ELEMENT, AND ORGANIC ELECTROLUMINESCENT ELEMENT PRODUCED USING SAME

This application is the National Phase of International Patent Application No. PCT/JP2012/006074, filed Sep. 25, 2012, which claims the benefit of priority from Japanese Patent Application No. 2011-213330, filed Sep. 28, 2011. The contents of these applications are incorporated herein by reference in their entirety.

TECHNICAL FIELD

The invention relates to a material for an organic electroluminescence device, and an organic electroluminescence device.

BACKGROUND ART

Organic electroluminescence (EL) devices are divided to into two types, i.e. a fluorescent type and a phosphorescent type. For each type, an optical device design has been studied according to the emission mechanism. For the phosphorescent organic EL device, it is known that due to its emission properties, a high-performance device cannot be obtained by simple application of the fluorescent device technique. The reason therefor is generally considered as follows.

The phosphorescent emission utilizes triplet excitons and thus uses a compound having a large energy gap in an emitting layer, since the energy gap value (hereinafter also referred to as singlet energy) of a compound is normally larger than the triplet energy value (referred to as the difference in energy between the lowest excited triplet state and the ground state in the invention) of the compound.

Therefore, in order to confine the triplet energy of a phosphorescent dopant material in an emitting layer efficiently, it is preferred that a host material having a larger triplet energy than a phosphorescent dopant material be used in the emitting layer. In addition, it is preferred that an electron-transporting layer and a hole-transporting layer be provided adjacent to the emitting layer, and a compound having a triplet energy larger than that of the phosphorescent dopant material be used in the electron-transporting layer and the hole-transporting layer.

As seen above, designing an organic EL device based on the traditional design concept leads to the use in the phosphorescent organic EL device a compound having a larger energy gap than that of a compound used in the fluorescent organic EL device, thereby to increase the driving voltage of the whole organic EL device.

In addition, a hydrocarbon-based compound having a high oxidation resistance and a high reduction resistance, which is useful for the fluorescent device, has a broad pi-electron cloud, and hence it has a small energy gap. Hence, for the phosphorescent organic EL device, such a hydrocarbon-based compound is unlikely to be selected, but an organic compound containing a hetero atom such as oxygen or nitrogen is rather selected. Consequently, the phosphorescent organic EL device has a problem that it has a shorter life as compared with the fluorescent organic EL device.

Further, the device performance is greatly affected by the fact that the relaxation rate of triplet excitons of a phosphorescent dopant material is very slower than that of singlet excitons thereof. That is, the emission from singlet excitons is expected to be efficient, since the rate of the relaxation leading to the emission is so rapid that excitons are unlikely to diffuse to the neighboring layers of an emitting layer (hole-transporting layer or electron-transporting layer, for example). On the other hand, since emission from triplet excitons is spin-forbidden and has a slow relaxation rate, the triplet excitons are likely to diffuse to the neighboring layers, so that the triplet excitons are thermally energy-deactivated unless the phosphorescent dopant material is a specific phosphorescent compound. In short, in the phosphorescent organic EL device, control of electrons and holes in the recombination region is more important as compared with the fluorescent organic EL device.

For the above reasons, enhancement of the performance of the phosphorescent organic EL device requires material selection and device design different from those of the fluorescent organic EL device.

Particularly, in the case of a phosphorescent organic EL device emitting blue light, it is preferred that a compound having a large triplet energy be used in an emitting layer and their neighboring layers as compared with a phosphorescent organic EL device emitting green to red light. Specifically, in order to obtain blue phosphorescent emission, it is ideal that a host material used in the emitting layer have a triplet energy of 3.0 eV or more. In order to obtain such materials, it has been required to design molecules according to a new concept which are different from those for materials for the fluorescent device and materials for the phosphorescent device emitting green to red light.

Under such conditions, as a material for a phosphorescent organic EL device emitting blue light, a compound having a structure in which plural heterocyclic rings are combined has been studied. For example, Patent Document 1 discloses a compound having a 3,3'-biscarbazole as a mother skeleton and a substituent which is adjacent to the carbon atom in each carbazole skeleton involved in the bond of the carbazoles. The document discloses the structure in which the biscarbazole is twisted by introducing an alkyl group to the substituent to retain the triplet energy high.

Patent Document 2 discloses a compound having a 3,3'-biscarbazole as a mother skeleton and a substituent which is adjacent to the carbon atom in each carbazole skeleton involved in the bond of the carbazoles. This document states advantageous effects that driving voltage is lowered and durability is improved are attained by using this compound as a host material of a phosphorescent device.

RELATED ART DOCUMENTS

Patent Documents

Patent Document 1: WO2006/061759
Patent Document 2: JP-A-2006-352046

SUMMARY OF THE INVENTION

The invention is aimed at providing a compound suitable for a material for a phosphorescent organic EL device, in particular for a blue phosphorescent device.

In order to retain a high luminous efficiency in the phosphorescent organic EL device, a material which can confine high triplet energy in an emitting layer is preferable. In order to retain a high triplet energy state, it is important to control the molecular skeleton of the material which is in the triplet energy state.

The inventors have found that a compound which comprises two carbazole skeletons being bonded at a specific part and in which a specific substituent is introduced to the carbon atom adjacent to the bonding position of the two carbazole skeletons only in the one carbazole skeleton can retain high triplet energy.

In addition, in order to lower the driving voltage of an organic EL device, a material having a small barrier at injection of holes and electrons to an emitting layer is preferable. The inventors have found that the injection barrier of holes to an emitting layer can be lowered by bonding two carbazole skeletons at a specific position.

Further, the inventors have found that in a phosphorescent device, which requires high triplet energy, the above-mentioned compounds which can satisfy the above-mentioned characters simultaneously contribute largely to lower the driving voltage while retaining high luminous efficiency.

Moreover, traditionally, in order to retain high triplet energy even in the excited triplet state, severe material designing has been conducted. Specifically, the molecular structure is prevented from changing between the ground state and the excited state by introducing many substituents to the atoms adjacent to each other in the identical aromatic ring among the aromatic rings constituting a material for an organic EL device.

However, such designing often lowers the material stability against heat, thereby rending the material unstable due to heat during deposition. At the same time, the designing often shortens the driving life of a device. Optimizing the number of substituents on the carbon atom adjacent to the bonding position of carbazole skeletons allows an organic thin film to be formed stably even when deposited, thereby to obtain an organic EL device having high luminous efficiency without lowering the driving life. The invention was completed based on the following finding.

According to the invention, the following material for an organic electroluminescence device and organic electroluminescence device are provided.

1. A compound represented by the following formula (1):

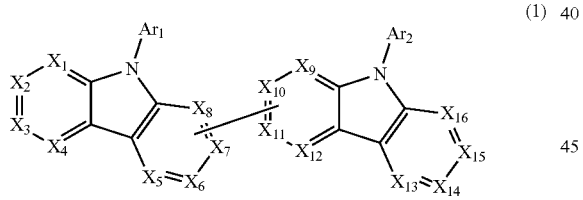

wherein in the formula (1),

Ar$_1$ and Ar$_2$ are independently a substituted or unsubstituted aryl group including 6 to 18 ring carbon atoms, a substituted or unsubstituted heteroaryl group including 5 to 18 ring atoms, or a substituted or unsubstituted alkyl group including 1 to 20 carbon atoms;

X$_1$ to X$_4$ and X$_{13}$ to X$_{16}$ are independently CR$_1$, CH or N;

one of X$_5$ to X$_8$ is a carbon atom bonding to one of X$_9$ to X$_{12}$, and at least one of X$_5$ to X$_8$ that is adjacent to the carbon atom bonding to one of X$_9$ to X$_{12}$ is CR$_2$;

one of X$_9$ to X$_{12}$ is a carbon atom bonding to one of X$_5$ to X$_8$, and X$_9$ to X$_{12}$ that is adjacent to the carbon atom bonding to one of X$_5$ to X$_8$ is CH or N;

the remaining X$_5$ to X$_8$ and the remaining X$_9$ to X$_{12}$ are CR$_1$, CH or N; and R$_1$ and R$_2$ are independently a substituted or unsubstituted aryl group including 6 to 18 ring carbon atoms, or a substituted or unsubstituted heteroaryl group including 5 to 18 ring atoms.

2. The compound according to 1, wherein X$_9$ to X$_{12}$ that is not the carbon atom bonding to one of X$_5$ to X$_8$ are CH or N.

3. The compound according to 1 which is selected from the group consisting of compounds represented by the following formulas (2) to (17):

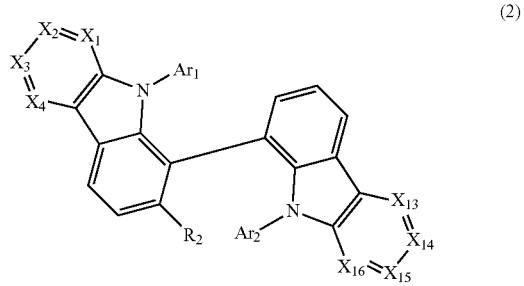

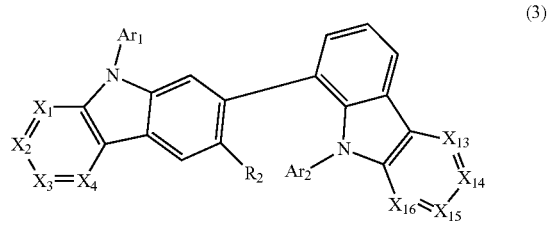

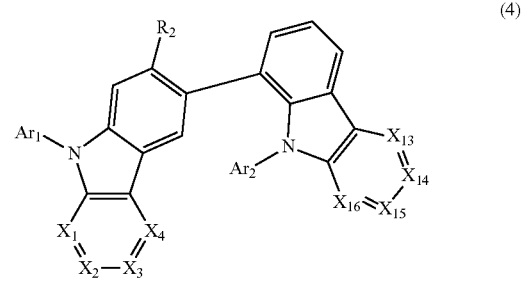

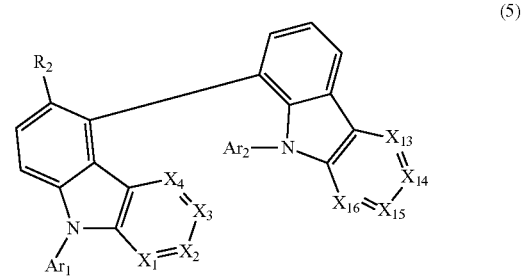

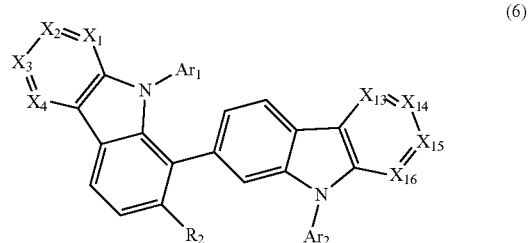

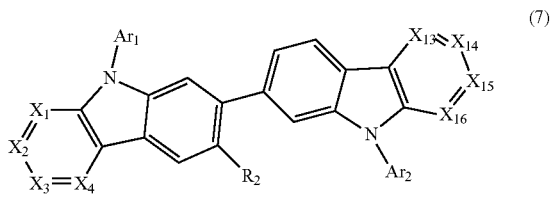

-continued
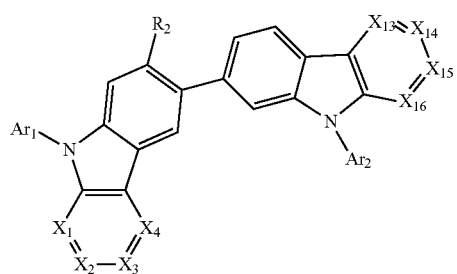
(8)
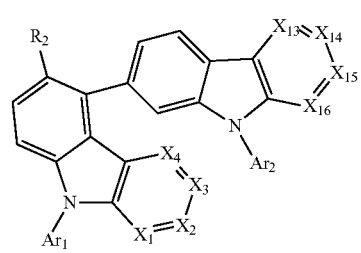
(9)
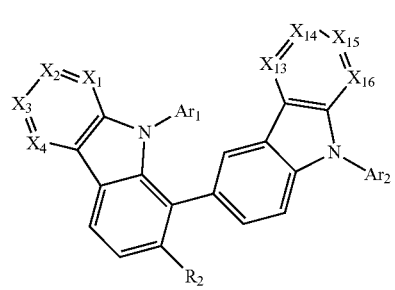
(10)
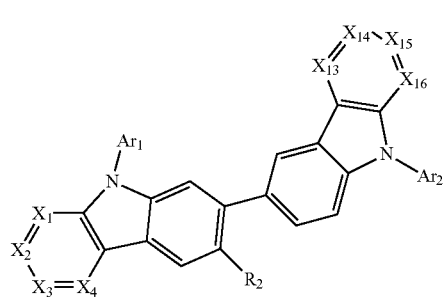
(11)
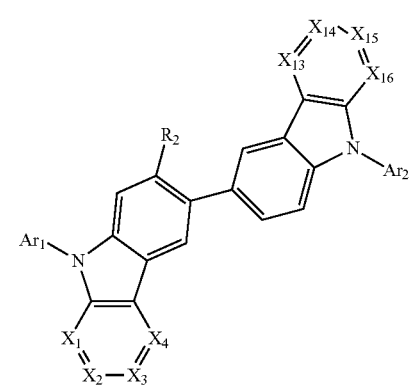
(12)
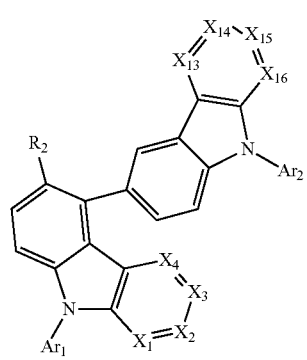
(13)
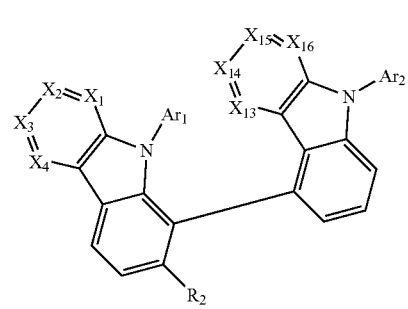
(14)
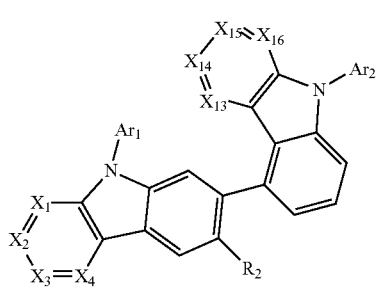
(15)
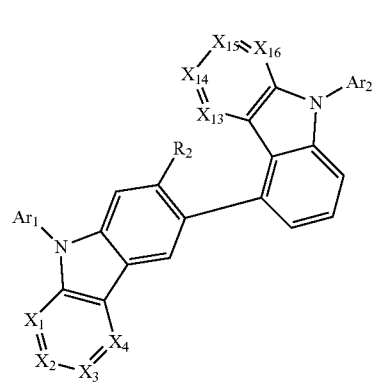
(16)

-continued

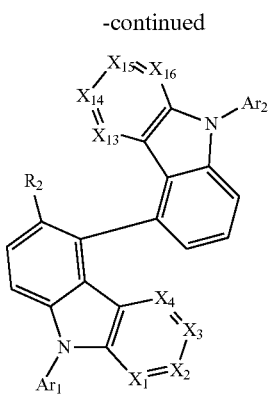

(17)

wherein, in the formulas (2) to (17), $Ar_1$, $Ar_2$, $R_2$, $X_1$ to $X_4$ and $X_{13}$ to $X_{16}$ are as defined in the formula (1).

4. A material for an organic electroluminescence device comprising the compound according to any of 1 to 3.

5. An organic electroluminescence device comprising one or more organic thin film layers including an emitting layer between a cathode and an anode, at least one layer of the organic thin film layers comprising the material for an organic electroluminescence device according to 4.

6. The organic electroluminescence device according to 5, wherein the organic thin film layers comprise one or more emitting layers, and at least one of the emitting layers comprises the material for an organic electroluminescence device and a phosphorescent material.

7. The organic electroluminescence device according to 6, wherein the excited triplet energy of the phosphorescent material is 1.8 eV or more and less than 2.9 eV.

8. The organic electroluminescence device according to 6 or 7, wherein the phosphorescent material comprises a metal complex, the metal complex comprising a metal atom selected from Ir, Pt, Os, Au, Cu, Re and Ru, and a ligand.

9. The organic electroluminescence device according to 8, wherein the ligand comprises an ortho-metal bond with the metal atom.

10. The organic electroluminescence device according to any of 6 to 9, wherein the maximum value of emission wavelengths is 430 nm or more and 720 nm or less.

11. The organic electroluminescence device according to any of 5 to 11, wherein an electron-transporting region is between the emitting layer and the cathode, the electron-transporting region comprising the material for an organic electroluminescence device.

12. The organic electroluminescence device according to any of 5 to 11, wherein a hole-transporting region is between the emitting layer and the anode, the hole-transporting region comprising the material for an organic electroluminescence device.

13. The organic electroluminescence device according to any of 5 to 10, wherein at least one of two organic thin film layers adjacent to the emitting layer comprises the material for an organic electroluminescence device, and the excited triplet energy of the material for an organic electroluminescence device of this adjacent layer is 2.5 eV or more.

14. The organic electroluminescence device according to any of 5 to 13, wherein the organic thin film comprises an electron-transporting layer or an electron-injecting layer between the cathode and the emitting layer, and the electron-transporting layer or electron-injecting layer comprises an aromatic ring compound including a nitrogen-containing six-membered ring or a nitrogen-containing five-membered ring skeleton, or a fused aromatic ring compound including a nitrogen-containing six-membered ring or a nitrogen-containing five-membered ring skeleton.

According to the invention, an organic EL device of which the drive life is not lowered and the luminous efficiency is high can be provided.

MODE FOR CARRYING OUT THE INVENTION

Figure 1:
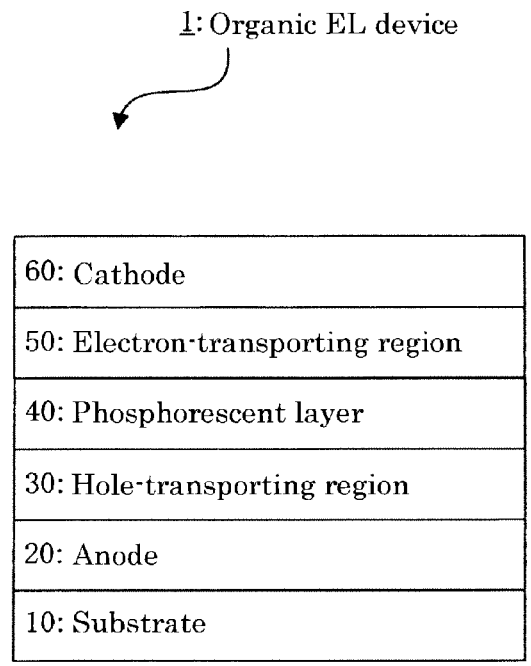
FIG. 1 is a schematic view showing the layer construction according to one embodiment of the organic EL device of the invention.

The compound of the invention is characterized by being represented by the following formula (1).

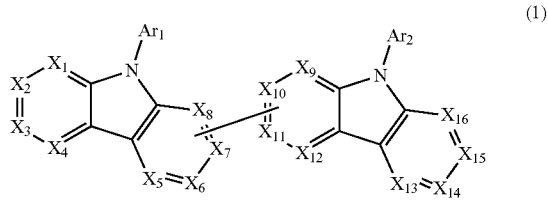

(1)

In the formula (1), $Ar_1$ and $Ar_2$ are independently a substituted or unsubstituted aryl group including 6 to 18 carbon atoms that form a ring (hereinafter referred to as the "ring carbon atoms"), a substituted or unsubstituted heteroaryl group including 5 to 18 ring atoms, or a substituted or unsubstituted alkyl group including 1 to 20 carbon atoms;

$X_1$ to $X_4$ and $X_{13}$ to $X_{16}$ are independently $CR_1$, CH or N, preferably CH or N, and more preferably CH;

one of $X_5$ to $X_8$ is a carbon atom bonding to one of $X_9$ to $X_{12}$, at least one of $X_5$ to $X_8$ which is adjacent to the carbon atom bonding to one of $X_9$ to $X_{12}$ is $CR_2$, and at least one of $X_5$ to $X_8$ which is adjacent to the carbon atom bonding to one of $X_9$ to $X_{12}$ is preferably $CR_2$;

one of $X_9$ to $X_{12}$ is a carbon atom bonding to one of $X_5$ to $X_8$, $X_9$ to $X_{12}$ which is adjacent to the carbon atom bonding to one of $X_5$ to $X_8$ is CH or N, and $X_9$ to $X_{12}$ which is adjacent to the carbon atom bonding to one of $X_5$ to $X_8$ is preferably CH;

the remainder of $X_5$ to $X_8$ and the remainder of $X_9$ to $X_{12}$ are $CR_1$, CH or N, $X_9$ to $X_{12}$ which is not the carbon atom bonding to one of $X_5$ to $X_8$ is preferably CH or N, more preferably CH, and $X_5$ to $X_8$ which is not the carbon atom bonding to one of $X_9$ to $X_{12}$ and is not $CR_2$ is preferably CH or N, more preferably CH; and $R_1$ and $R_2$ are independently a substituted or unsubstituted aryl group including 6 to 18 ring carbon atoms, or a substituted or unsubstituted heteroaryl group including 5 to 18 atoms that form a ring (hereinafter referred to as the "ring atoms").

In the specification, the aryl group includes a monocyclic aromatic hydrocarbon ring group and a fused aromatic hydrocarbon ring group obtained by fusing plural hydrocarbon rings. The heteroaryl group includes a monocyclic hetero aromatic ring group, and a hetero fused aromatic ring group obtained by fusing plural hetero aromatic rings, and a hetero fused aromatic ring group obtained by fusing an aromatic hydrocarbon ring and a hetero aromatic ring.

Specific examples of the aryl group including 6 to 18 ring carbon atoms include a phenyl group, a triphenylenyl group, a fluorenyl group, a 9,9-dimethylfluorenyl group, a biphenyl group and a terphenyl group. A phenyl group and a biphenyl group are preferable.

The above-mentioned aryl group preferably includes 6 to 12 ring carbon atoms.

Meanwhile, the "carbon atoms that form a ring" means carbon atoms constituting a saturated ring, an unsaturated ring or an aromatic ring. The "ring carbon atoms" means the number of carbon atoms constituting a saturated ring, an unsaturated ring or an aromatic ring, excluding the number of carbon atoms included in substituents of these rings.

Specific examples of the heteroaryl group including 5 to 18 ring atoms include a pyrrolyl group, a pyrazinyl group, a pyridinyl group, an indolyl group, an isoindolyl group, an imidazolyl group, a furyl group, a benzofuranyl group, an isobenzofuranyl group, a dibenzofuranyl group, a dibenzothiophenyl group, a carbazolyl group, a phenylcarbazolyl group, an acridinyl group, a phenothiazinyl group, a phenoxazinyl group, an oxazolyl group, an oxadiazolyl group, a furazanyl group, a thienyl group, a benzothiophenyl group, an azacarbazolyl group, an azadibenzofuranyl group and an azadibenzothiophenyl group. A dibenzofuranyl group, a dibenzothiophenyl group, a carbazolyl group and a phenylcarbazolyl group are preferable.

The above-mentioned heteroaryl group preferably includes 5 to 13 ring atoms.

Meanwhile, the "atoms that form a ring" means atoms constituting a saturated ring, an unsaturated ring or an aromatic ring. The "ring atoms" means the number of atoms constituting a saturated ring, an unsaturated ring or an aromatic ring, excluding the number of carbon atoms included in substituents of these rings.

Specific examples of the alkyl group including 1 to 20 carbon atoms include a linear or branched alkyl group, specifically a methyl group, an ethyl group, a propyl group, an isopropyl group, an n-butyl group, an isobutyl group, a sec-butyl group, a tert-butyl group, an n-pentyl group, an n-hexyl group, an n-heptyl group and an n-octyl group. A methyl group, an ethyl group, a propyl group, an isopropyl group, an n-butyl group, an isobutyl group, a sec-butyl group and a tert-butyl group are preferable. A methyl group, an ethyl group, a propyl group, an isopropyl group, an n-butyl group, an s-butyl group and a t-butyl group are more preferable.

When the above-mentioned aryl group and heteroaryl group has a substituent, specific examples of the substituent include an alkyl group, alkoxy group or fluoroalkyl group including 1 to 20 carbon atoms, an aryl group or aryloxy group including 6 to 18 ring carbon atoms, a heteroaryl group including 5 to 18 ring atoms, a group formed by bonding an aryl group including 6 to 18 ring carbon atoms and a heteroaryl group including 5 to 18 ring atoms, an aralkyl group including 7 to 30 carbon atoms, a halogen atom, a cyano group, a substituted or unsubstituted silyl group and a germanium group. These substituents may be further substituted by the above-mentioned substituents.

When the above-mentioned alkyl group has a substituent, as the specific example of the substituent, the above-mentioned substituent of an aryl group and a heteroaryl group excluding an alkyl group including 1 to 20 carbon atoms can be given. These substituents may be further substituted by the above-mentioned substituents.

The alkoxy group is represented by —OY. Examples of Y include the above-mentioned examples for an alkyl group. Specific examples of the alkoxy group include a methoxy group and an ethoxy group.

The ayloxy group is represented by —OZ. Examples of Z include the above-mentioned examples for an aryl group. Specific examples of the aryloxy group include a phenoxy group.

As the fluoroalkyl group, the above-mentioned alkyl group substituted by one or more fluorine atoms can be given. Specifically, a fluoromethyl group, a difluoromethyl group, a trifluoromethyl group, a fluoroethyl group, a 2,2,2-trifluoroethyl group, a pentafluoroethyl group or the like can be given. A trifluoromethyl group and a pentafluoroethyl group are preferable.

The aralkyl group is represented by —Y—Z. Examples of Y include examples of the alkylene group corresponding to the above-mentioned examples for the alkyl group. Examples of Z include the above-mentioned examples for the aryl group. The aryl part of the aralkyl group preferably includes 6 to 20 carbon atoms, with 6 to 12 carbon atoms being particularly preferable. The alkyl part of the aralkyl group preferably includes 1 to 10 carbon atoms, with 1 to 6 carbon atoms being particularly preferable. For example, a benzyl group, a phenylethyl group, a 2-phenylpropane-2-yl group or the like can be given.

In the invention, the hydrogen atom includes isotopes which have a different number of neutrons, i.e., protium, deuterium and tritium.

Preferable examples of $R_2$ include a substituted or unsubstituted phenyl group, a substituted or unsubstituted dibenzofuranyl group, a substituted or unsubstituted dibenzothiophenyl group, a substituted or unsubstituted carbazolyl group, a substituted or unsubstituted azadibenzofuranyl group, a substituted or unsubstituted azadibenzothiophenyl group, a substituted or unsubstituted azacarbazolyl group, a substituted or unsubstituted pyridyl group, a substituted or unsubstituted pyrimidinyl group and a substituted or unsubstituted triazinyl group.

Preferable examples of $Ar_1$ include a substituted or unsubstituted phenyl group, a substituted or unsubstituted dibenzofuranyl group, a substituted or unsubstituted dibenzothiophenyl group, a substituted or unsubstituted carbazolyl group, a substituted or unsubstituted azadibenzofuranyl group, a substituted or unsubstituted azadibenzothiophenyl group, a substituted or unsubstituted azacarbazolyl group, a substituted or unsubstituted pyridyl group, a substituted or unsubstituted pyrimidinyl group and a substituted or unsubstituted triazinyl group.

Preferable examples of $Ar_2$ include a substituted or unsubstituted phenyl group, a substituted or unsubstituted dibenzofuranyl group, a substituted or unsubstituted dibenzothiophenyl group, a substituted or unsubstituted carbazolyl group, a substituted or unsubstituted azadibenzofuranyl group, a substituted or unsubstituted azadibenzothiophenyl group, a substituted or unsubstituted azacarbazolyl group, a substituted or unsubstituted pyridyl group, a substituted or unsubstituted pyrimidinyl group and a substituted or unsubstituted triazinyl group.

The compound of the invention can retain high triplet energy by introducing a proper substituent into the specific position of one carbazole ring, while it can preserve the stability against heat since the twisting of the bond of two carbazole rings can be suppressed due to the introduction of a substituent into only the one carbazole ring.

Thus, when the compound of the invention is used, a highly efficient organic EL device with a prolonged life can be produced.
The material for an organic EL device represented by the above-mentioned formula (1) is preferably selected from the group consisting of compounds represented by the following formulas (2) to (17).
(2)
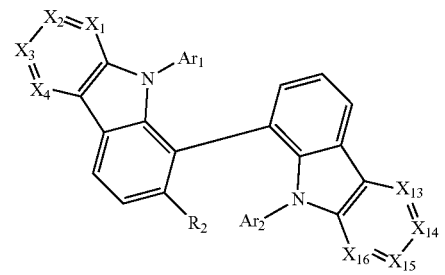
(3)
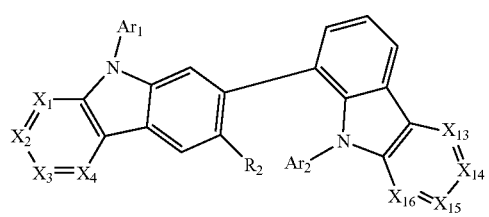
(4)
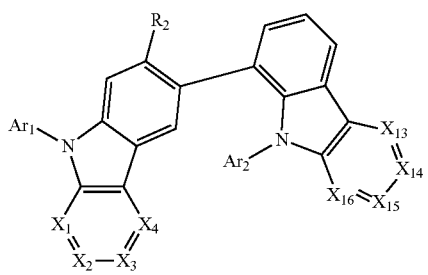
(5)
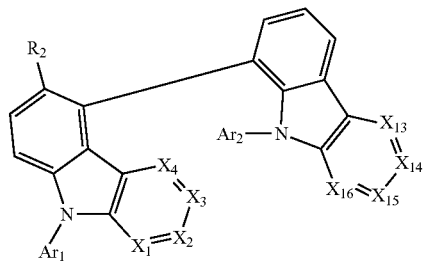
(6)
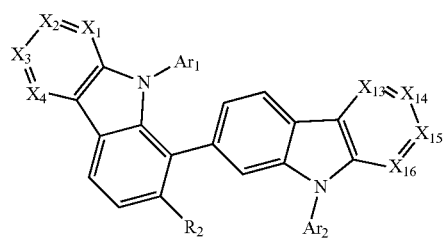
(7)
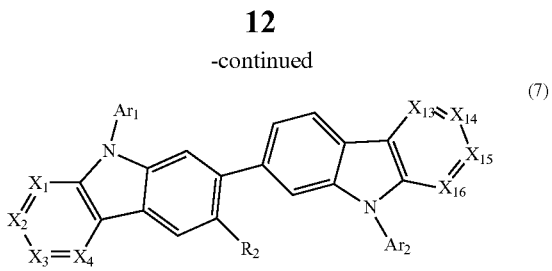
(8)
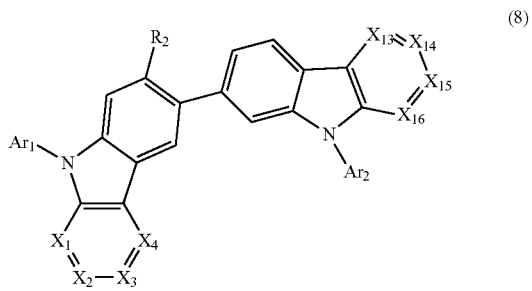
(9)
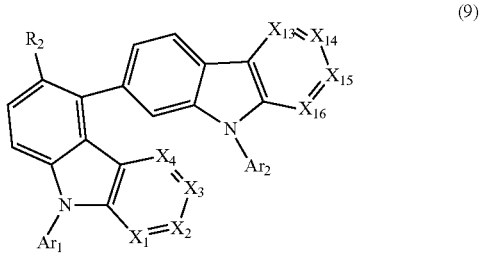
(10)
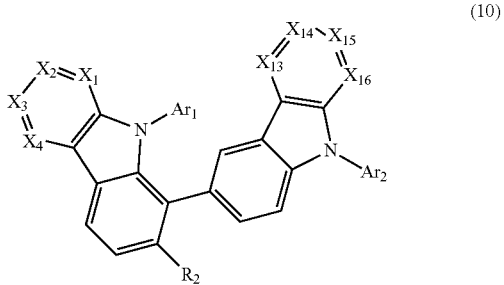
(11)
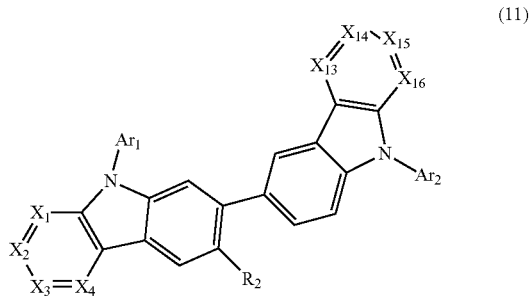

(12)
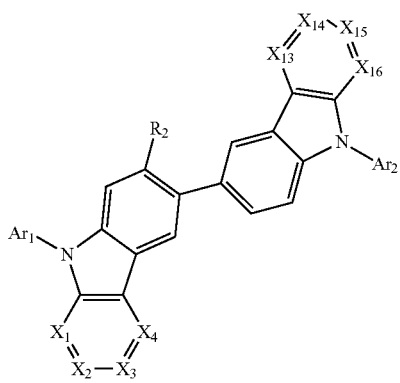
(13)
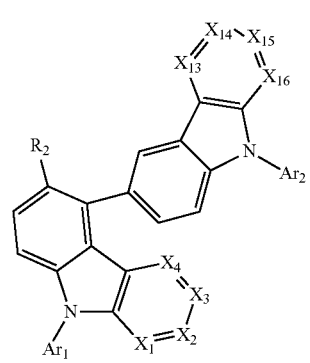
(14)
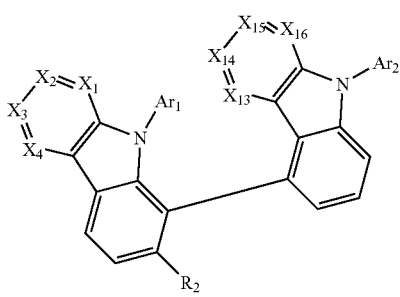
(15)
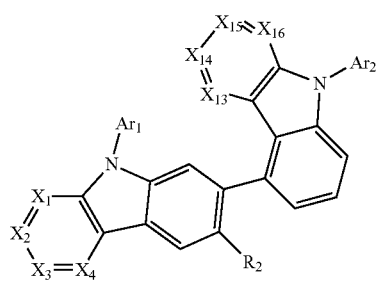
(16)
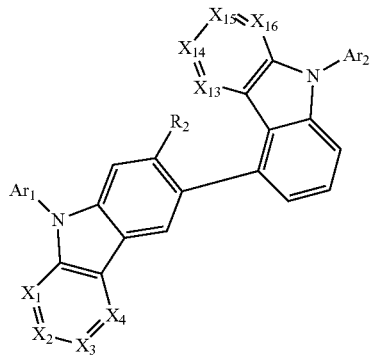
(17)
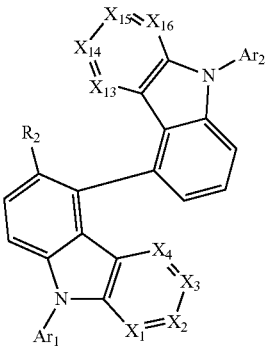
In the formulas (2) to (17), $Ar_1$, $Ar_2$, $R_2$, $X_1$ to $X_4$ and $X_{13}$ to $X_{16}$ are as described in the above-mentioned formula (1).
Specific examples of the compounds represented by the above-mentioned formulas (2) to (17) are shown below.
Compounds represented by the formula (2):
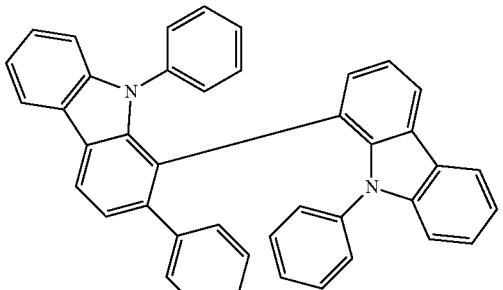
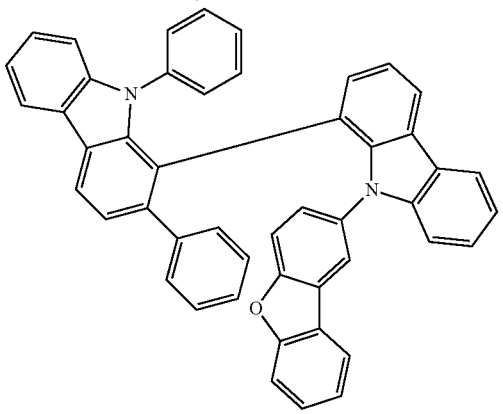

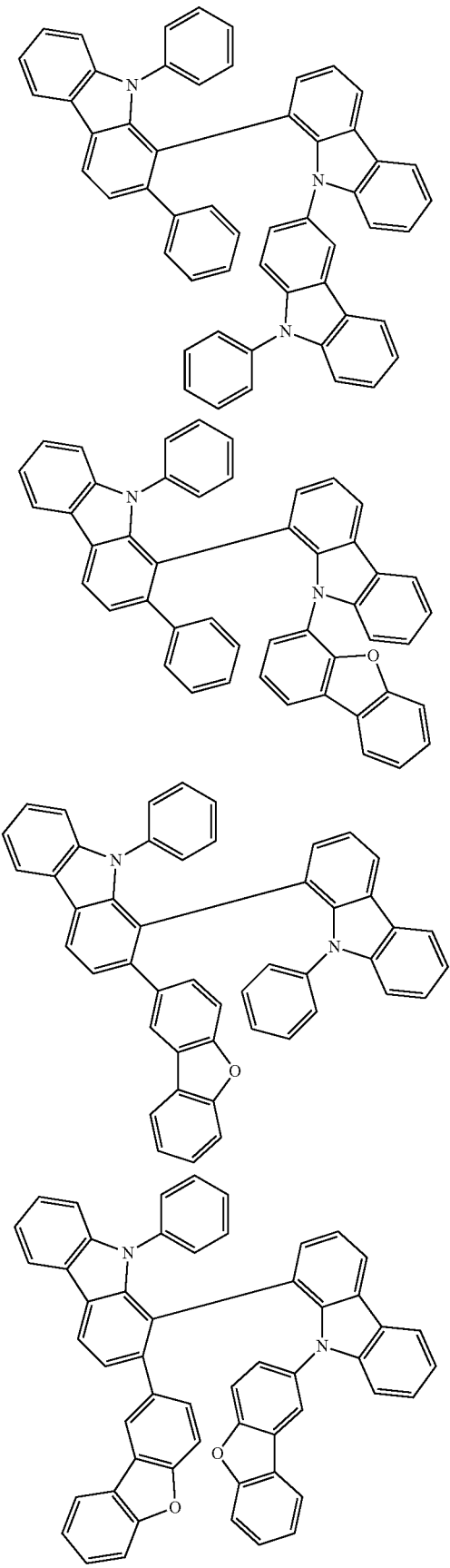
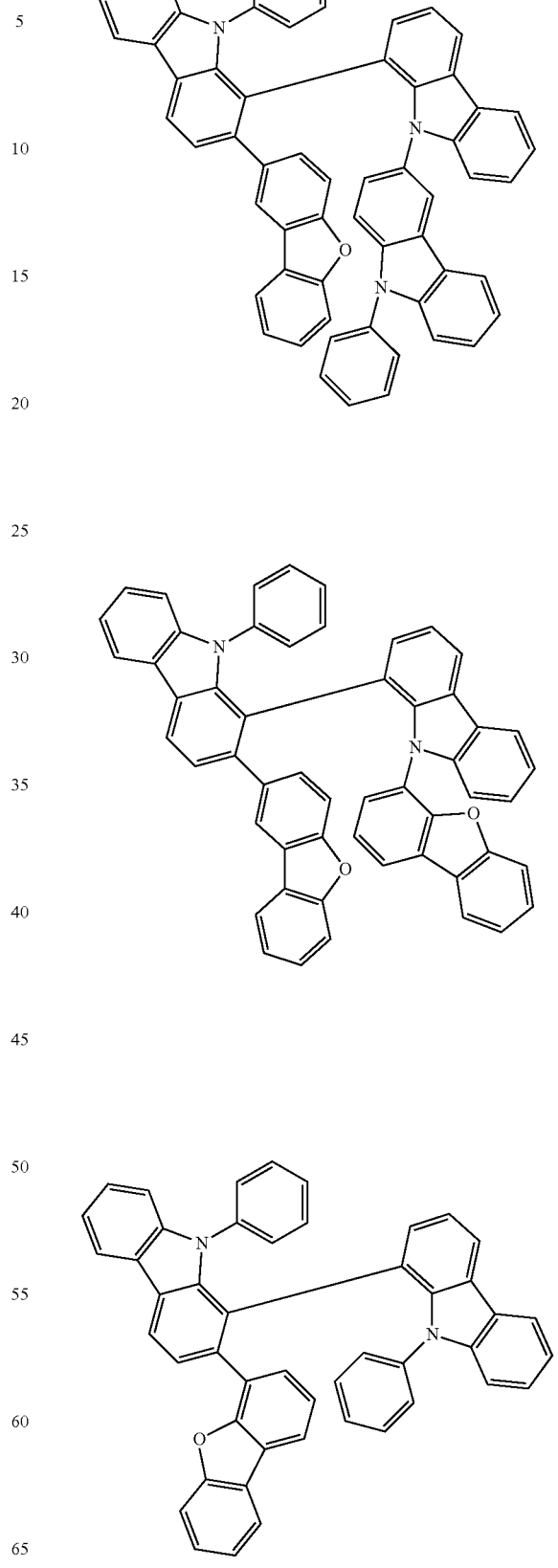

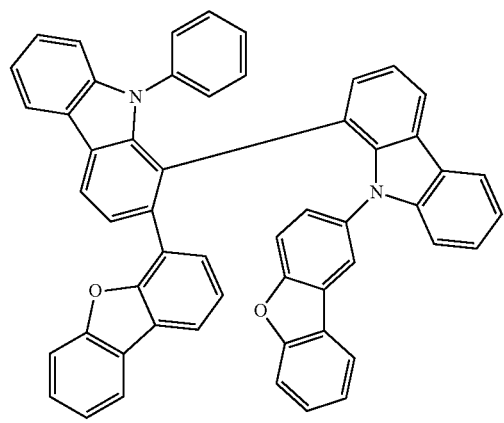
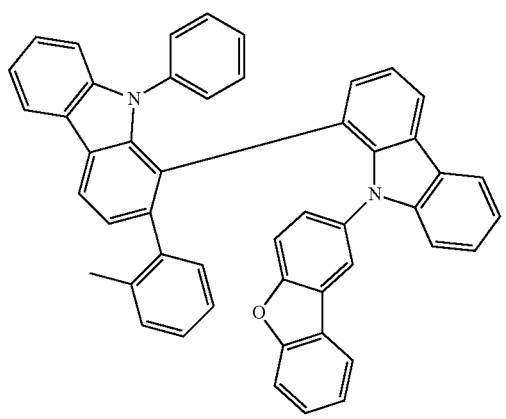
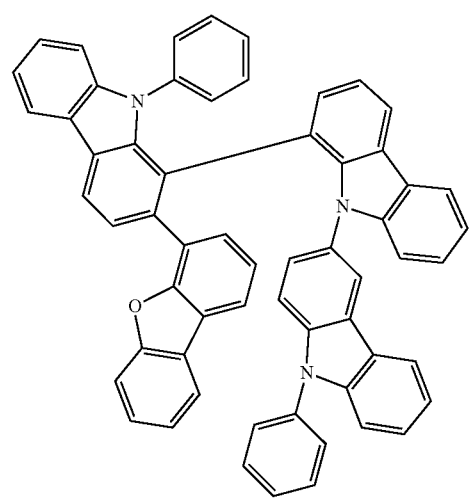
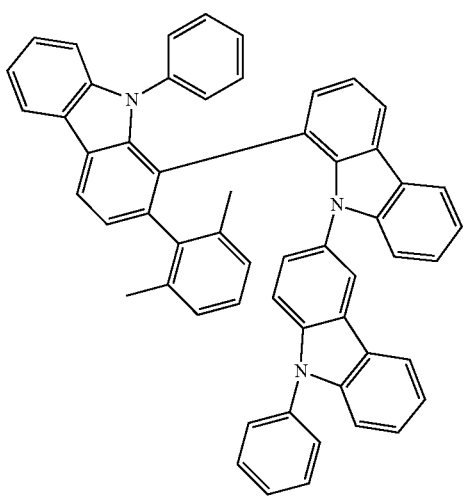
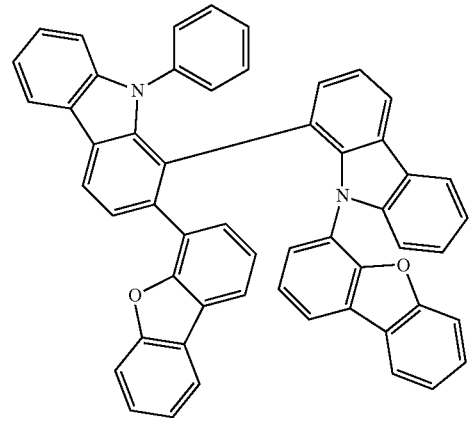
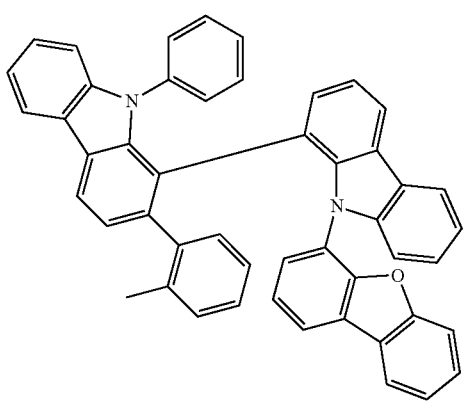
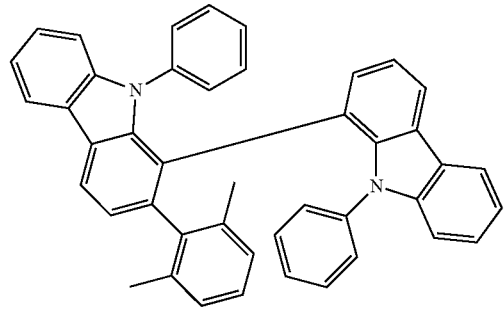

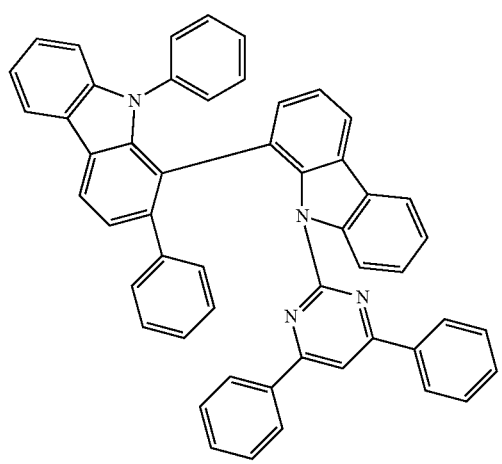
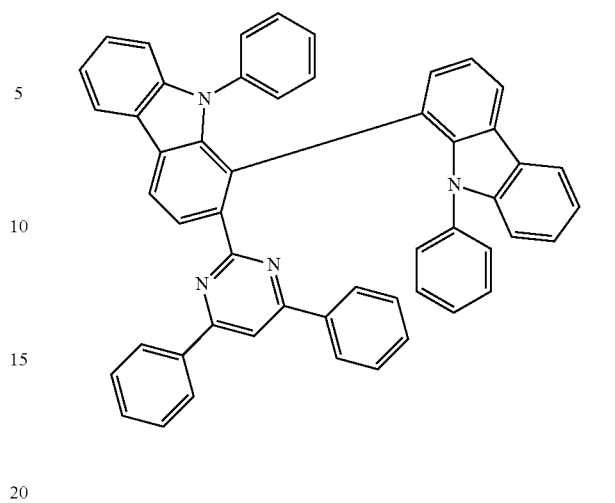
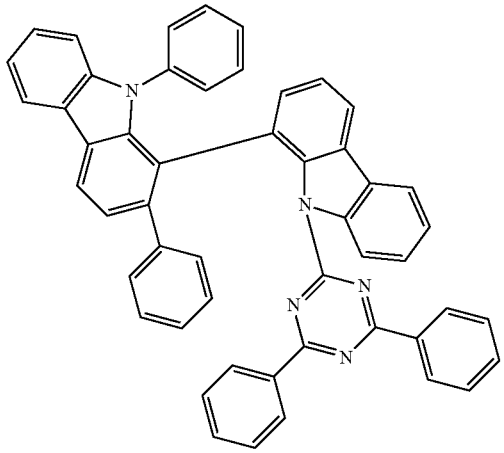
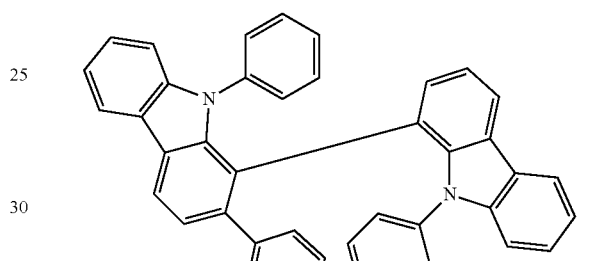
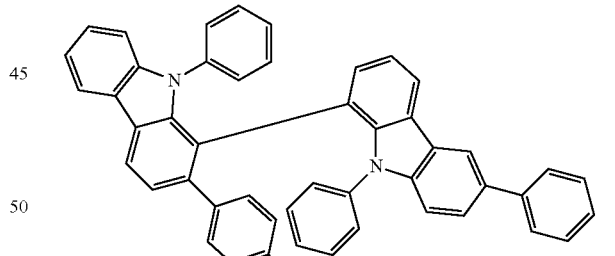
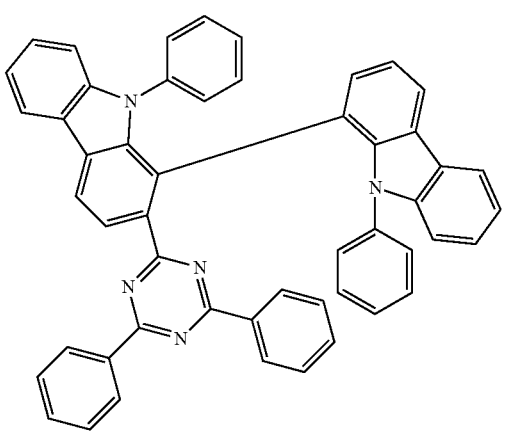
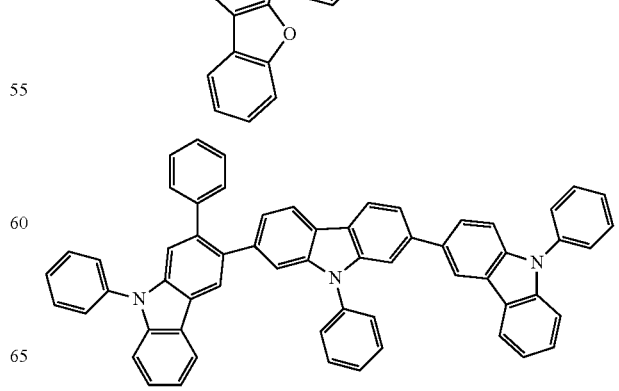

21
-continued
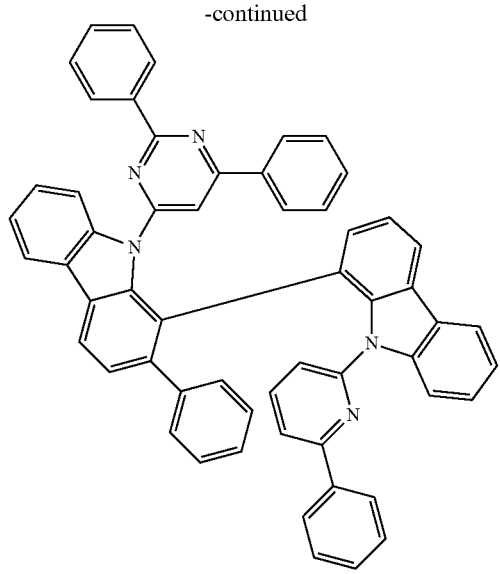
Compounds represented by the formula (3):
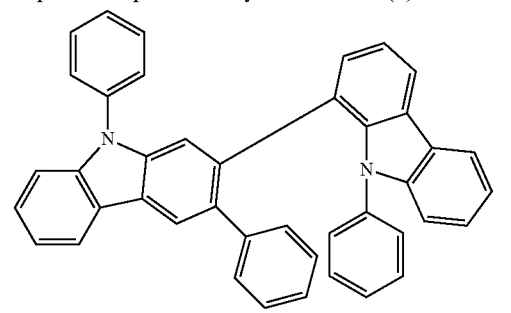
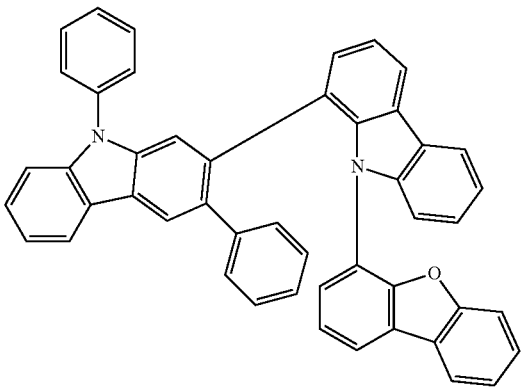
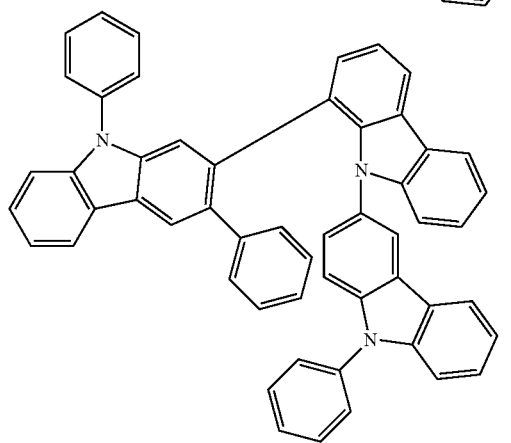
22
-continued
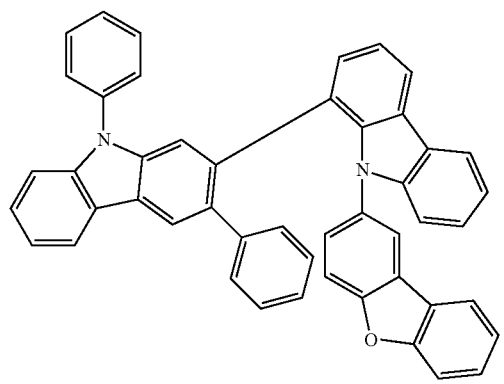
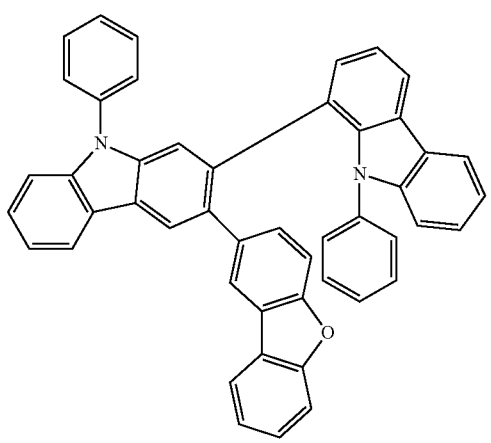
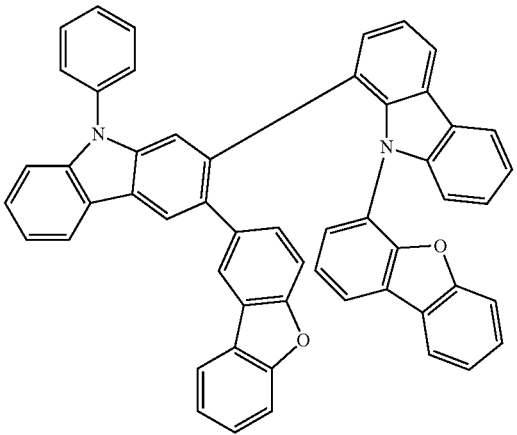

23
-continued
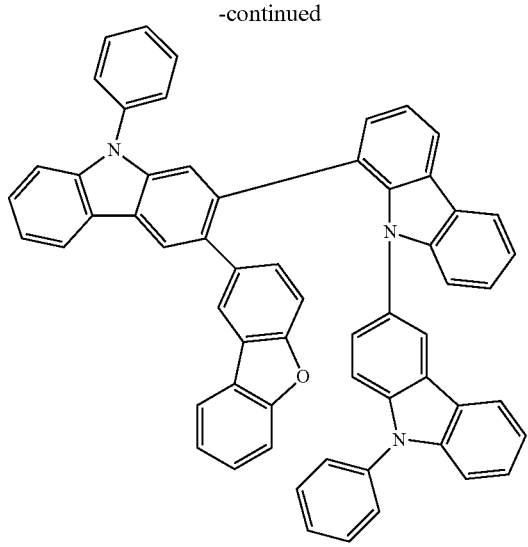
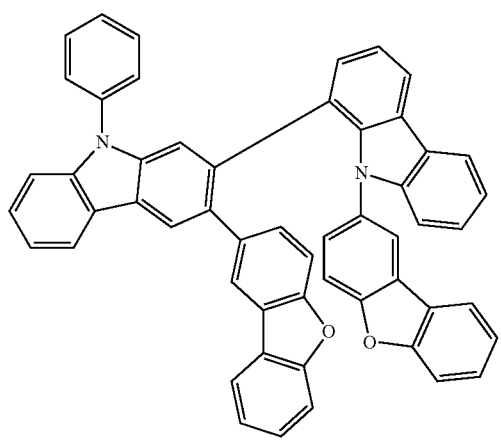
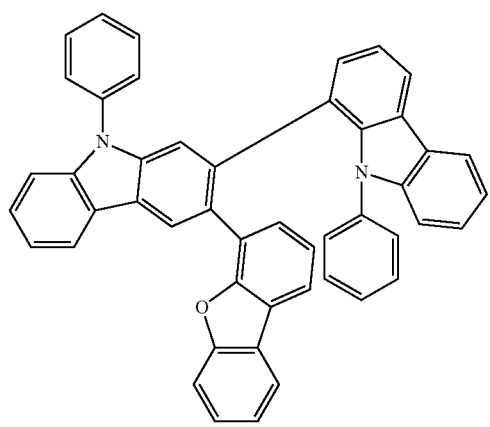
24
-continued
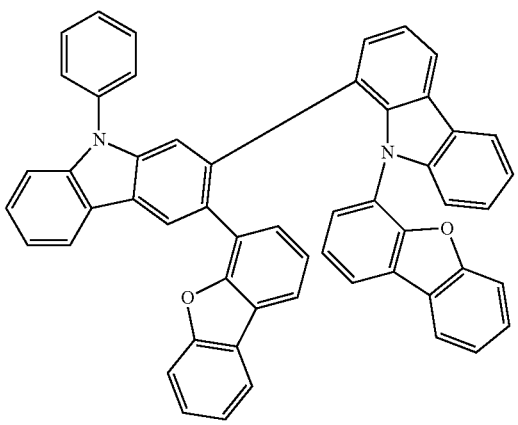
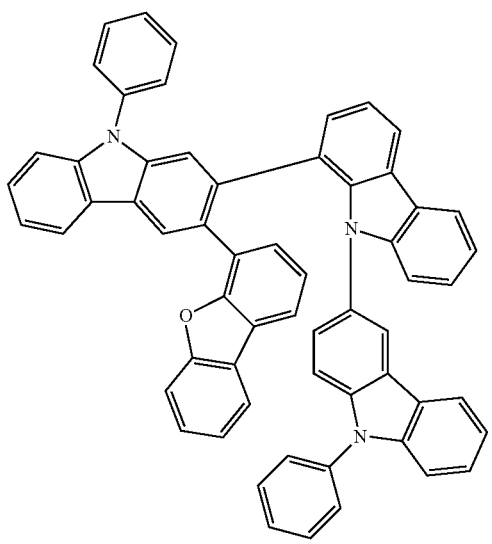
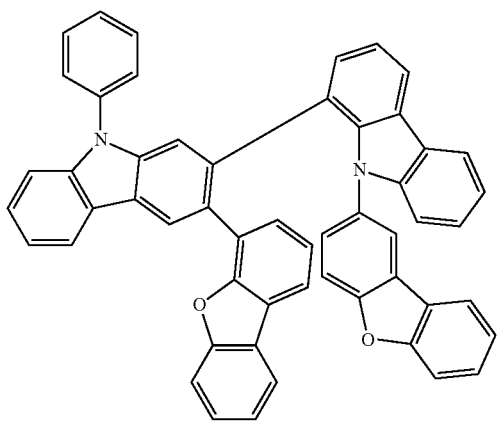

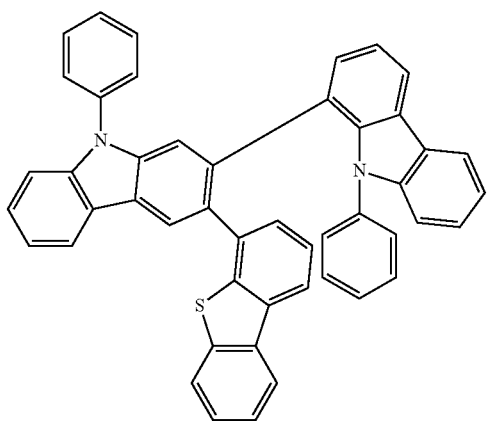
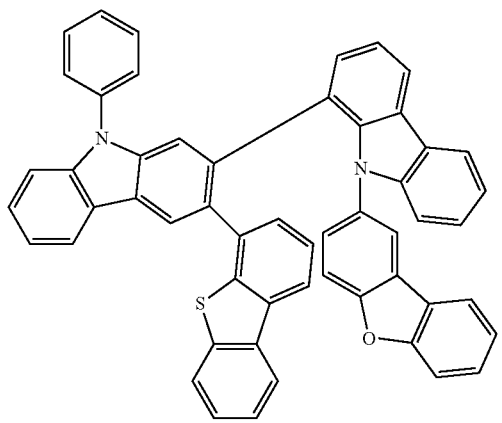
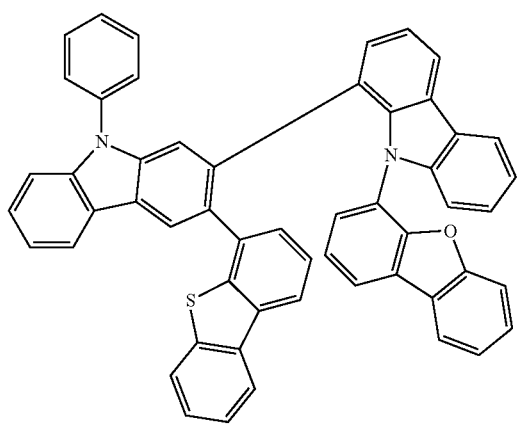
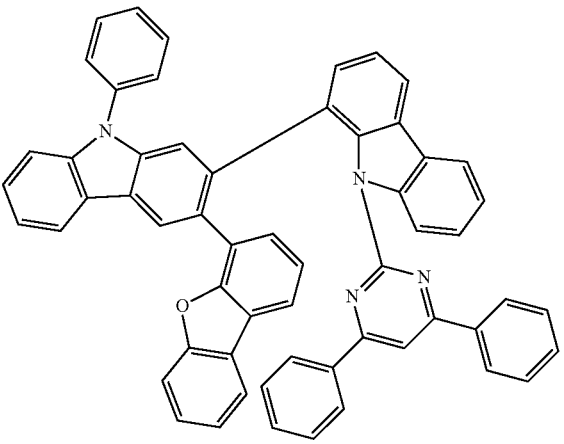
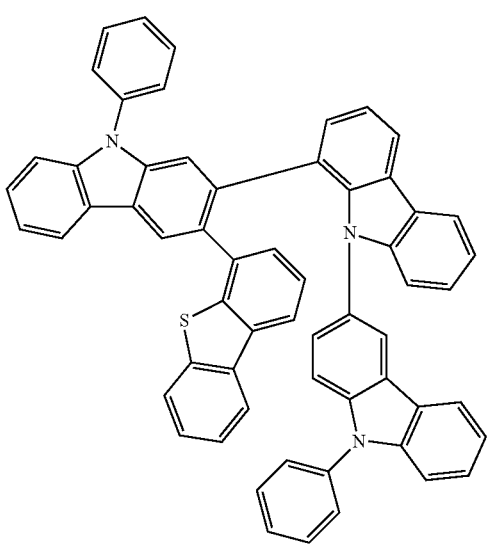
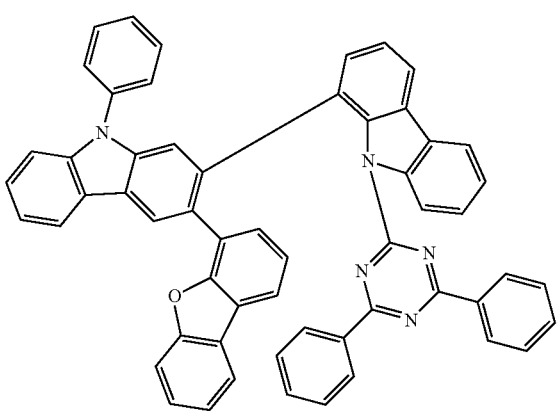

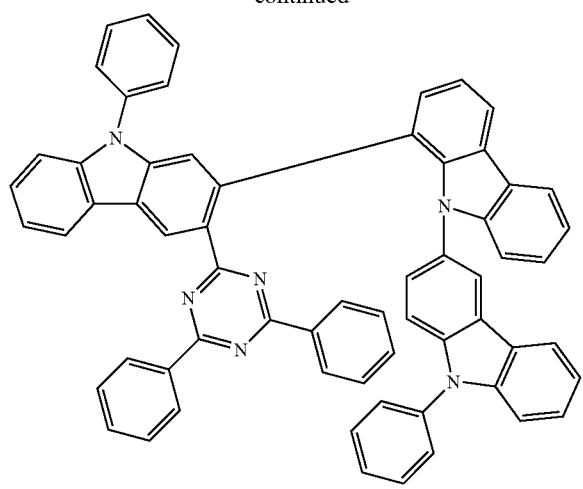
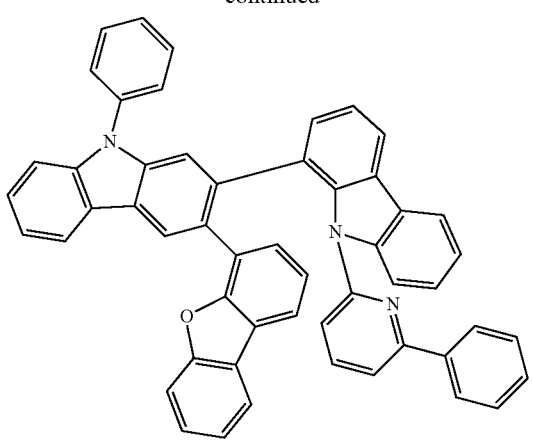
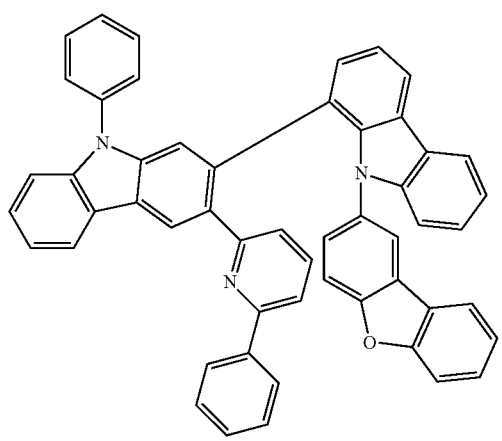
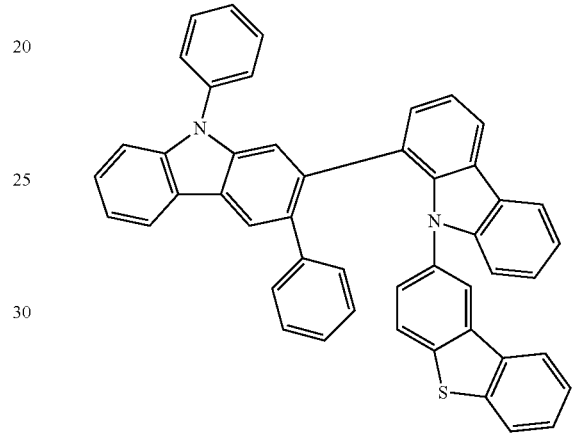
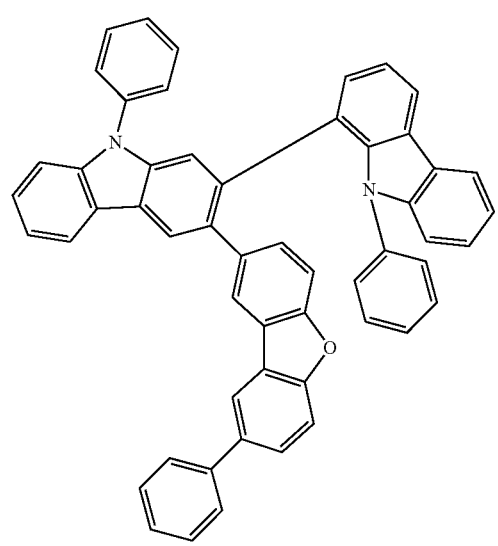
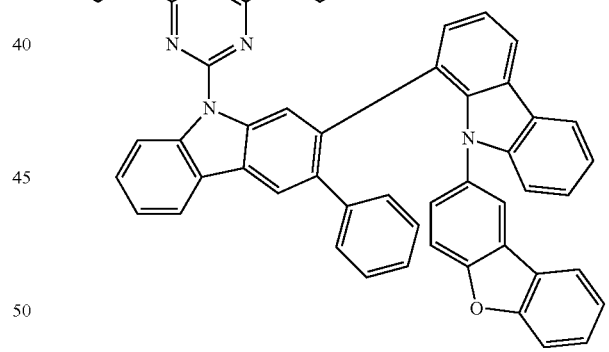
Compounds represented by the formula (4):
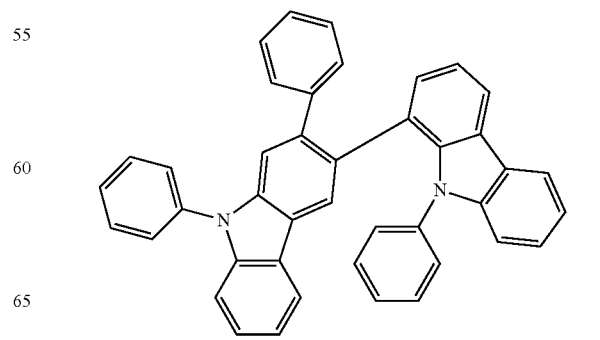

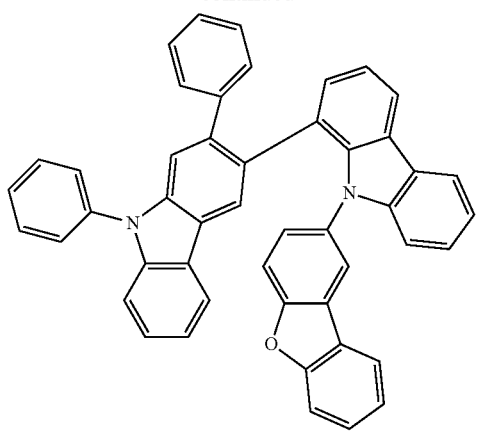
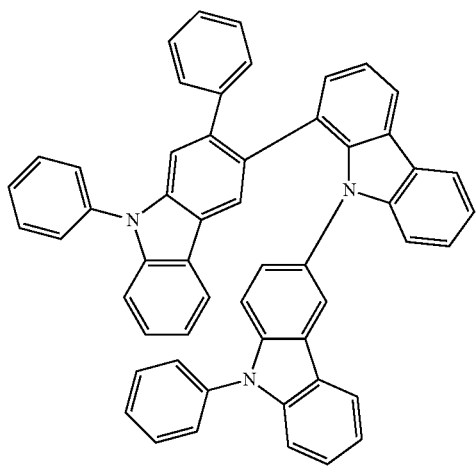
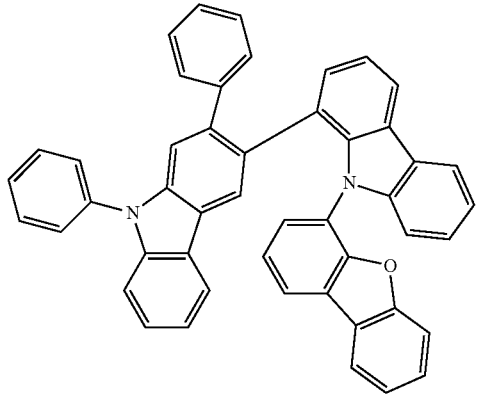
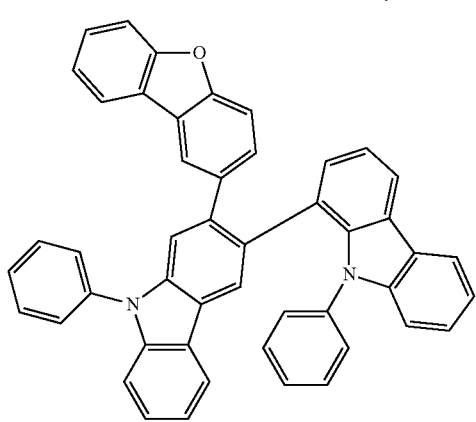
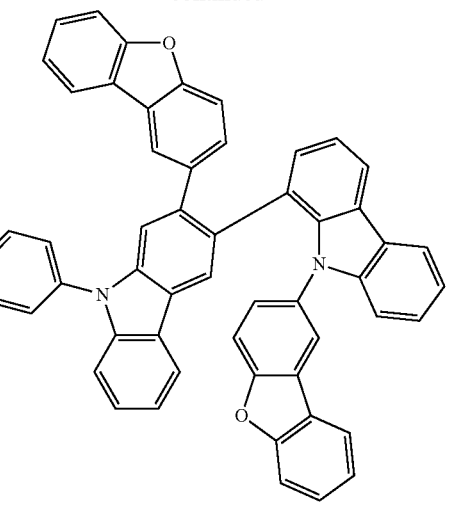
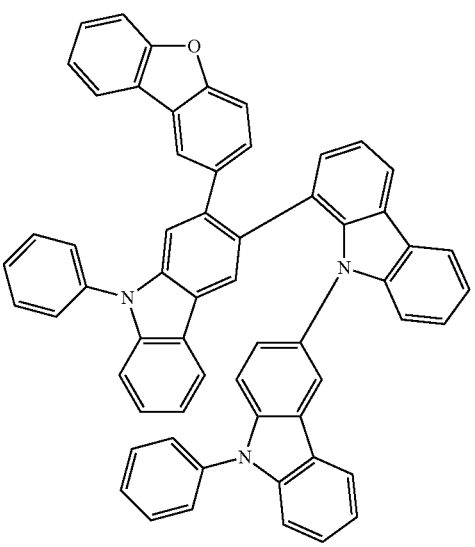
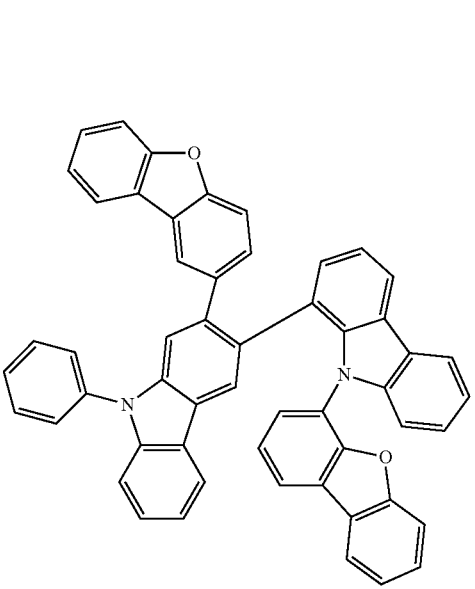

31
-continued
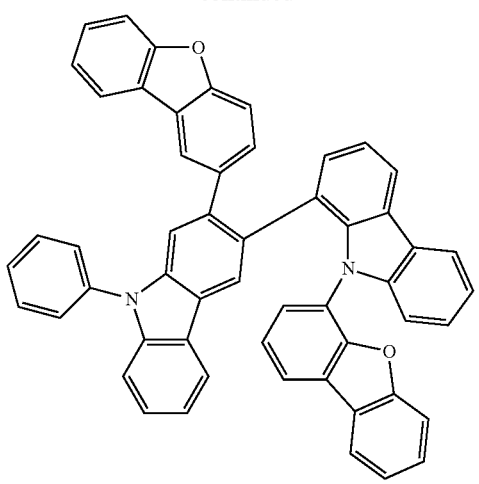
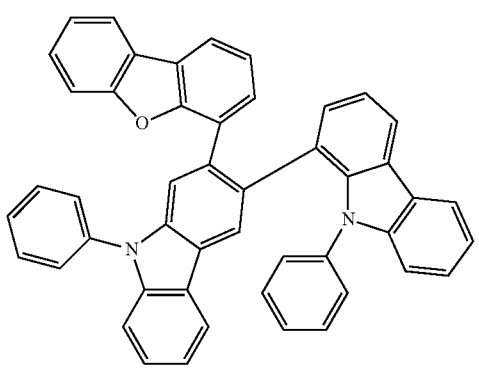
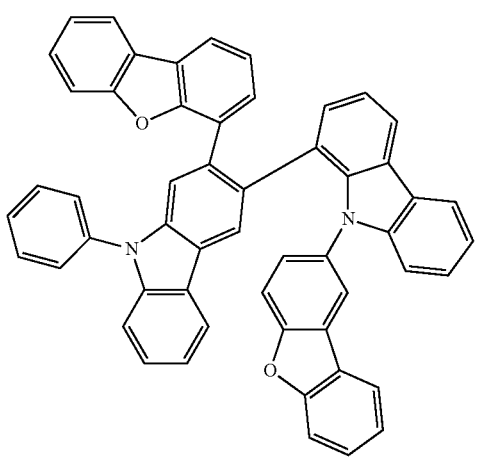
32
-continued
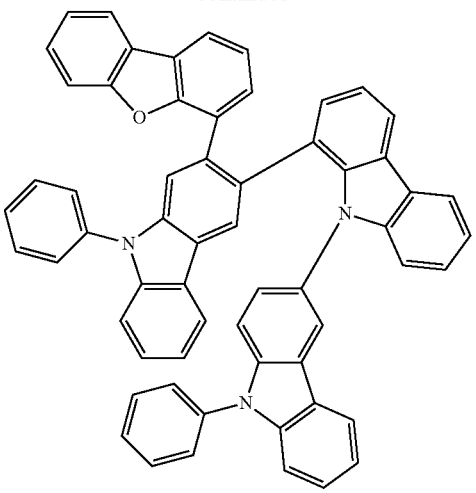
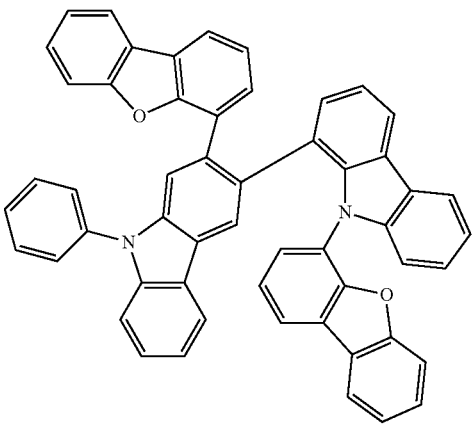 [SMILES: c1ccc(-n2c3ccccc3c3cc(-c4cccc5c6ccccc6n(-c6cccc7c6oc6ccccc67)c45)c(-c4cccc5c4oc4ccccc45)cc32)cc1]
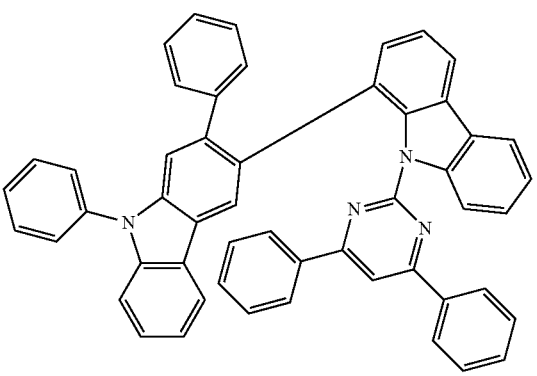
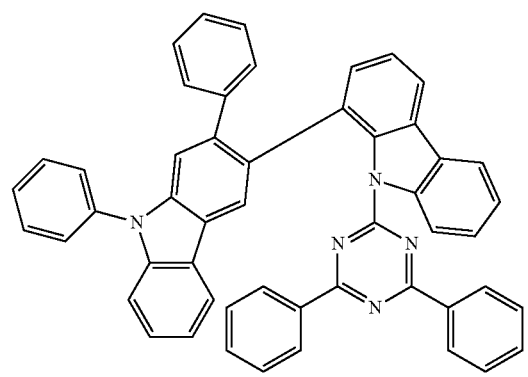

33
-continued
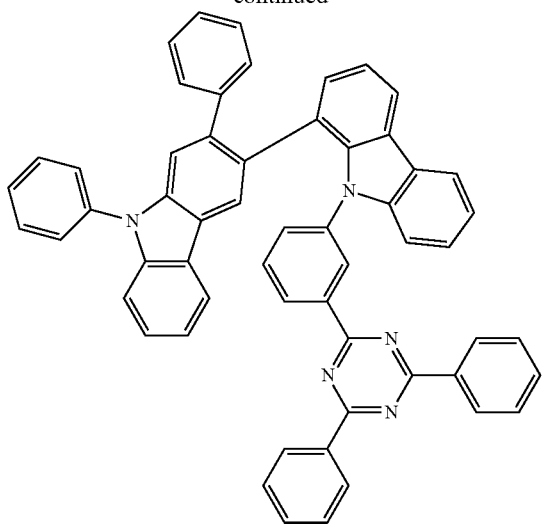
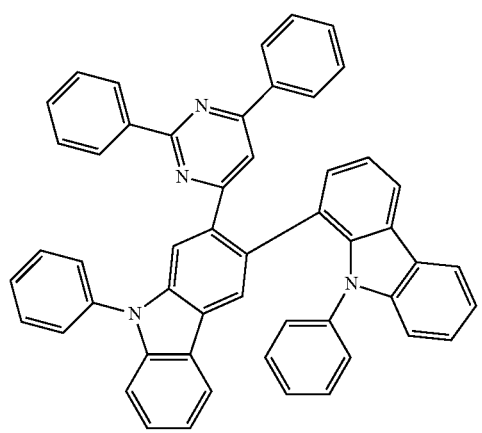
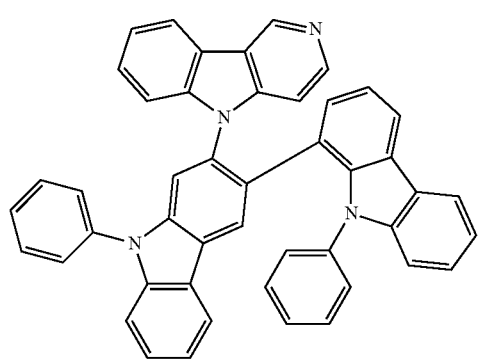
34
-continued
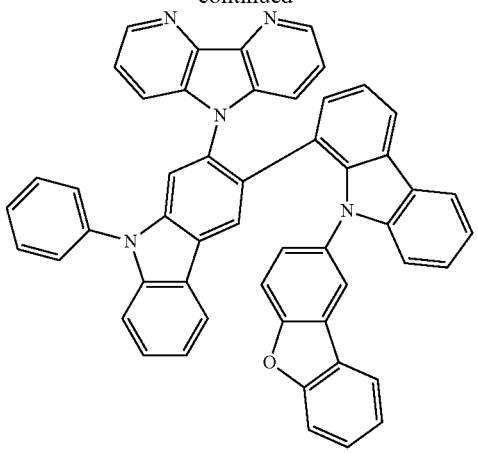
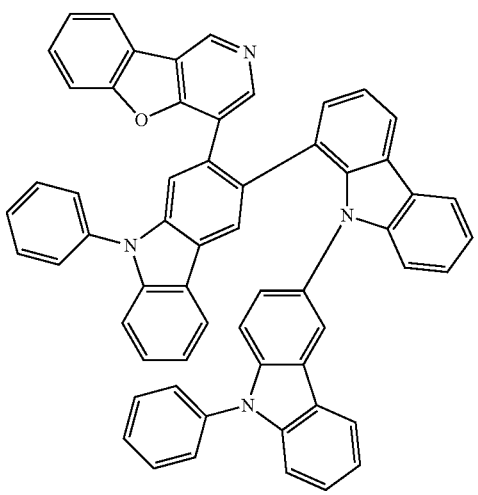
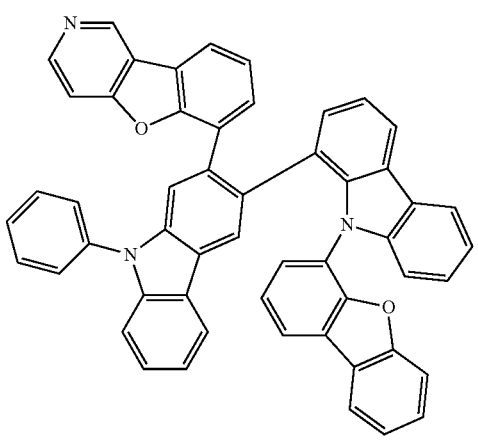

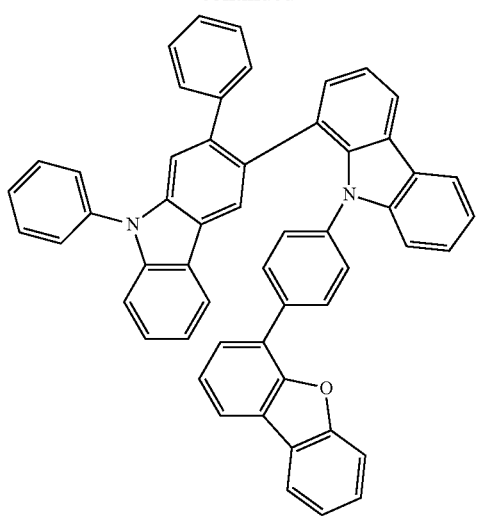
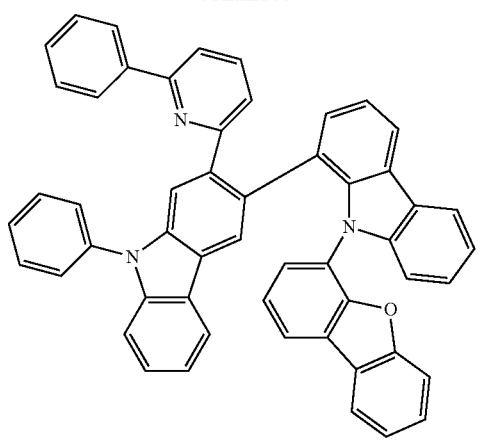
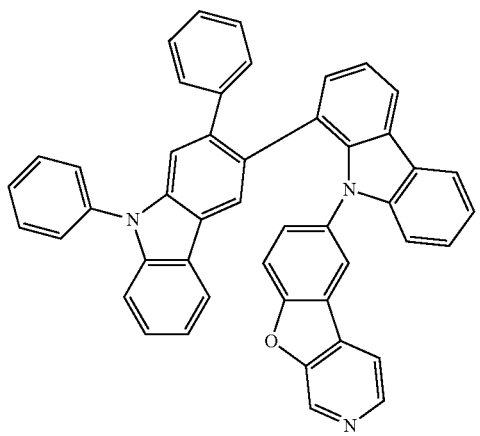
Compounds represented by the formula (5):
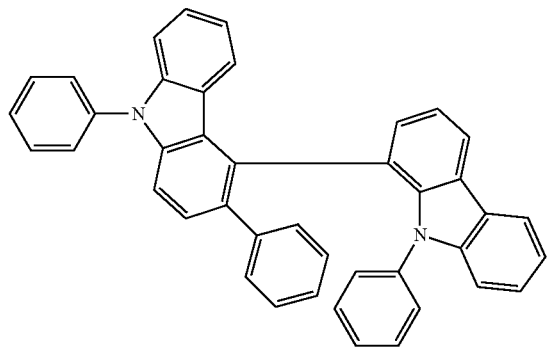
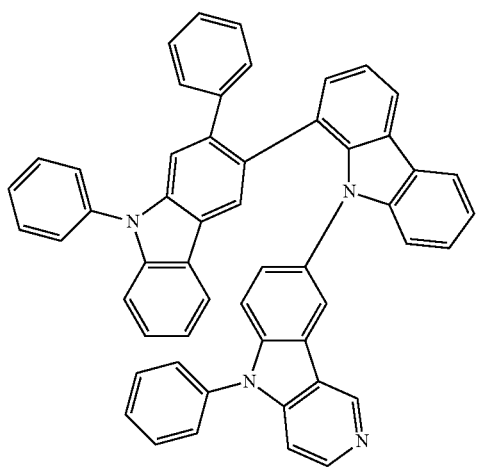
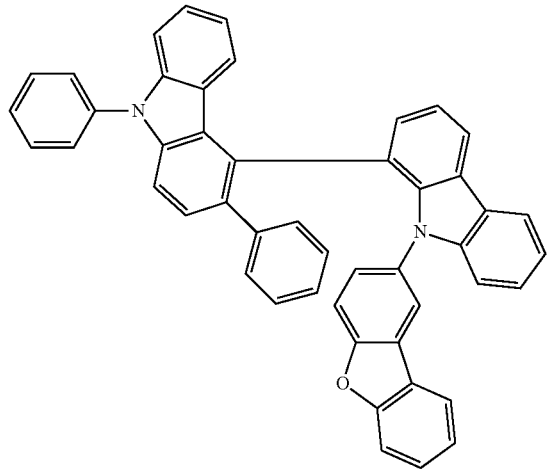

37
-continued
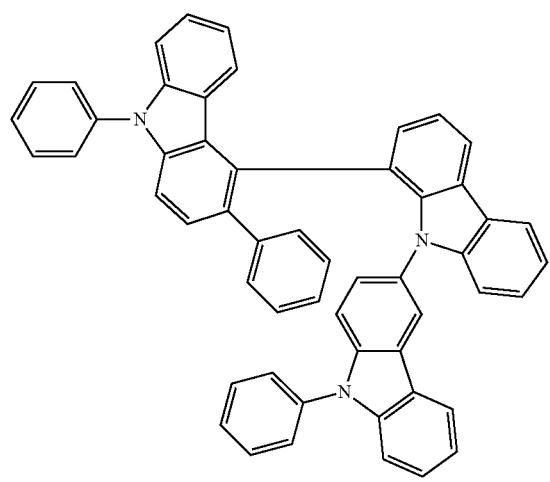
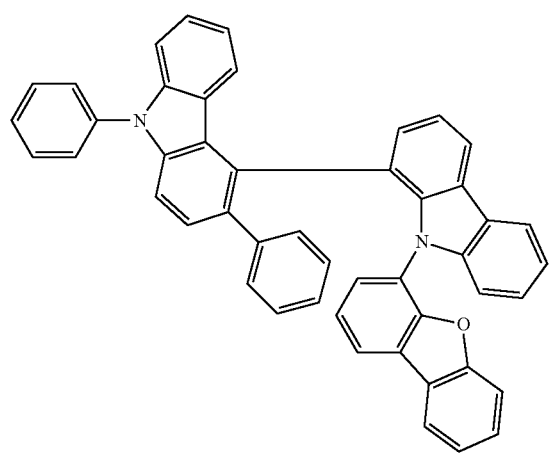
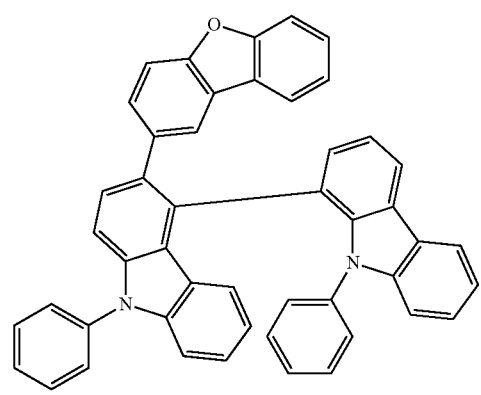
38
-continued
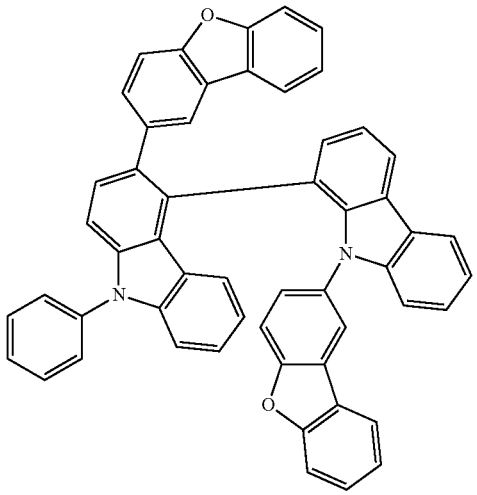
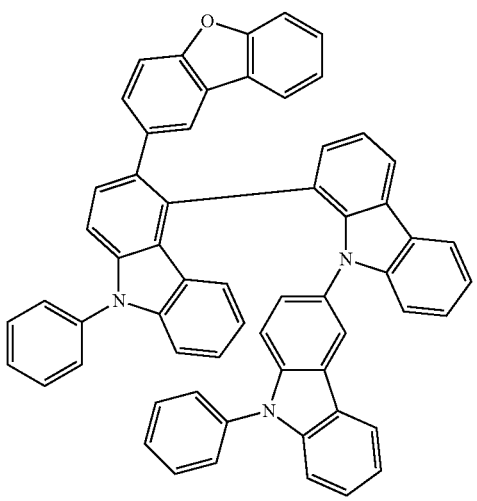
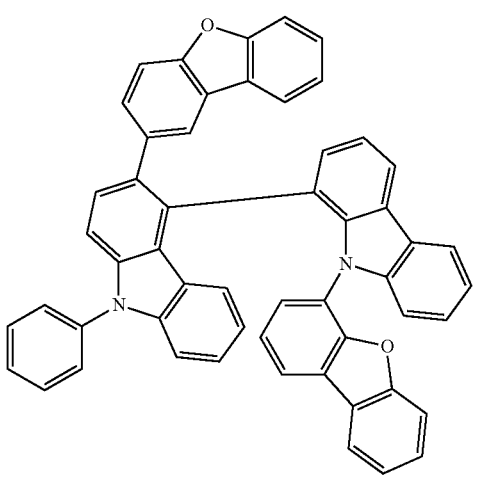

39
-continued
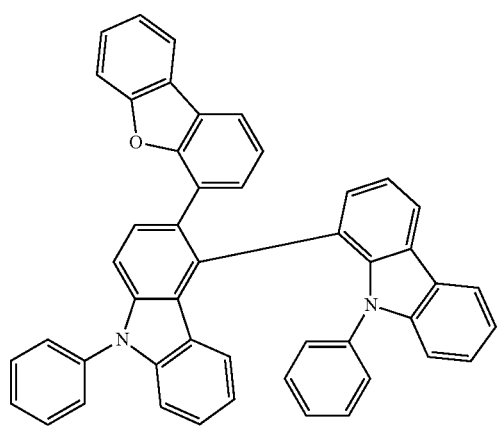
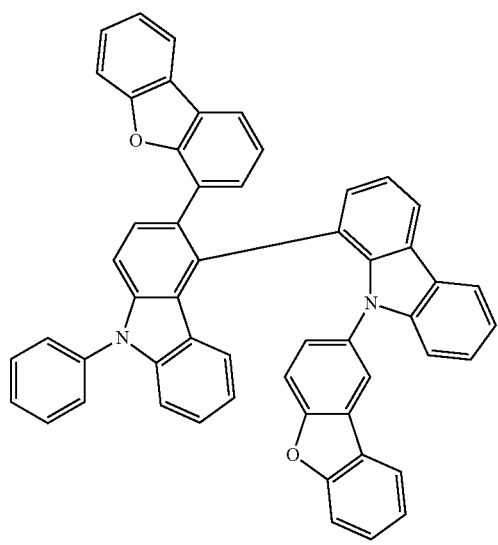
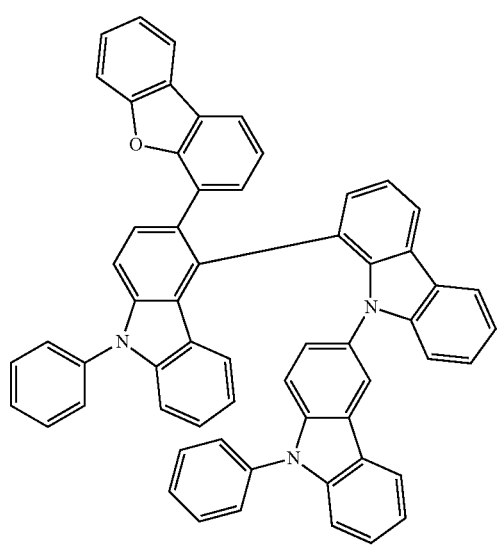
40
-continued
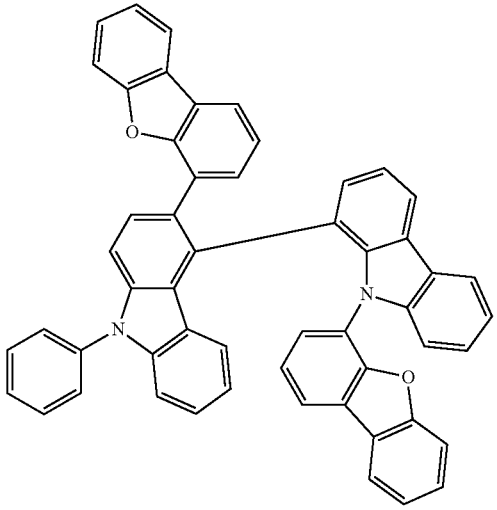
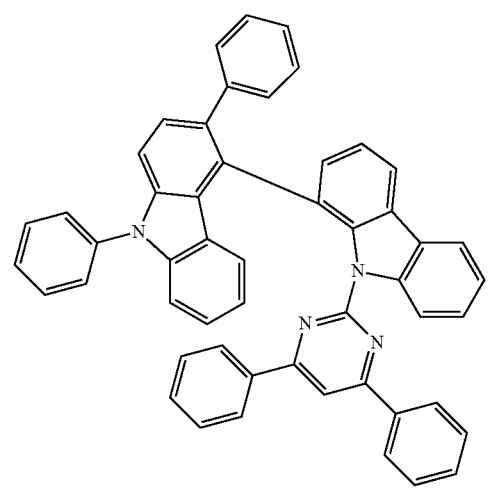
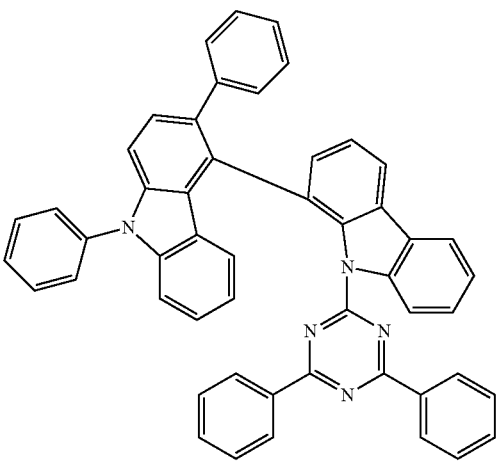

41
-continued
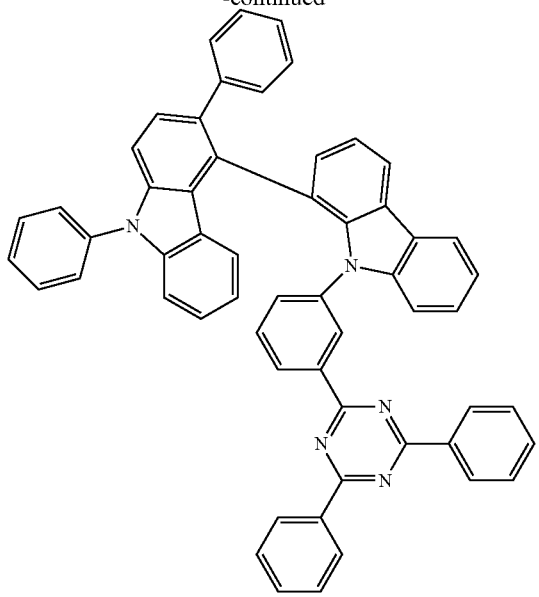
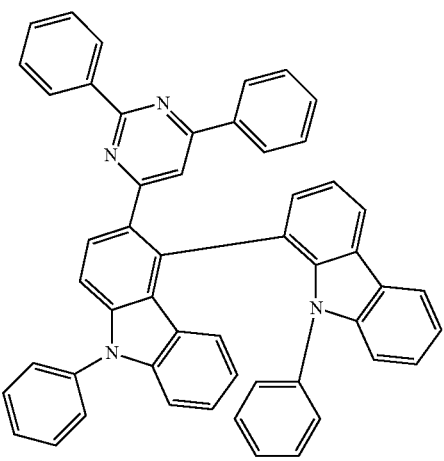
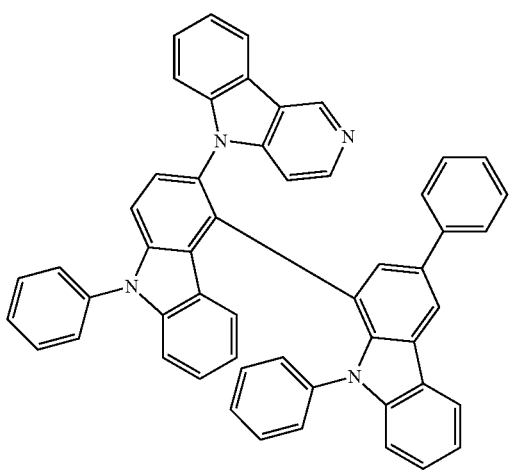
42
-continued
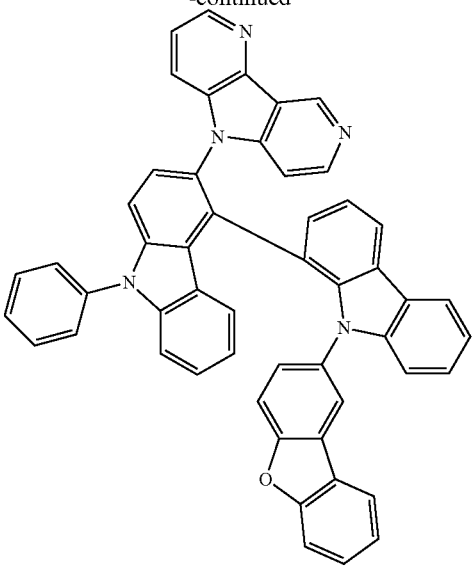
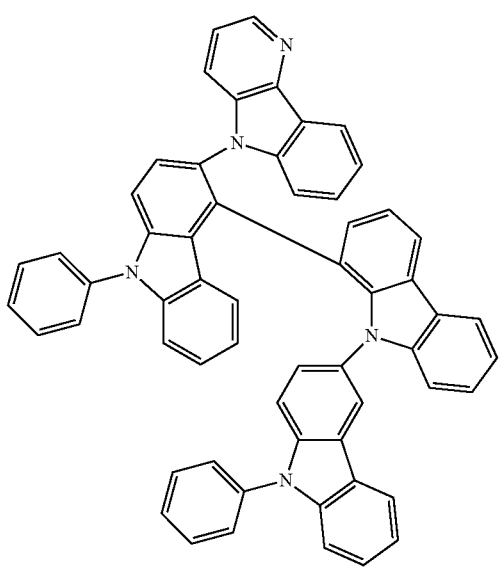
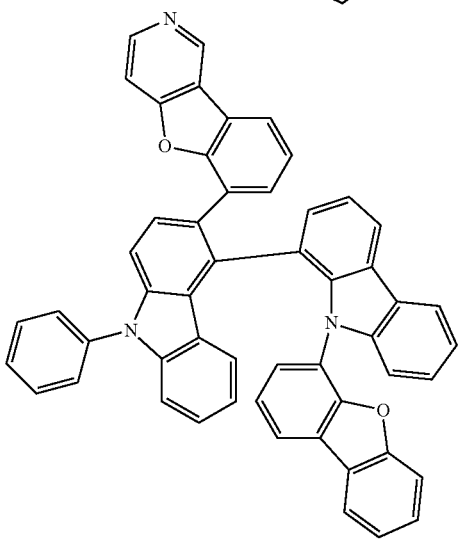

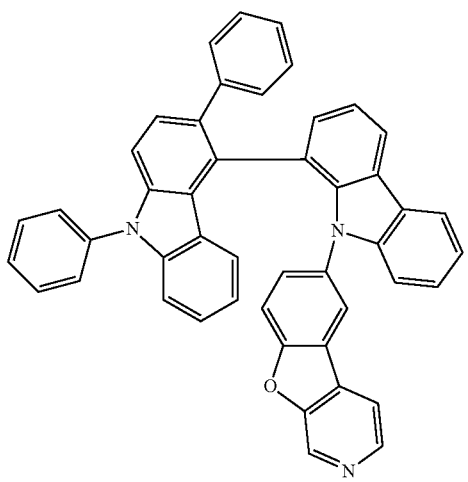
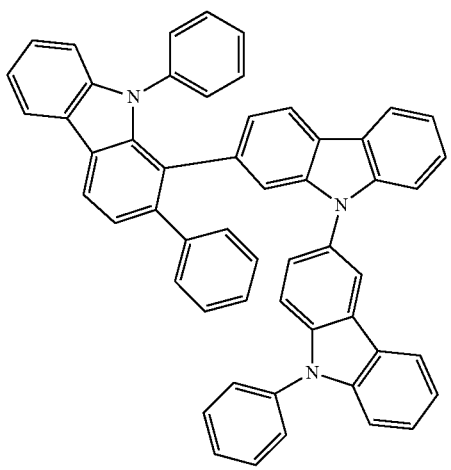
Compounds represented by the formula (6):
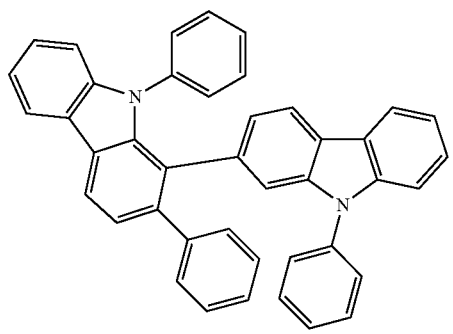
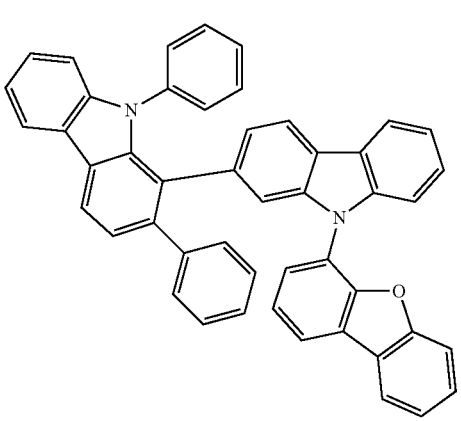
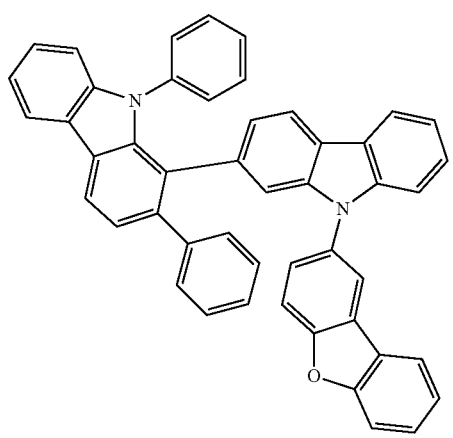
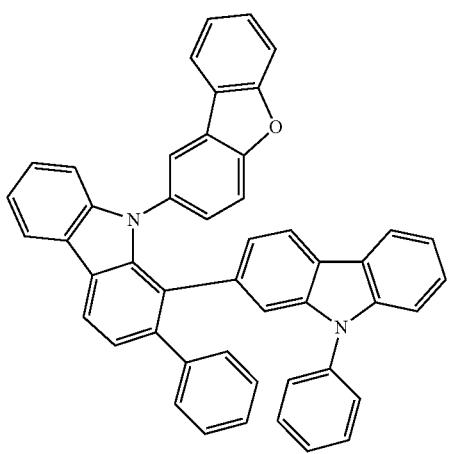

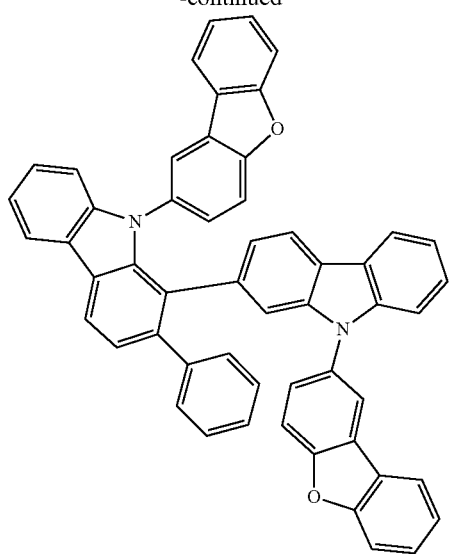
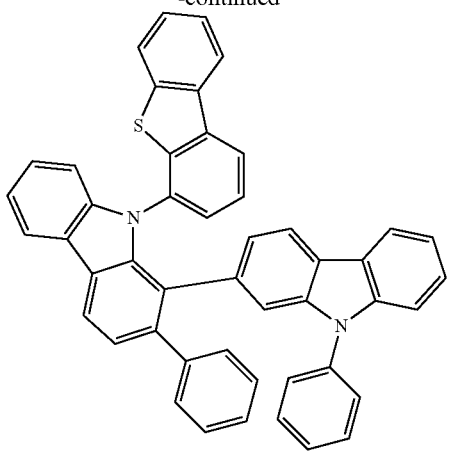
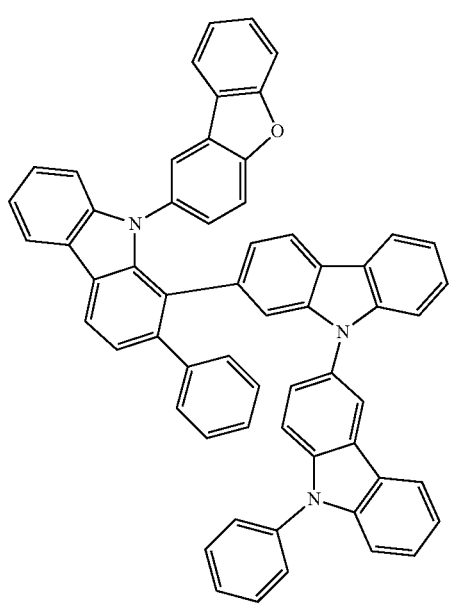
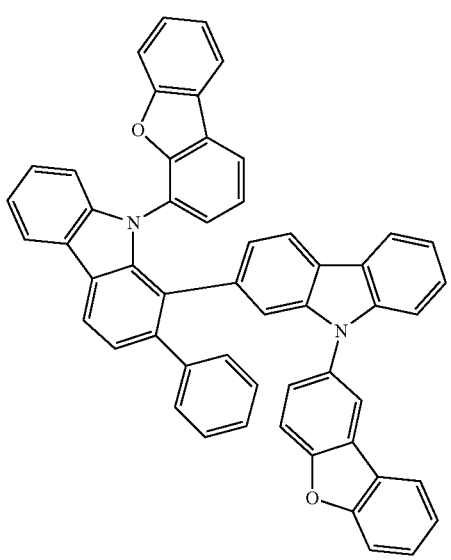
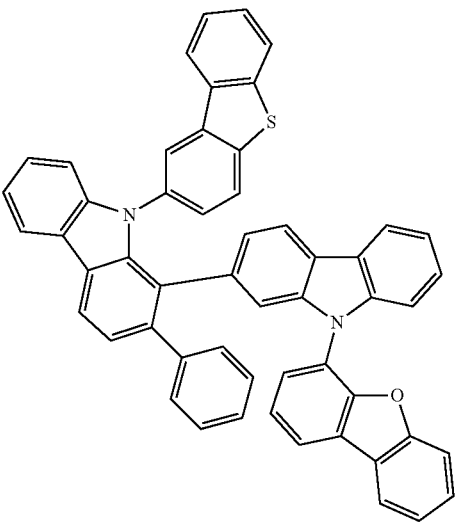
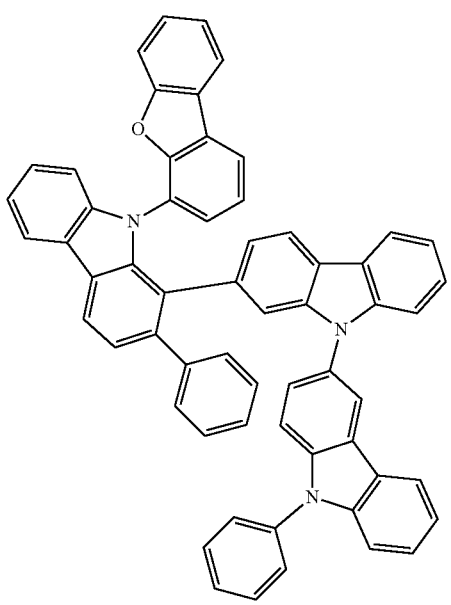

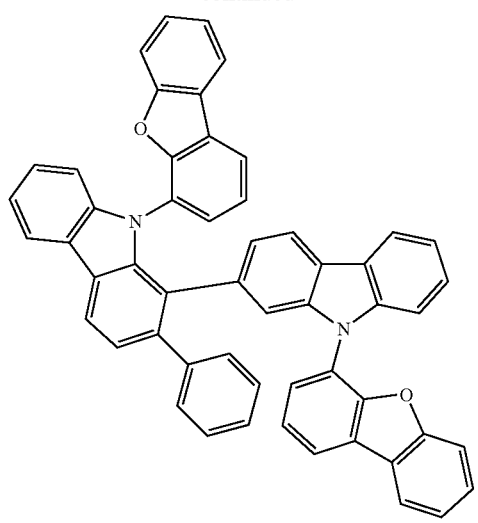
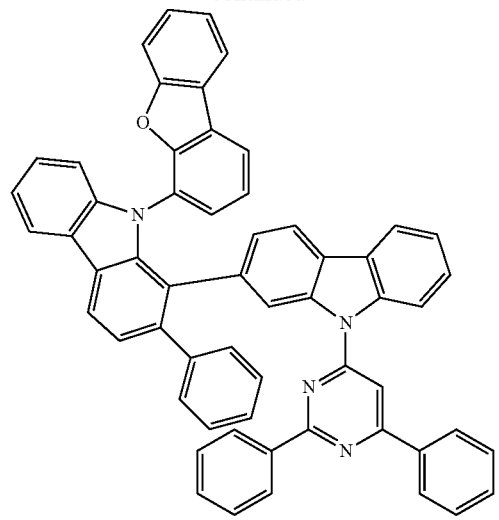
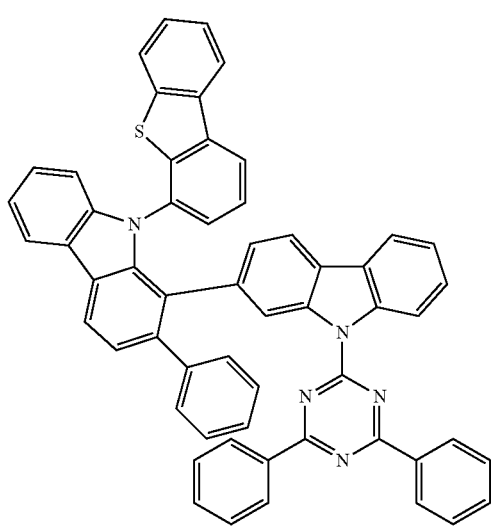
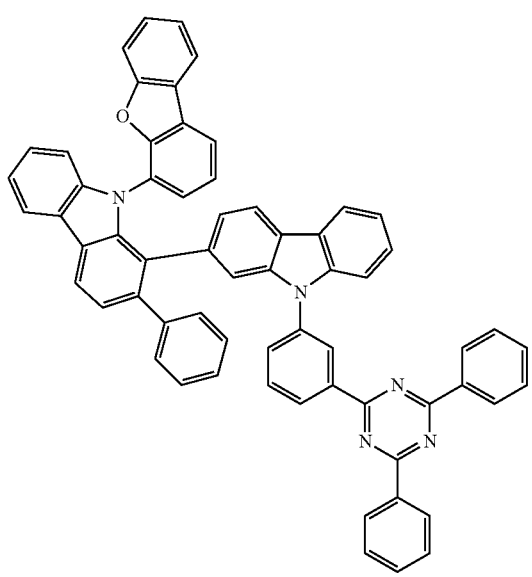
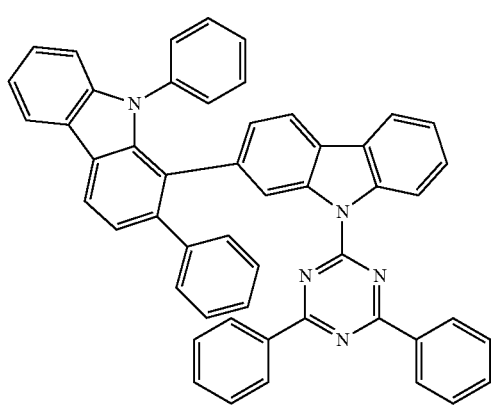
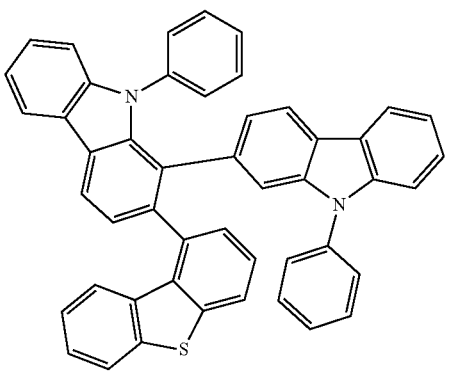

-continued
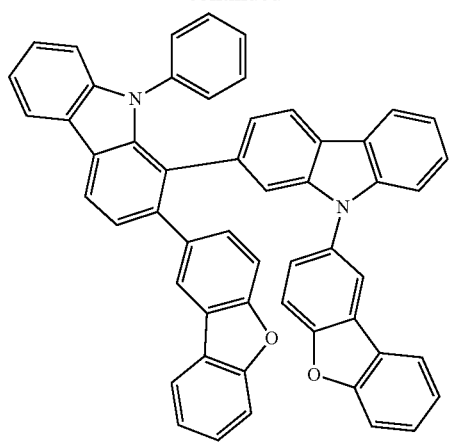
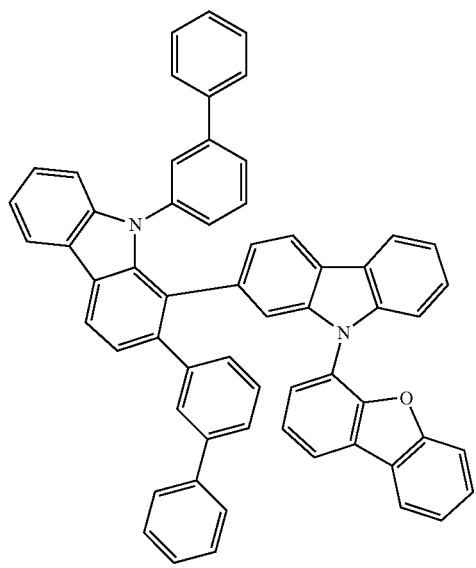
Compounds represented by the formula (7):
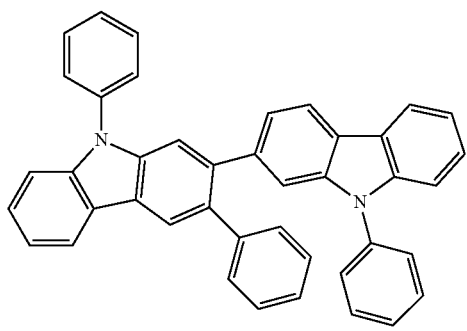
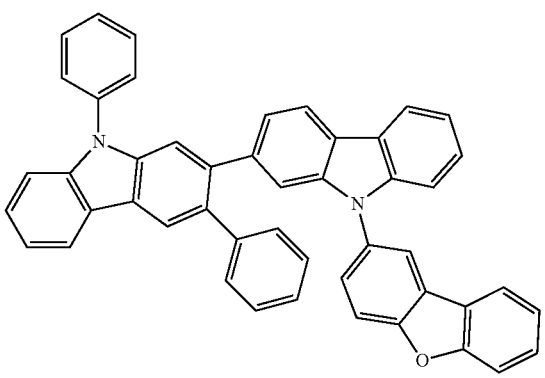
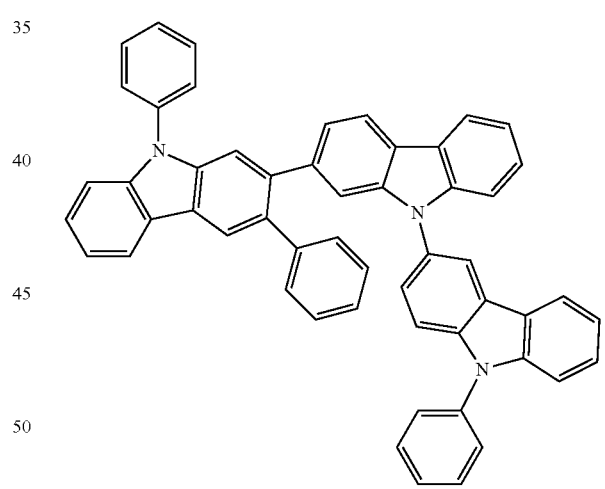
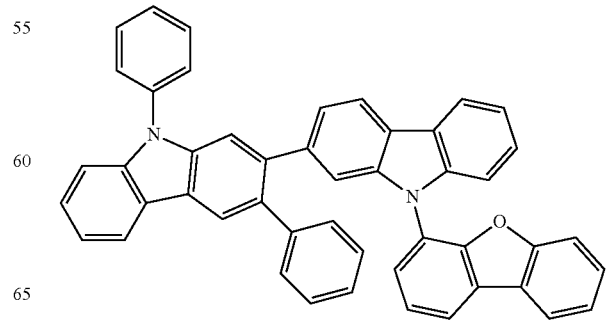

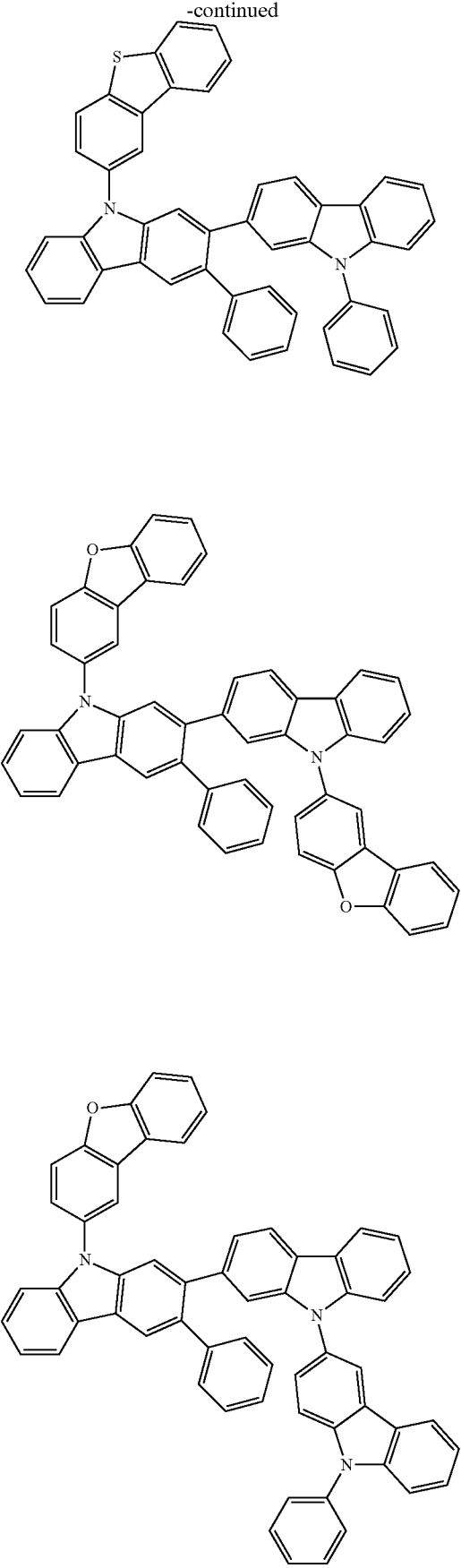

-continued
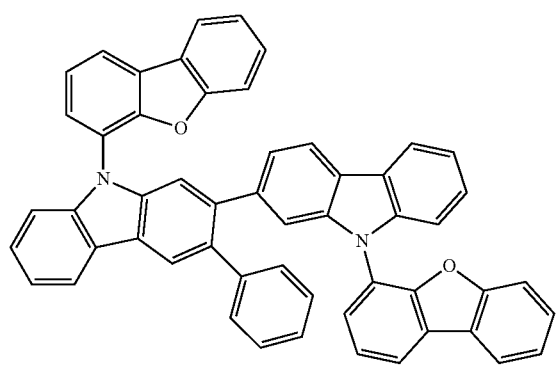
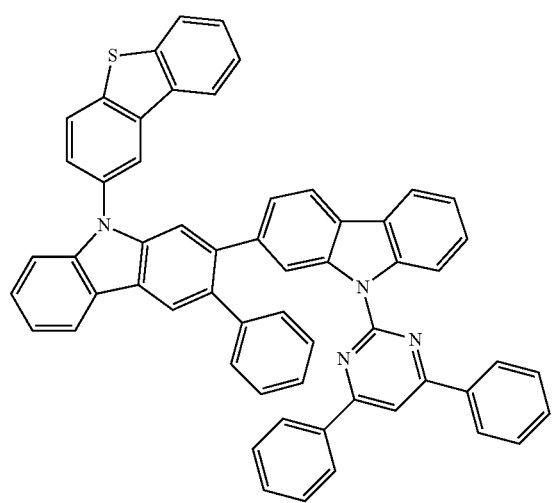
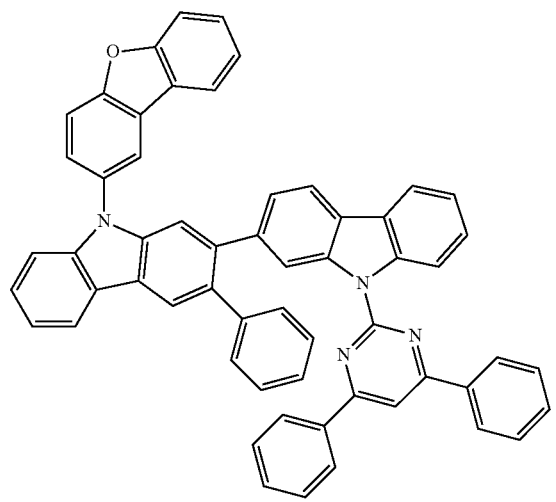
-continued
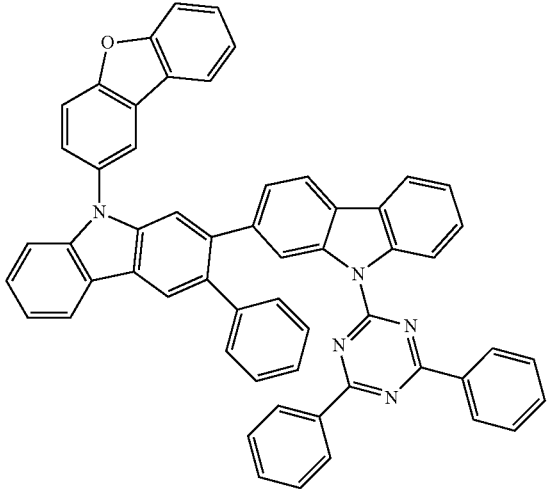
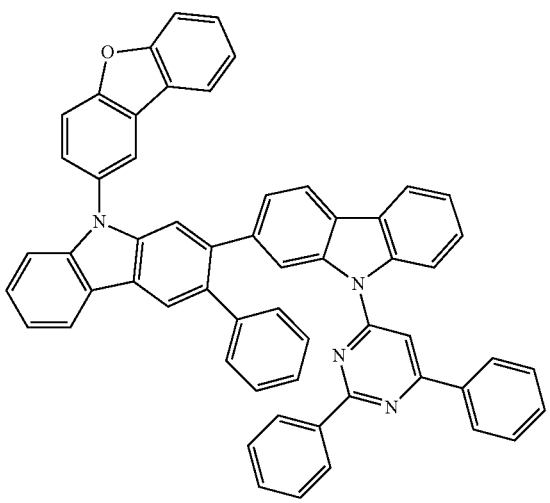
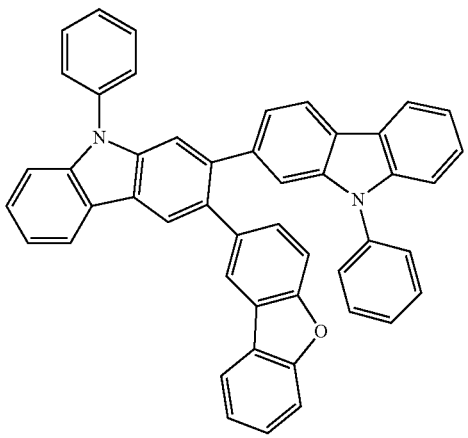

55
-continued
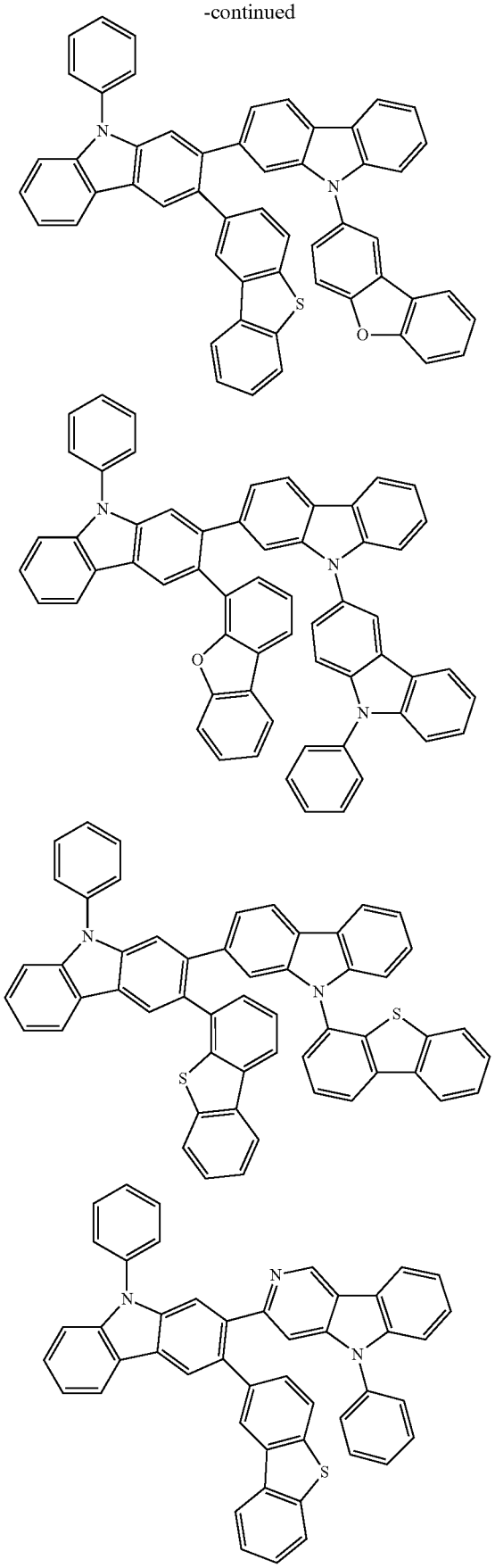
56
-continued
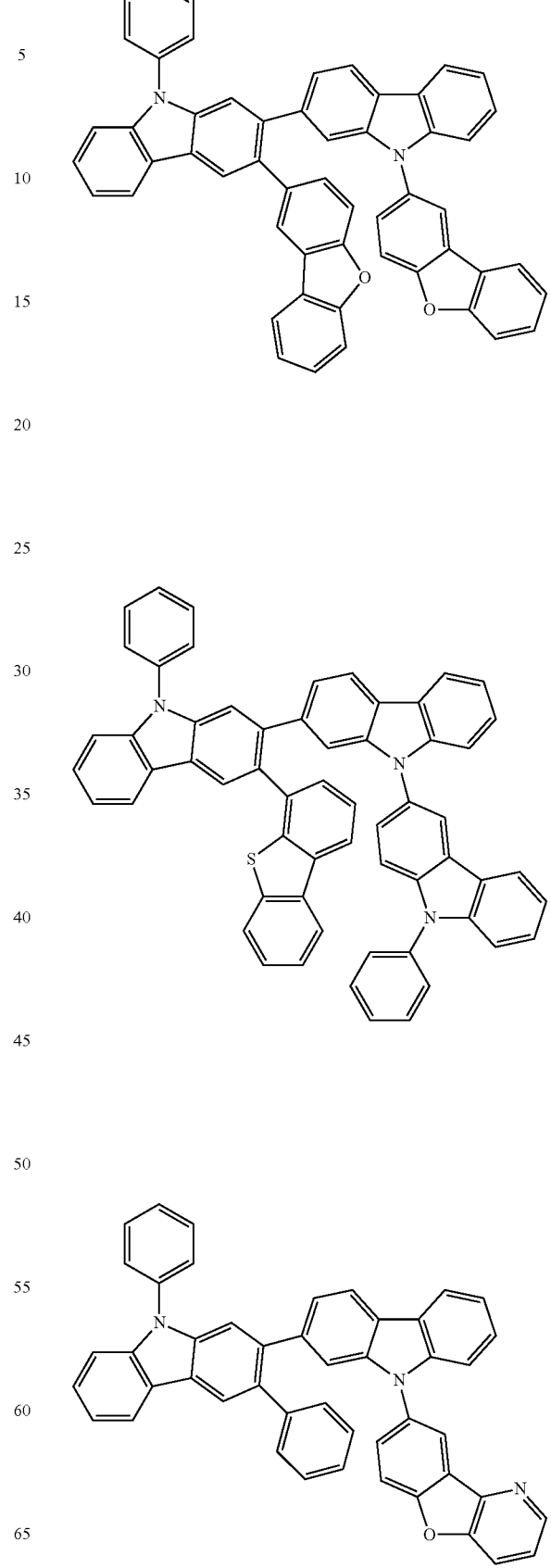

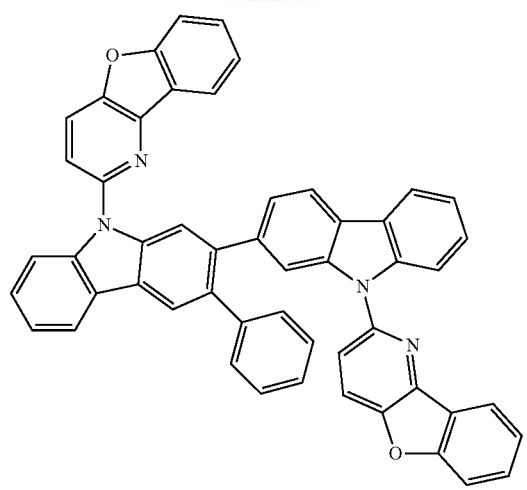
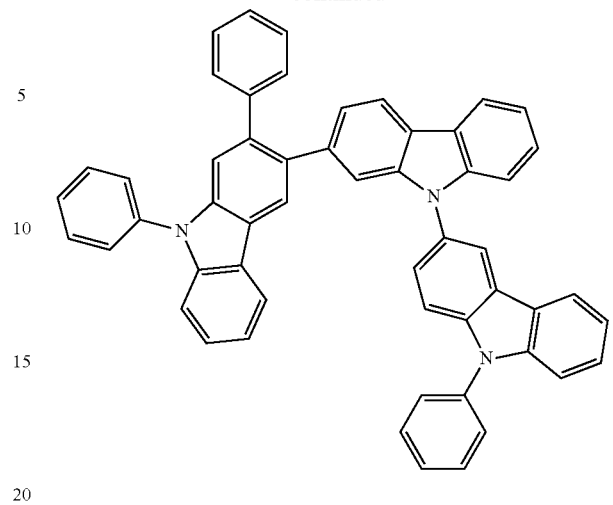
Compounds represented by the formula (8):
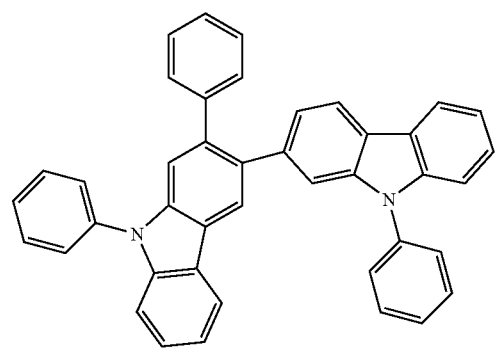
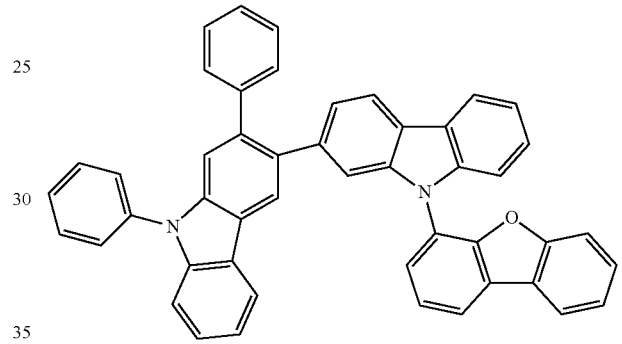
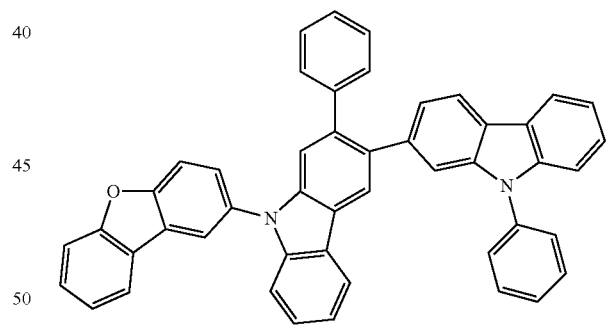
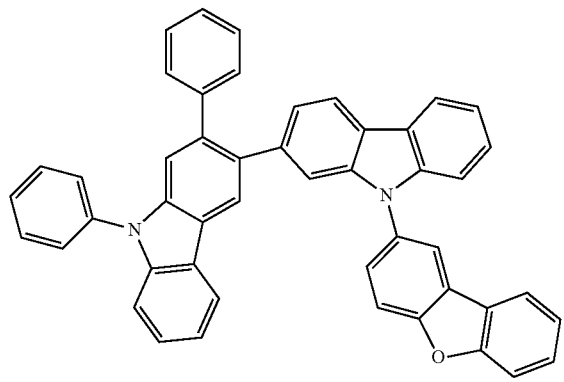
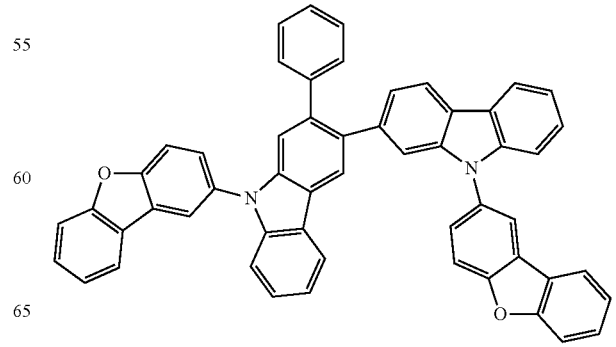

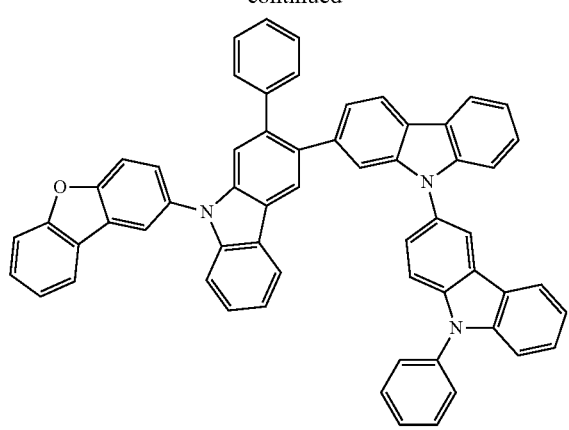
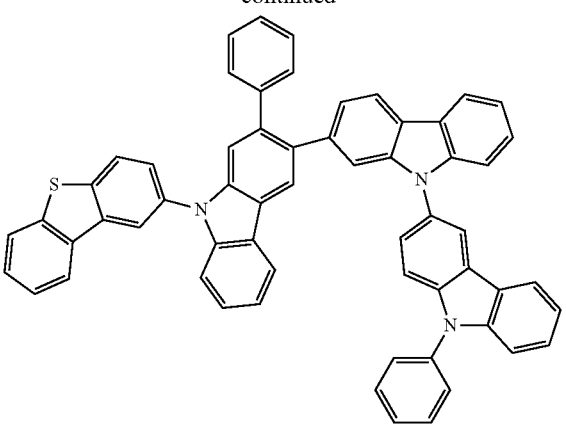
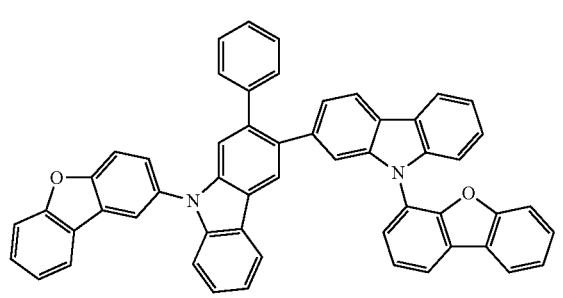
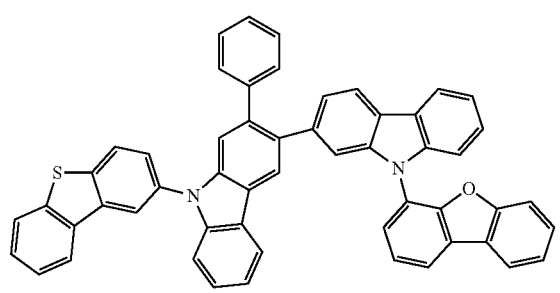
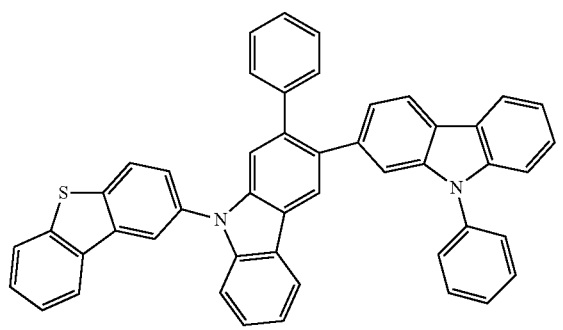
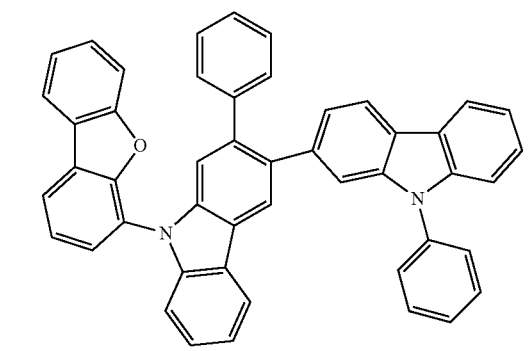
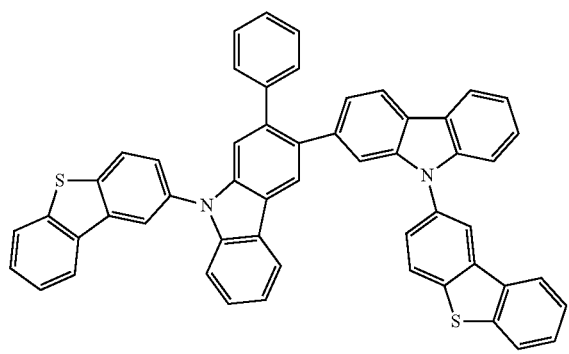
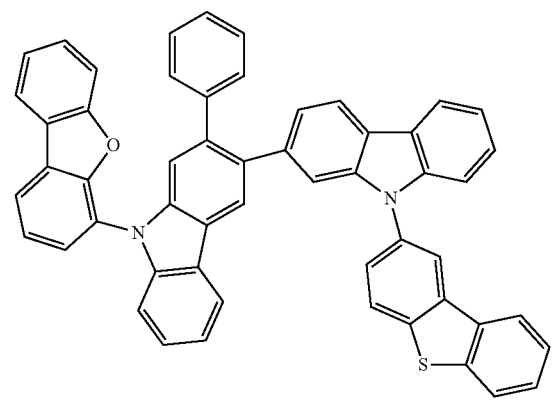

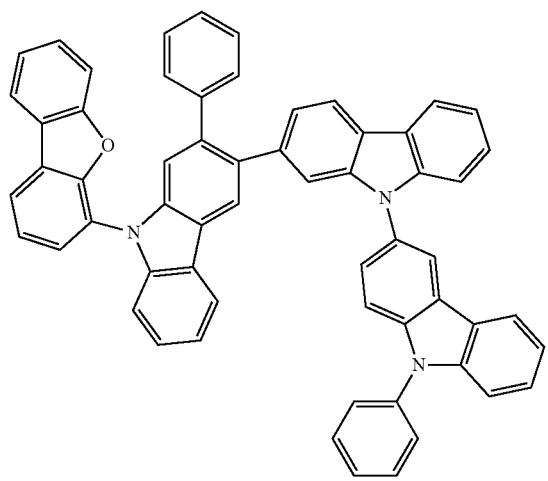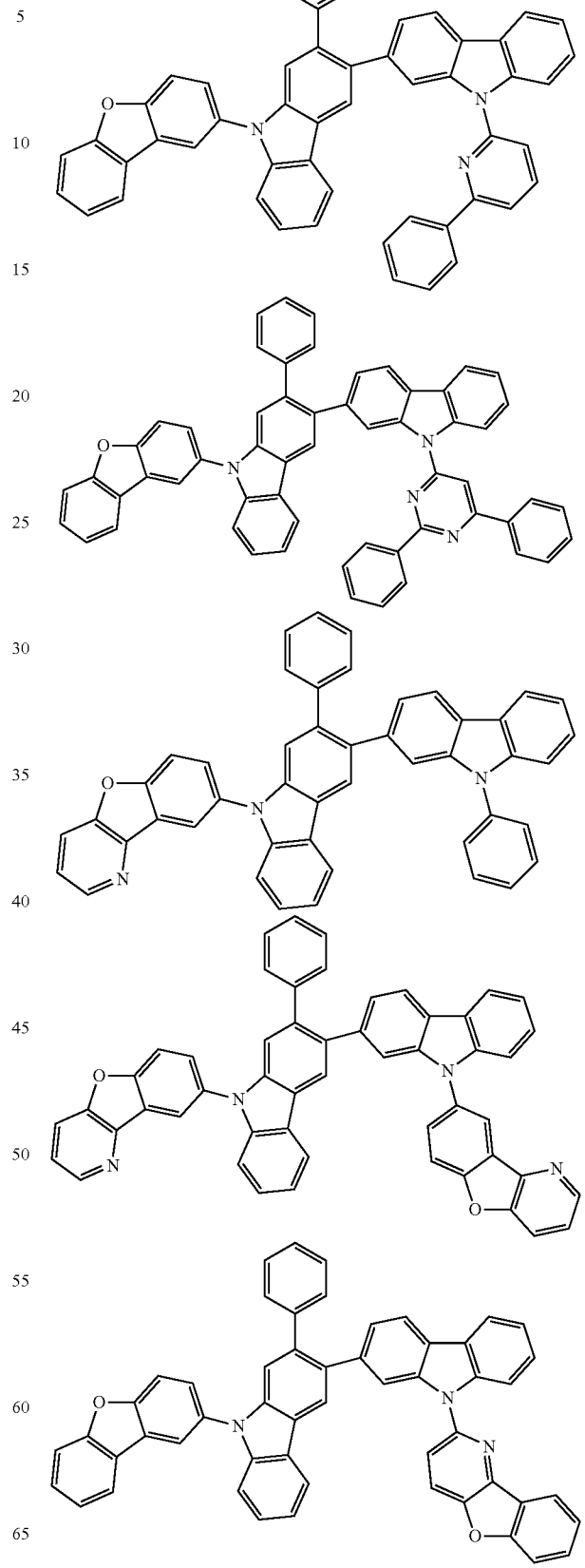

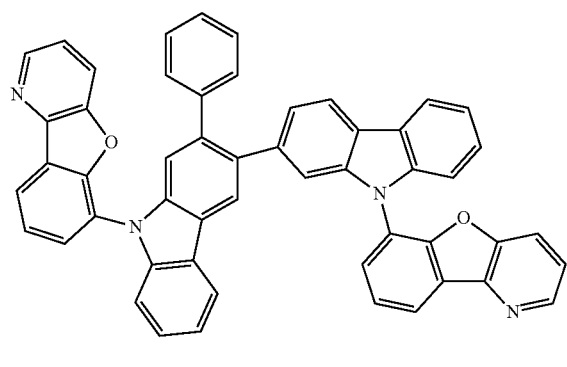 [SMILES: c1ccc(-c2cc3c(cc2-c2ccc4c5ccccc5n(-c5cccc6c5oc5cccnc56)c4c2)c2ccccc2n3-c2cccc3c2oc2cccnc23)cc1]
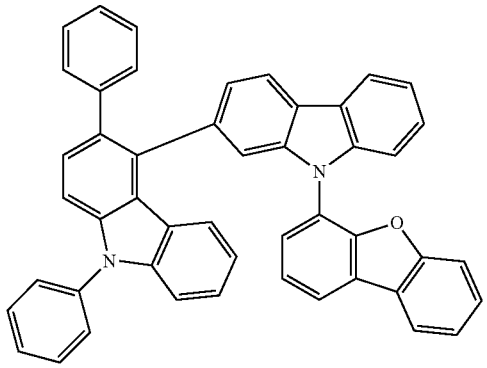
Compounds represented by the formula (9):
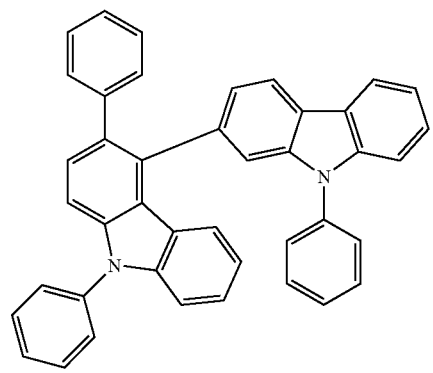
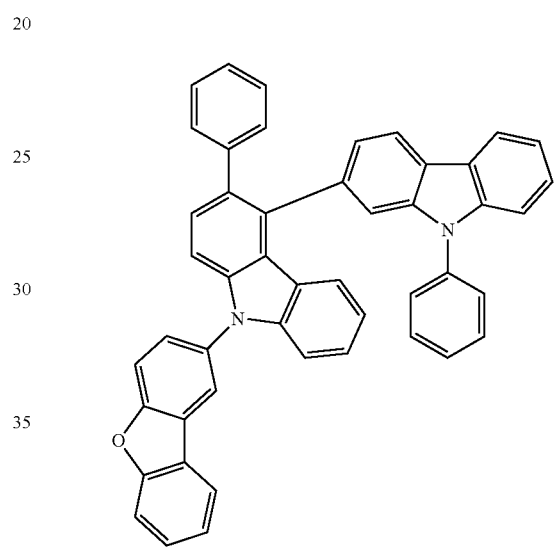
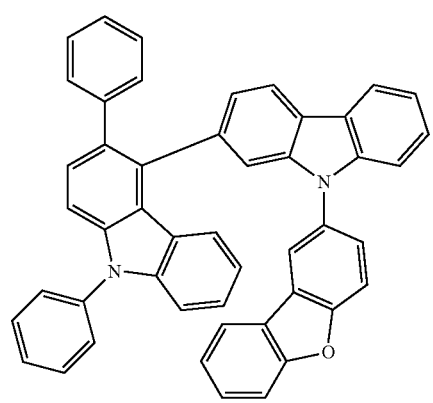 [SMILES: c1ccc(-c2ccc3c(c2-c2ccc4c5ccccc5n(-c5ccc6sc7ccccc7c6c5)c4c2)c2ccccc2n3-c2ccccc2)cc1]
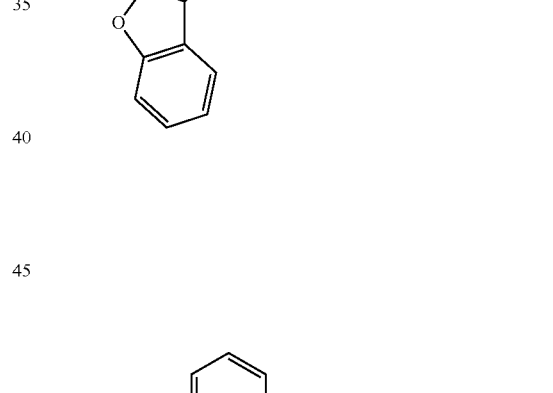
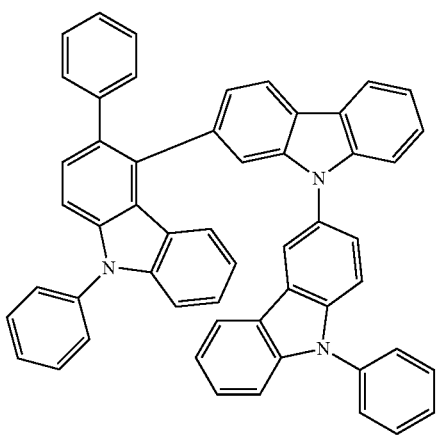
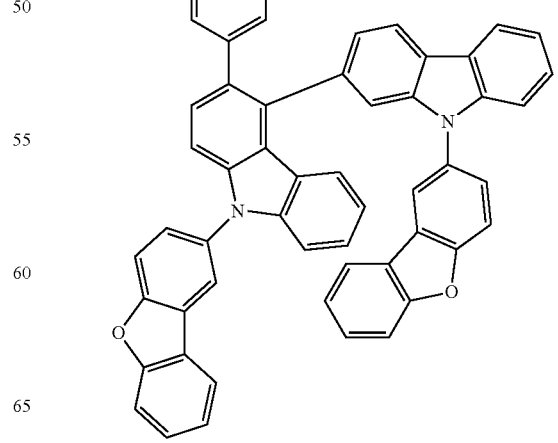

65
-continued
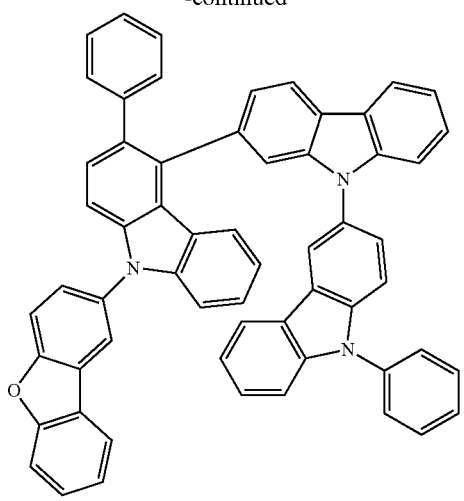
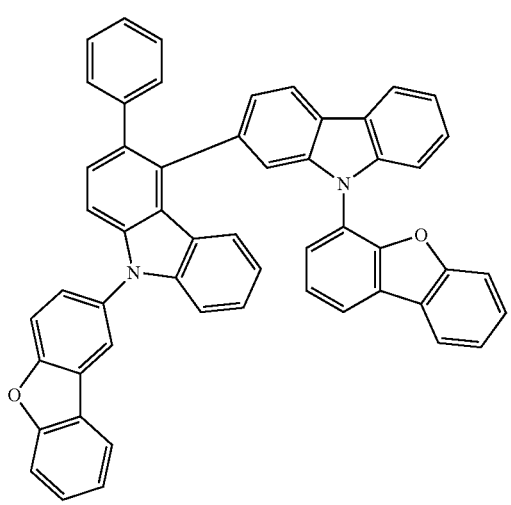
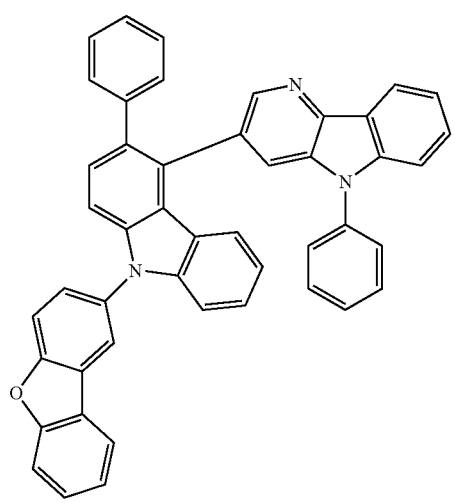
66
-continued
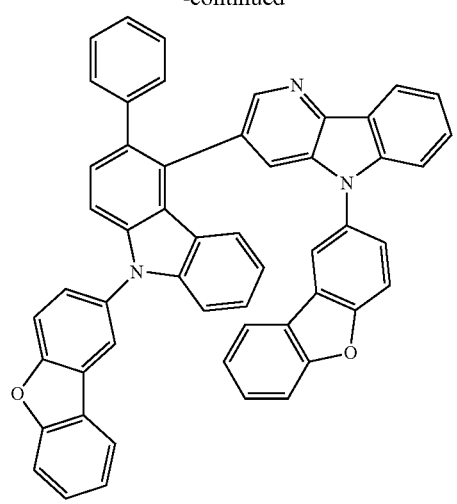
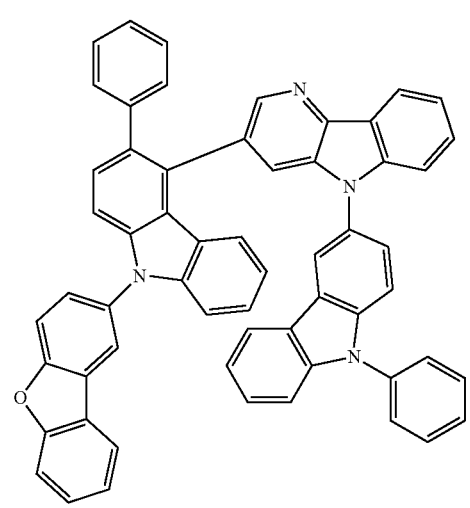
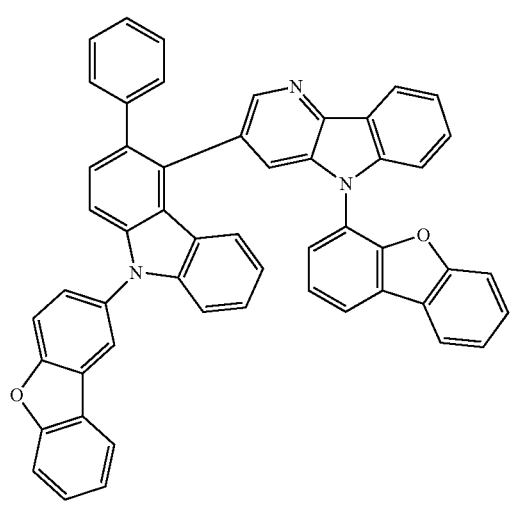

67
-continued
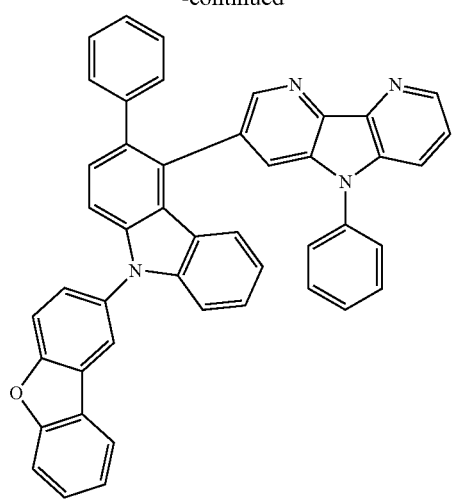
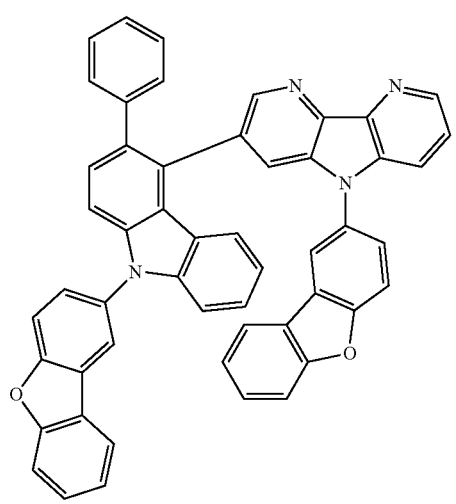
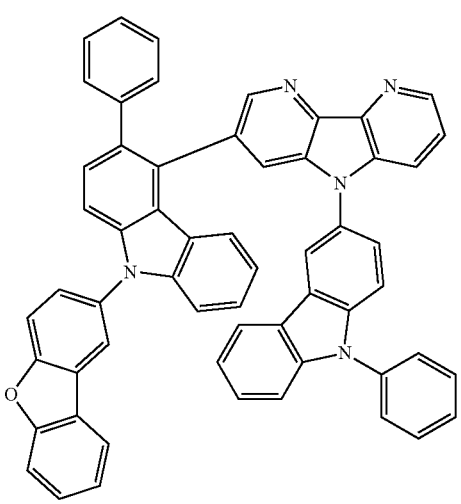
68
-continued
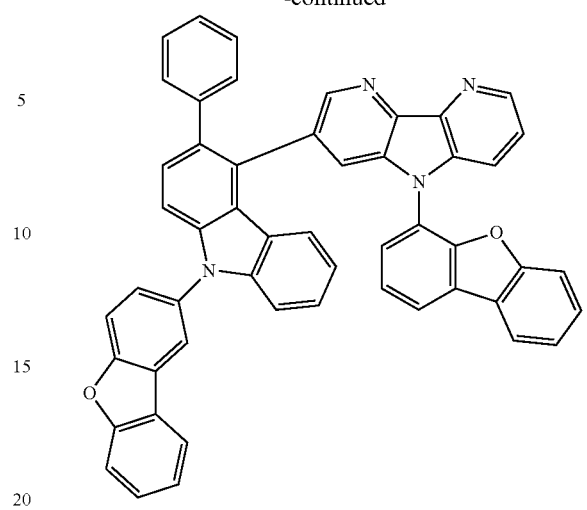
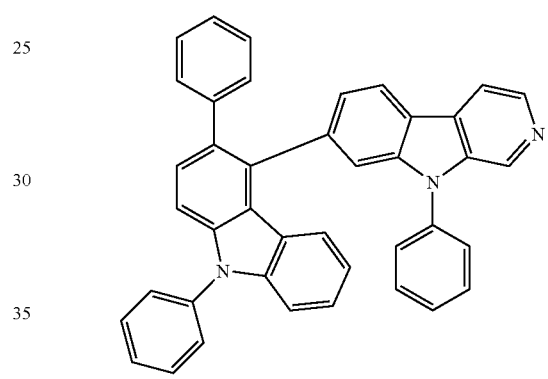
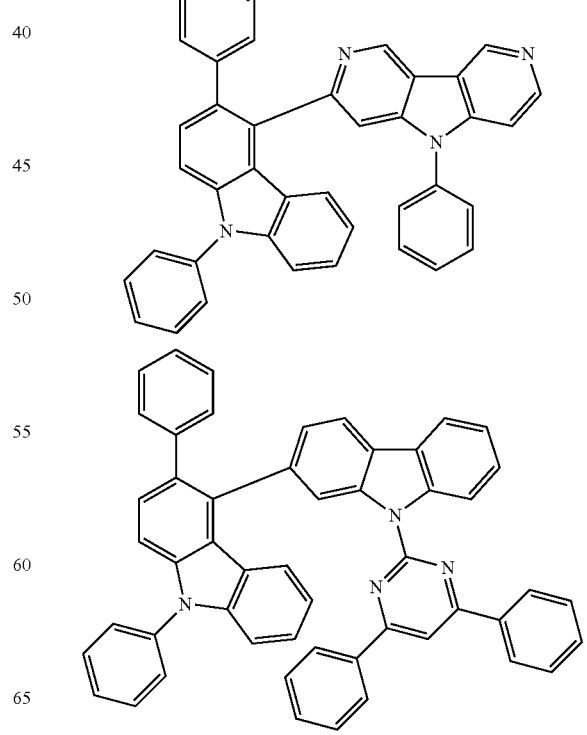

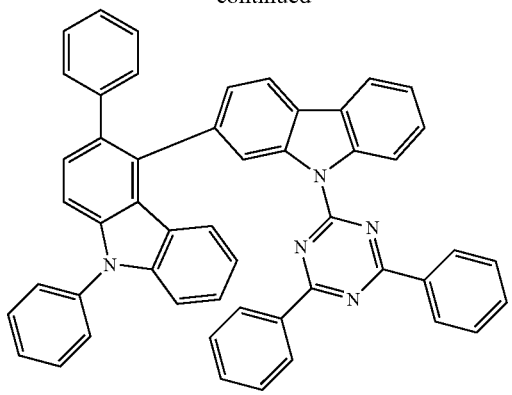
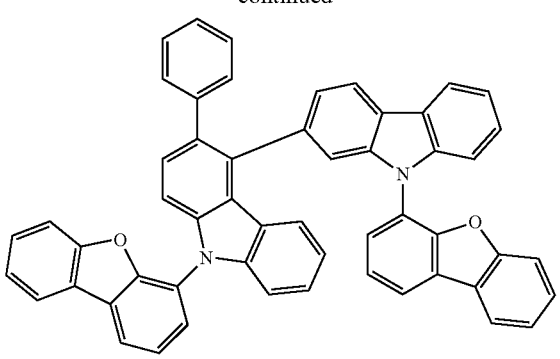
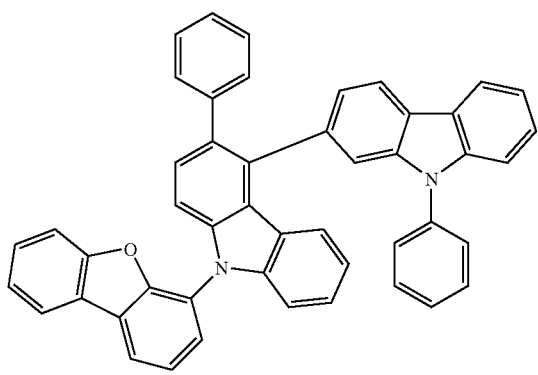
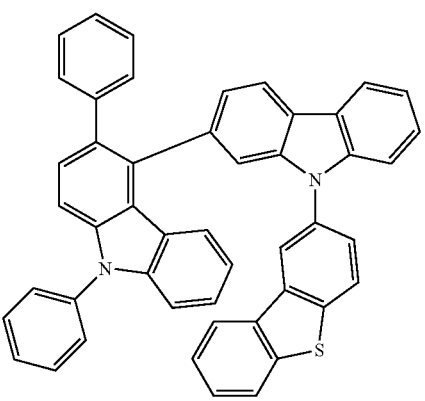
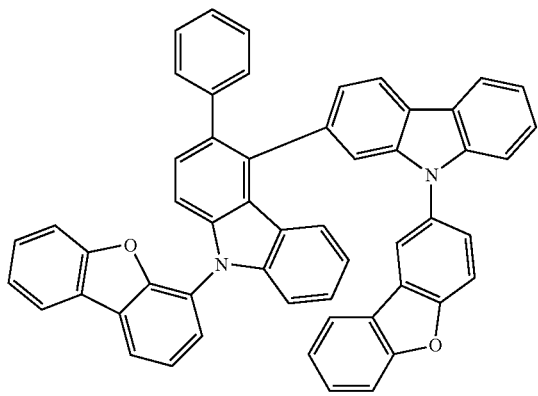
Compounds represented by the formula (10):
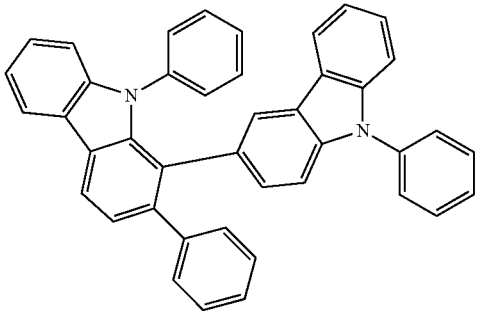
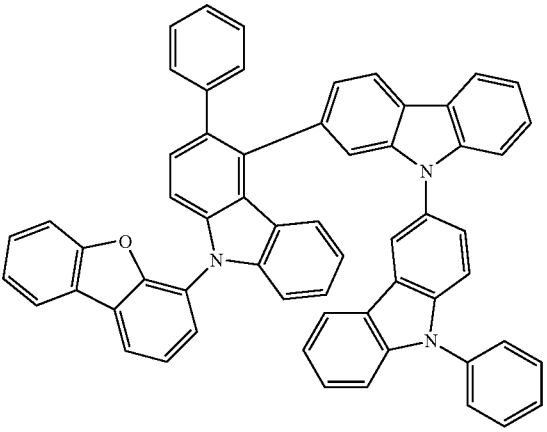
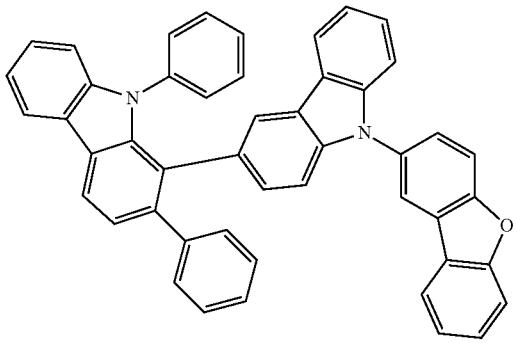

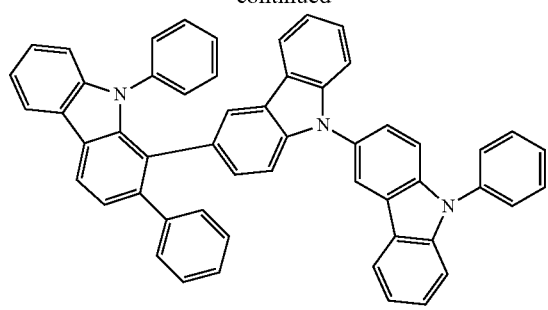
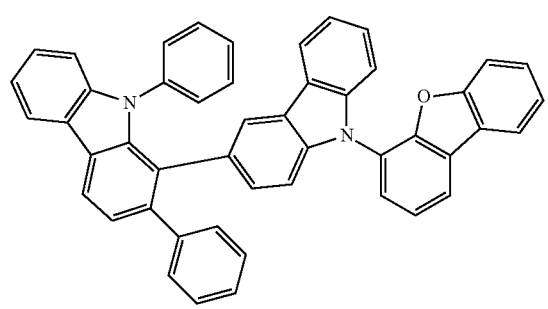
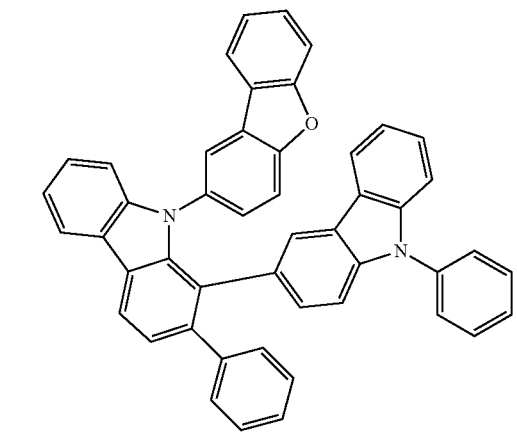
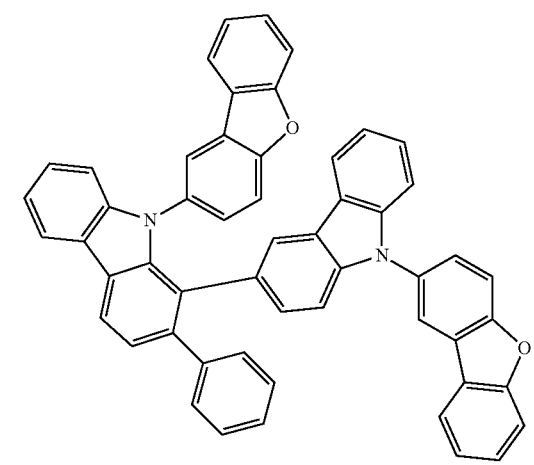
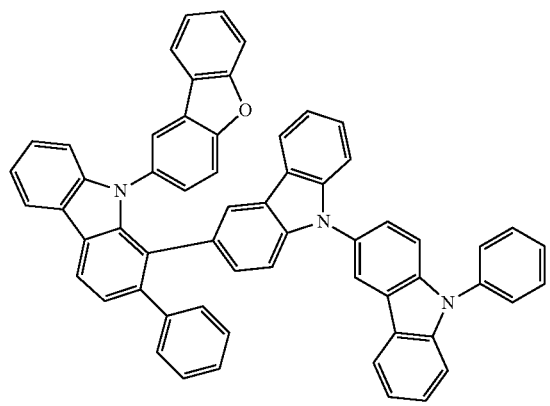
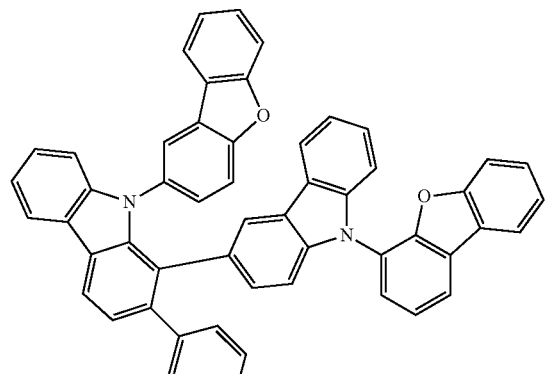
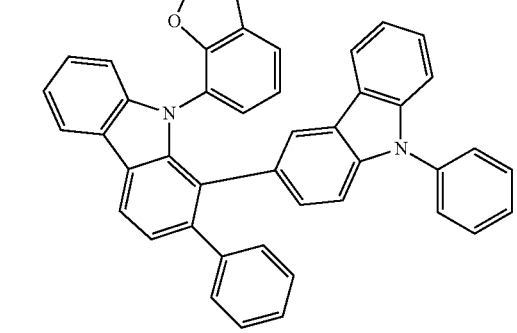
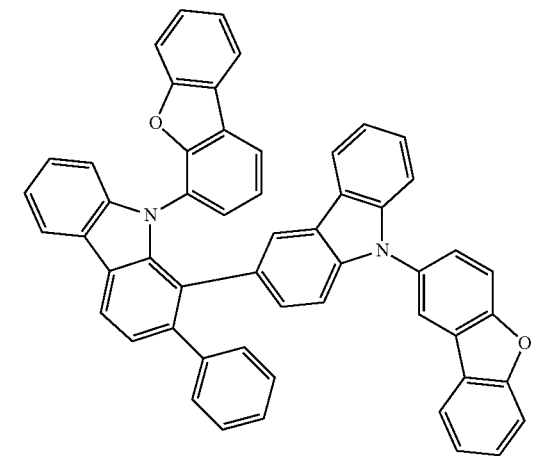

73
-continued
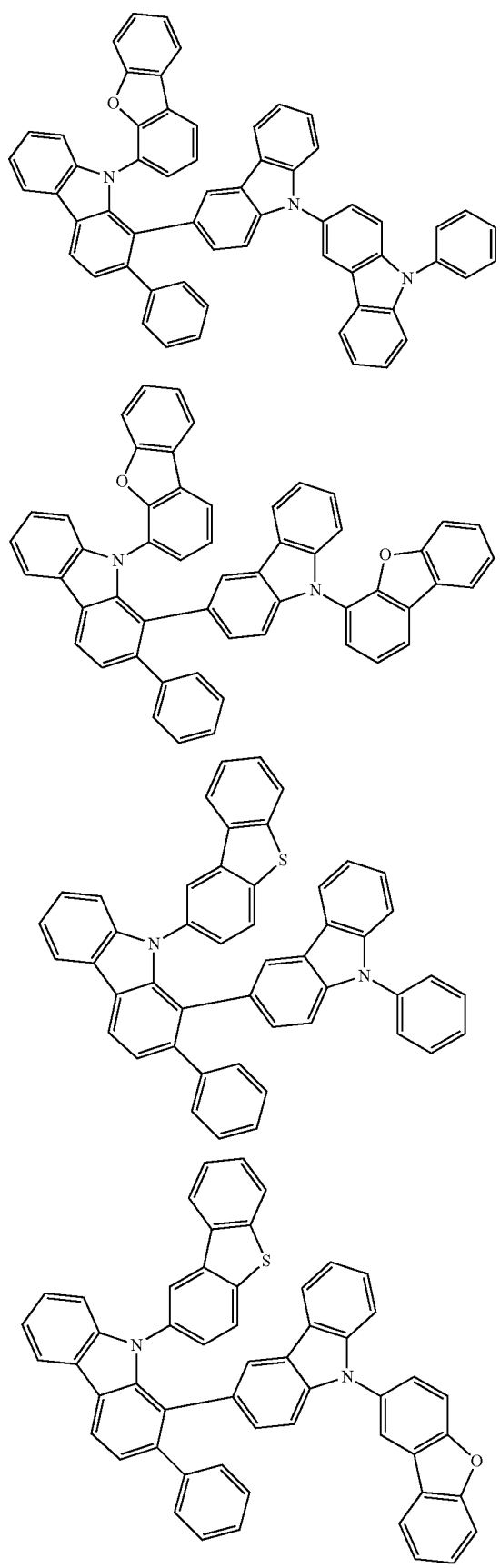
74
-continued
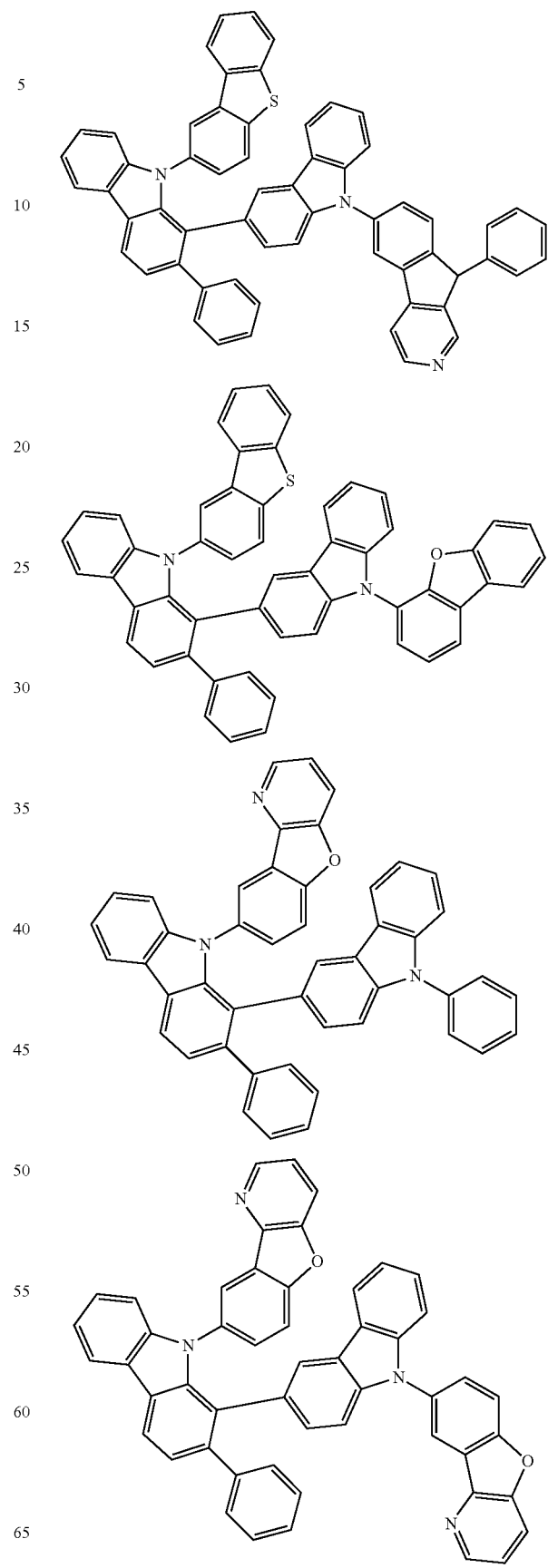

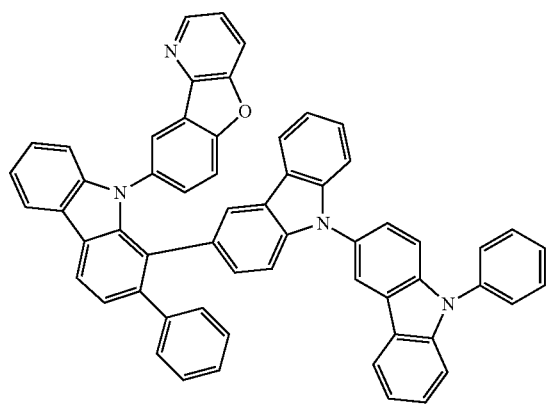
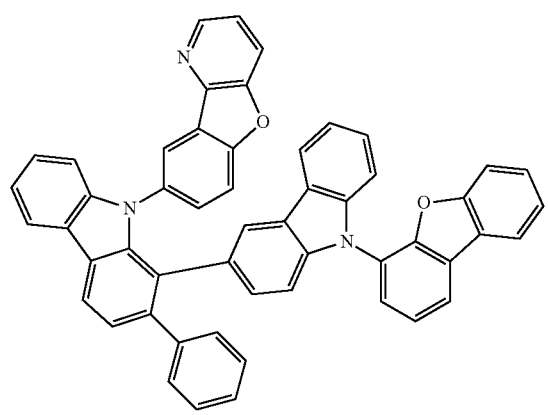
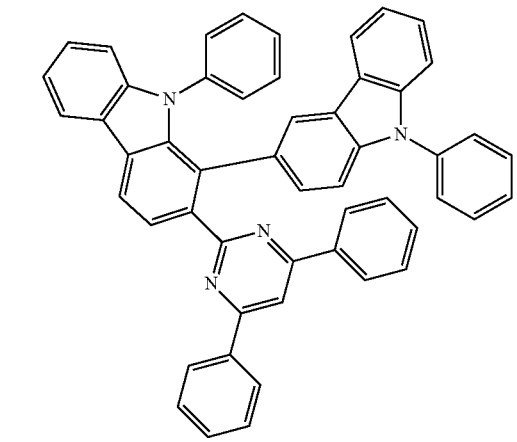
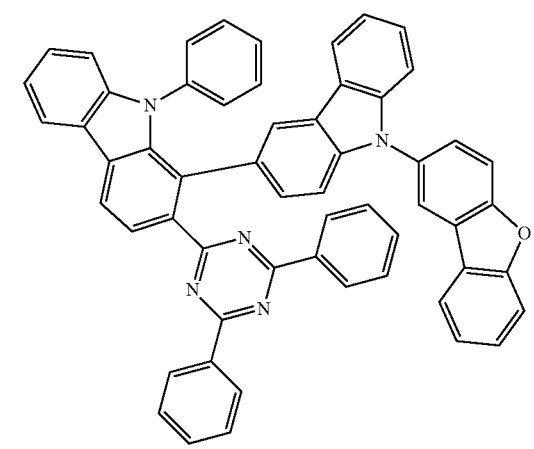
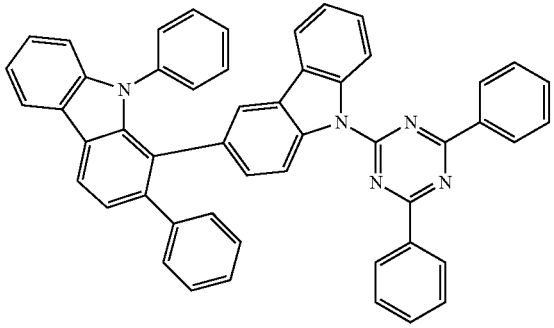
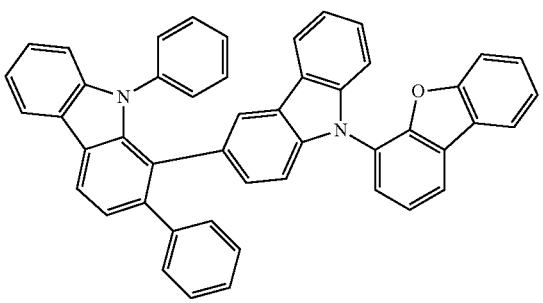
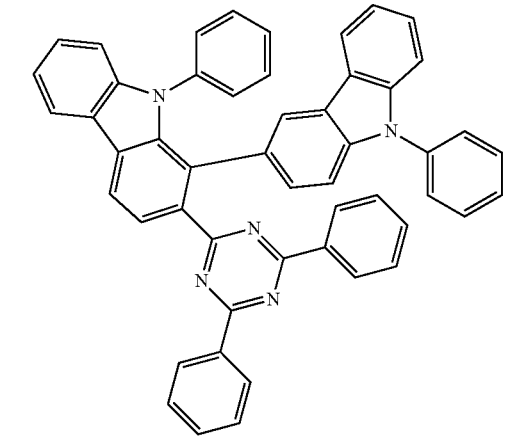
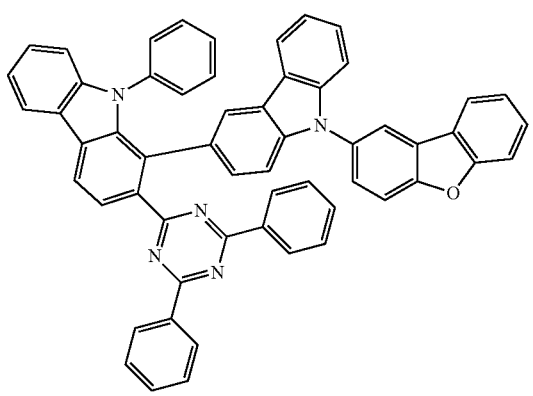 [SMILES: c1ccc(-c2nc(-c3ccccc3)nc(-c3ccc4c5ccccc5n(-c5ccccc5)c4c3-c3ccc4c(c3)c3ccccc3n4-c3ccc4oc5ccccc5c4c3)n2)cc1]

Compounds represented by the formula (11):
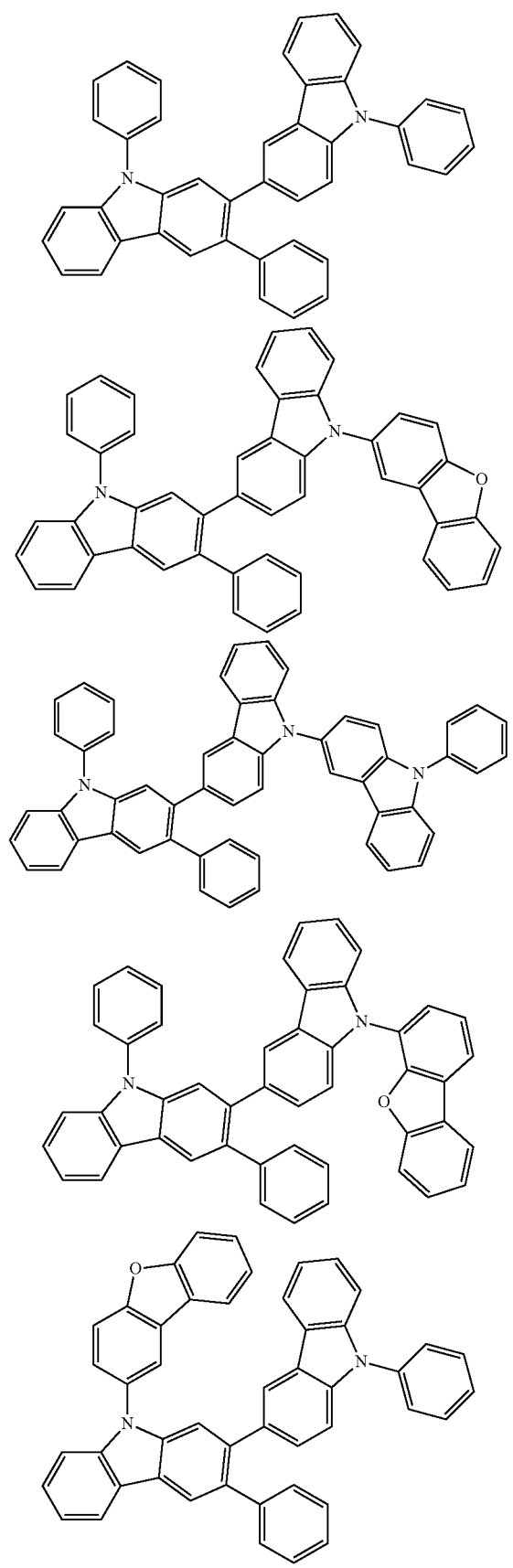
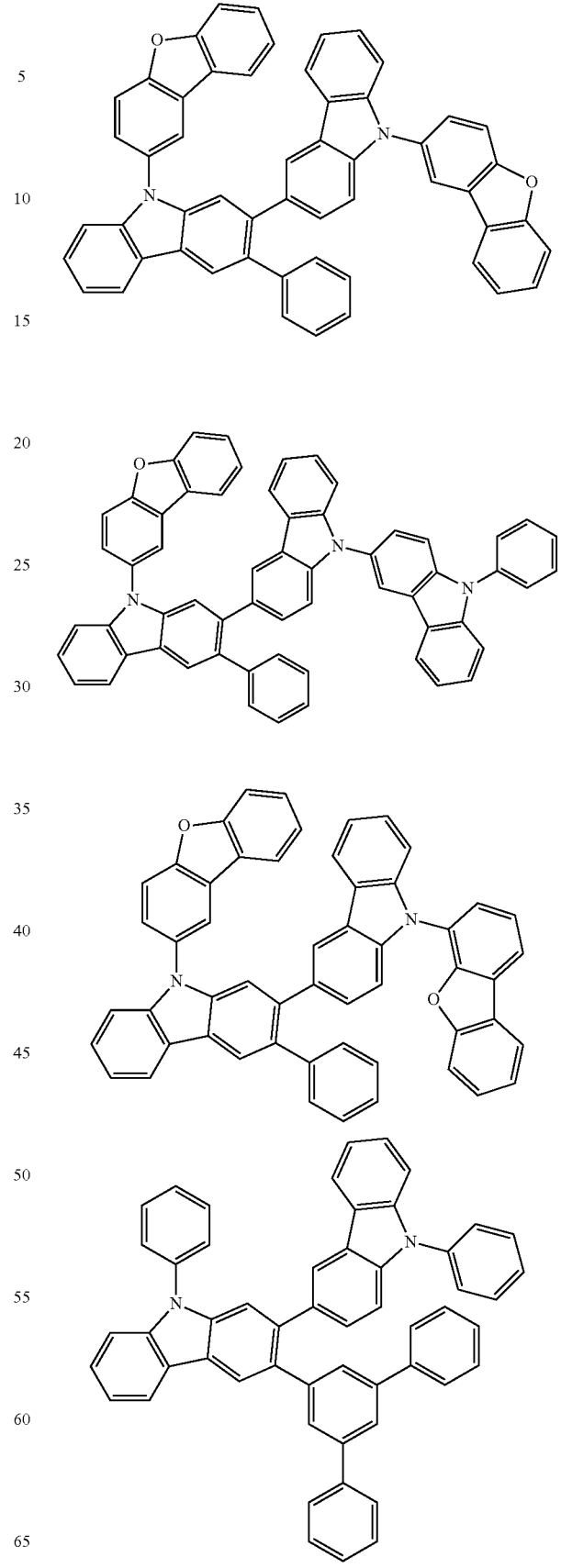

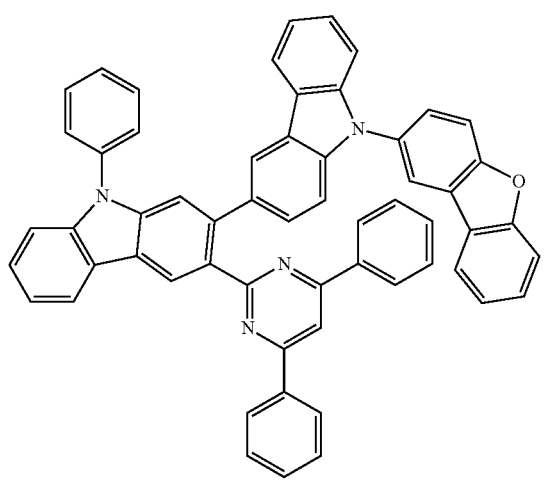
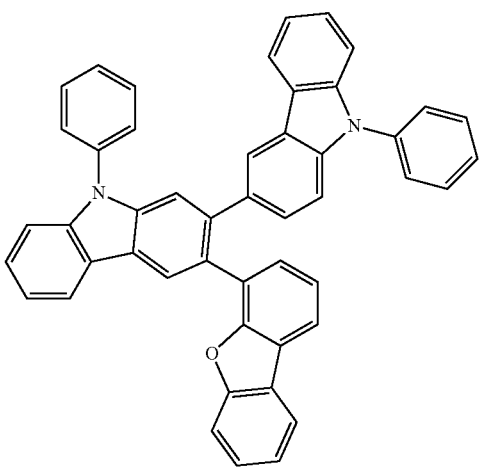
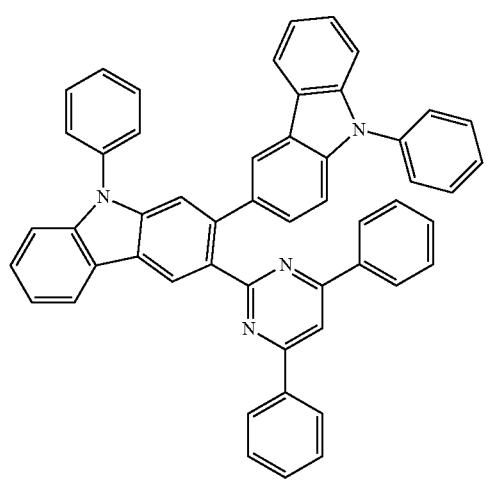
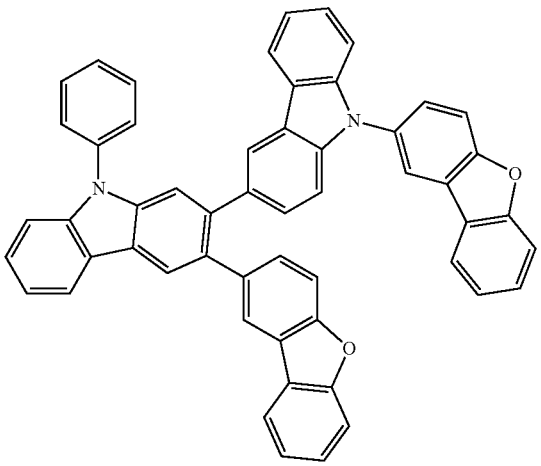
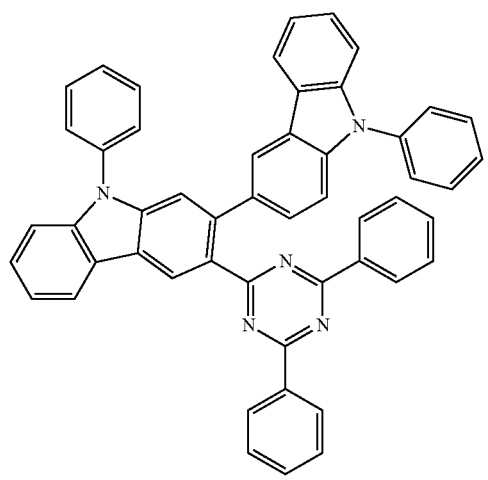
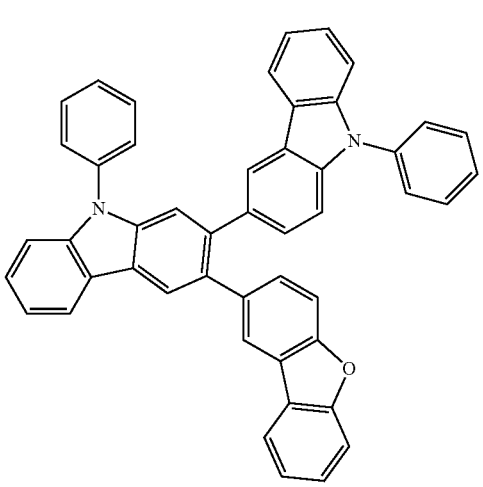

81
-continued
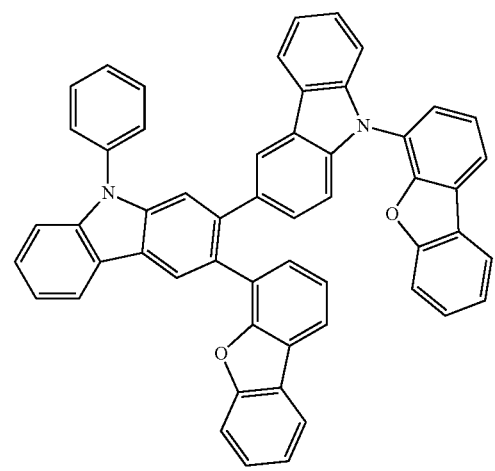
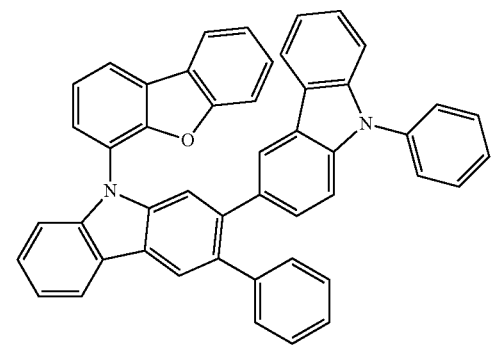
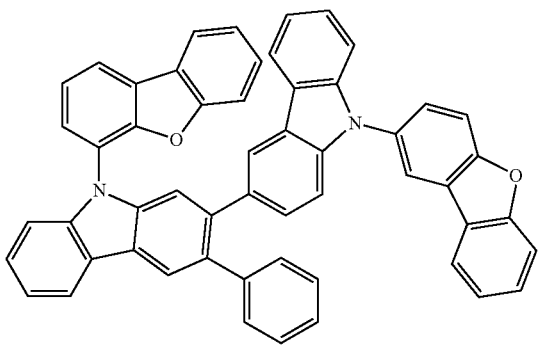
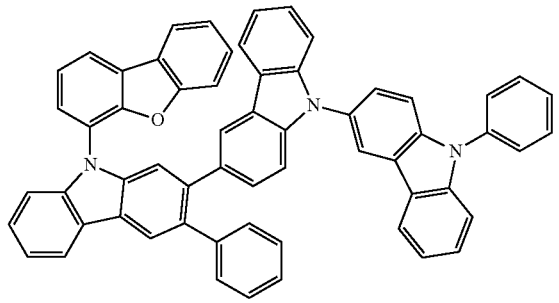
82
-continued
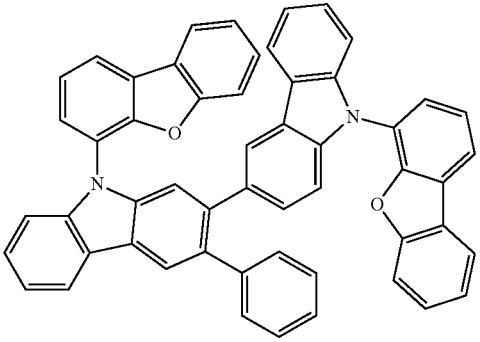
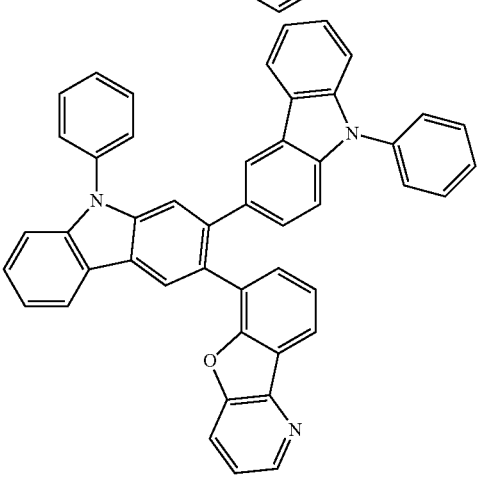
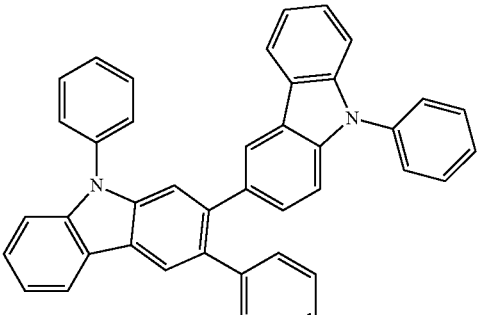
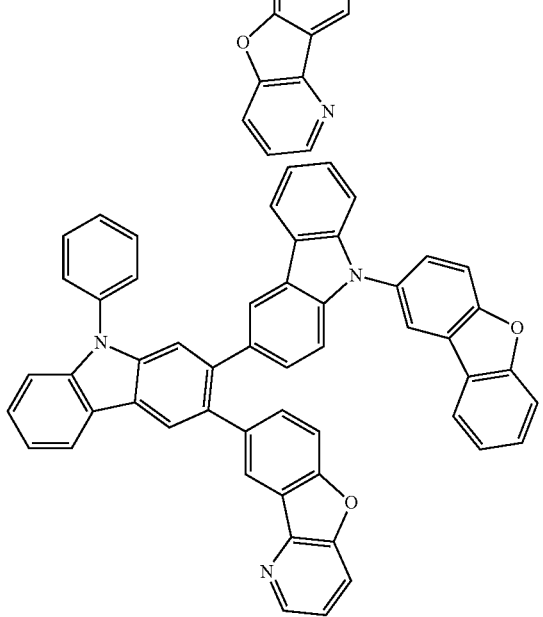

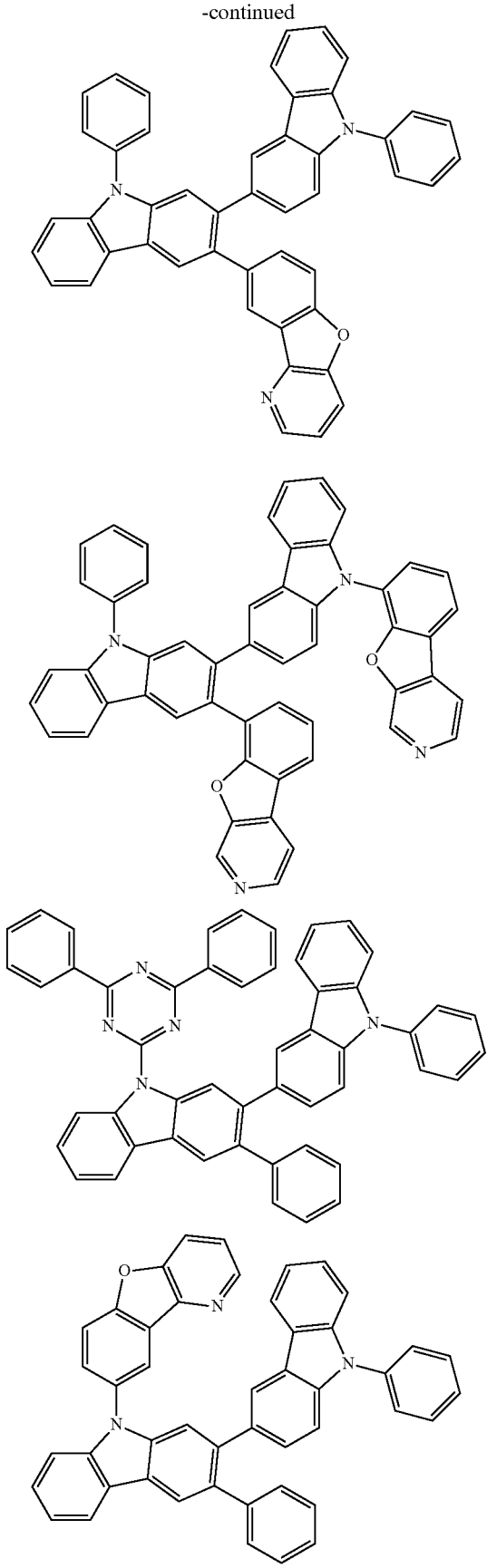
Compounds represented by the formula (12):
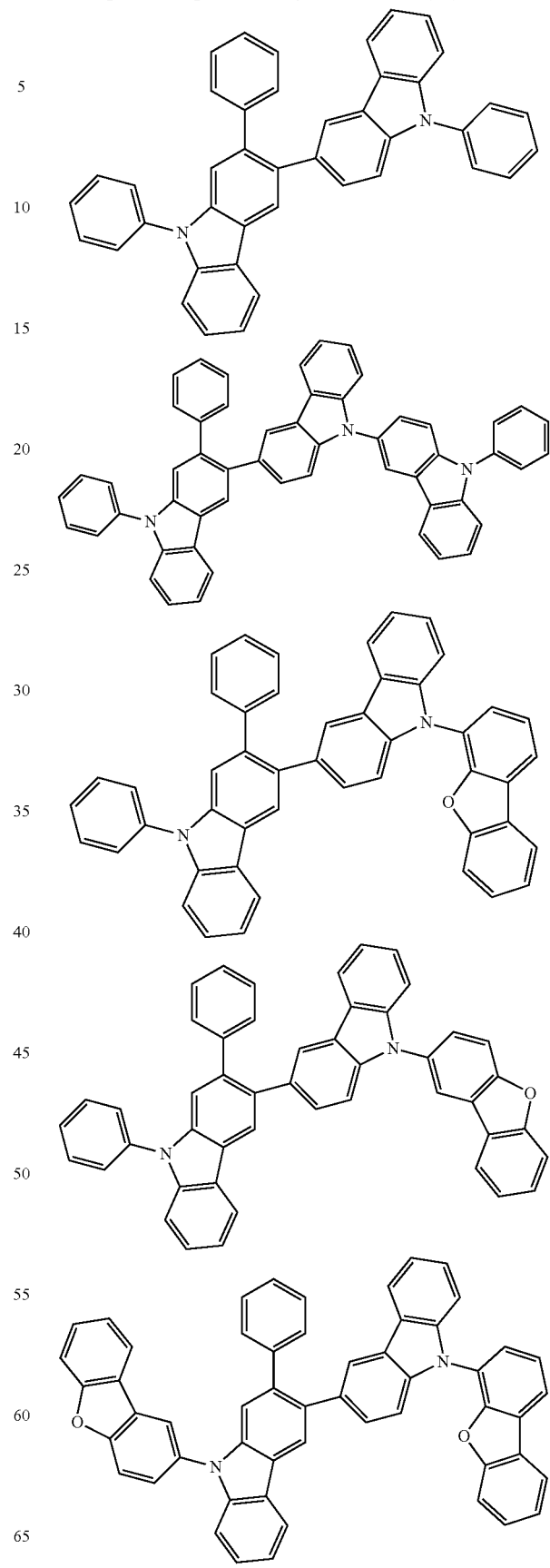

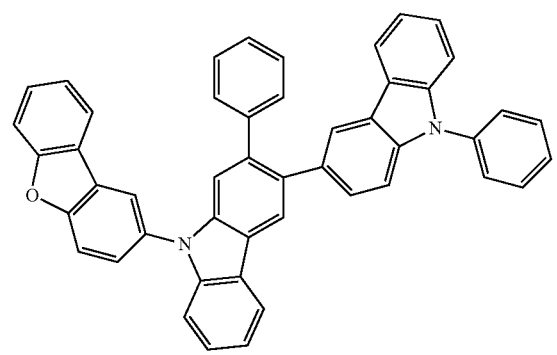
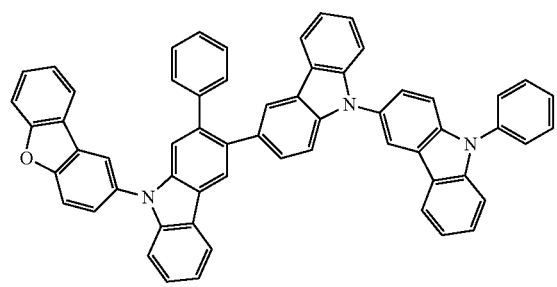
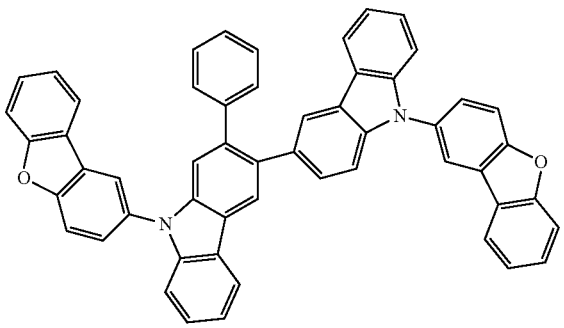
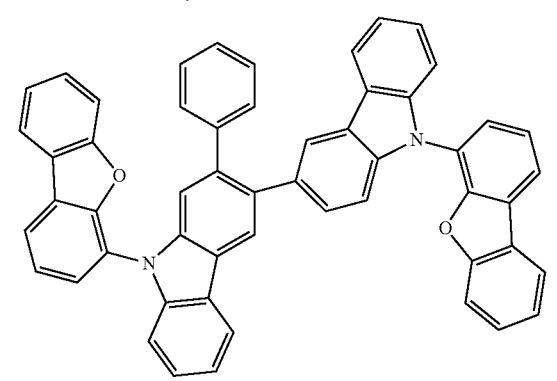
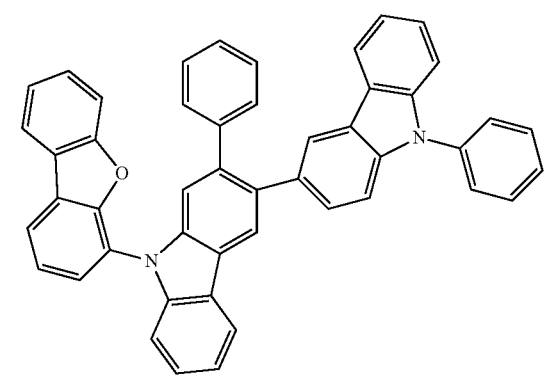
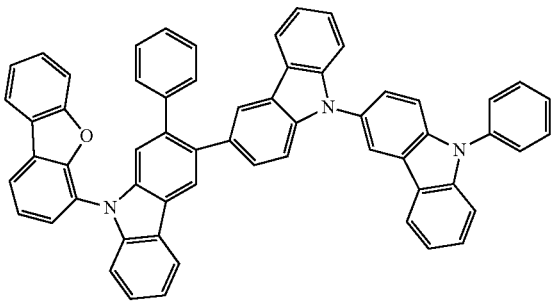
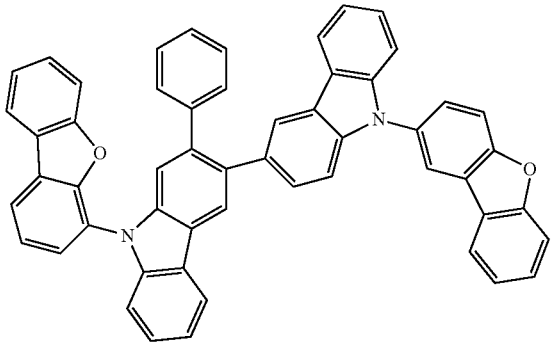
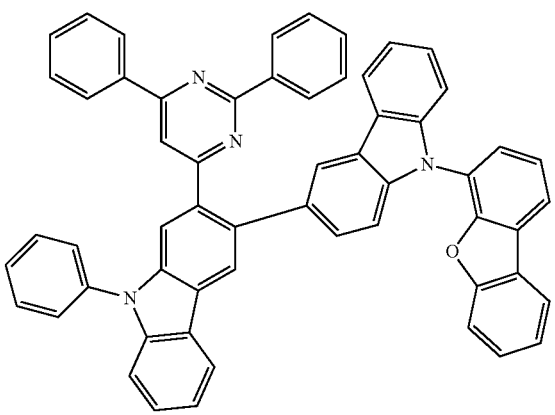
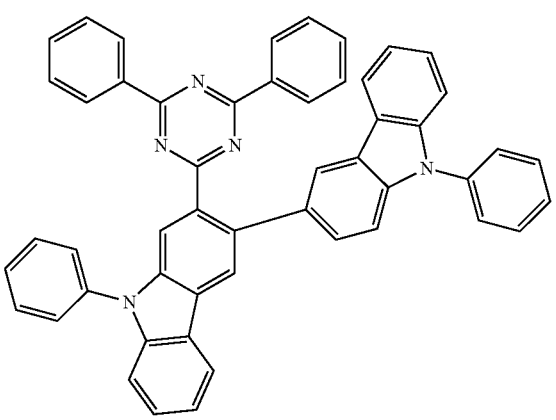

87
-continued
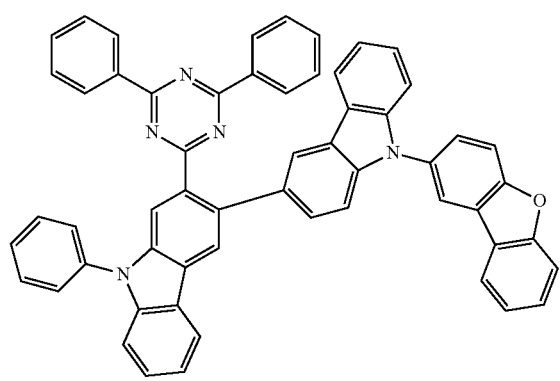
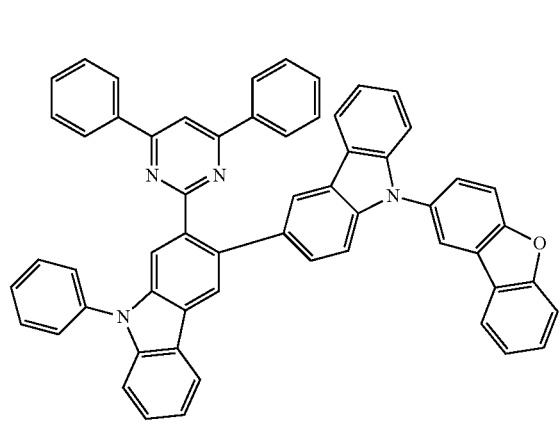
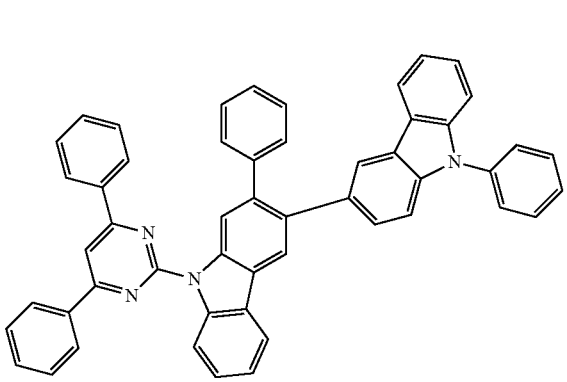
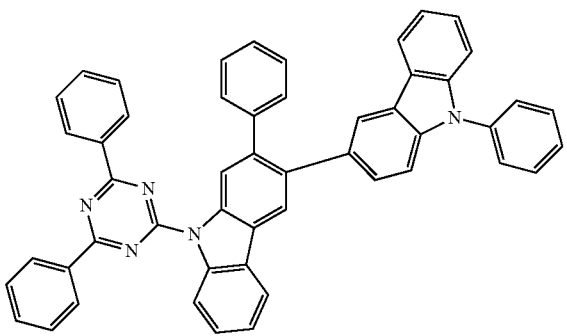
88
-continued
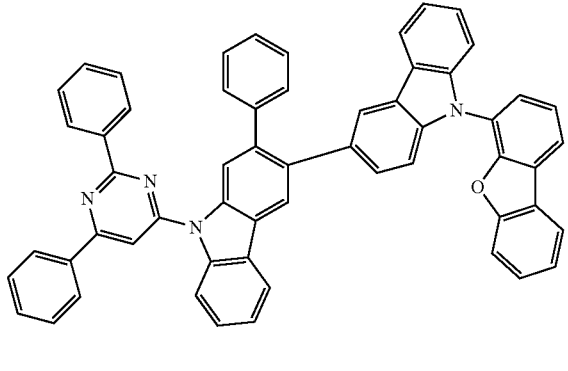
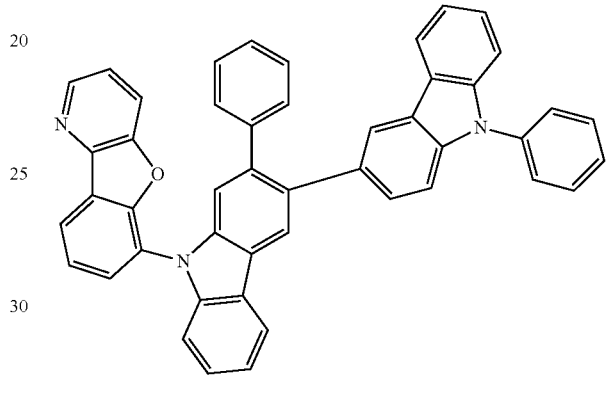
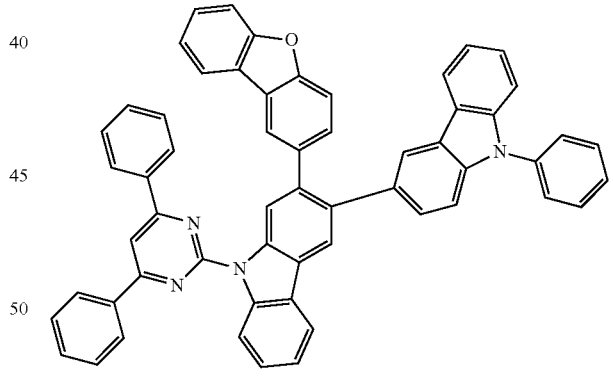
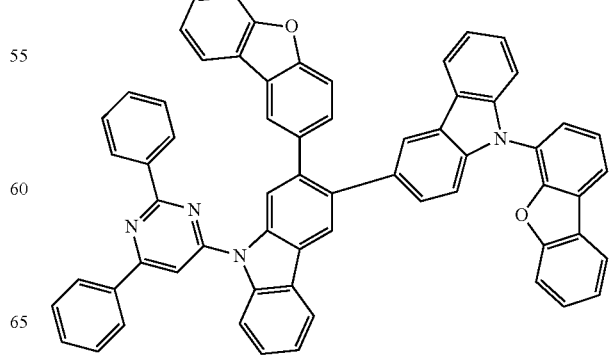

-continued
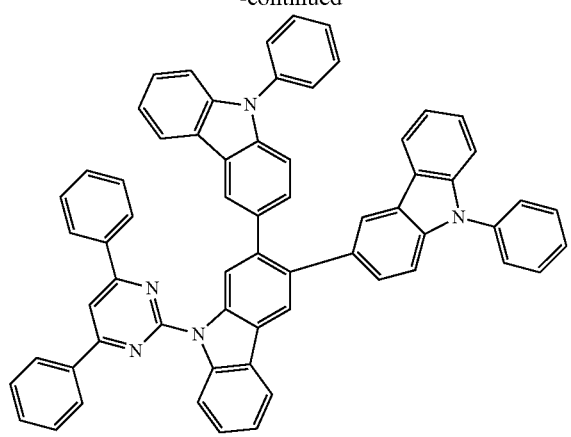
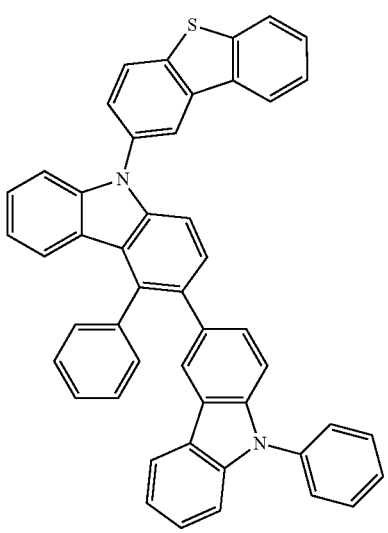
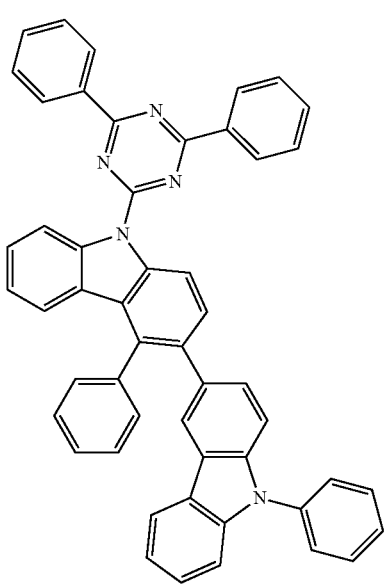
Compounds represented by the formula (13):
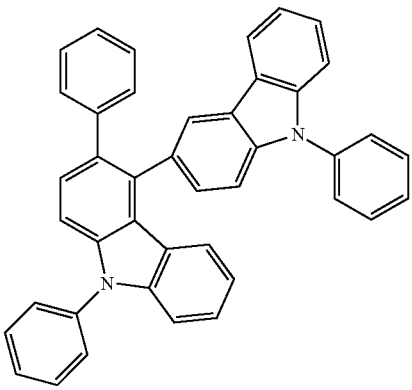
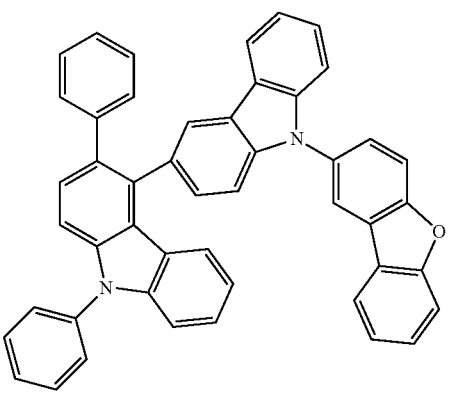
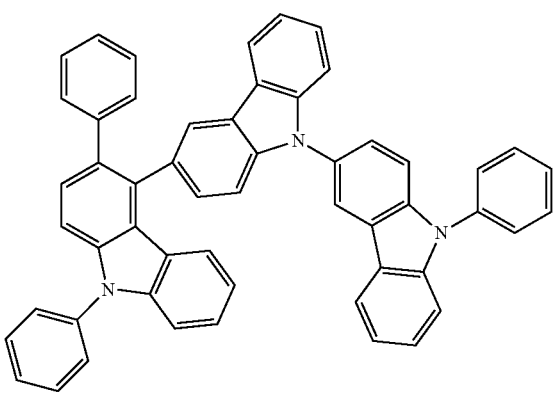
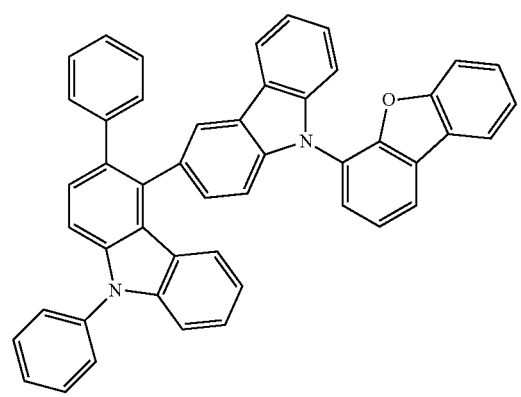

91
-continued
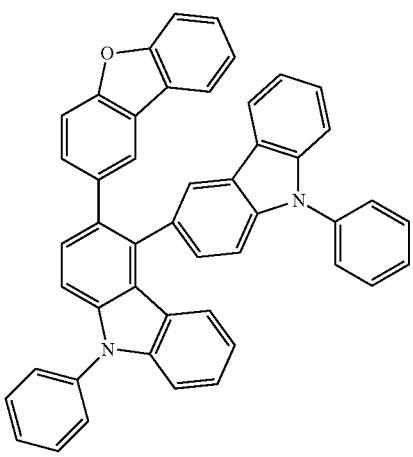
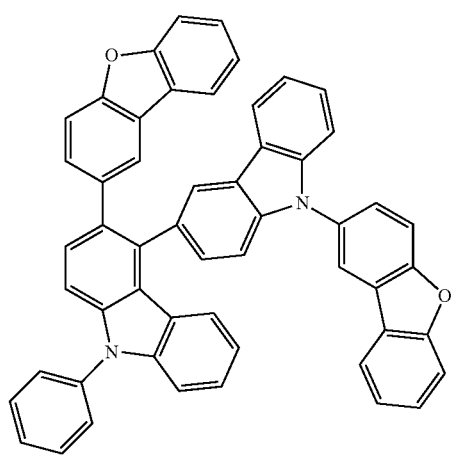
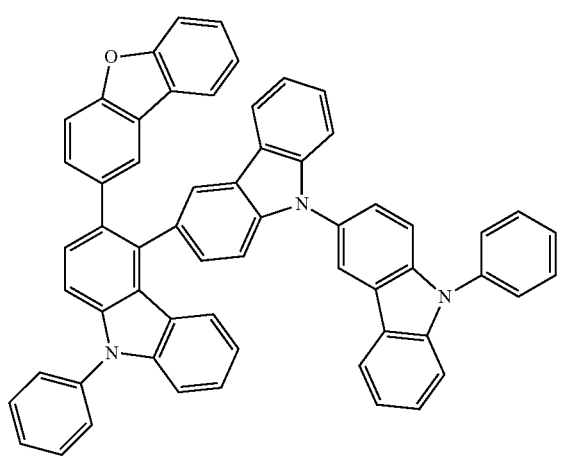
92
-continued
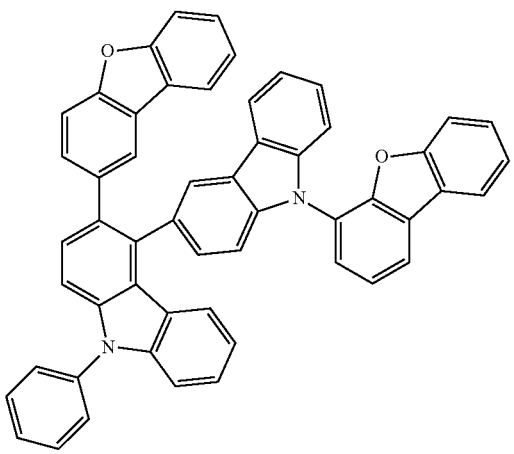
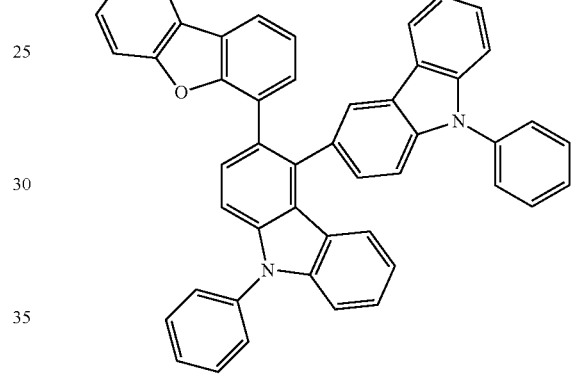
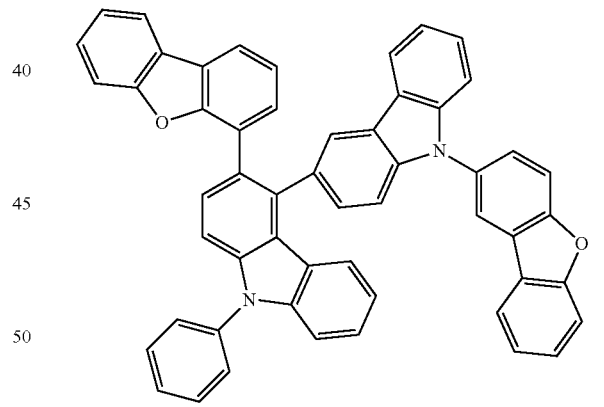
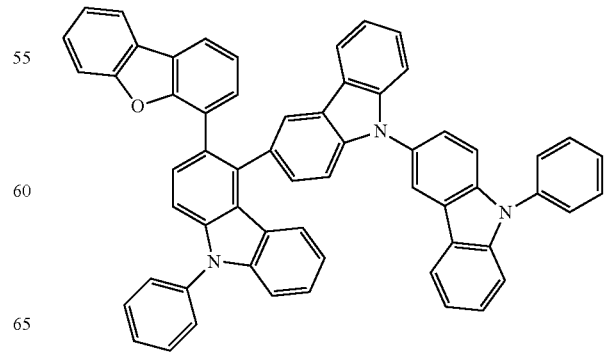

93
-continued
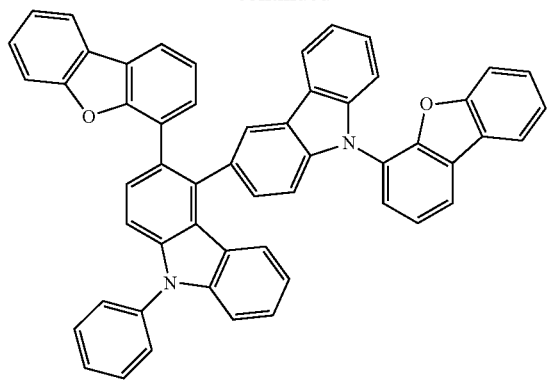
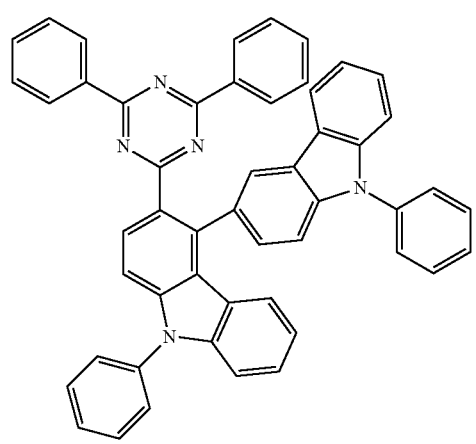
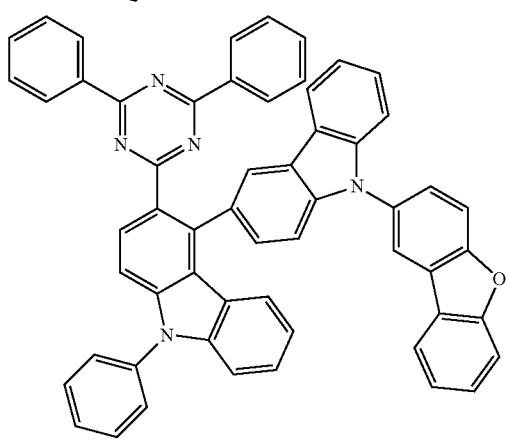
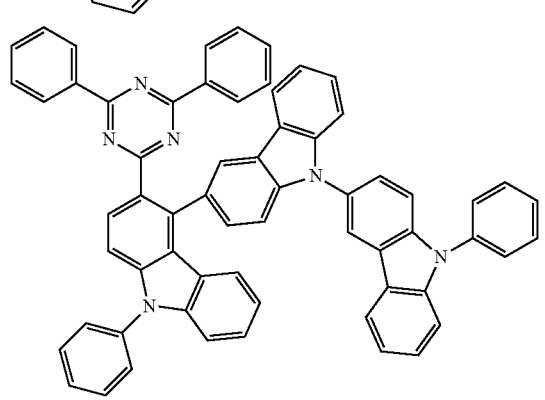
94
-continued
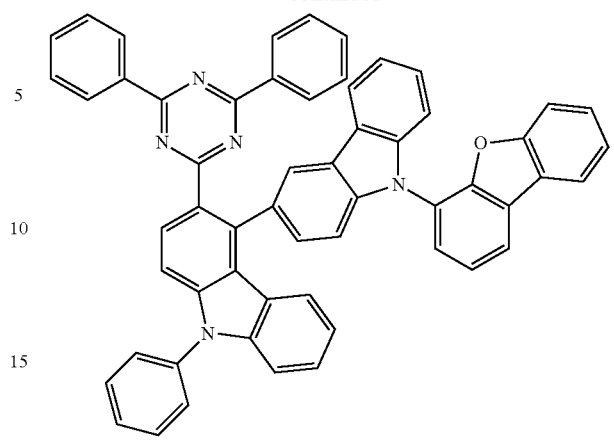
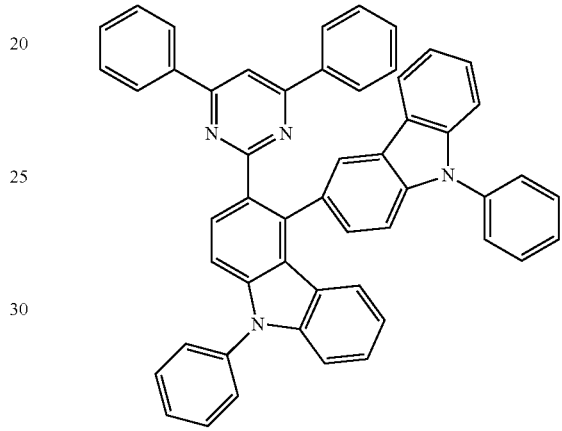
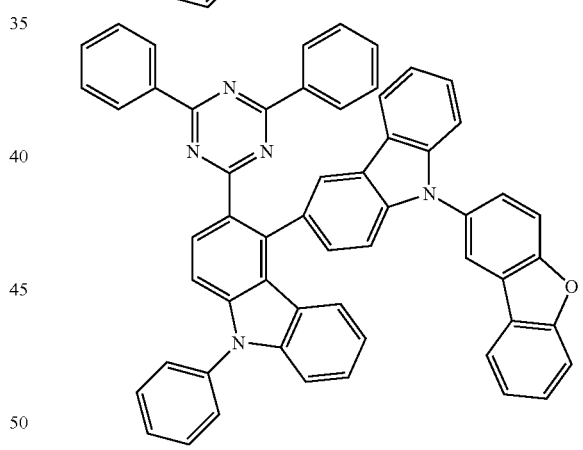
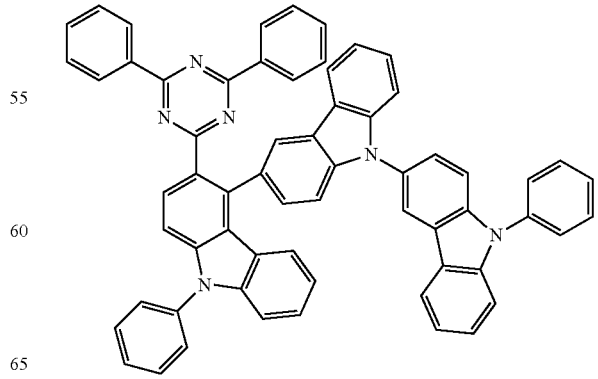

95
-continued
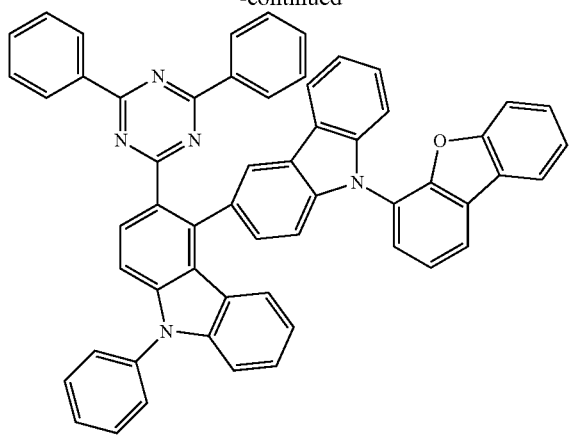
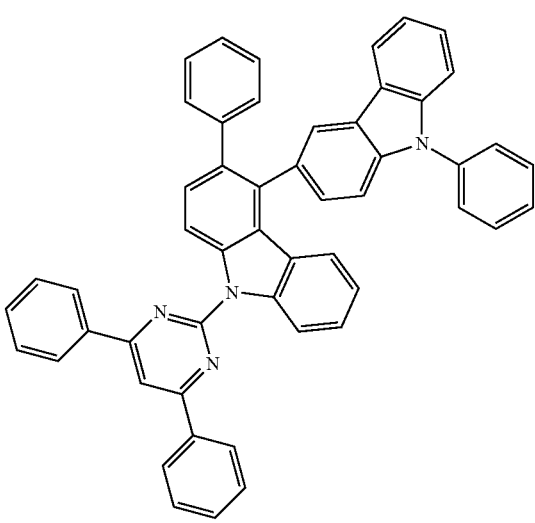
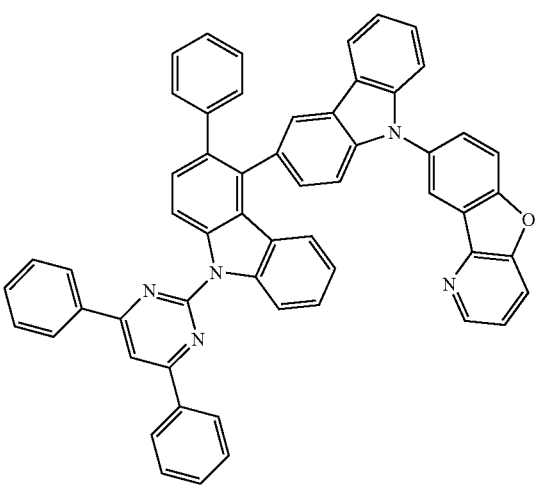
96
-continued
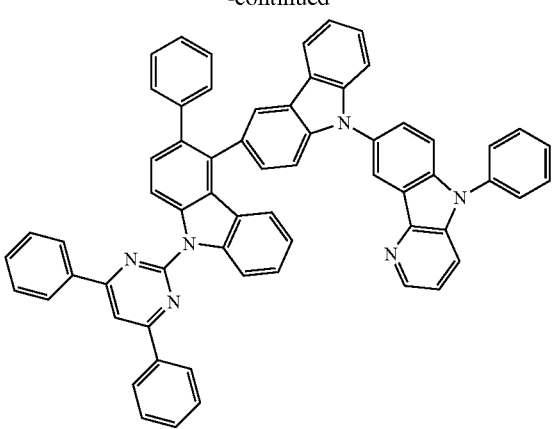
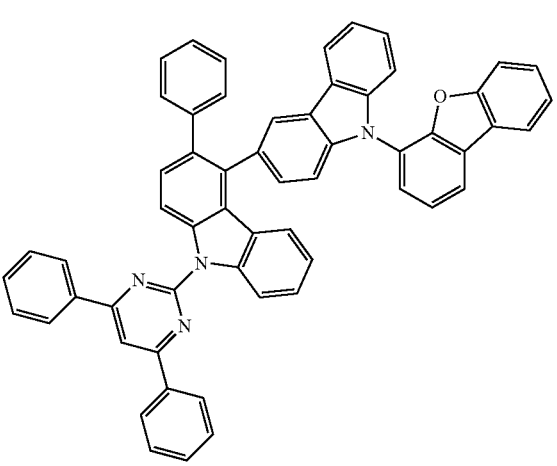
Compounds represented by the formula (14):
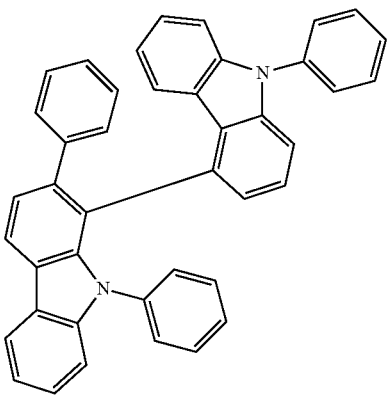

97
-continued
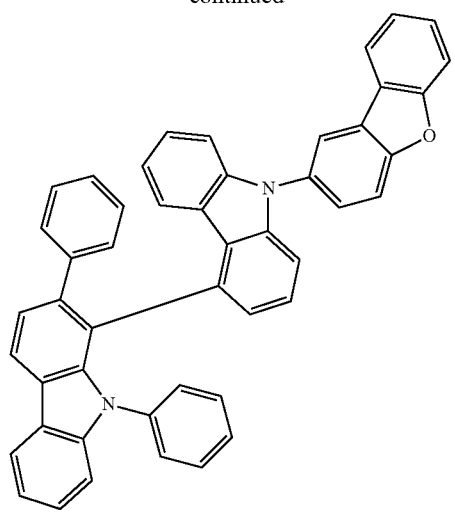
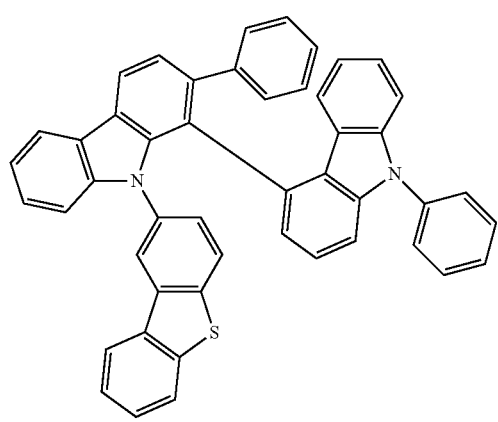
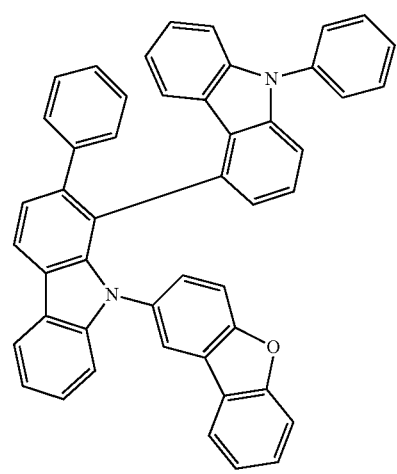
98
-continued
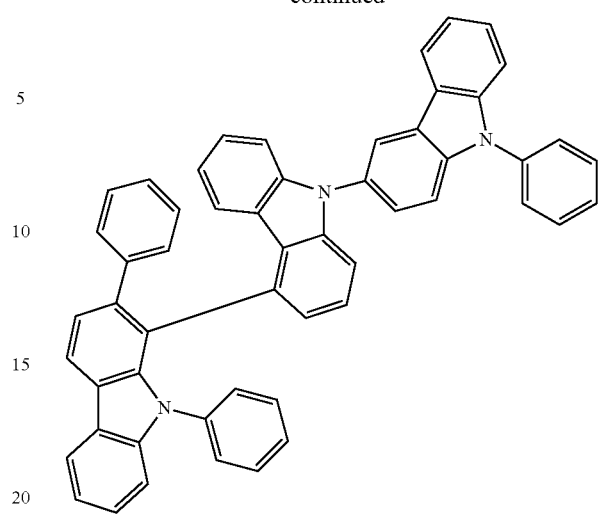
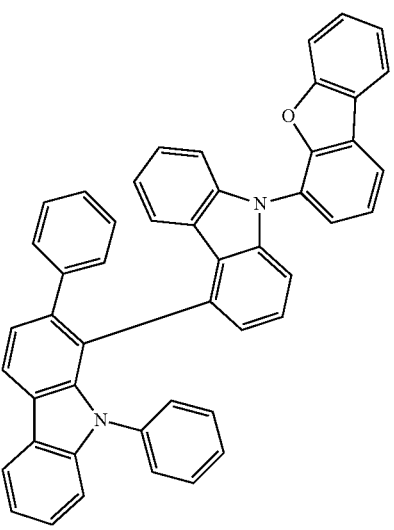
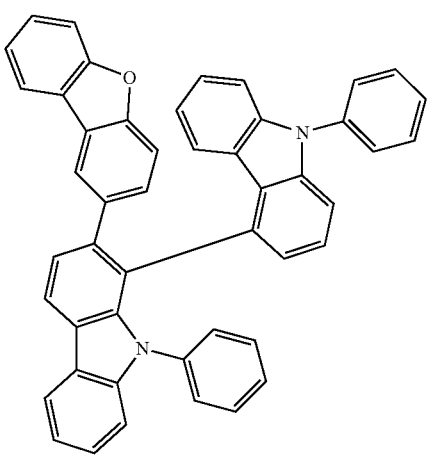

99
-continued
100
-continued
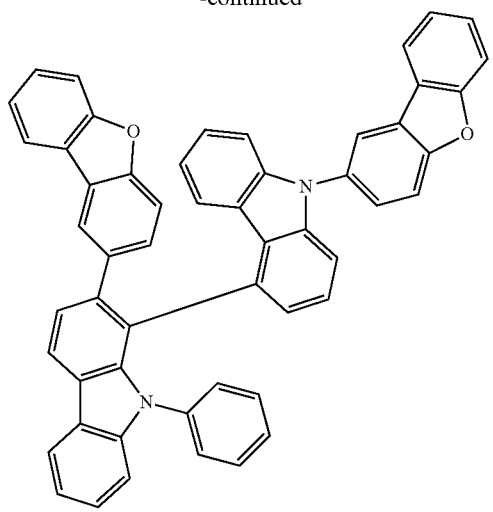
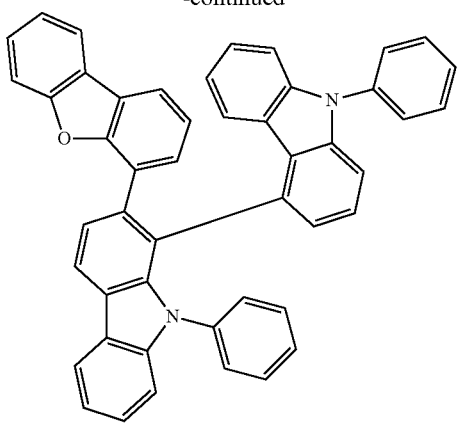

101
-continued
102
-continued
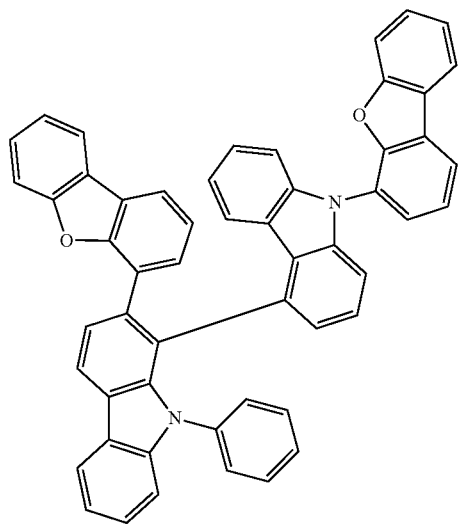
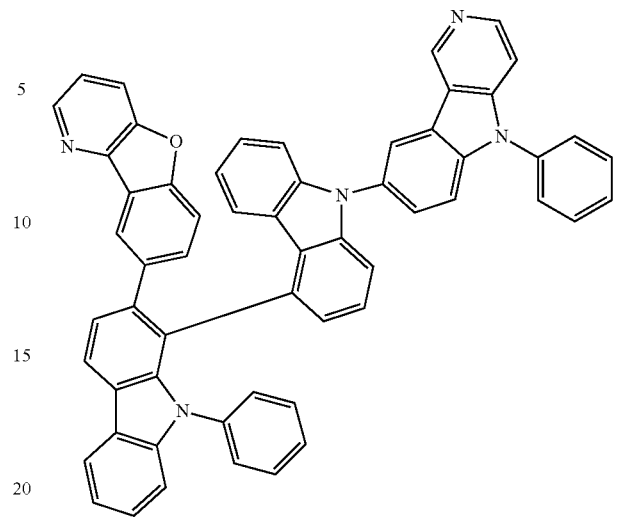
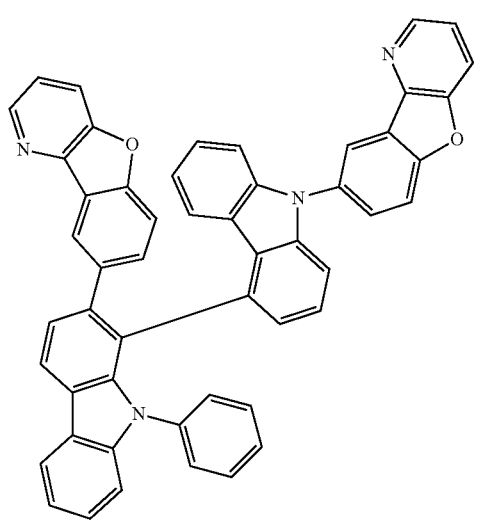
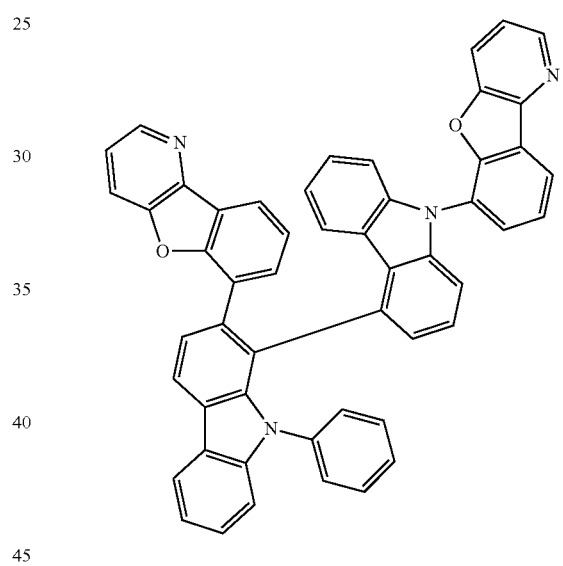

103
-continued
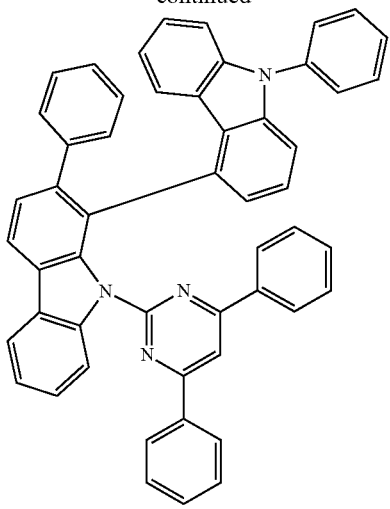
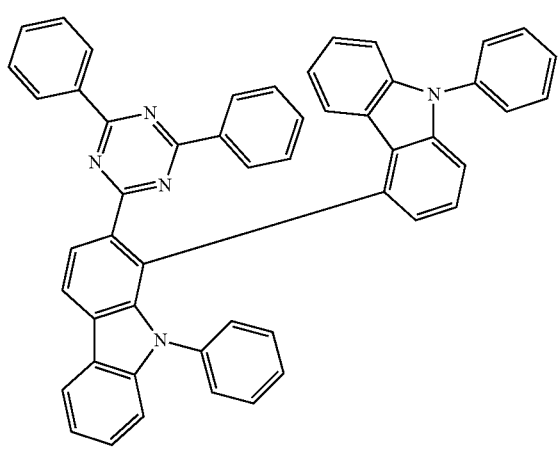
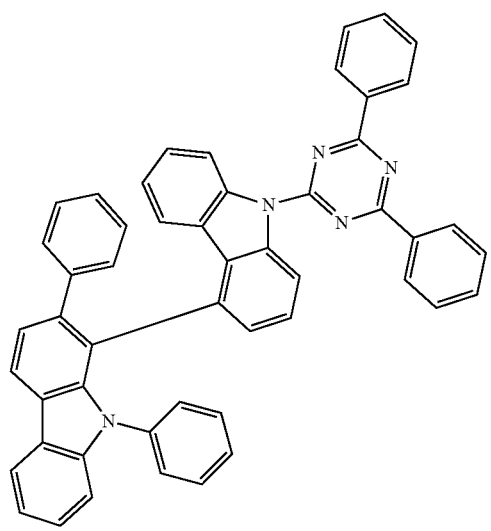
104
-continued
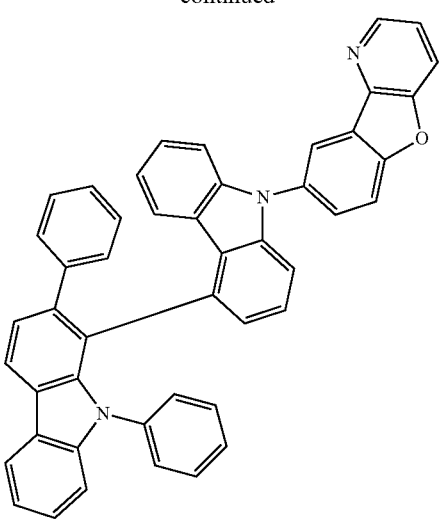
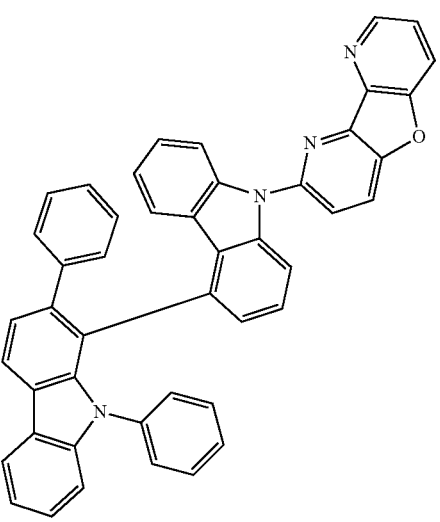
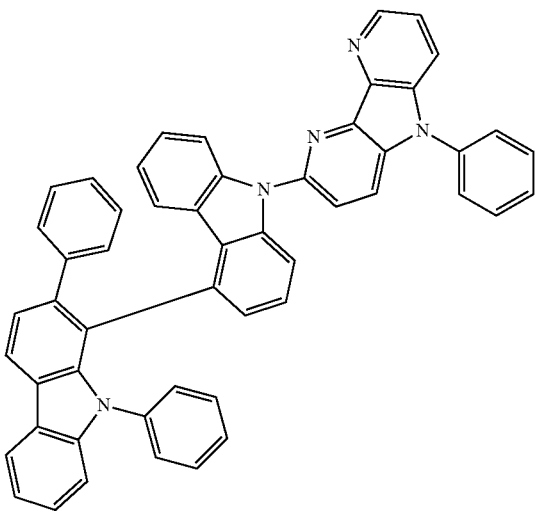

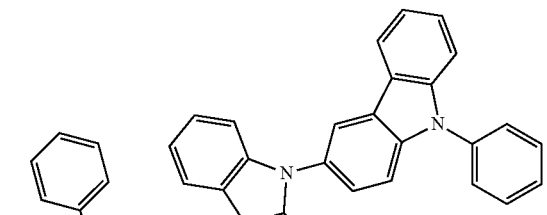
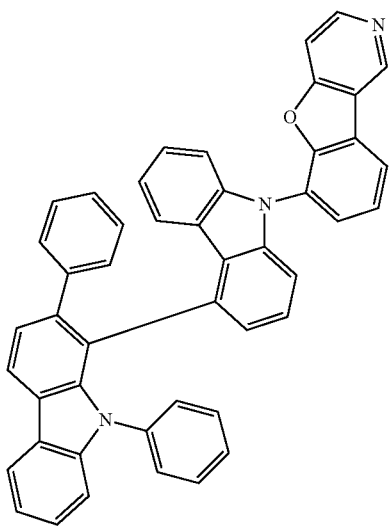 [SMILES: c1ccc(-c2ccc3c4ccccc4n(-c4ccccc4)c3c2-c2cccc3c2c2ccccc2n3-c2cccc3c2oc2ccncc23)cc1]
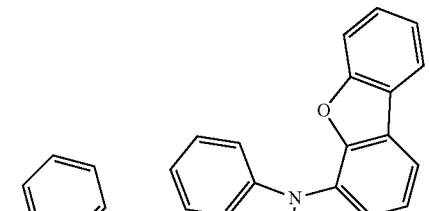
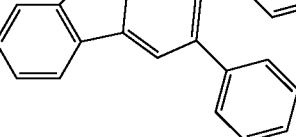
Compounds represented by the formula (15):
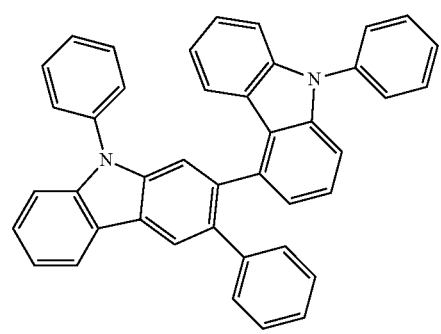
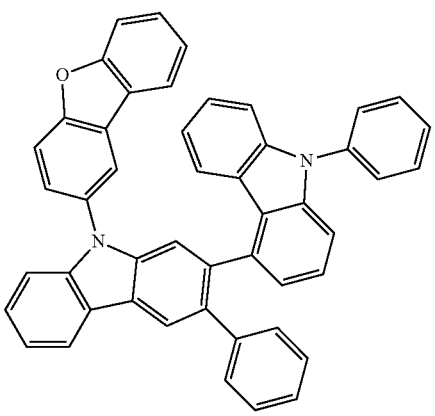
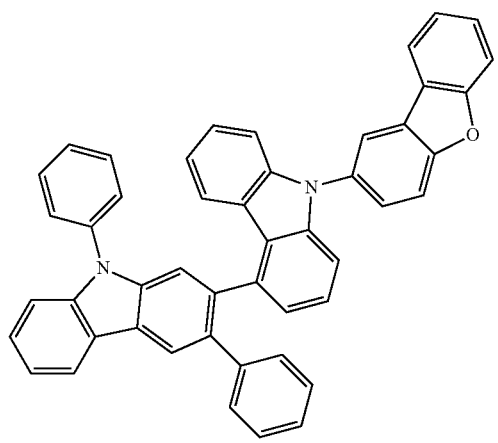
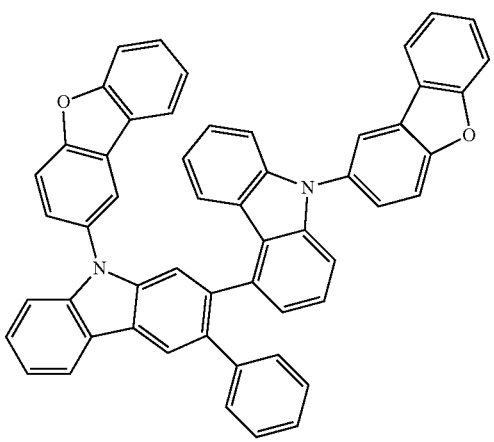

107
-continued
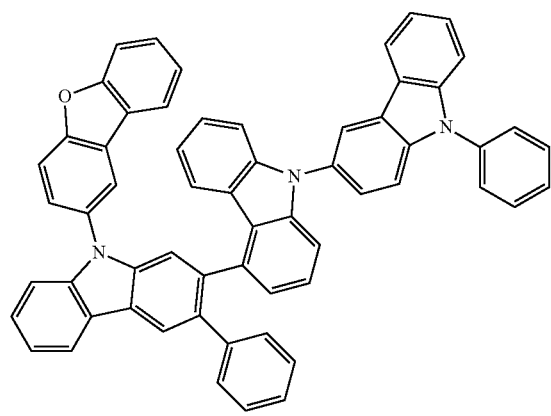
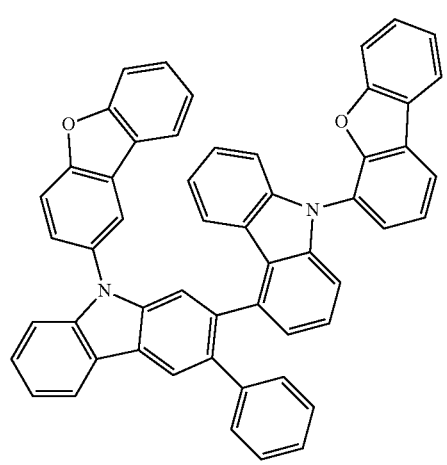
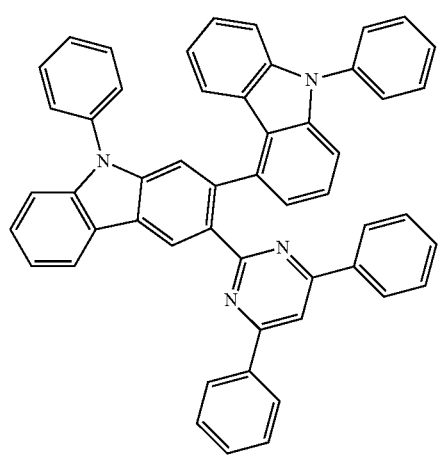
108
-continued
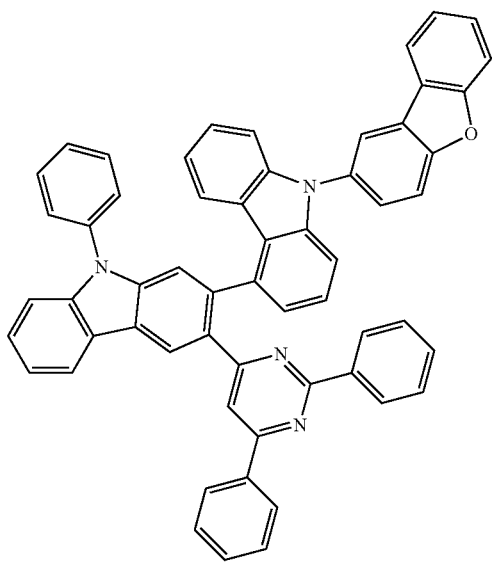
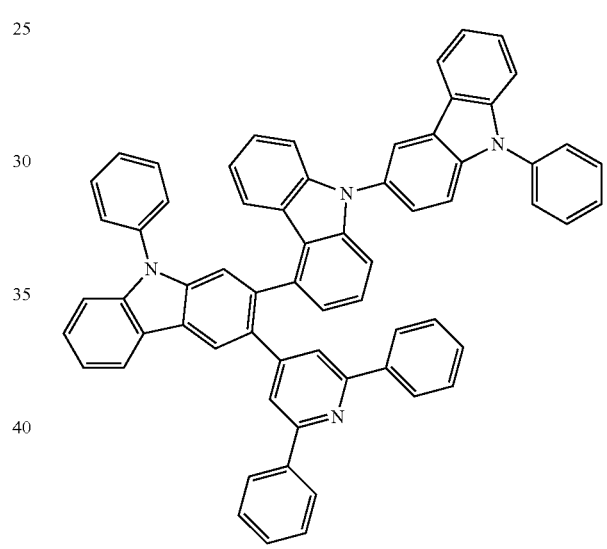
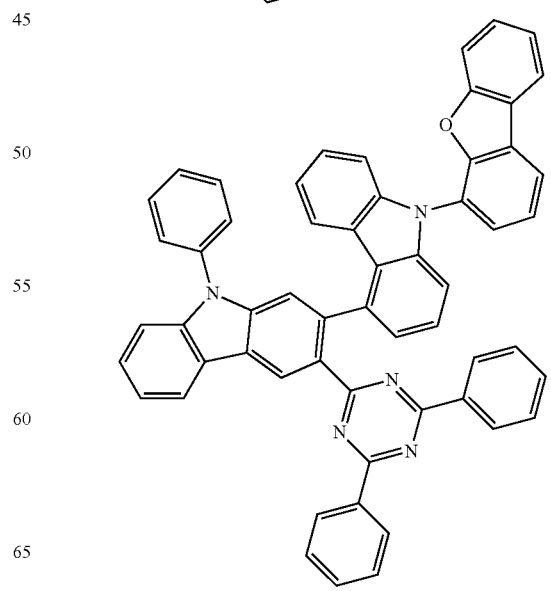

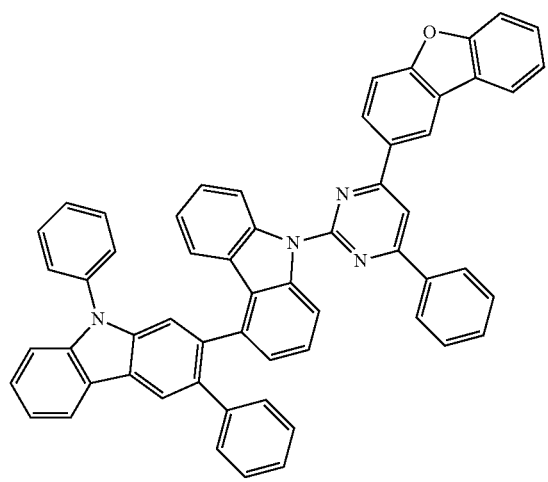
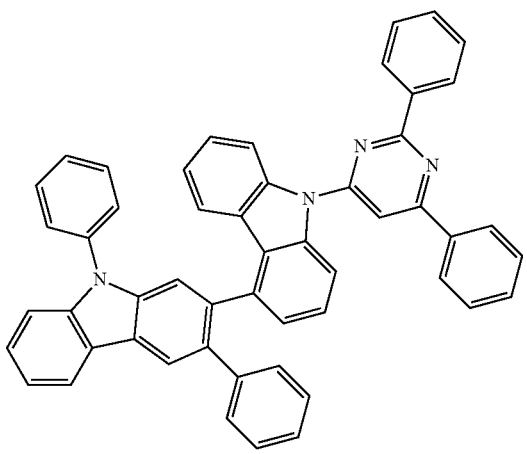
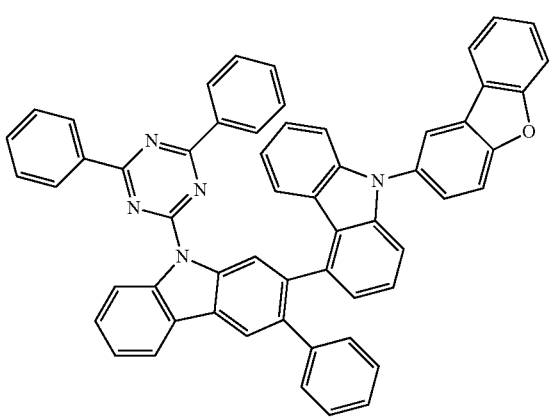
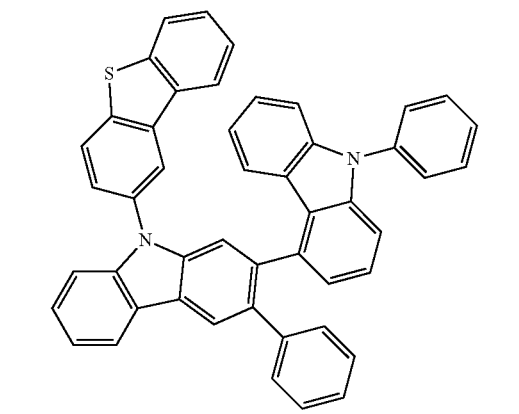
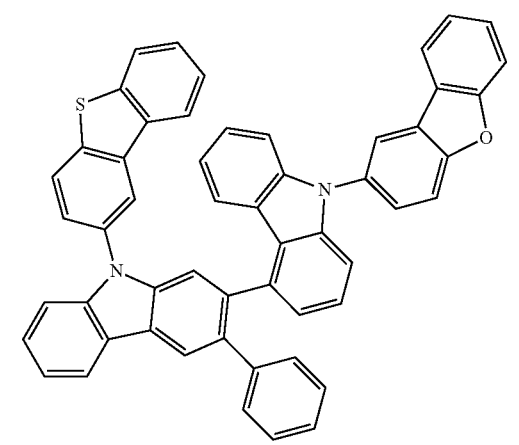
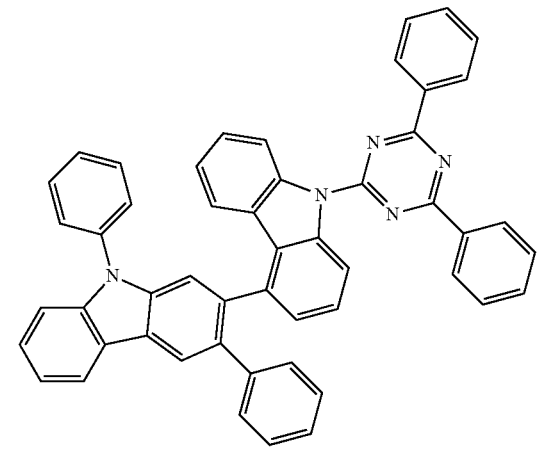
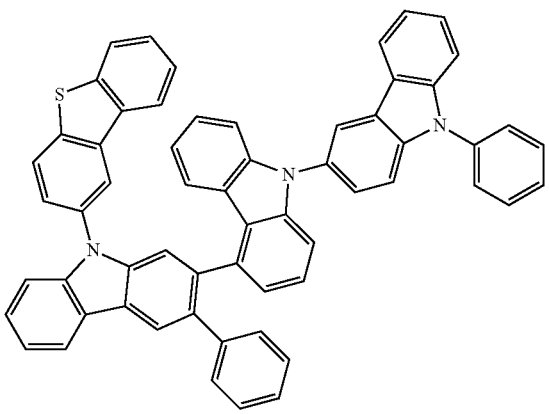

111
-continued
112
-continued
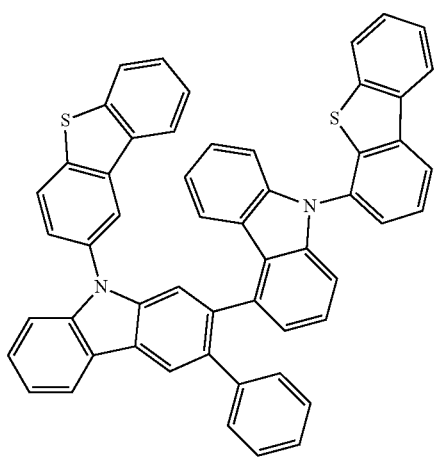
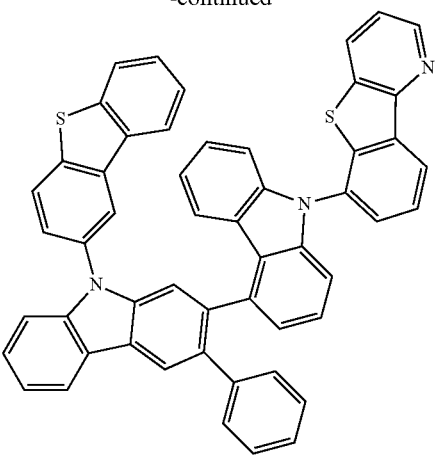
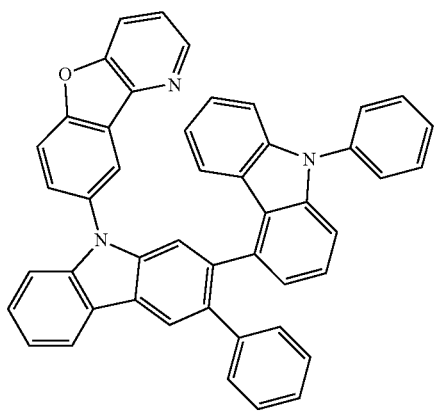
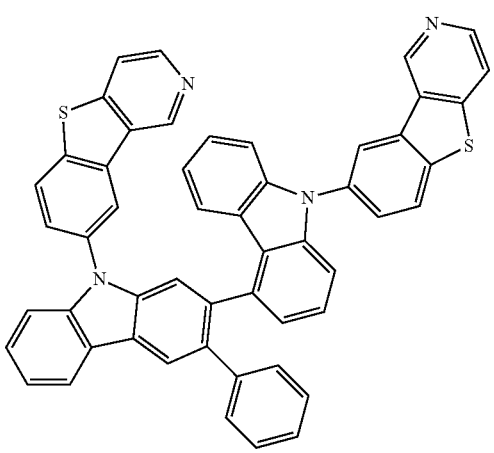
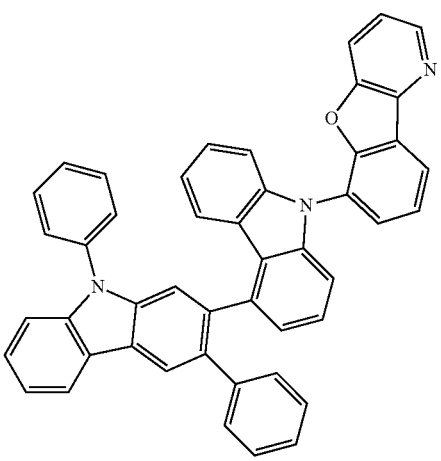
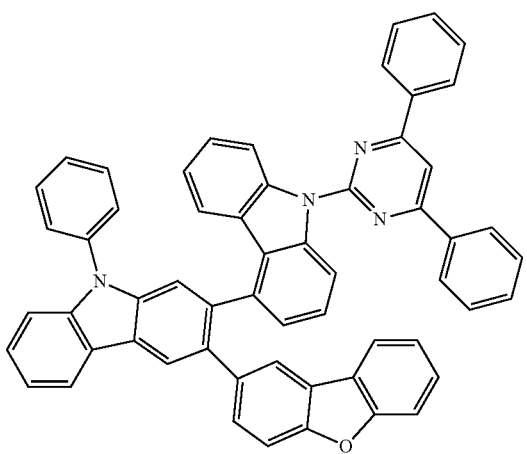

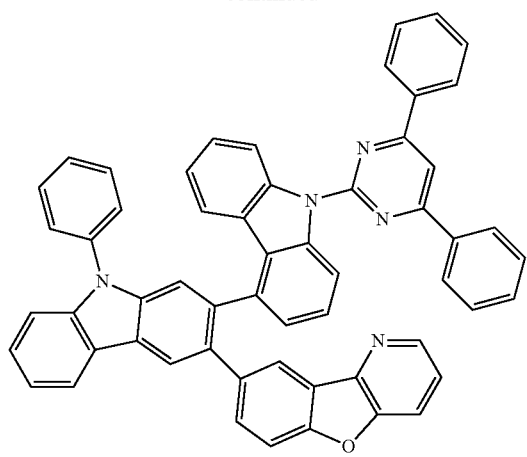
Compounds represented by the formula (16):
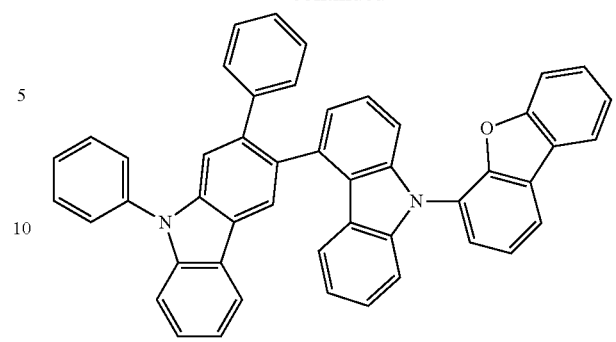
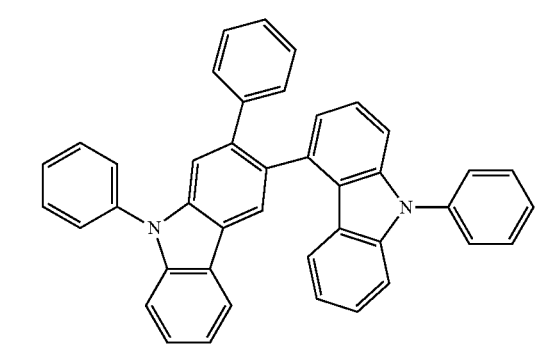
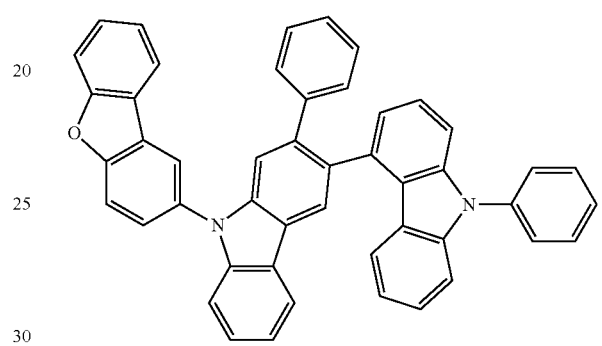
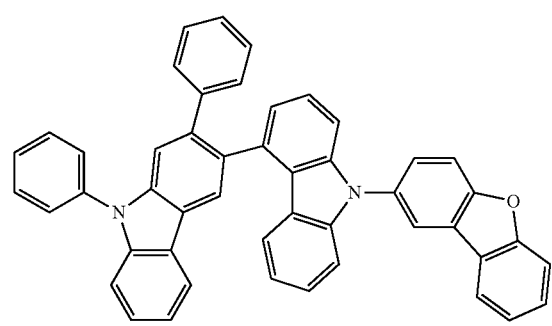
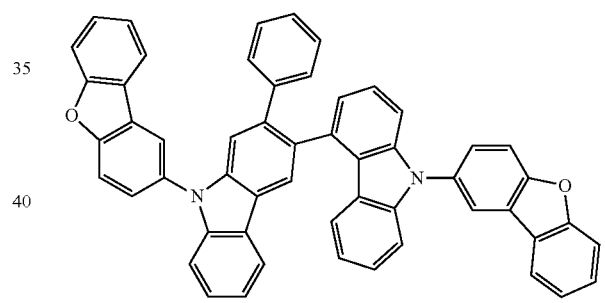
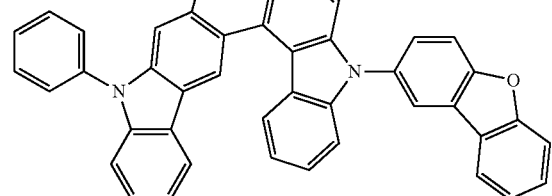
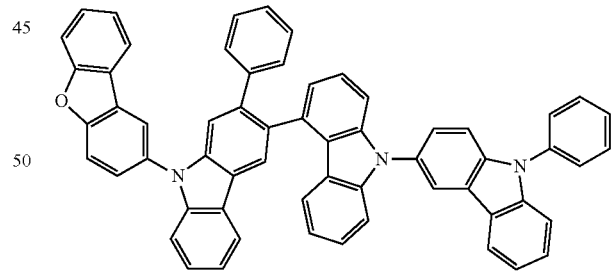
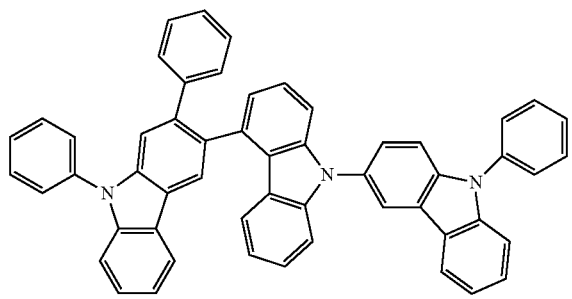
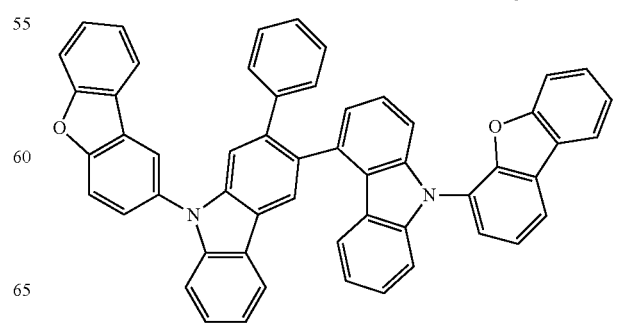

115
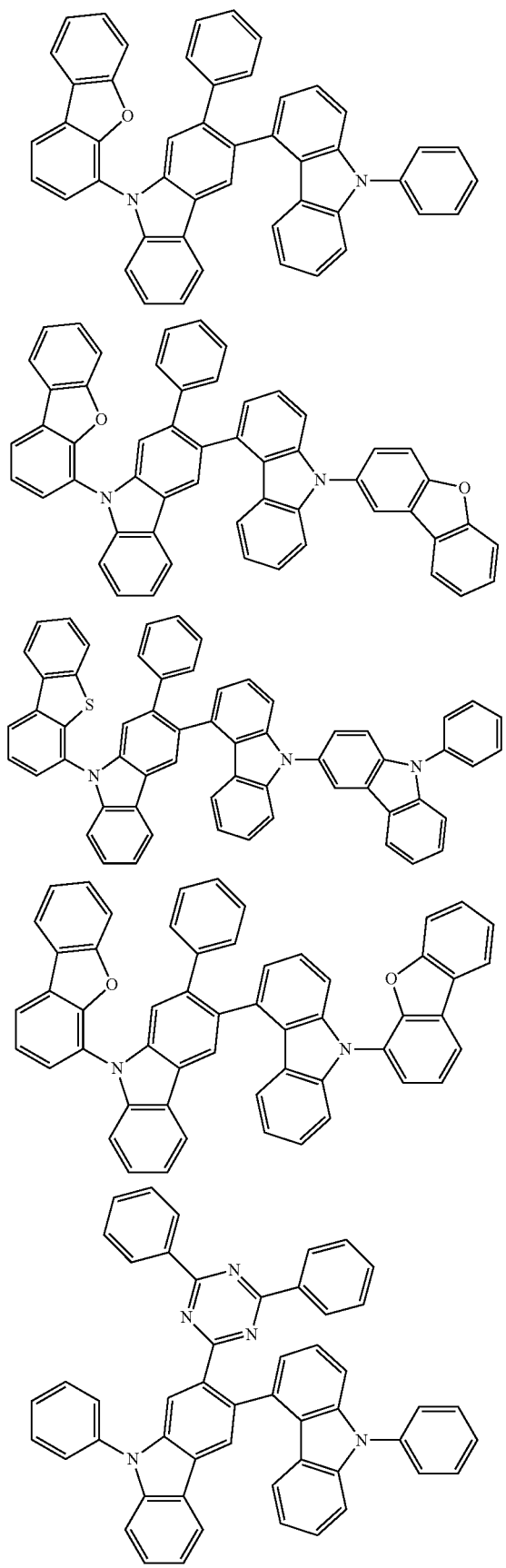
116
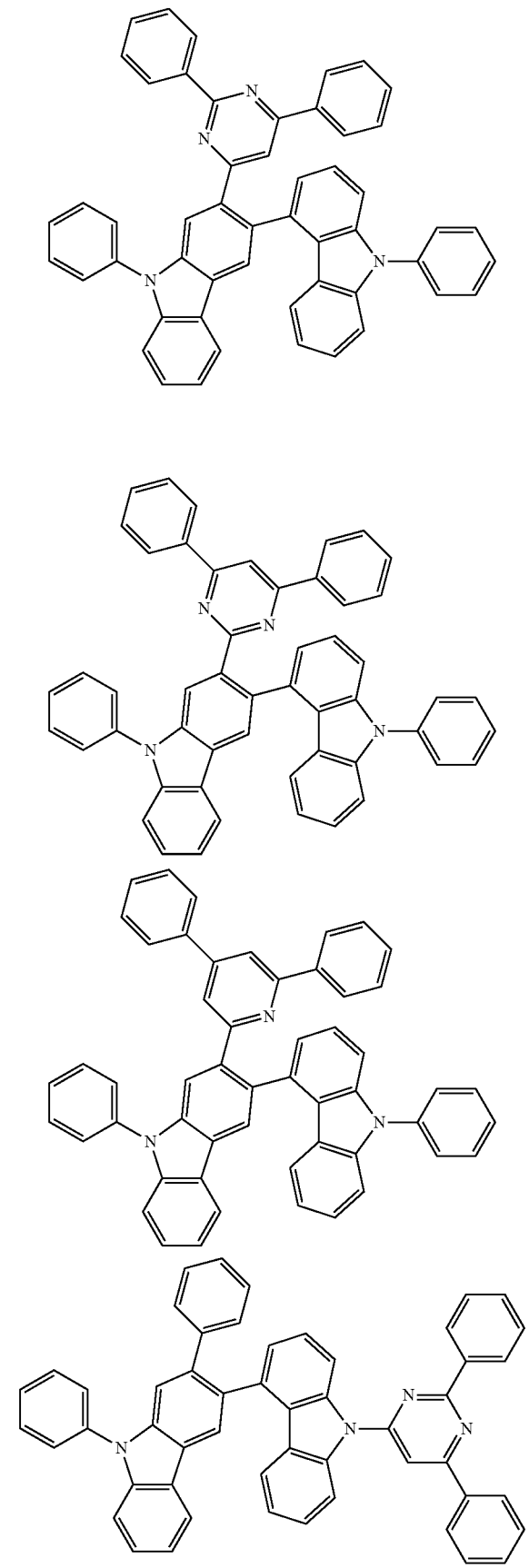

117
-continued
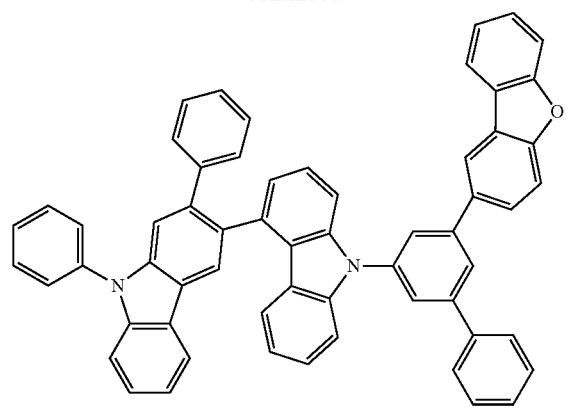
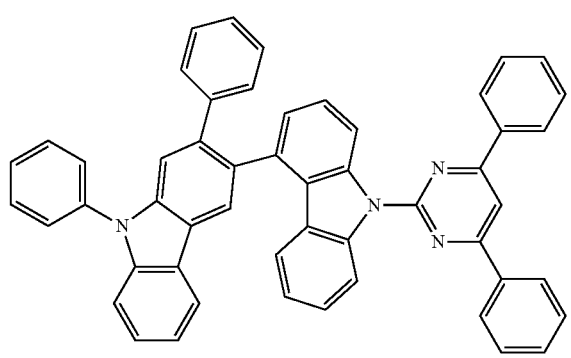
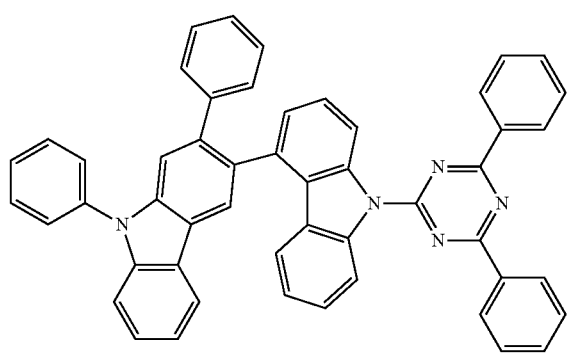
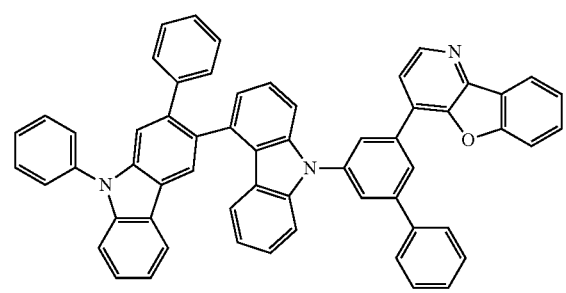
118
-continued
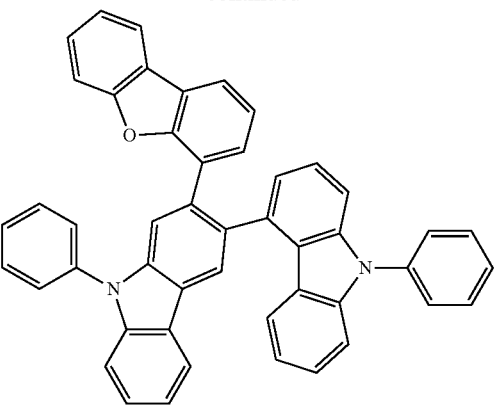
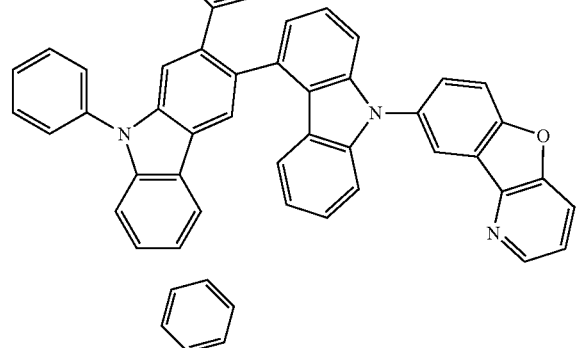
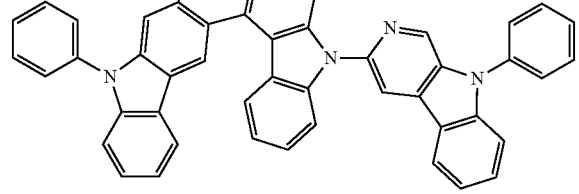
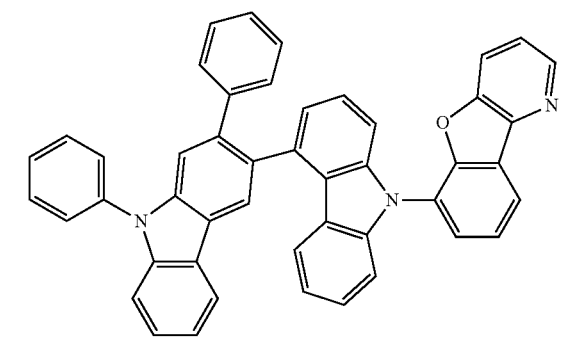
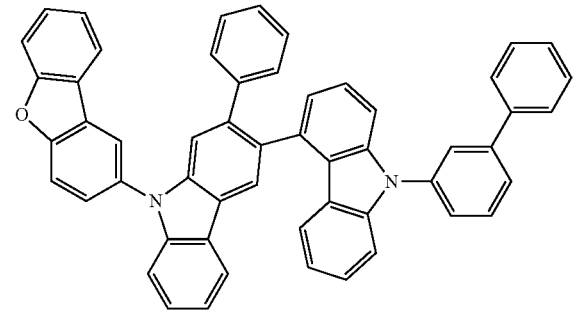

119
-continued
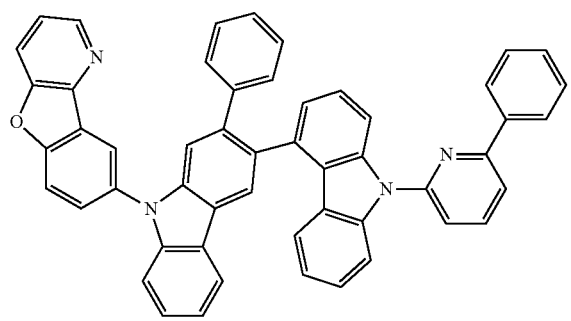
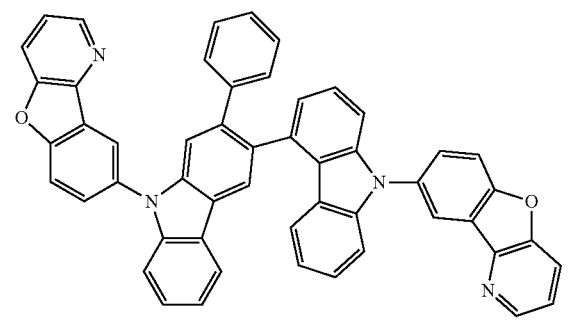
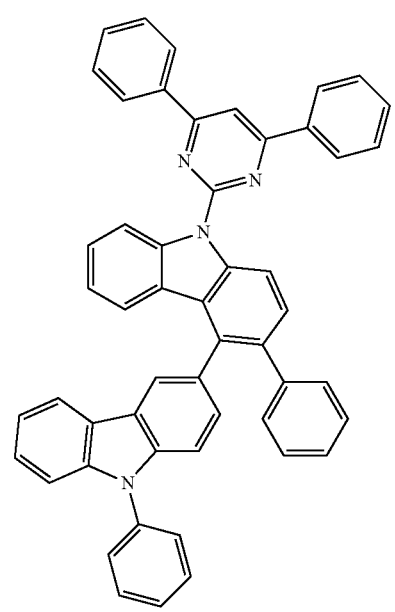
120
-continued
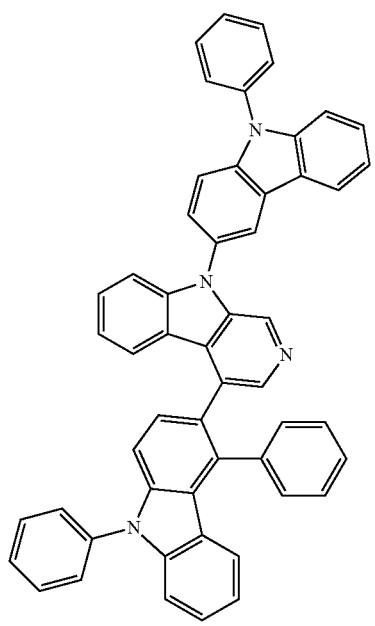
Compounds represented by the formula (17):
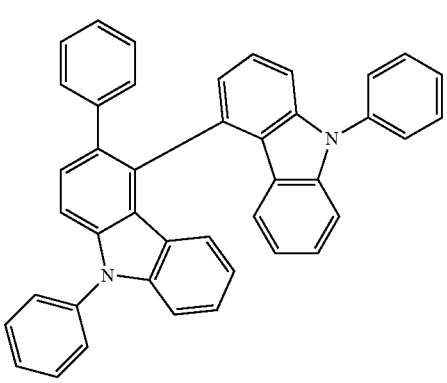
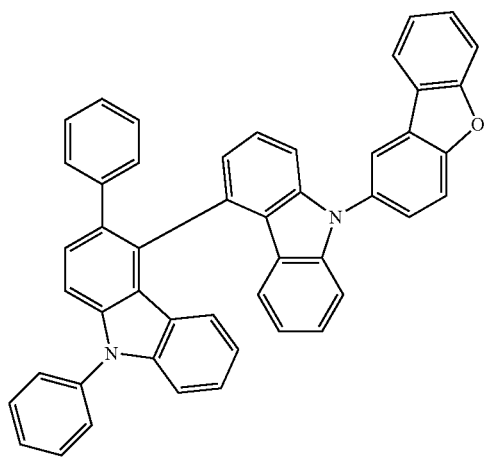

-continued
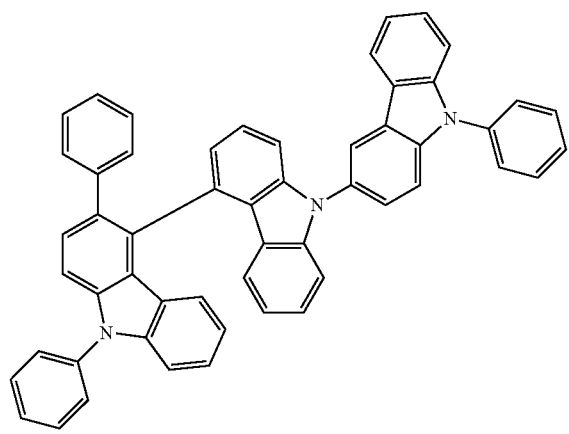
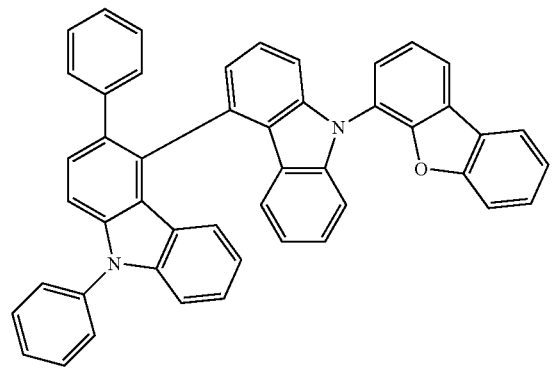
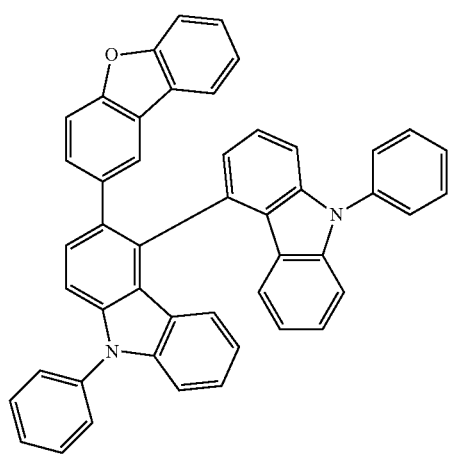
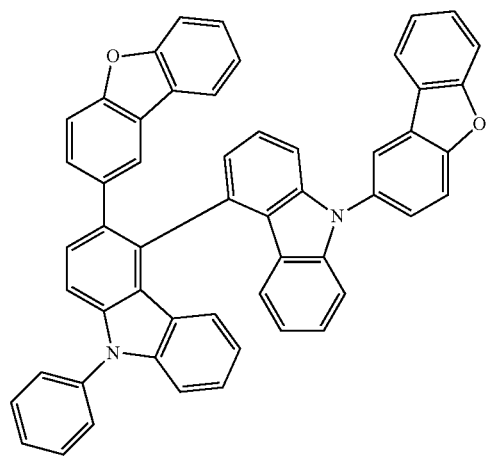
-continued
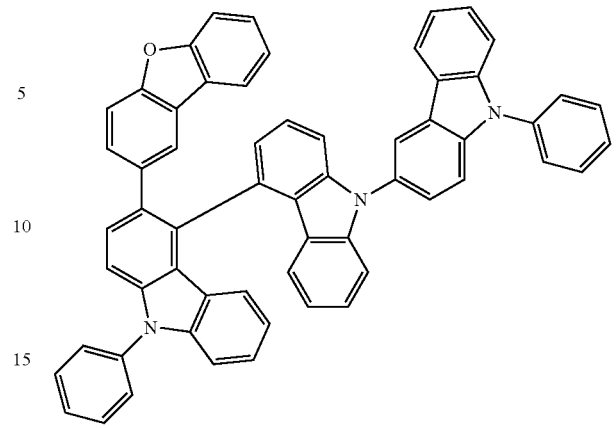
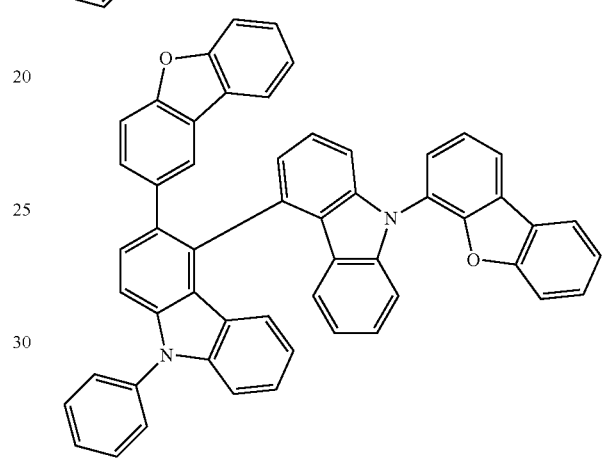
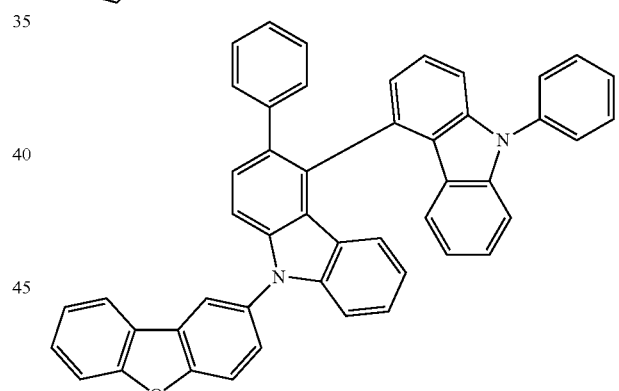
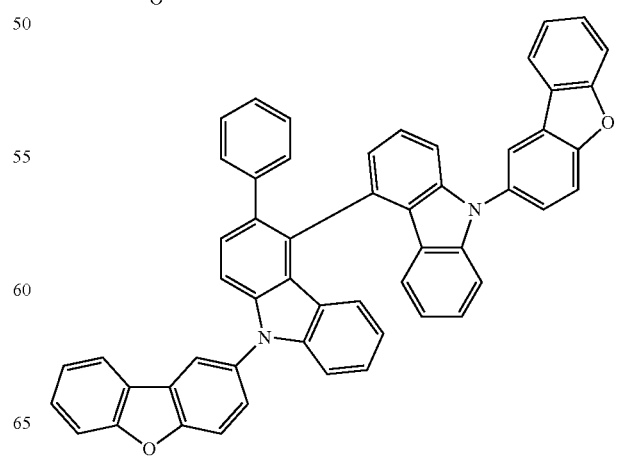

123
-continued
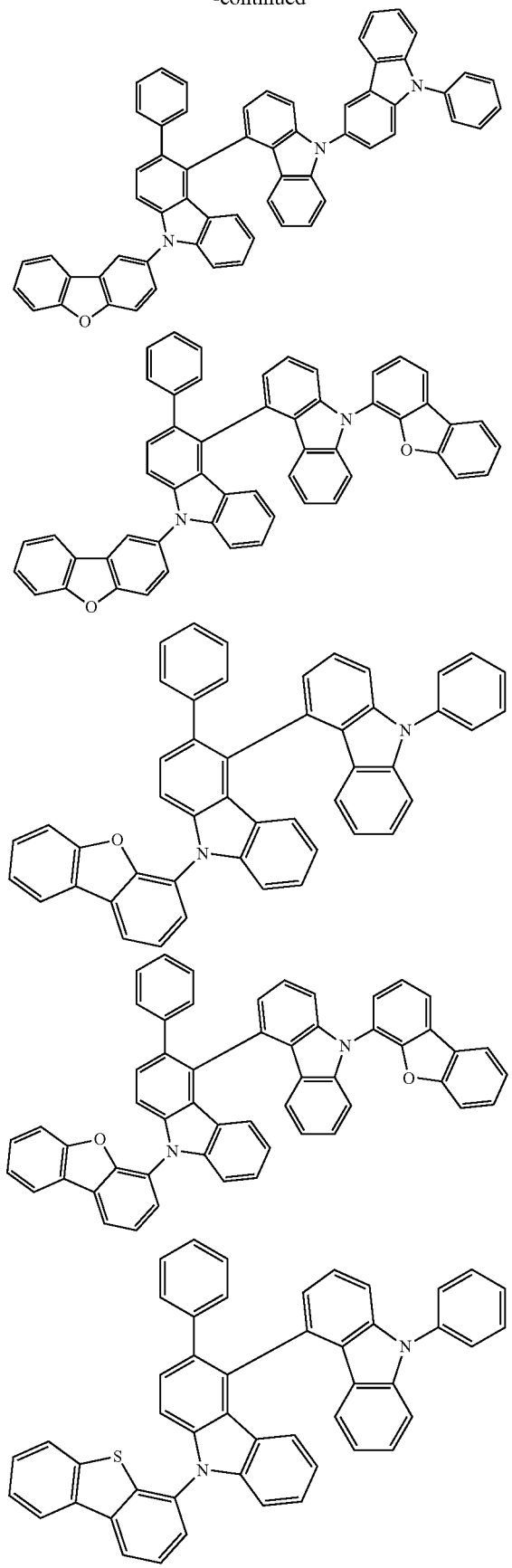
124
-continued
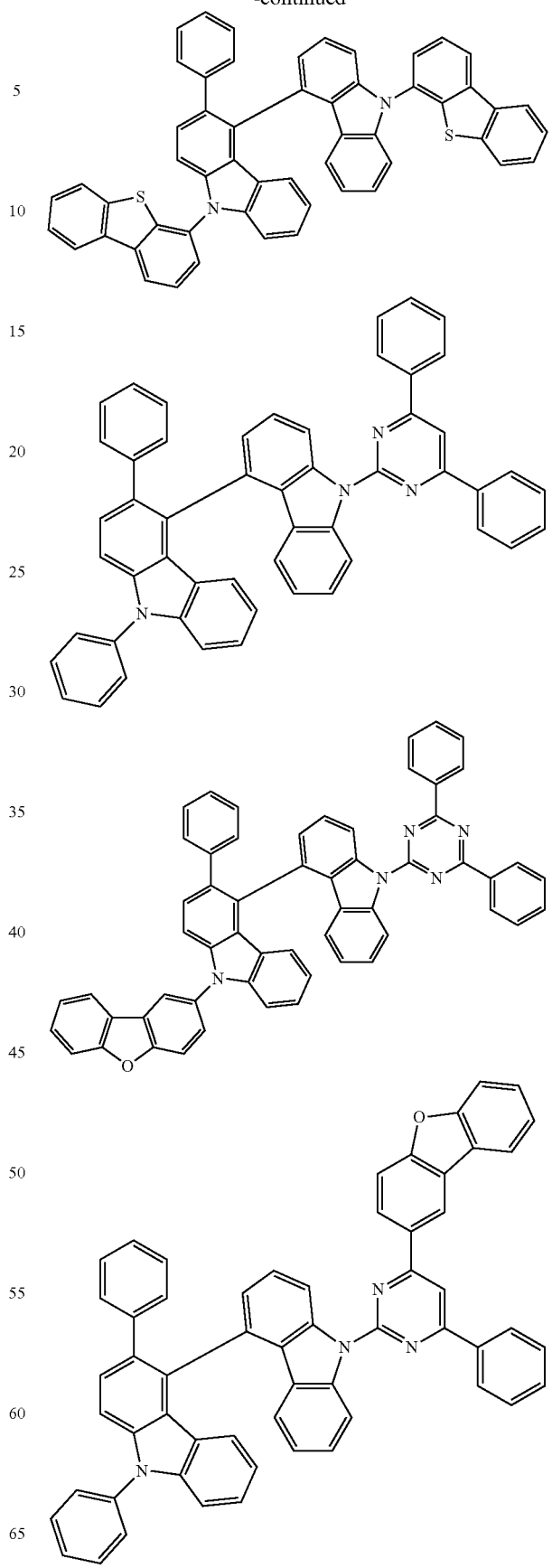

125
-continued
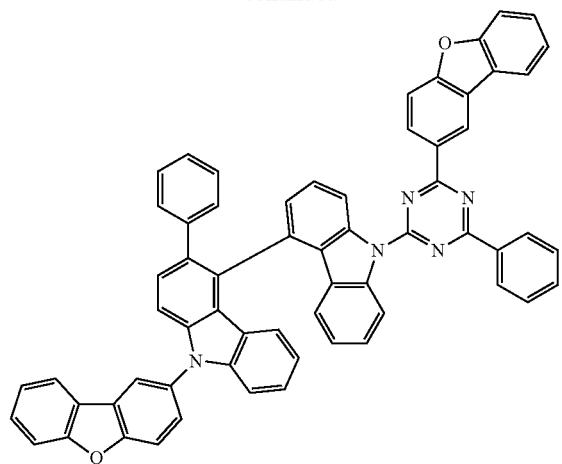
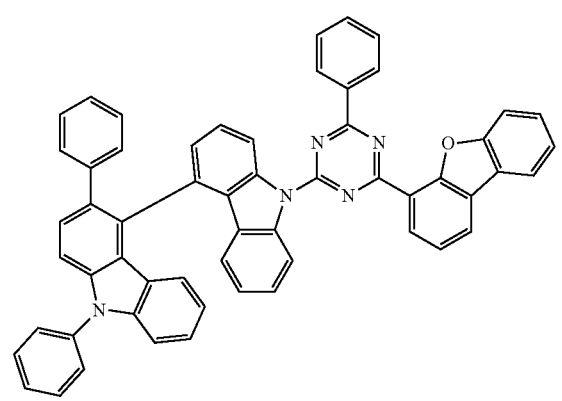
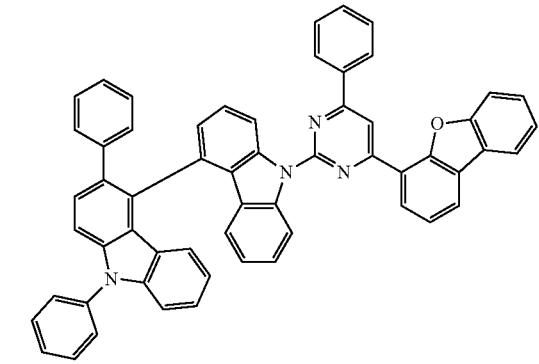
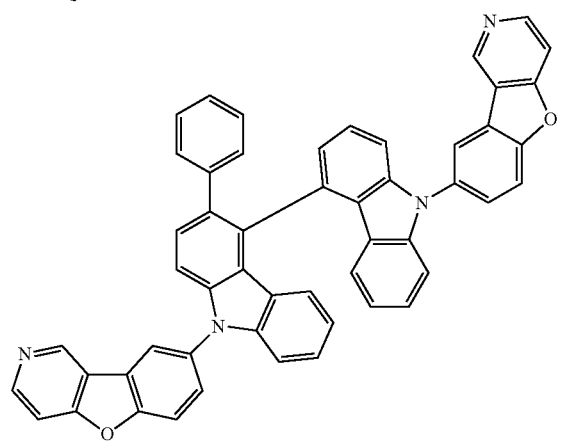
126
-continued
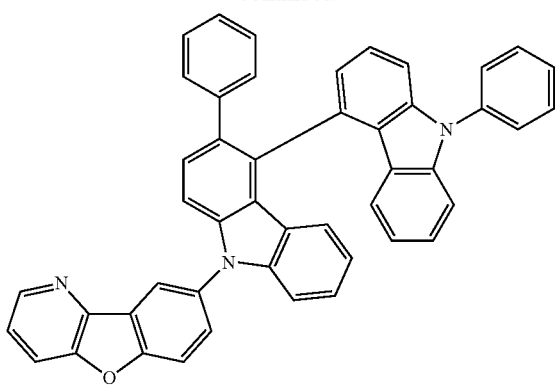
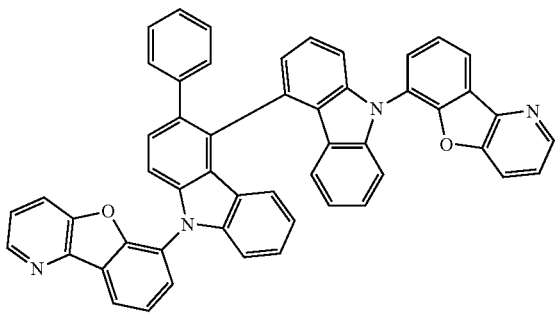
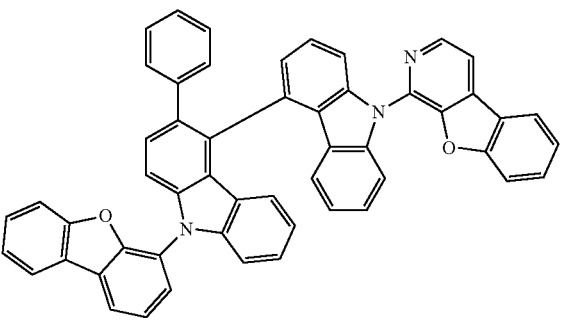
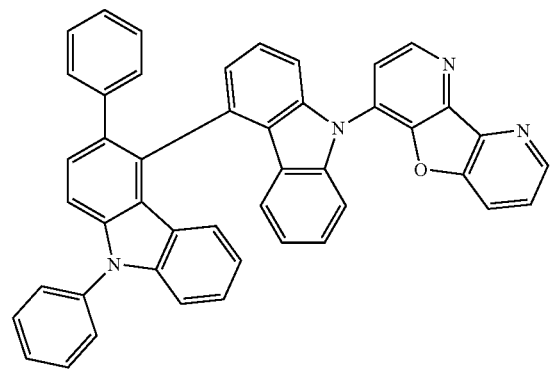

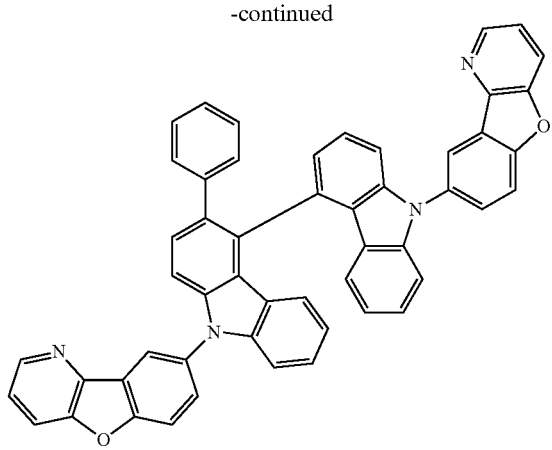

The compound of the invention can be produced according to the synthesis examples described later.

The material for an organic EL device of the invention is characterized by containing the above-mentioned compound of the invention.

The material for an organic EL device of the invention can be suitably used as a material for an organic thin film layer constituting an organic EL device.

The material for an organic EL device of the invention is particularly preferable as a material for an emitting layer, and layers adjacent to an emitting layer, e.g. a hole blocking layer or an electron blocking layer, in a phosphorescent organic EL device.

Subsequently, the organic EL device of the invention will be explained.

The organic EL device of the invention comprises one or more organic thin film layers including an emitting layer between an anode and a cathode. The material for an organic EI device of the invention is contained in at least one of the organic thin film layers. When the material for an organic EL device of the invention is contained in each of plural layers of the device, the materials for an organic EL device may be the same or different.

FIG. 1 is a schematic view showing a layer construction according to one embodiment of the organic EL device of the invention.

The organic EL device 1 has a construction in which an anode 20, a hole-transporting region 30, a phosphorescent emitting layer 40, an electron-transporting zone 50 and a cathode 60 are stacked on a substrate 10 in this order. The hole-transporting zone 30 means a hole-transporting layer, a hole-injecting layer or the like. Similarly, the electron-transporting zone 50 means an electron-transporting layer, an electron-injecting layer or the like. Although these cannot be formed, it is preferred that one or more layers be formed. In this device, each organic layer provided in the hole-transporting zone 30, a phosphorescent emitting layer 40 and each organic layer provided in the electron-transporting zone 50 correspond to the above-mentioned organic thin film layers. Of these organic thin film layers, at least one layer contains the material for an organic EL device of the invention. By this, an organic EL device which has a high luminous efficiency while retaining a good driving life can be provided.

Meanwhile, in the organic thin film layer containing the material for an organic EL device of the invention, the content of the material is preferably 1 to 100% by weight.

In the organic EL device of the invention, the material for an organic EL device of the invention is preferably contained in the phosphorescent emitting layer 40, and in particular, is preferably used as a host material in an emitting layer. Since the material of the invention has sufficiently large triplet energy, even if a blue phosphorescent dopant material is used, the triplet energy of the phosphorescent dopant material can be efficiently confined in an emitting layer. Meanwhile, the material of the invention can be used not only in a blue emitting layer but also in an emitting layer which emits light having a longer wave length (green to red or the like).

The phosphorescent emitting layer contains a phosphorescent emitting material (phosphorescent dopant). As the phosphorescent dopant, metal complex compounds can be given. Preferable is a compound having a metal atom selected from Ir, Pt, Os, Au, Cu, Re and Ru and a ligand. The ligand preferably has an ortho-metal bond.

In respect of a high phosphorescent quantum yield and capability of improving external quantum yield of an emitting device, the phosphorescent dopant is preferably a compound having a metal atom selected from Ir, Os and Pt. Further preferable are a metal complex such as an iridium complex, an osmium complex and a platinum complex. Among them, an iridium complex and a platinum complex are more preferable, and an ortho-metalated iridium complex is most preferable. The dopant may be used singly or in combination of two or more.

The additive concentration of a phosphorescent dopant in a phosphorescent emitting layer is, but not particularly limited to, preferably 0.1 to 30% by weight, with 0.1 to 20% by weight being more preferable.

Moreover, it is preferred that the material of the invention be used in layers adjacent to the phosphorescent emitting layer 40. For example, in the device shown in FIG. 1, when layers containing the material of the invention (adjacent layers nearer to the anode) are formed between the hole-transporting region 30 and the phosphorescent emitting layer 40, the layers function as an electron-blocking layer or an exciton-barrier layer.

On the other hand, when layers containing the material of the invention (adjacent layers nearer to the cathode) are formed between the phosphorescent emitting layer 40 and the electron-transporting region 50, the layers function as a hole-blocking layer or an exciton-barrier layer.

Meanwhile, the blocking (barrier) layer is the layer which blocks transporting of carriers or diffusion of excitons. The organic layer which prevents electrons from leaking from an emitting layer into a hole-transporting region is mainly defined as the electron-blocking layer. The organic layer which prevents holes from leaking from an emitting layer into an electron-transporting region is often defined as the hole-blocking layer. In addition, the organic layer which prevents triplet excitons generated in an emitting layer from diffusing to the peripheral layers having lower triplet energy than that of the emitting layer is often defined as the exciton-barrier layer (triplet-blocking layer).

Moreover, it is also possible to use the material of the invention in the layers adjacent to the phosphorescent emitting layer 40, and further in other organic thin film layers which bond to the adjacent layers.

Moreover, when two or more emitting layers are formed, the material of the invention can be suitably used in spacing layers formed between the emitting layers.

Figure 2:
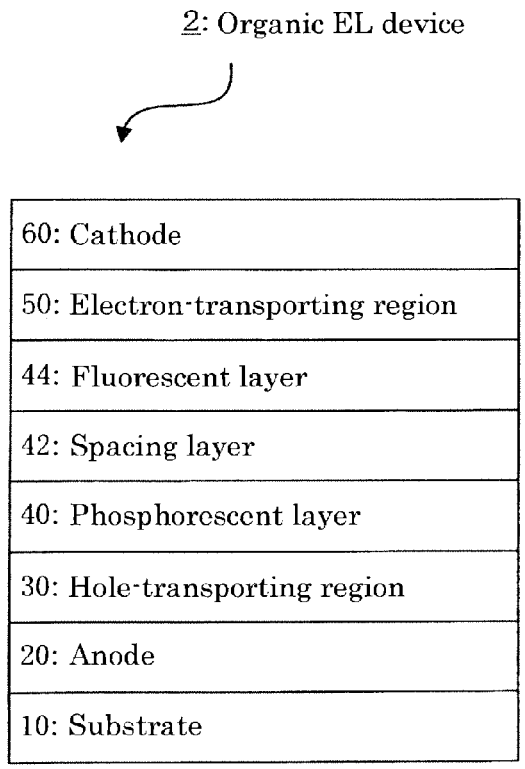
FIG. 2 is a schematic view showing the layer construction according to another embodiment of the organic EL device of the invention.

FIG. 2 is a schematic view showing the layer construction according to another embodiment of the organic EL device of the invention.

The organic EL device 2 is an example of a hybrid-type organic EL device, in which a phosphorescent emitting layer and a fluorescent emitting layer are stacked.

The organic EL device 2 has the same construction as the organic EL device 1 mentioned above, except that a spacing layer 42 and a fluorescent emitting layer 44 are formed between a phosphorescent emitting layer 40 and an electron-transporting region 50. In the construction in which the phosphorescent emitting layer 40 and the fluorescent emitting layer 44 are stacked, for preventing excitons generated in the phosphorescent emitting layer 40 from diffusing into the fluorescent emitting layer 44, the spacing layer 42 may be provided between the fluorescent emitting layer 44 and the phosphorescent emitting layer 40. Since the material of the invention has a large triplet energy, it can function as a spacing layer.

In the organic EL device 2, for example, by allowing the phosphorescent emitting layer to emit yellow light and by allowing the fluorescent emitting layer to emit blue light, an organic EL device which emits white light can be obtained. Meanwhile, in this embodiment, the phosphorescent emitting layer and the fluorescent emitting layer are each formed as a single layer. However, the configuration is not limited thereto, and they may be each formed as two or more layers. Their manner of formation can be selected appropriately depending on the intended use such as lightning or a display device. For example, when a full-color emitting device is realized by utilizing white emitting devices and color filters, the phosphorescent emitting layer and the fluorescent emitting layer preferably include emissions in the plural wave length regions such as red, green and blue (RGB), or red, green, blue and yellow (RGBY) in respect of color rendering properties.

In addition to the above-mentioned embodiments, the organic EL device of the invention can employ various known structures. Further, the emission from an emitting layer can be outcoupled from the anode side, the cathode side or the both sides.

(Electron-Donating Dopant and Organic Metal Complex)

The organic EL device of the invention preferably comprises at least one of an electron-donating dopant and an organic metal complex in the interface region between a cathode and an organic thin film layer.

By this structure, the organic EL device can have an improved luminance and a prolonged life.

As the electron-donating dopant, at least one selected from an alkali metal, an alkali metal compound, an alkaline-earth metal, an alkaline-earth metal compound, a rare-earth metal and a rare-earth metal compound can be given.

As the organic metal complex, at least one selected from an organic metal complex including an alkali metal, an organic metal complex including an alkaline-earth metal and an organic metal complex including a rare-earth metal can be given.

As the alkali metal, lithium (Li) (work function: 2.93 eV), sodium (Na) (work function: 2.36 eV), potassium (K) (work function: 2.28 eV), rubidium (Rb) (work function: 2.16 eV), cesium (Cs) (work function: 1.95 eV) and the like can be given. One having a work function of 2.9 eV or less is particularly preferable. Of these, K, Rb and Cs are preferable, Rb or Cs is further preferable, and Cs is most preferable.

As the alkaline-earth metal, calcium (Ca) (work function: 2.9 eV), strontium (Sr) (work function: 2.0 eV or more and 2.5 eV or less), barium (Ba) (work function: 2.52 eV) and the like can be given. One having a work function of 2.9 eV or less is particularly preferable.

As the rare-earth metal, scandium (Sc), yttrium (Y), cerium (Ce), terbium (Tb), ytterbium (Yb) and the like can be given. One having a work function of 2.9 eV or less is particularly preferable.

The preferable metals of the above-mentioned metals have a particularly high reducing ability, and hence can provide the resulting organic EL device with an improved luminance and a prolonged life by adding a relative small amount of the metal to an electron-injecting region.

Examples of the alkali metal compound include an alkali oxide such as lithium oxide ($Li_2O$), cesium oxide ($Cs_2O$) or potassium oxide ($K_2O$), and an alkali halide such as lithium fluoride (LiF), sodium fluoride (NaF), cesium fluoride (CsF) or potassium fluoride (KF). Of these, lithium fluoride (LiF), lithium oxide ($Li_2O$) and sodium fluoride (NaF) are preferable.

Examples of the alkaline-earth metal compound include barium oxide (BaO), strontium oxide (SrO), calcium oxide (CaO), and mixtures thereof such as barium strontium acid ($Ba_xSr_{1-x}O$) (0<x<1) and barium calcium acid ($Ba_xCa_{1-x}O$) (0<x<1). Of these, BaO, SrO and CaO are preferred.

Examples of the rare-earth metal compound include ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$) and terbium fluoride ($TbF_3$). Of these, $YbF_3$, $ScF_3$ and $TbF_3$ are preferable.

The organic metal complexes are not particularly limited as long as the complexes each contain, as a metal ion, at least one of alkali metal ions, alkaline-earth metal ions, and rare-earth metal ions, as mentioned above. Meanwhile, preferred examples of the ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluborane, bipyridyl, phenanthroline, phthalocyanine, porphyrin, cyclopentadiene, β-diketones, azomethines, and derivatives thereof.

For the addition form of the electron-donating dopant and the organic metal complex, it is preferred that the electron-donating dopant and the organic metal complex be formed in a shape of a layer or an island in the interfacial region. A preferred method for the formation is a method in which an organic substance as a light emitting material or an electron-injecting material for forming the interfacial region is deposited at the same time as at least one of the electron-donating dopant and the organic metal complex is deposited by a resistant heating deposition method, thereby dispersing at least one of the electron-donating dopant and the organic metal complex reducing dopant in the organic substance. The disperse concentration by molar ratio of the organic substance to the electron-donating dopant and/or the organic metal complex is normally 100:1 to 1:100, preferably 5:1 to 1:5.

In a case where at least one of the electron-donating dopant and the organic metal complex is formed into the shape of a layer, the light emitting material or electron injecting material which serves as an organic layer in the interface is formed into the shape of a layer. After that, at least one of the electron-donating dopant and the organic metal complex is solely deposited by the resistant heating deposition method to form a layer preferably having a thickness of 0.1 nm or more and 15 nm or less.

In a case where at least one of the electron-donating dopant and the organic metal complex is formed into the shape of an island, the light emitting material or the electron injecting material which serves as an organic layer in the interface is formed into the shape of an island. After that, at least one of the electron-donating dopant and the organic metal complex is solely deposited by the resistant heating deposition method to form an island preferably having a thickness of 0.05 nm or more and 1 nm or less.

In addition, the ratio of the main component (the emitting material or the electron-injecting material) to at least one of the electron-donating dopant and the organic metal complex in the organic EL device of the invention is preferably 5:1 to 1:5, more preferably 2:1 to 1:2 in terms of a molar ratio.

In the organic EL device of the invention, the composition of layers other than those using the above-mentioned material of an organic EL device of the invention is not particularly limited. As the composition of the layers, known materials and the like can be used. Hereinafter, the layers of the device according to the embodiment 1 will be briefly explained. However, the materials applied to the organic EL device of the invention are not limited to the following.
(Substrate)

As the substrate, a glass plate, a polymer plate or the like can be used.

As the glass plate, particularly, soda-lime glass, barium/strontium-containing glass, lead glass, aluminosilicate glass, borosilicate glass, barium borosilicate glass, quartz or the like can be given. As the polymer plate, polycarbonate, acrylic resin, polyethylene terephthalate, polyethersulfone, polysulfone or the like can be given.
(Anode)

The anode is formed of a conductive material, for example. A conductive material having a work function larger than 4 eV is suitable.

Examples of the above-mentioned conductive material include carbon, aluminum, vanadium, iron, cobalt, nickel, tungsten, silver, gold, platinum, palladium or the like and an alloy thereof, a tin oxide used in ITO substrate or NESA substrate, a metal oxide such as indium oxide, and an organic conductive resin such as polythiophene and polypyrrole.

The anode can be formed in the form of two or more layers if needed.

(Cathode)

The cathode is formed of a conductive material, for example. A conductive material having a work function smaller than 4 eV is suitable.

Examples of the above-mentioned conductive material include magnesium, calcium, tin, lead, titanium, yttrium, lithium, ruthenium, manganese, aluminum, lithium fluoride or the like, and alloys thereof, but not limited thereto.

Further, representative examples of the above-mentioned alloys include magnesium/silver, magnesium/indium, lithium/aluminum or the like, but not limited thereto. The ratio of the alloy can be selected appropriately by controlling the temperature of a deposition source, the atmosphere, the vacuum level or the like.

The cathode may be formed in the form of two or more layers if needed. The cathode can be prepared by forming a thin film of the above-mentioned conductive material by deposition, sputtering or the like.

When emission from an emitting layer is outcoupled through a cathode, it is preferred that the transmittance for emission of the cathode be larger than 10%.

In addition, the sheet resistance as a cathode is preferably several hundred $\Omega/\square$ or less. The thickness is normally 10 nm to 1 µm, with 50 to 200 nm being preferable.
(Emitting Layer)

When a phosphorescent emitting layer is formed by using materials other than the material for an organic EL device of the invention, materials which are known as a material for a phosphorescent emitting layer can be used. Specifically, reference can be made to the Japanese patent application 2005-517938 or the like.

The organic EL device of the invention may comprise a fluorescent emitting layer as the device shown in FIG. 2. As the fluorescent emitting layer, known materials can be used.

The emitting layer can be a double-host (often referred to as host/co-host) type. Specifically, in the emitting layer, an electron-transporting host and a hole-transporting host may be combined to control the carrier balance.

The emitting layer also can be of a double-dopant type. By incorporating two or more kinds of dopant materials having a high quantum yield to the emitting layer, each dopant emits. For example, there may be a case that a yellow emitting layer is realized by co-depositing a host, and a red dopant and a green dopant.

The emitting layer may be a single layer, or have a stacked structure. When the emitting layer has a stacked structure, due to the accumulation of electrons and holes in the interface of the emitting layers, the recombination region can be concentrated in the interface of the emitting layers interface, thereby increasing the quantum efficiency.
(Hole-Injecting Layer and Hole-Transporting Layer)

The hole-injecting/transporting layer helps holes to be injected to an emitting layer and transports the injected holes to an emitting region. It has a large hole mobility and normally a small ionization energy of 5.6 eV or less.

As the material for a hole-injecting/transporting layer, materials which can transport holes to an emitting layer at lower electric field intensity are preferable. In addition, it is preferred that the hole mobility be at least $10^{-4}$ cm$^2$/V·second when an electric field intensity of $10^4$ to $10^6$ V/cm is applied, for example.

Specific examples of materials for a hole-injecting layer and a hole-transporting layer include triazole derivatives (see U.S. Pat. No. 3,112,197 and others), oxadiazole derivatives (see U.S. Pat. No. 3,189,447 and others), imidazole derivatives (see JP-B-37-16096 and others), polyarylalkane derivatives (see U.S. Pat. Nos. 3,615,402, 3,820,989 and 3,542,544, JP-B-45-555 and 51-10983, JP-A-51-93224, 55-17105, 56-4148, 55-108667, 55-156953 and 56-36656, and others), pyrazoline derivatives and pyrazolone derivatives (see U.S. Pat. Nos. 3,180,729 and 4,278,746, JP-A-55-88064, 55-88065, 49-105537, 55-51086, 56-80051, 56-88141, 57-45545, 54-112637 and 55-74546, and others), phenylene diamine derivatives (see U.S. Pat. No. 3,615,404, JP-B-51-10105, 46-3712, 47-25336 and 54-119925, and others), arylamine derivatives (see U.S. Pat. Nos. 3,567,450, 3,240,597, 3,658,520, 4,232,103, 4,175,961 and 4,012,376, JP-B-49-35702 and 39-27577, JP-A-55-144250, 56-119132 and 56-22437, DE1,110,518, and others), amino-substituted chalcone derivatives (see U.S. Pat. No. 3,526,501, and others), oxazole derivatives (ones disclosed in U.S. Pat. No. 3,257,203, and others), styrylanthracene derivatives (see JP-A-56-46234, and others), fluorenone derivatives (JP-A-54-110837, and others), hydrazone derivatives (see U.S. Pat. No. 3,717,462, JP-A-54-59143, 55-52063, 55-52064, 55-46760, 57-11350, 57-148749 and 2-311591, and others), stilbene derivatives (see JP-A-61-210363, 61-228451, 61-14642, 61-72255, 62-47646, 62-36674, 62-10652, 62-30255, 60-93455, 60-94462, 60-174749 and 60-175052, and others), silazane derivatives (U.S. Pat. No. 4,950,950), polysilanes (JP-A-2-204996), and aniline copolymers (JP-A-2-282263).

Further, an inorganic compound such as P-type Si and P-type SiC can be used as the hole-injecting material.

As the material for a hole-injecting/transporting layer, a cross-linking material can be used. As the cross-linking hole-injecting/transporting layer, a layer formed of the cross-linking agent disclosed in Chem. Mater. 2008, 20, 413-422, Chem. Mater. 2011, 23(3), 658-681, WO2008108430, WO2009102027, WO2009123269, WO2010016555, WO2010018813 or the like insolubilized by heat, light or the like can be given, for example.

(Electron-Injecting Layer and Electron-Transporting Layer)

The electron-injecting/transporting layer helps electrons to be injected to an emitting layer and transports the injected electrons to an emitting region. It has a large electron mobility.

In the organic EL device, it is known that since emitting light is reflected by an electrode (a cathode, for example), emission outcoupled directly from an anode interfered with emission after being reflected by the electrode. In order to utilize the interference effect efficiently, the film thickness of the electron injecting/transporting layer is appropriately selected to be several nm to several μm. When the film thickness is particularly large, it is preferred that the electron mobility be at least $10^{-5}$ cm$^2$/Vs or more at an applied electric field intensity of $10^4$ to $10^6$ V/cm in order to avoid an increase in voltage.

As the electron-transporting material used in the electron-injecting/transporting layer, an aromatic hetero ring compound containing one or more hetero atoms in the molecule is preferably used, with a nitrogen-containing ring derivative being particularly preferable. Further, as the nitrogen-containing ring derivative, an aromatic ring having a nitrogen-containing six-membered ring or five-membered ring skeleton, or a fused aromatic ring compound having a nitrogen-containing six-membered ring or five-membered ring skeleton is preferable. Examples thereof include compounds containing a pyridine ring, a pyrimidine ring, a triazine ring, a benzimidazole ring, a phenanthroline ring, a quinazoline ring or the like in the skeleton.

In addition, an organic layer with a semiconductor property may be formed by doping a donor material (n) or doping an acceptor material (P). Representative examples of N-doping include one obtained by doping an electron-transporting material with a metal such as Li or Cs. Representative examples of P-doping include one obtained by doping a hole-transporting material with an acceptor material such as F4TCNQ (see Japan Patent No. 3695714, for example).

Each layer of the organic EL device of the invention can be formed by using known methods including the dry-type film formation such as vacuum deposition, sputtering, plasma ion-plating or the like and the wet-type film formation such as spin coating, dipping, flow coating or the like.

The film thickness of each layer is not particularly limited, but should be set to be a proper thickness. If the film thickness is too large, a large applied voltage is required in order to obtain the predetermined light output, thereby leading to low efficiency. If the film thickness is too small, due to generation of pinholes or the like, sufficient luminance cannot be obtained when an electric field is applied. Normally, the film thickness is preferably 5 nm to 10 μm, and the range of 10 nm to 0.2 μm is further preferable.

EXAMPLES

The invention will be explained in more detail with reference to Synthesized Examples, Examples and the like below. However the invention is not limited to these Synthesized Examples and Examples and the like.

m

Synthesis Example 1 (Synthesis of Intermediate 3)

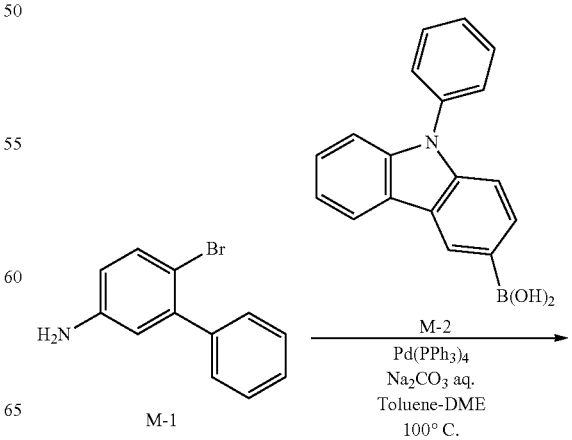

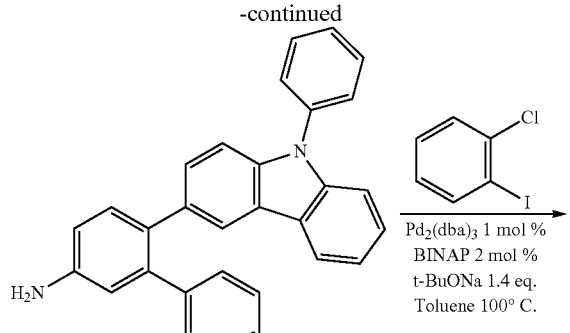

Intermediate 1

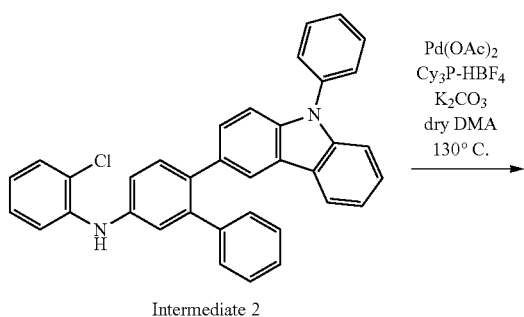

Intermediate 2

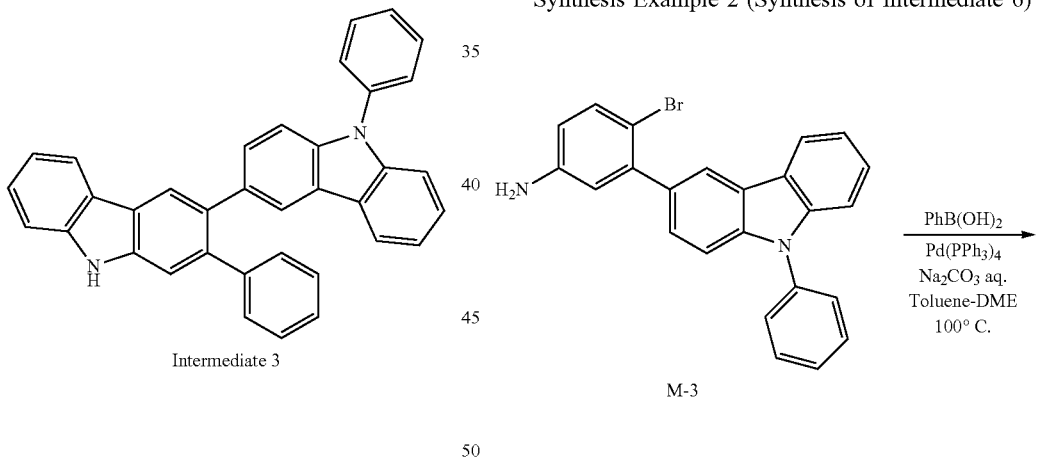

Intermediate 3

Under an argon atmosphere, 2.3 g (8.06 mmol) of M-2, 279 mg (0.242 mmol) of tetrakis(triphenylphosphine)palladium(0) and 2.0 g (8.06 mmol) of M-1 dissolved in 12 mL of dried toluene were placed in a three-necked flask. Further, 12 mL of dried dimethoxyethane and 12 mL of a 2M aqueous solution of sodium carbonate were added. The resulting mixture was heated under reflux while stirring for 15 hours. The reaction mixture was cooled to room temperature. After addition of water, the mixture was stirred for an hour at room temperature, followed by extraction with toluene. After separating, an organic layer was washed with saturated saline, and dried with anhydrous sodium sulfate. Under reduced pressure, the solvent is distilled away, and a residue was purified by silica-gel column chromatography to obtain 3.1 g of intermediate 1 (yield: 92%).

Under an argon atmosphere, 3.12 g (7.6 mmol) of the intermediate 1, 70 mg (0.076 mmol) of tris(dibenzylideneacetone)dipalladium(0), 95 mg (0.152 mmol) of 2,2'-bis(diphenylphosphino)-1,1'-binaphthyl (BINAP), 1.02 g (10.6 mmol) of sodium t-butoxide and 38 mL of dried toluene were placed in a three-necked flask. Further, 2.7 g (11.4 mmol) of 1,2-chloroiodobenzene was added, and the resulting mixture was stirred for 8 hours while heating under reflux. The reaction mixture was cooled to room temperature, and purified by silica-gel column chromatography to obtain 2.34 g of intermediate 2 (yield: 57%).

Under an argon atmosphere, 2.34 g (4.49 mmol) of the intermediate 2, 11 mL of dried dimethylacetamide, 20 mg (0.090 mmol) of palladium acetate, 66 mg (0.180 mmol) of tricyclohexylphosphine tetrafluoroborate and 1.24 g (8.98 mmol) of potassium carbonate were placed in a three-necked flask. The mixture was stirred for 15 hours while heating to 130° C. The reaction mixture was cooled to room temperature. Water was added to the mixture, followed extraction with dichloromethane at room temperature. After filtration of insoluble matters, an organic layer obtained by separating was washed with saturated saline and dried with anhydrous sodium sulfate. Under reduced pressure, the solvent was distilled away, and a residue was purified by silica gel column chromatography to obtain 1.2 g of intermediate 3 (yield: 55%).

The solids obtained were measured for the molecular weight by FD mass spectrum. As a result, the molecular weight was found to be 484.

Synthesis Example 2 (Synthesis of Intermediate 6)

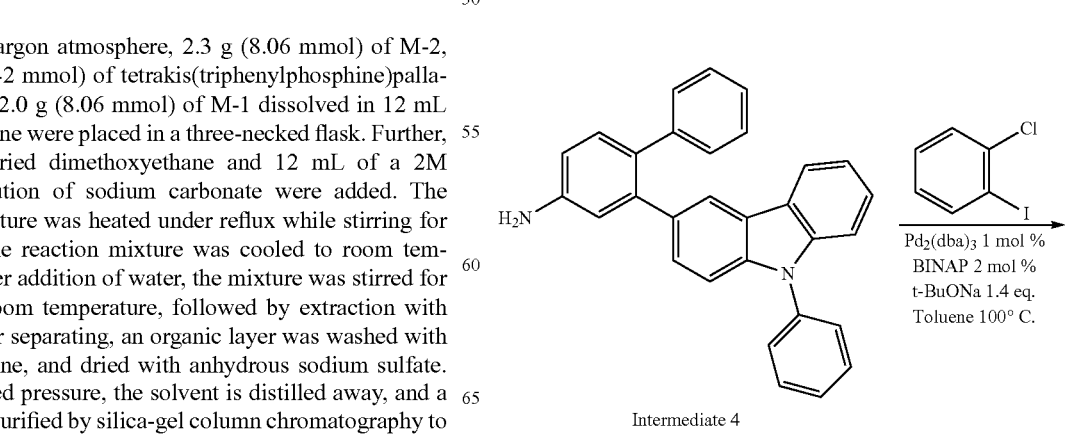

Intermediate 4

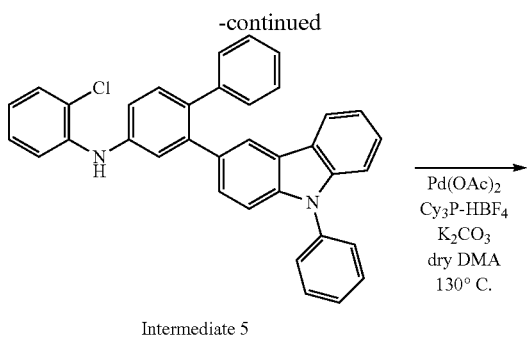

Intermediate 5

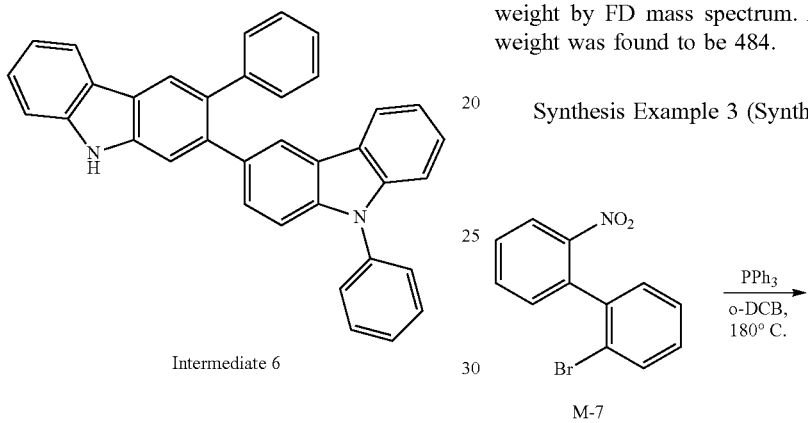

Intermediate 6

Under an argon atmosphere, 22.9 g (55.5 mmol) of M-3, 1.92 mg (1.67 mmol) of tetrakis(triphenylphosphine)palladium(0), 25.1 g (61.1 mmol) of phenylboronic acid, 83 mL of dried toluene, 83 mL of dried dimethoxyethane and 83 mL of a 2M aqueous solution of sodium carbonate were placed in a three-necked flask. The mixture was heated under reflux while stirring for 8 hours. The reaction mixture was cooled to room temperature. After addition of water, the mixture was stirred for an hour at room temperature, followed by extraction with toluene. After separating, an organic layer was washed with saturated saline, and dried with anhydrous sodium sulfate. Under reduced pressure, a solvent was distilled away, and a residue was purified by silica-gel column chromatography to obtain 19.5 g of intermediate 4 (yield: 86%).

Under an argon atmosphere, 19.5 g (47.6 mmol) of the intermediate 4, 436 mg (0.476 mmol) of tris(dibenzylideneacetone)dipalladium(0), 592 mg (0.951 mmol) of BINAP, 6.4 g (66.6 mmol) of sodium t-butoxide and 238 mL of dried toluene were placed in a three-necked flask. Further, 17.0 g (71.4 mmol) of 1,2-iodochlorobenzene was added. The resulting mixture was stirred for 7 hours while heating under reflux. The reaction mixture was cooled to room temperature. After addition of water, the mixture was stirred for an hour at room temperature, followed by extraction with toluene. After separating, an organic phase was washed with saturated saline, and dried with anhydrous sodium sulfate. Under reduced pressure, the solvent was distilled away, and a residue was purified by silica-gel column chromatography to obtain 12.9 g of intermediate 5 (yield: 52%).

Under an argon atmosphere, 12.0 g (23 mmol) of the intermediate 5, 55 mL of dried dimethylacetamide, 103 mg (0.46 mmol) of palladium acetate, 339 mg (0.92 mmol) of triscyclohexylphosphine tetrafluoroborate salt and 6.36 g (46 mmol) of potassium carbonate were placed in a three-necked flask. The mixture was stirred for 15 hours while heating to 130° C. The reaction mixture was cooled to room temperature, and water was added to the mixture, followed extraction with dichloromethane at room temperature. After filtration of insoluble matters, an organic layer obtained by separating was washed with saturated saline and dried with anhydrous sodium sulfate. Under reduced pressure, a solvent was distilled away, and a residue was purified by silica gel column chromatography to obtain 6.2 g of intermediate 6 (yield: 56%).

The solids obtained were measured for the molecular weight by FD mass spectrum. As a result, the molecular weight was found to be 484.

Synthesis Example 3 (Synthesis of Intermediate 7)

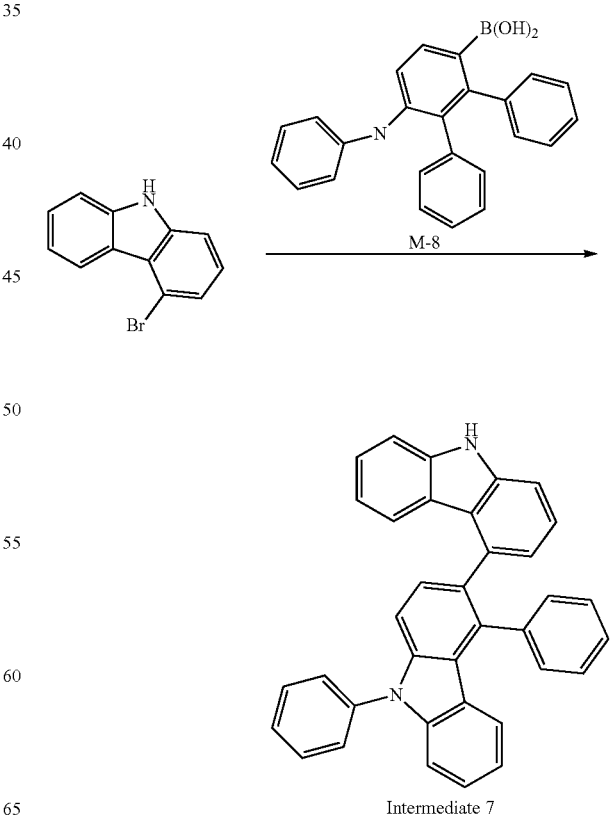

Intermediate 7

Under an argon atmosphere, 38.6 g (147 mmol) of triphenylphosphine, 16.3 g (58.8 mmol) of M-7, and 65 mL of dichlorobenzene were placed in a three-necked flask. The mixture was heated under reflux while stirring for 18 hours. The reaction mixture was cooled to room temperature and purified by silica-gel column chromatography to obtain 9.4 g of 4-bromocarbazole (yield: 65%).

Under an argon atmosphere, 4.0 g (16.3 mmol) of 4-bromocarbazole, 5.9 g (16.3 mmol) of M-8, 36 mg (0.16 mmol) of palladium acetate, 112 mg (0.32 mmol) of 2-(dicyclohexylphosphino)biphenyl, 6.8 g (32 mmol) of tripotassium phosphate and 70 mL of toluene were placed in a three-necked flask. The mixture was stirred while heating under reflux for 20 hours. The reaction mixture was cooled to room temperature, and a saturated aqueous solution of sodium hydrogen carbonate was added to the mixture, followed extraction with dichloromethane at room temperature. An organic layer obtained by separating was dried with anhydrous sodium sulfate. Under reduced pressure, the solvent was distilled away, and a residue was purified by silica gel column chromatography to obtain 4.2 g of intermediate 7 (yield: 53%).

The solids obtained were measured for the molecular weight by FD mass spectrum. As a result, the molecular weight was found to be 484.

Synthesis Example 4 (Synthesis of Intermediate 9)

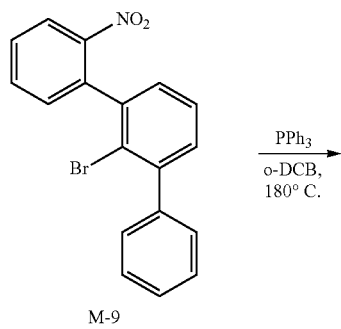

M-9

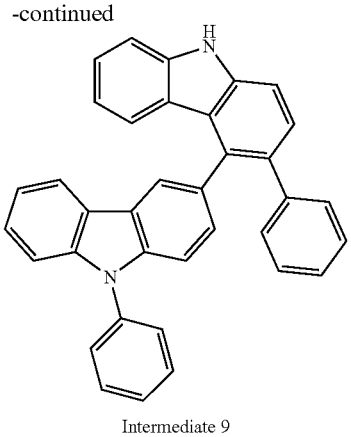

Intermediate 9

Under an argon atmosphere, 51 g (194 mmol) of triphenylphosphine, 27.5 g (77.7 mmol) of M-9 and 80 mL of o-dichlorobenzene were placed in a three-necked flask. The mixture was heated under reflux while stirring for 18 hours. The reaction mixture was cooled to room temperature, and purified by silica-gel column chromatography to obtain 12.3 g of intermediate 8 (yield: 49%).

Under an argon atmosphere, 5.5 g (17 mmol) of intermediate 8, 4.9 g (17 mmol) of M-2, 39 mg (0.17 mmol) of palladium acetate, 120 mg (0.34 mmol) of 2-(dicyclohexylphosphino)biphenyl, 7.3 g (34 mmol) of tripotassium phosphate and 75 mL of toluene were placed in a three-necked flask. The mixture was stirred while heating under reflux for 20 hours. The reaction mixture was cooled to room temperature, and a saturated aqueous solution of sodium hydrogen carbonate was added to the mixture, followed by extraction with dichloromethane at room temperature. An organic layer obtained by separating was dried with anhydrous sodium sulfate. Under reduced pressure, the solvent was distilled away, and a residue was purified by silica gel column chromatography to obtain 3.3 g of intermediate 9 (yield: 40%).

The solids obtained were measured for the molecular weight by FD mass spectrum. As a result, the molecular weight was found to be 484.

Synthesis Example 5 (Synthesis of Intermediate 10)

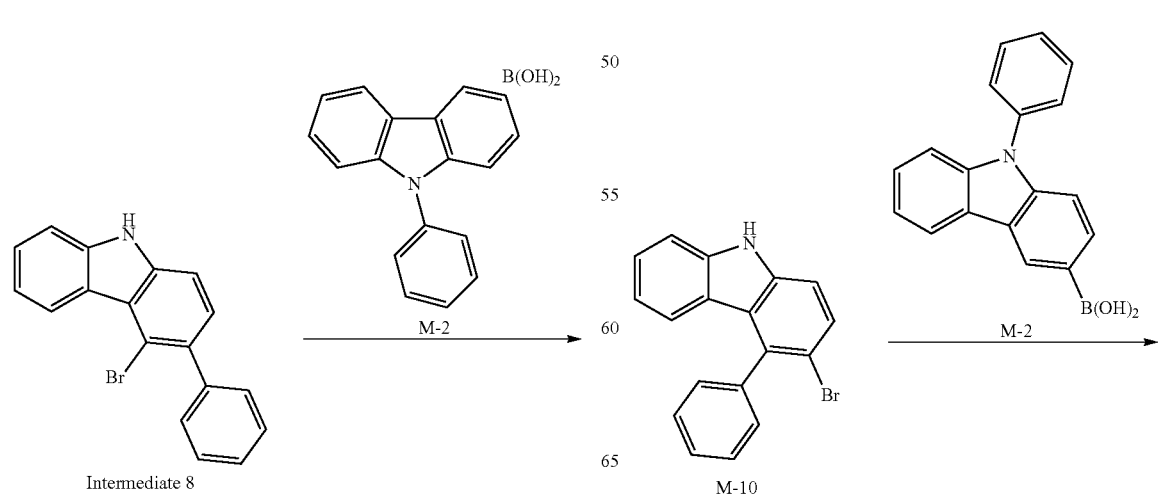

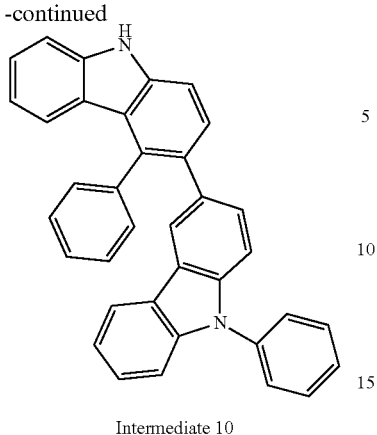

Intermediate 10

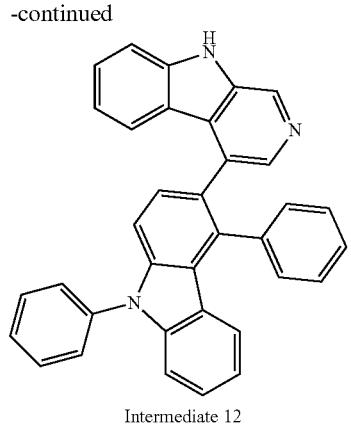

Intermediate 12

Under an argon atmosphere, 5.5 g (17 mmol) of intermediate M-10, 4.9 g (17 mmol) of M-2, 39 mg (0.17 mmol) of palladium acetate, 120 mg (0.34 mmol) of 2-(dicyclohexylphosphino)biphenyl, 7.3 g (34 mmol) of tripotassium phosphate and 75 mL of toluene were placed in a three-necked flask. The mixture was stirred while heating under reflux for 20 hours. The reaction mixture was cooled to room temperature, and a saturated aqueous solution of sodium hydrogen carbonate was added to the mixture, followed by extraction with dichloromethane at room temperature. An organic layer obtained by separating was dried with anhydrous sodium sulfate. Under reduced pressure, the solvent was distilled away, and a residue was purified by silica gel column chromatography to obtain 5.0 g of intermediate 10 (yield: 61%).

The solids obtained were measured for the molecular weight by FD mass spectrum. As a result, the molecular weight was found to be 484.

Synthesis Example 6 (Synthesis of Intermediate 12)

Under an argon atmosphere, 24 g (91.5 mmol) of triphenylphosphine, 10.2 g (36.6 mmol) of M-11 and 45 mL of o-dichlorobenzene were placed in a three-necked flask. The mixture was heated under reflux while stirring for 17 hours. The reaction mixture was cooled to room temperature, and purified by silica-gel column chromatography to obtain 6.1 g of intermediate 11 (yield: 67%).

Under an argon atmosphere, 6.1 g (24.7 mmol) of the intermediate 11, 9.0 g (24.7 mmol) of M-8, 56 mg (0.25 mmol) of palladium acetate, 172 mg (0.5 mmol) of 2-(dicyclohexylphosphino)biphenyl, 10.7 g (50 mmol) of tripotassium phosphate and 85 mL of toluene were placed in a three-necked flask. The mixture was stirred while heating under reflux for 20 hours. The reaction mixture was cooled to room temperature, and a saturated aqueous solution of sodium hydrogen carbonate was added to the mixture, followed by extraction with dichloromethane at room temperature. An organic layer obtained by separating was dried with anhydrous sodium sulfate. Under reduced pressure, the solvent was distilled away, and a residue was purified by silica gel column chromatography to obtain 7.0 g of intermediate 12 (yield: 58%).

The solids obtained were measured for the molecular weight by FD mass spectrum. As a result, the molecular weight was found to be 485.

Synthesis Example 7 (Synthesis of Compound A)

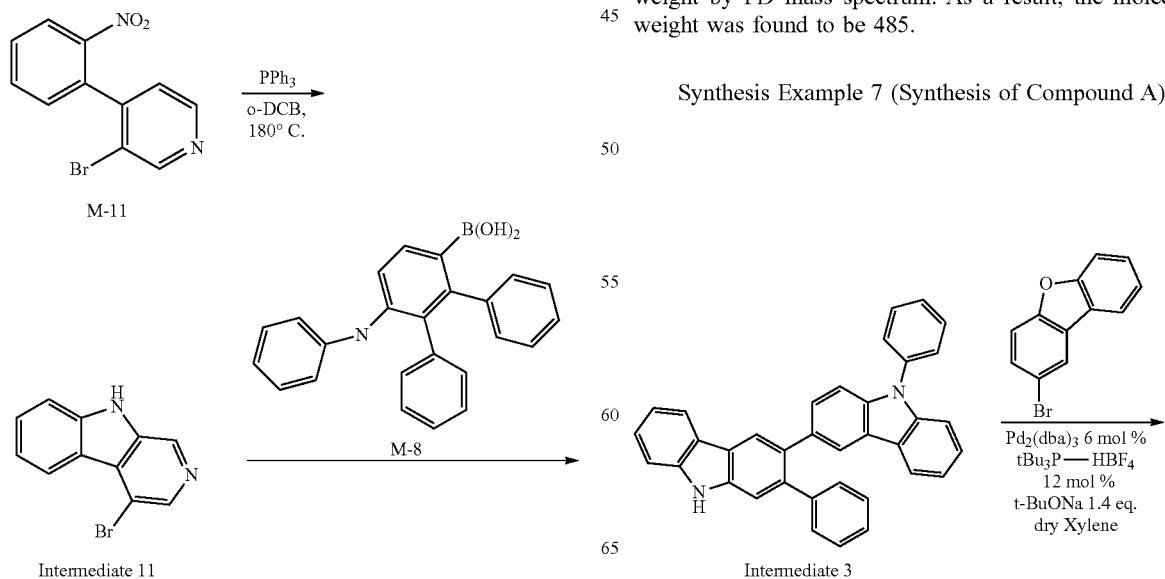

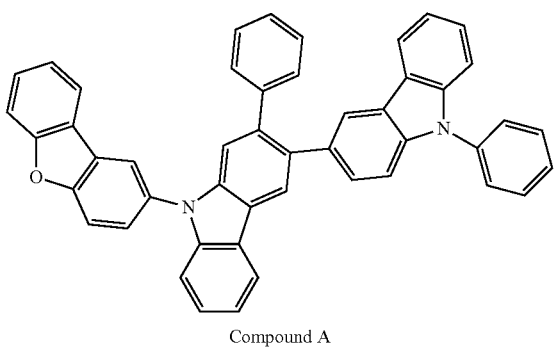

Compound A

Under an argon atmosphere, 3.0 g (6.2 mmol) of intermediate 3, 1.53 g (6.2 mmol) of 2-bromodibenzofuran, 341 mg (0.372 mmol) of tris(dibenzylideneacetone)dipalladium (0), 218 mg (0.75 mmol) of tri-t-butylphosphine tetrafluoroborate 834 mg (8.68 mmol) of sodium t-butoxide and 50 mL of dried xylene were placed in a three-necked flask. The mixture was heated under reflux while stirring for 20 hours. The reaction mixture was cooled to room temperature. After filtration by means of Celite (registered trademark, manufactured by Celite Corporation), the solvent was distilled away under reduced pressure. A residue was purified by silica gel column chromatography and was subjected to recrystallization, whereby 1.5 g of compound A was obtained (yield: 37%).

The solids obtained were measured for the molecular weight by FD mass spectrum. As a result, the molecular weight was found to be 650.

Synthesis Example 8 (Synthesis of Compound B)

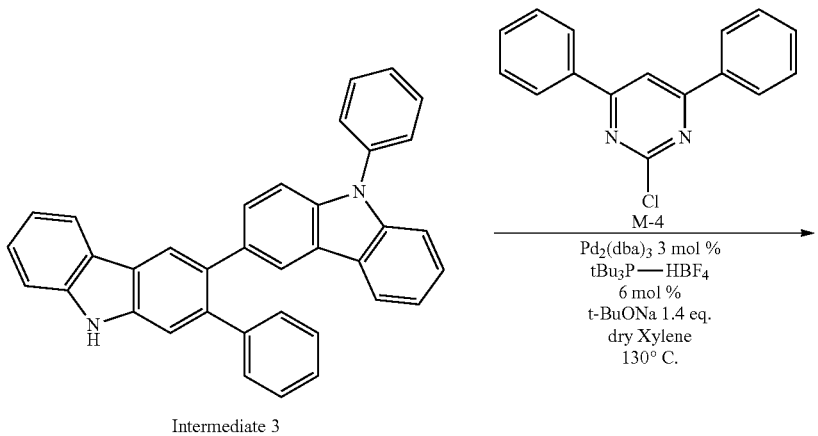

Intermediate 3

Pd$_2$(dba)$_3$ 3 mol %
tBu$_3$P—HBF$_4$ 6 mol %
t-BuONa 1.4 eq.
dry Xylene
130° C.

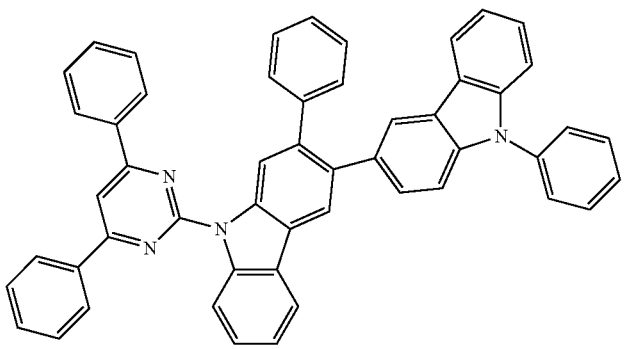

Compound B

Under an argon atmosphere, 3.0 g (6.2 mmol) of intermediate 3, 1.66 g (6.2 mmol) of M-4, 170 mg (0.186 mmol) of tris(dibenzylidene acetone)dipalladium(0), 109 mg (0.38 mmol) of tri-t-butylphosphine tetrafluoroborate and 50 mL of dried xylene were placed in a three-necked flask. The mixture was heated under reflux while stirring. Further, 834 mg (8.68 mmol) of sodium t-butoxide was added and the resulting mixture was stirred for 2 hours. The reaction mixture was cooled to room temperature. By adding methanol, a precipitate was filtered off. A recrystallization was conducted to obtain 2.9 g of the compound B (yield: 66%).

The solids obtained were measured for the molecular weight by FD mass spectrum. As a result, the molecular weight was found to be 714.

Synthesis Example 9 (Synthesis of Compound C)

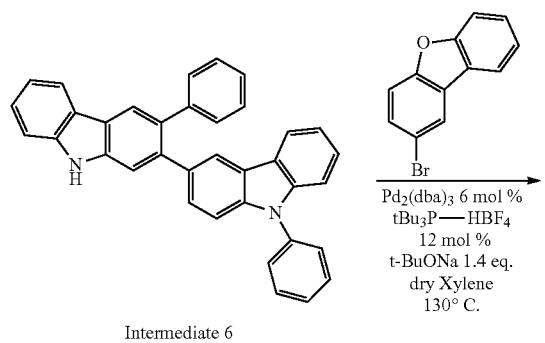

Intermediate 6

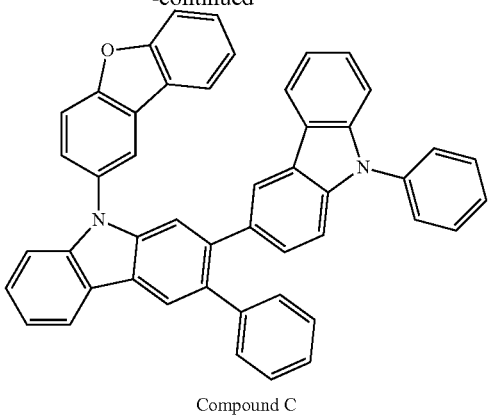

Compound C

Under an argon atmosphere, 3.0 g (6.2 mmol) of intermediate 6, 1.53 g (6.2 mmol) of 2-bromodibenzofuran, 341 mg (0.372 mmol) of tris(dibenzylidene acetone)dipalladium (0), 218 mg (0.75 mmol) of tri-t-butylphosphine tetrafluoroborate salt, 834 mg (8.68 mmol) of sodium t-butoxide and 50 mL of dried xylene were placed in a three-necked flask. The mixture was heated under reflux while stirring for 20 hours. The reaction mixture was cooled to room temperature. After filtration by means of Celite, the solvent was distilled away under reduced pressure. A residue was purified by silica gel column chromatography and was subjected to recrystallization, whereby 2.1 g of compound C was obtained (yield: 52%).

The solids obtained were measured for the molecular weight by FD mass spectrum. As a result, the molecular weight was found to be 650.

Synthesis Example 10 (Synthesis of Compound D)

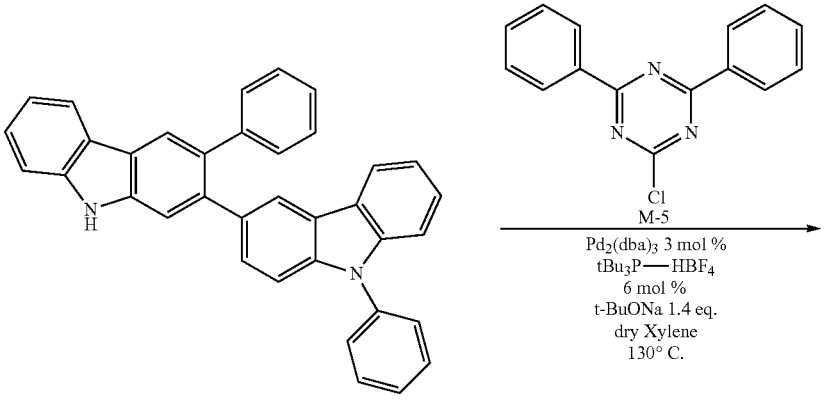

Intermediate 6

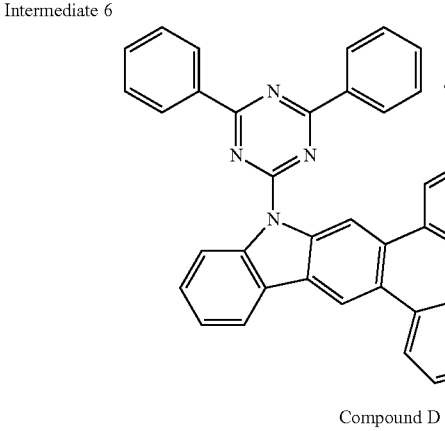

Compound D

Under an argon atmosphere, 3.0 g (6.2 mmol) of intermediate 6, 1.66 g (6.2 mmol) of M-5, 170 mg (0.186 mmol) of tris(dibenzylidene acetone)dipalladium(0), 109 mg (0.38 mmol) of tri-t-butylphosphine tetrafluoroborate salt and 50 mL of dried xylene were placed in a three-necked flask. The mixture was heated under reflux while stirring. Further, 834 mg (8.68 mmol) of sodium t-butoxide was added and the resulting mixture was stirred for 10 hours. The reaction mixture was cooled to room temperature. By adding methanol, a precipitate was collected by filtration. A recrystallization was conducted to obtain 1.8 g of compound D (yield: 40%).

The solids obtained were measured for the molecular weight by FD mass spectrum. As a result, the molecular weight was found to be 715.

Synthesis Example 11 (Synthesis of Compound E)

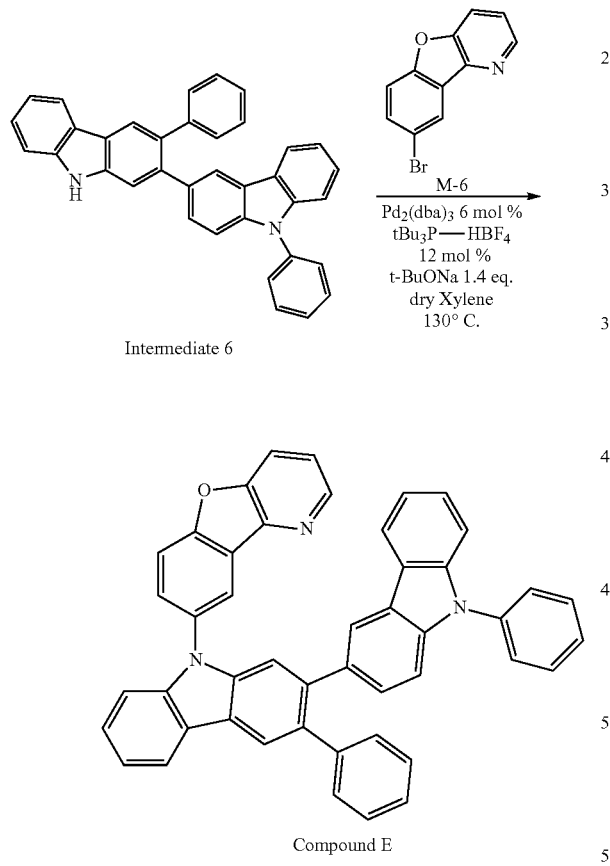

Compound E

Under an argon atmosphere, 3.0 g (6.2 mmol) of intermediate 6, 1.54 g (6.2 mmol) of M-6, 341 mg (0.372 mmol) of tris(dibenzylideneacetone)dipalladium(0), 218 mg (0.75 mmol) of tri-t-butylphosphine tetrafluoroborate, 834 mg (8.68 mmol) of sodium t-butoxide and 50 mL of dried xylene were placed in a three-necked flask. The mixture was heated under reflux while stirring for 24 hours. The reaction mixture was cooled to room temperature. After filtration by means of Celite, the solvent was distilled away under reduced pressure. A residue was purified by silica gel column chromatography and was subjected to recrystallization, whereby 2.5 g of compound E was obtained (yield: 62%).

The solids obtained were measured for the molecular weight by FD mass spectrum. As a result, the molecular weight was found to be 651.

Synthesis Example 12 (Synthesis of Compound F)

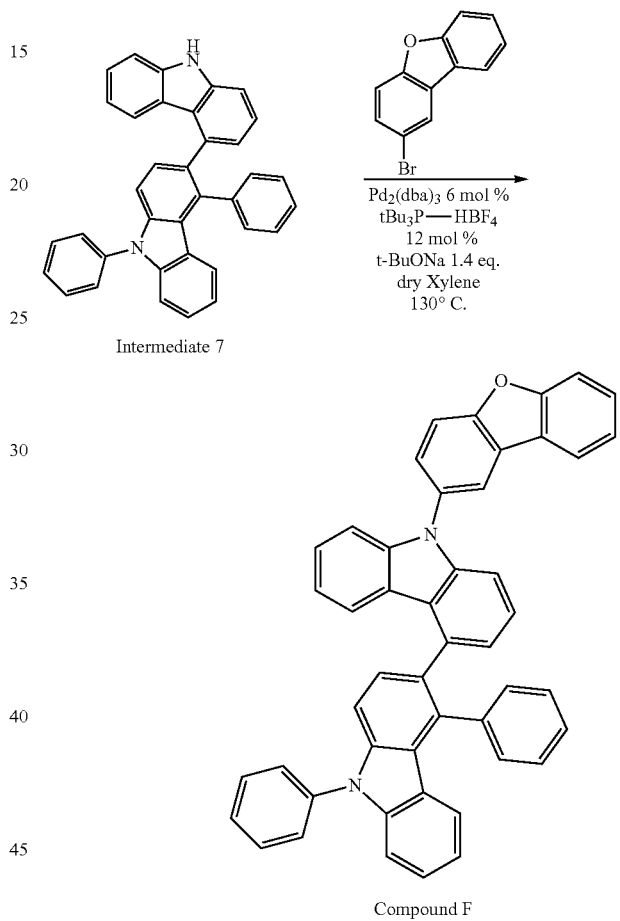

Compound F

Under an argon atmosphere, 4.0 g (8.3 mmol) of the intermediate 7, 2.05 g (8.3 mmol) of 2-bromodibenzofuran, 454 mg (0.496 mmol) of tris(dibenzylideneacetone)dipalladium(0), 290 mg (1.0 mmol) of tri-t-butylphosphine tetrafluoroborate, 1.11 g (11.6 mmol) of sodium t-butoxide and 70 mL of dried xylene were placed in a three-necked flask. The mixture was heated under reflux while stirring for 20 hours. The reaction mixture was cooled to room temperature. After filtration by means of Celite, the solvent was distilled away under reduced pressure. A residue was purified by silica gel column chromatography and was subjected to recrystallization, whereby 2.9 g of compound F was obtained (yield: 54%).

The solids obtained were measured for the molecular weight by FD mass spectrum. As a result, the molecular weight was 650.

Synthesis Example 13 (Synthesis of Compound G)

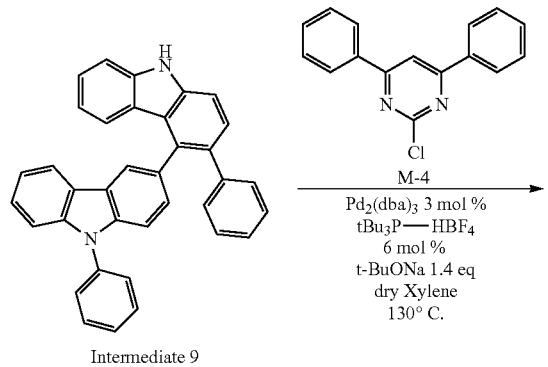

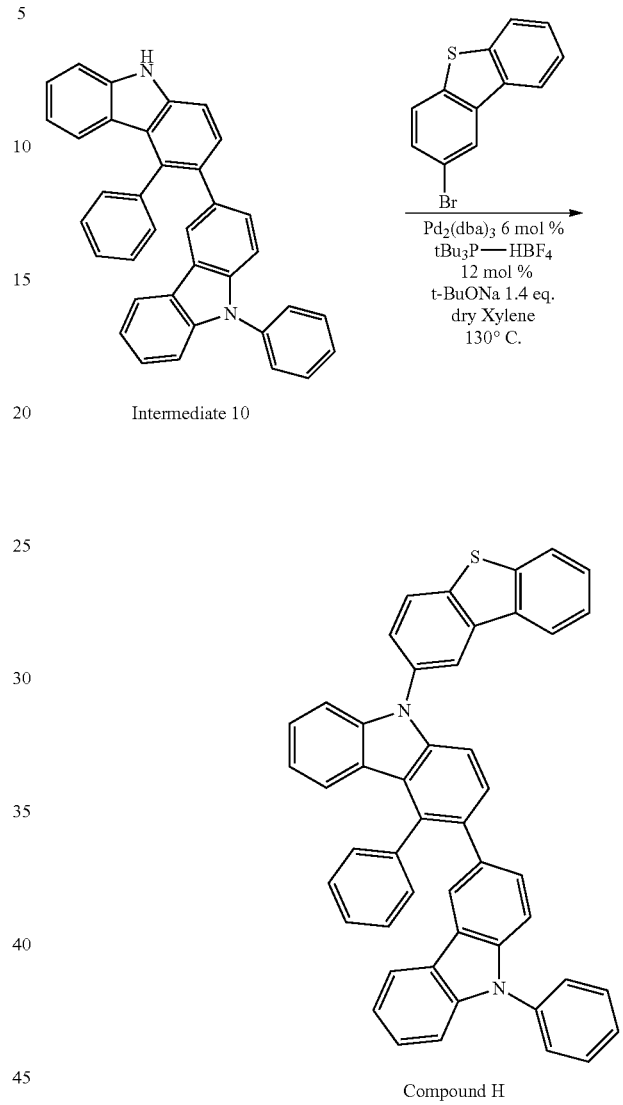

Synthesis Example 14 (Synthesis of Compound H)

Under an argon atmosphere, 3.0 g (6.2 mmol) of the intermediate 9, 1.66 g (6.2 mmol) of M-4, 170 mg (0.186 mmol) of tris(dibenzylideneacetone)dipalladium(0), 109 mg (0.38 mmol) of tri-t-butylphosphine tetrafluoroborate and 50 mL of dried xylene were placed in a three-necked flask. The mixture was heated under reflux while stirring. Further, 834 mg (8.68 mmol) of sodium t-butoxide was added and the resulting mixture was stirred for 2 hours. The reaction mixture was cooled to room temperature. By adding methanol, a precipitate was collected by filtration. A recrystallization was conducted to obtain 1.6 g of compound G (yield: 36%).

The solids obtained were measured for the molecular weight by FD mass spectrum. As a result, the molecular weight was found to be 714.

Under an argon atmosphere, 2.5 g (5.2 mmol) of intermediate 10, 1.37 g (5.2 mmol) of 2-bromodibenzothiophene, 284 mg (0.310 mmol) of tris(dibenzylideneacetone)dipalladium(0), 182 mg (0.63 mmol) of tri-t-butylphosphine tetrafluoroborate, 695 mg (7.26 mmol) of sodium t-butoxide and 50 mL of dried xylene were placed in a three-necked flask. The mixture was heated under reflux while stirring for 20 hours. The reaction mixture was cooled to room temperature. After filtration by means of Celite, the solvent was distilled away under reduced pressure. A residue was purified by silica gel column chromatography and was subjected to recrystallization, whereby 1.8 g of compound H was obtained (yield: 52%).

The solids obtained were measured for the molecular weight by FD mass spectrum. As a result, the molecular weight was found to be 666.

Synthesis Example 15 (Synthesis of Compound I)
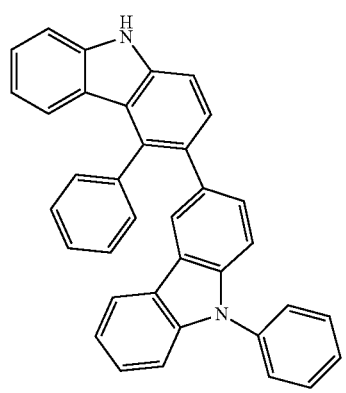
Intermediate 10
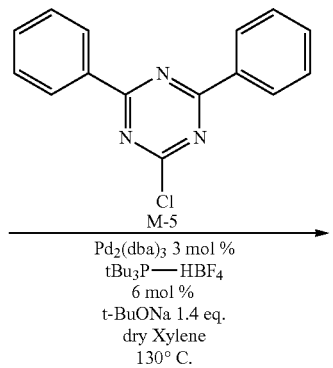
M-5
Pd$_2$(dba)$_3$ 3 mol %
tBu$_3$P—HBF$_4$
6 mol %
t-BuONa 1.4 eq.
dry Xylene
130° C.
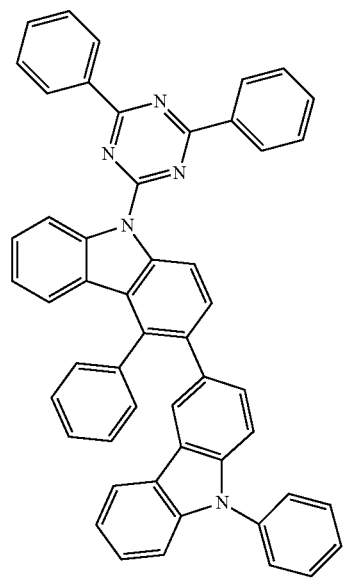
Compound I Under an argon atmosphere, 2.5 g (5.2 mmol) of intermediate 10, 1.34 g (5.2 mmol) of M-5, 143 mg (0.156 mmol) of tris(dibenzylideneacetone)dipalladium(0), 91.4 mg (0.32 mmol) of tri-t-butylphosphine tetrafluoroborate and 50 mL of dried xylene were placed in a three-necked flask. The mixture was heated under reflux while stirring. Further, 699 mg (7.28 mmol) of sodium t-butoxide was added and the resulting mixture was stirred for 10 hours. The reaction mixture was cooled to room temperature. By adding methanol, a precipitate was filtered off. A recrystallization was conducted to obtain 2.2 g of compound I (yield: 59%).

The solids obtained were measured for the molecular weight by FD mass spectrum. As a result, the molecular weight was found to be 715.

Synthesis Example 16 (Synthesis of Compound J)

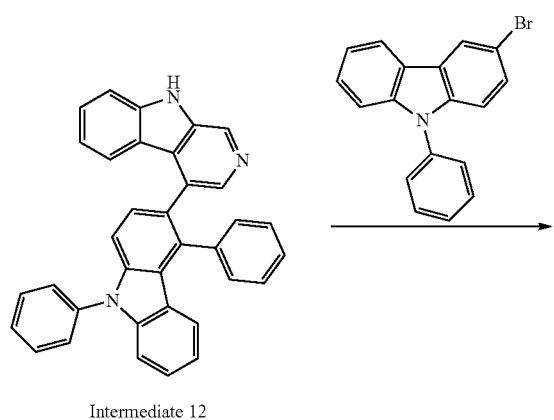

Intermediate 12

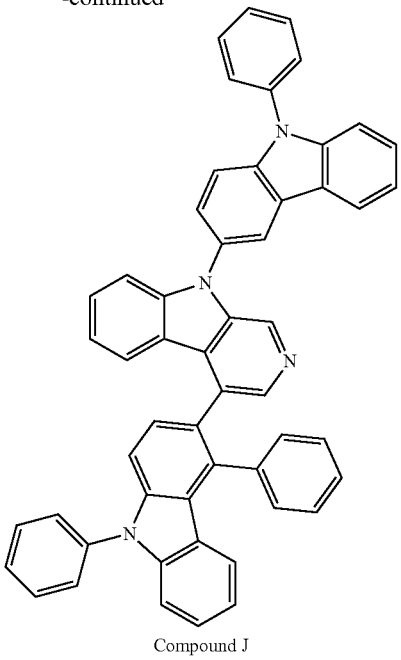

Compound J

Under an argon atmosphere, 3.5 g (7.2 mmol) of intermediate 12, 2.3 g (7.2 mmol) of 3-bromo-9-phenylcarbazole, 395 mg (0.432 mmol) of tris(dibenzylideneacetone)dipalladium(0), 253 mg (0.87 mmol) of tri-t-butylphosphine tetrafluoroborate, 966 mg (10.1 mmol) of sodium t-butoxide and 70 mL of dried xylene were placed in a three-necked flask. The mixture was heated under reflux while stirring for 20 hours. The reaction mixture was cooled to room temperature. After filtration by means of Celite, the solvent was distilled away under reduced pressure. A residue was purified by silica gel column chromatography and was subjected to recrystallization, whereby 3.5 g of compound J was obtained (yield: 67%).

The solids obtained were measured for the molecular weight by FD mass spectrum. As a result, the molecular weight was found to be 726.

The structural formulas of the compounds used in the following Examples and Comparative Examples are shown below.

Compound 1

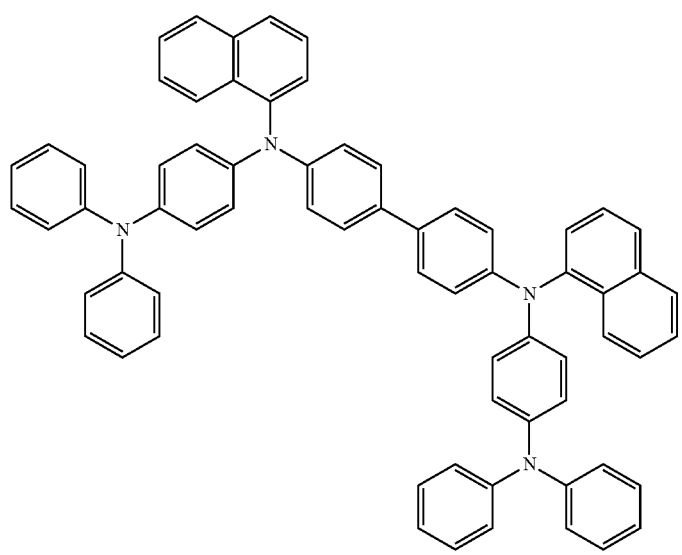

-continued
Compound 2
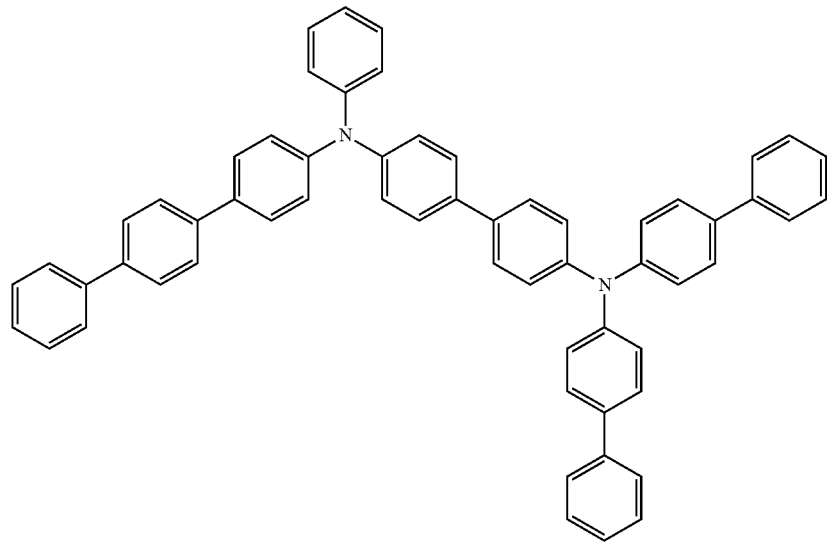
Compound 3
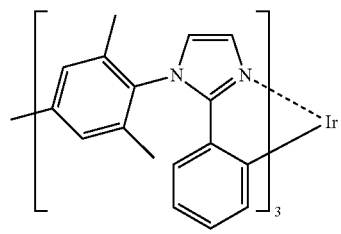
Compound 4
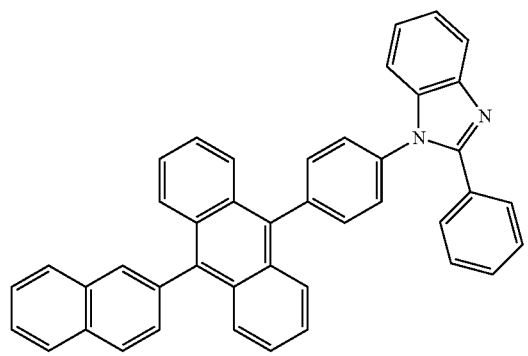
Compound 5
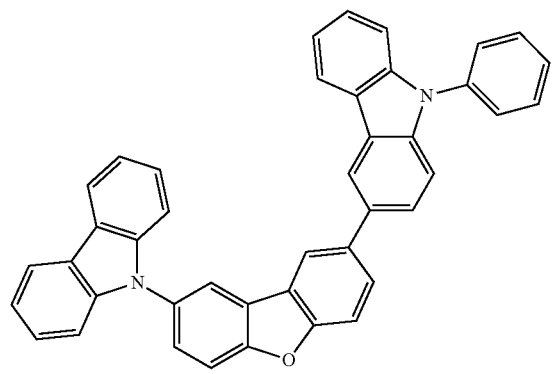
Compound A
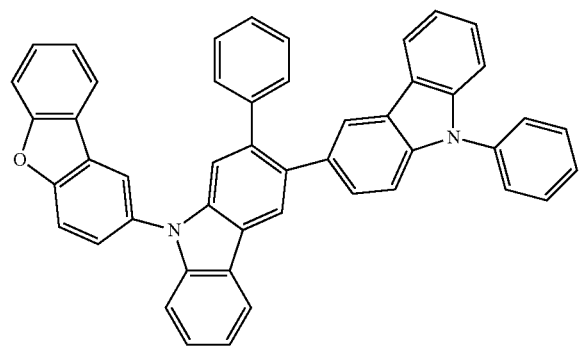

-continued
Compound C
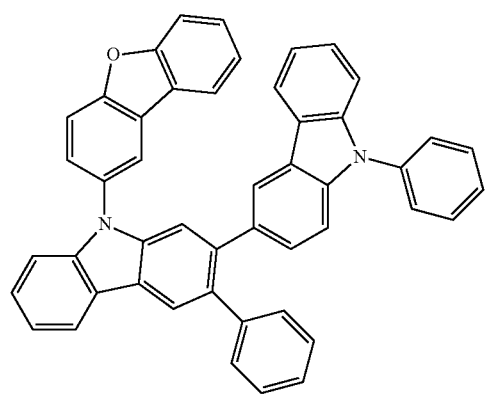
Compound F
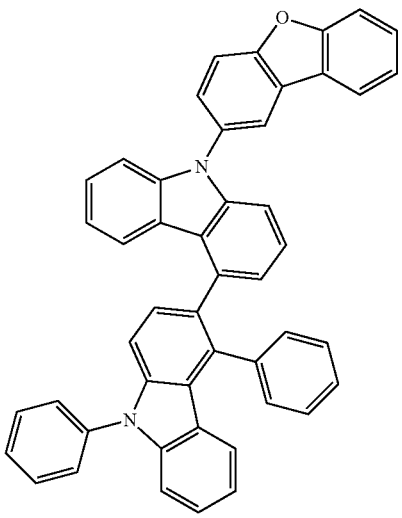
Compound H
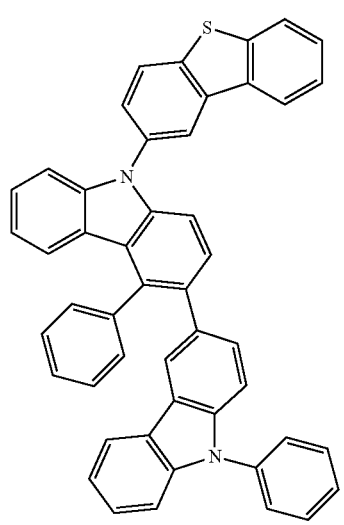
Compound J
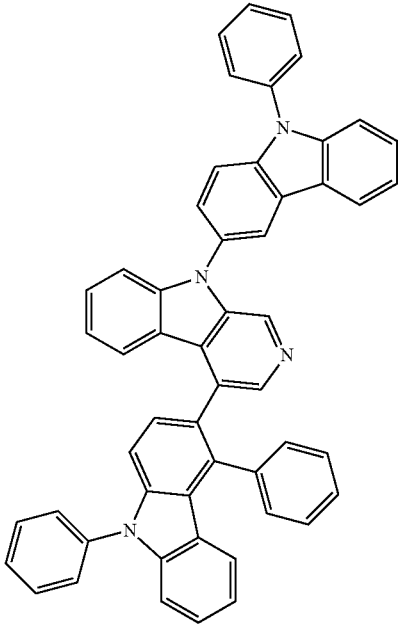
Compound E
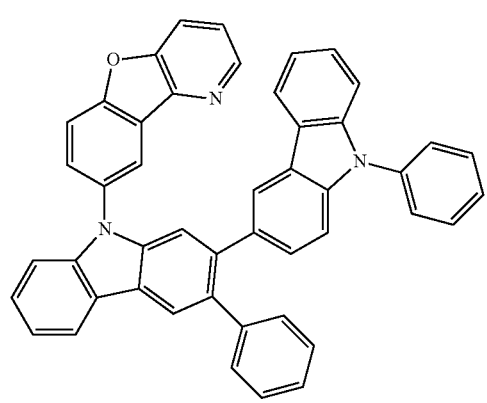
Comparative compound A
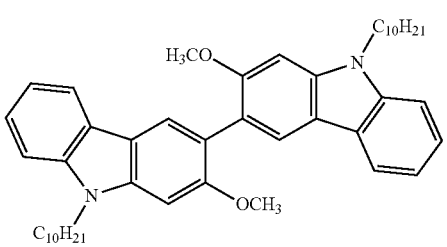

-continued
Comparative compound B
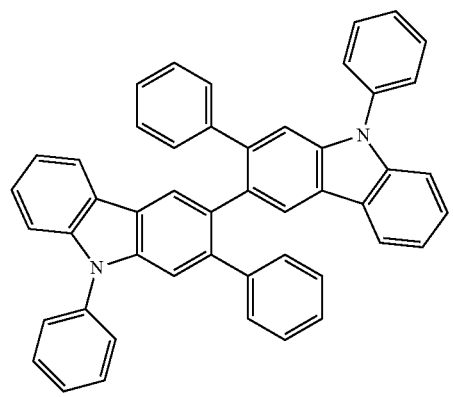
Comparative compound C
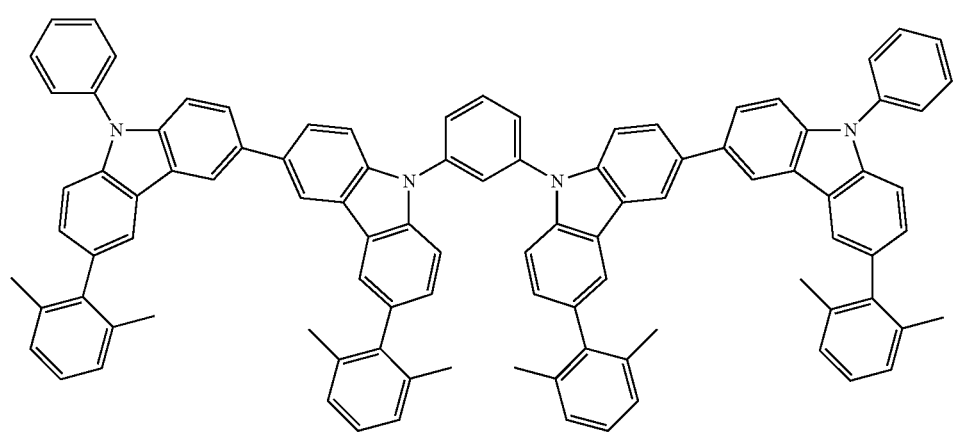
Compound 6
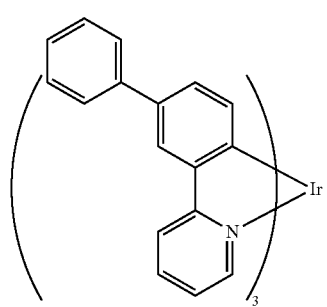
Compound B
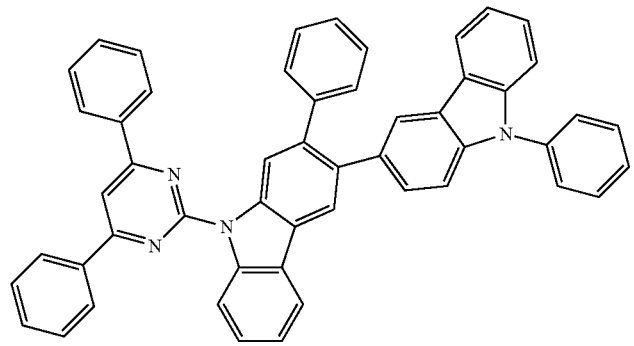

-continued

Compound D

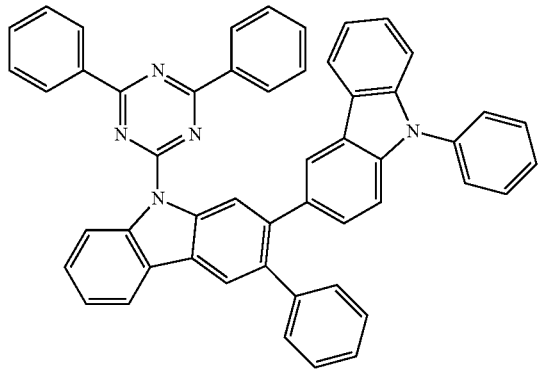

Compound G

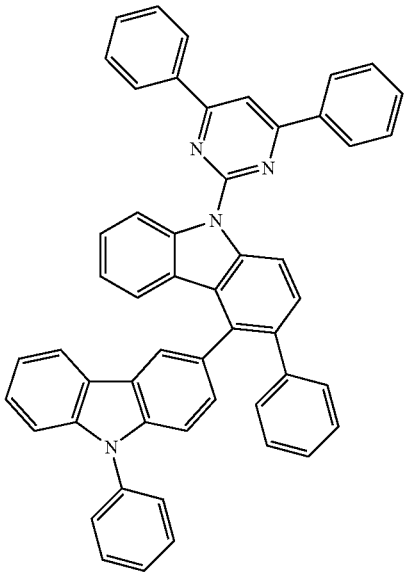

Compound I

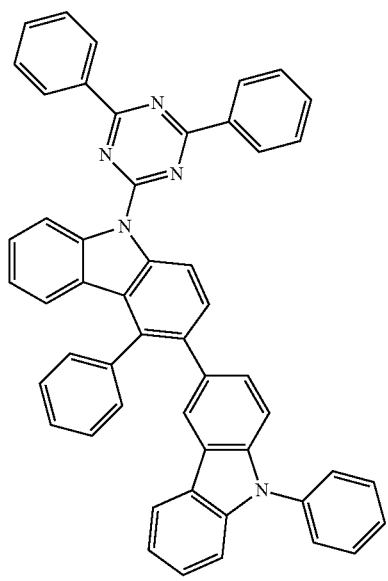

(Organic EL Device)

Example 1

A glass substrate, measuring 25 mm×75 mm×1.1 mm, with an ITO transparent electrode (manufactured by Geomatics Co.) was subjected to ultrasonic cleaning in isopropyl alcohol for 5 minutes and then UV ozone cleaning for 30 minutes.

The cleaned glass substrate with transparent electrode lines was mounted on a substrate holder in a vacuum deposition apparatus. Compound 1 was deposited on the surface of the glass substrate on which the transparent electrode lines had been formed so as to cover the transparent electrode to form a 20 nm-thick film as a hole-injecting layer. Next, on this film, compound 2 was deposited to form a 60 nm-thick film as a hole-transporting layer.

On the hole-transporting layer, compound A as a phosphorescent host material and compound 3 as a phosphorescent material were co-deposited to form a 50 nm-thick film as a phosphorescent layer. In the phosphorescent layer, the concentration of compound A was 80 mass %, and the concentration of compound 3 was 20 mass %.

Subsequently, on the phosphorescent layer, compound 5 was deposited to form a 10 nm-thick film as a hole blocking layer. Further, compound 4 was deposited to form a 10 nm thick film as an electron-transporting layer. After that, LiF film with a thickness of 1 nm and metal Al film with a thickness of 80 nm were stacked sequentially to obtain a cathode. Meanwhile, the LiF film as an electron-injecting electrode was formed at the rate of 1 Å/min.

(Luminescent Performance Evaluation of Organic EL Device)

Organic EL devices obtained were allowed to emit by DC driving and measured for the luminance and the current density. The voltage and luminous efficiency (external quantum efficiency) at a current density of 1 mA/cm$^2$ was determined. In addition, the luminance 50% life time at an initial luminance of 3000 cd/cm² (the time taken for the luminance to decrease to 50%) was determined. The results of the luminescent performance evaluations are shown in Table 1.

Examples 2 to 6

Organic EL devices were fabricated and evaluated in the same method as in Example 1, except that compounds shown in the following Table 1 were used instead of compound A as a phosphorescent host material. The results are shown in Table 1.

Comparative Examples 1 to 3

Organic EL devices were fabricated and evaluated in the same method as in Example 1, except that compounds shown in the following Table 1 were used instead of compound A as a phosphorescent host material.

Comparative compound C has a large molecular weight and thus a deposited film could not be obtained. As a result, an organic EL device could not be fabricated. Other results are shown in Table 1.

| | Emitting layer Host material | Voltage (V) | External quantum efficiency (%) | 50% reduction life time (hour) |
|---|---|---|---|---|
| Example 1 | Compound A | 5.9 | 16.6 | 520 |
| Example 2 | Compound C | 5.5 | 15.5 | 465 |
| Example 3 | Compound F | 5.8 | 17.5 | 430 |
| Example 4 | Compound H | 5.6 | 17.0 | 420 |
| Example 5 | Compound J | 5.2 | 17.3 | 315 |
| Example 6 | Compound E | 4.8 | 16.2 | 360 |
| Com. Ex. 1 | Com. Compound A | 5.9 | 14.4 | 85 |
| Com. Ex. 2 | Com. Compound B | 5.8 | 15.1 | 195 |
| Com. Ex. 3 | Com. Compound C | — | — | — |

Examples 7 and 8

Organic EL devices were fabricated and evaluated in the same method as in Example 1, except that compounds shown in Table 2 below were used instead of compound 5 in the hole blocking layer in Example 1. The results of Examples 7 and 8 are shown in Table 2, comparing to those of Example 1.

TABLE 2

| | Emitting layer Host material | Hole blocking material | Voltage (V) | External quantum efficiency (%) | 50% reduction life time (hour) |
|---|---|---|---|---|---|
| Example 1 | Compound A | Compound 5 | 5.9 | 16.6 | 520 |
| Example 7 | Compound A | Compound J | 5.1 | 16.9 | 530 |
| Example 8 | Compound A | Compound E | 4.5 | 18.6 | 520 |

Example 9

A glass substrate, measuring 25 mm×75 mm×1.1 mm, with an ITO transparent electrode (manufactured by Geomatics Co.) was subjected to ultrasonic cleaning in isopropyl alcohol for 5 minutes and then UV (Ultraviolet) ozone cleaning for 30 minutes.

The cleaned glass substrate with transparent electrode lines was mounted on a substrate holder in a vacuum deposition apparatus. Compound 1 was deposited on the surface of the glass substrate on which the transparent electrode lines had been formed so as to cover the transparent electrode to form a 40 nm-thick film as a hole-injecting layer. Next, on this film, compound 2 was deposited to form a 20 nm-thick film as a hole-transporting layer.

On the hole-transporting layer, the compound B as a phosphorescent host material and the compound 6 as a phosphorescent material were codeposited to form a 40 nm-thick film as a phosphorescent layer. In the phosphorescent layer, the concentration of compound B was 85 mass %, and the concentration of compound 6 was 15 mass %.

Subsequently, on the phosphorescent layer, compound 4 was deposited to form a 30 nm-thick film as an electron-transporting layer. After that, a LiF film with a thickness of 1 nm and a metal Al film with a thickness of 80 nm were stacked thereon sequentially to obtain a cathode. Meanwhile, the LiF film as an electron-injecting electrode was formed at the rate of 1 Å/min.

(Luminescent Performance Evaluation of Organic EL Device)

Organic EL devices obtained were allowed to emit by DC driven and measured for the luminance and the current density. The voltage and luminous efficiency (external quantum efficiency) at a current density of 1 mA/cm² was determined. In addition, the luminance 50% life time (the time taken for the luminance to decrease to 50%) at an initial luminance of 20,000 cd/m² was determined. The results of the luminescent performance evaluations are shown in Table 3.

Examples 10 to 12

Organic EL devices were fabricated and evaluated in the same method as in Example 9, except that compounds shown in the following Table 3 were used instead of compound B as a phosphorescent host material. The results are shown in Table 3.

Comparative Examples 4 to 6

Organic EL devices were fabricated and evaluated in the same method as in Example 9, except that compounds shown in the following Table 3 were used instead of compound A as a phosphorescent host material.

Comparative compound C used in Comparative Example 6 has a large molecular weight, and hence a deposited film was not obtained. As a result, an organic EL device could not be fabricated. The other results are shown in Table 3.

TABLE 3

| | Emitting layer Host material | Voltage (V) | External quantum efficiency (%) | 50% reduction life time (hour) |
|---|---|---|---|---|
| Example 9 | Compound B | 3.1 | 18.0 | 500 |
| Example 10 | Compound D | 3.0 | 17.9 | 450 |
| Example 11 | Compound G | 3.3 | 18.6 | 380 |
| Example 12 | Compound I | 3.2 | 18.5 | 360 |
| Com. Ex. 4 | Com. Compound A | 3.7 | 13.4 | 35 |
| Com. Ex. 5 | Com. Compound B | 3.5 | 14.0 | 160 |
| Com. Ex. 6 | Com. Compound C | — | — | — |

From the results of Examples 1 to 6 and Examples 9 to 12, it is found that when the compound of the invention was used in an emitting layer, a device having a higher luminous efficiency and a longer life compared with Comparative Examples could be obtained. Further, as shown in Examples 7 and 8, when the compound of the invention was used in a hole blocking layer, the driving voltage could be lowered remarkably.

INDUSTRIAL APPLICABILITY

The compound of the present invention can be used as a material for an organic EL device.

The organic EL device of the invention can be utilized for a planar emitting body such as a flat panel display of a wall-hanging television, a copier, a printer, a back light of a liquid crystal display, or a light source such as instruments, a sign board, a signal light or the like.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in this specification and the Japanese application specification claiming priority under the Paris Convention are incorporated herein by reference in its entirety.

The invention claimed is:

1. A compound represented by the following formula (1):

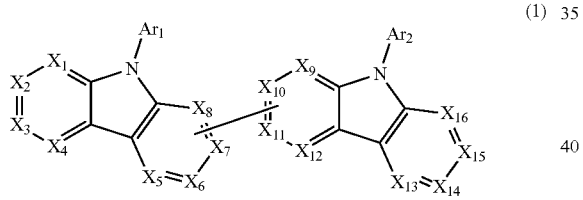

(1)

wherein in the formula (1),
Ar$_1$ and Ar$_2$ are independently a substituted or unsubstituted aryl group including 6 to 18 ring carbon atoms, a substituted or unsubstituted heteroaryl group including 5 to 18 ring atoms, or a substituted or unsubstituted alkyl group including 1 to 20 carbon atoms, at least one of Ar$_1$ and Ar$_2$ is a substituted or unsubstituted heteroaryl group including 5 to 18 ring atoms;
X$_1$ to X$_4$ and X$_{13}$ to X$_{16}$ are independently CR$_1$, CH or N;
one of X$_5$ to X$_8$ is a carbon atom bonding to one of X$_9$ to X$_{12}$, and at least one of X$_5$ to X$_8$ that is adjacent to the carbon atom bonding to one of X$_9$ to X$_{12}$ is CR$_2$;
one of X$_9$ to X$_{12}$ is a carbon atom bonding to one of X$_5$ to X$_8$, and X$_9$ to X$_{12}$ that is adjacent to the carbon atom bonding to one of X$_5$ to X$_8$ is CH or N;
the remaining X$_5$ to X$_8$ and the remaining X$_9$ to X$_{12}$ are CR$_1$, CH or N; and
R$_1$ and R$_2$ are independently a substituted or unsubstituted aryl group including 6 to 18 ring carbon atoms, or a substituted or unsubstituted heteroaryl group including 5 to 18 ring atoms.

2. The compound according to claim 1, wherein X$_9$ to X$_{12}$ that is not the carbon atom bonding to one of X$_5$ to X$_8$ are CH or N.

3. The compound according to claim 1, which is selected from the group consisting of compounds represented by the following formulas (2) to (17):

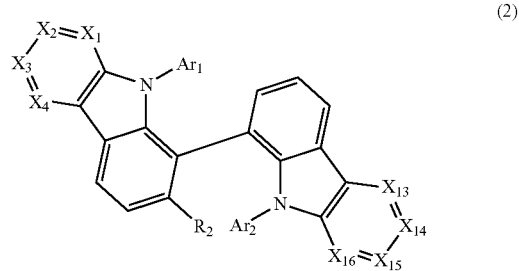

(2)

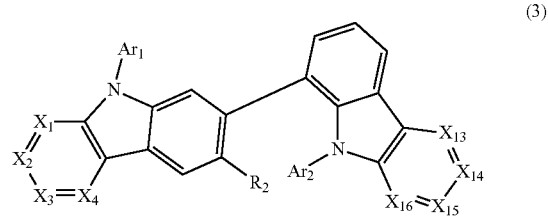

(3)

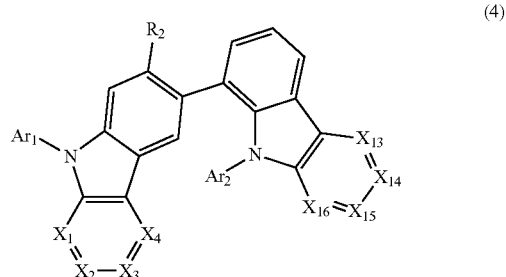

(4)

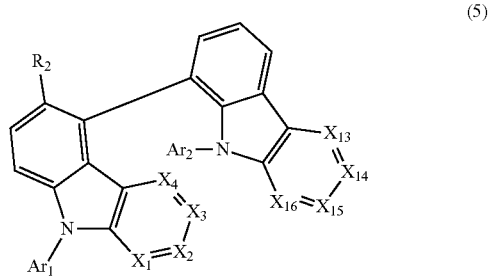

(5)

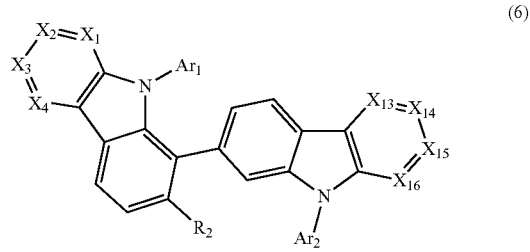

(6)

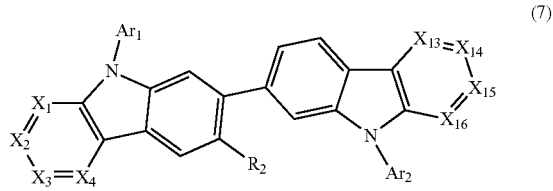

(7)

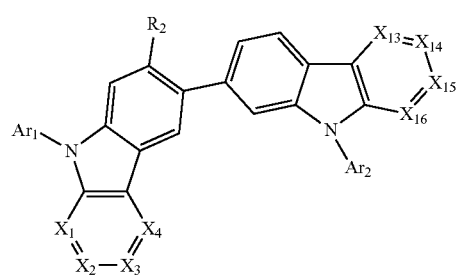
(8)
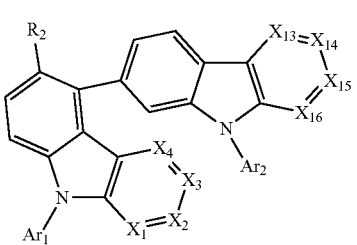
(9)
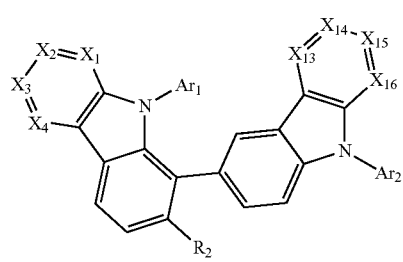
(10)
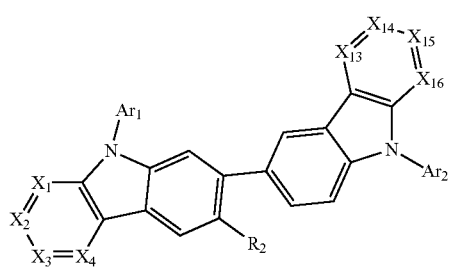
(11)
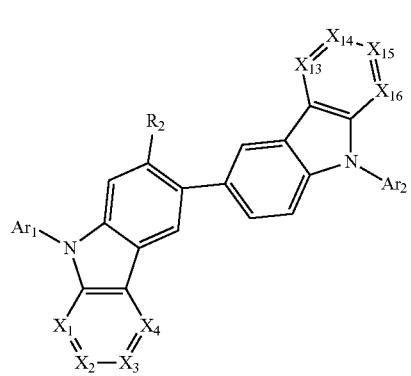
(12)
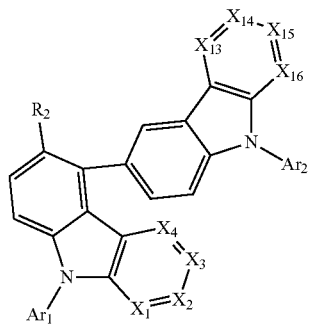
(13)
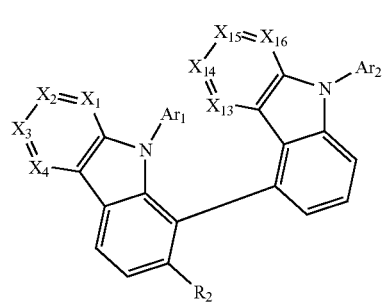
(14)
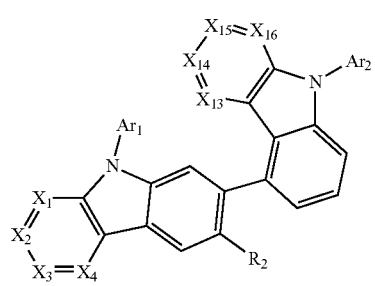
(15)
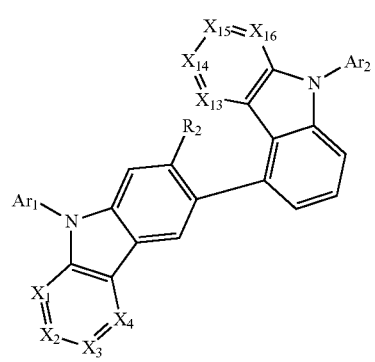
(16)
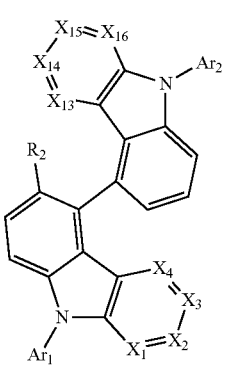
(17)

wherein, in the formulas (2) to (17), $Ar_1$, $Ar_2$, $R_2$, $X_1$ to $X_4$ and $X_{13}$ to $X_{16}$ are as defined in the formula (1).

4. A material for an organic electroluminescence device comprising the compound according to claim 1.

5. An organic electroluminescence device comprising one or more organic thin film layers including an emitting layer between a cathode and an anode, at least one layer of the organic thin film layers comprising the material for an organic electroluminescence device according to claim 4.

6. The organic electroluminescence device according to claim 5, wherein the organic thin film layers comprise one or more emitting layers, and at least one of the emitting layers comprises the material for an organic electroluminescence device and a phosphorescent material.

7. The organic electroluminescence device according to claim 6, wherein the excited triplet energy of the phosphorescent material is 1.8 eV or more and less than 2.9 eV.

8. The organic electroluminescence device according to claim 6, wherein the phosphorescent material comprises a metal complex, the metal complex comprising a metal atom selected from Ir, Pt, Os, Au, Cu, Re and Ru, and a ligand.

9. The organic electroluminescence device according to claim 8, wherein the ligand comprises an ortho-metal bond with the metal atom.

10. The organic electroluminescence device according to claim 6, wherein the maximum value of emission wavelengths is 430 nm or more and 720 nm or less.

11. The organic electroluminescence device according to claim 5, wherein an electron-transporting region is between the emitting layer and the cathode, the electron-transporting region comprising the material for an organic electroluminescence device.

12. The organic electroluminescence device according to claim 5, wherein a hole-transporting region is between the emitting layer and the anode, the hole-transporting region comprising the material for an organic electroluminescence device.

13. The organic electroluminescence device according to claim 5, wherein at least one of two organic thin film layers adjacent to the emitting layer comprises the material for an organic electroluminescence device, and the excited triplet energy of the material for an organic electroluminescence device of this adjacent layer is 2.5 eV or more.

14. The organic electroluminescence device according to claim 5, wherein the organic thin film comprises an electron-transporting layer or an electron-injecting layer between the cathode and the emitting layer, and the electron-transporting layer or electron-injecting layer comprises an aromatic ring compound including a nitrogen-containing six-membered ring or a nitrogen-containing five-membered ring skeleton, or a fused aromatic ring compound including a nitrogen-containing six-membered ring or a nitrogen-containing five-membered ring skeleton.

15. The compound according to claim 1, wherein $R_2$ is a substituted or unsubstituted phenyl group, a substituted or unsubstituted dibenzofuranyl group, a substituted or unsubstituted dibenzothiophenyl group, a substituted or unsubstituted carbazolyl group, a substituted or unsubstituted azadibenzofuranyl group, a substituted or unsubstituted azadibenzothiophenyl group, a substituted or unsubstituted azacarbazolyl group, a substituted or unsubstituted pyridyl group, a substituted or unsubstituted pyrimidinyl group or a substituted or unsubstituted triazinyl group.

16. The compound according to claim 3, wherein $R_2$ is a substituted or unsubstituted phenyl group, a substituted or unsubstituted dibenzofuranyl group, a substituted or unsubstituted dibenzothiophenyl group, a substituted or unsubstituted carbazolyl group, a substituted or unsubstituted azadibenzofuranyl group, a substituted or unsubstituted azadibenzothiophenyl group, a substituted or unsubstituted azacarbazolyl group, a substituted or unsubstituted pyridyl group, a substituted or unsubstituted pyrimidinyl group or a substituted or unsubstituted triazinyl group.

17. The compound according to claim 1, wherein $Ar_1$ is a substituted or unsubstituted phenyl group, a substituted or unsubstituted dibenzofuranyl group, a substituted or unsubstituted dibenzothiophenyl group, a substituted or unsubstituted carbazolyl group, a substituted or unsubstituted azadibenzofuranyl group, a substituted or unsubstituted azadibenzothiophenyl group, a substituted or unsubstituted azacarbazolyl group, a substituted or unsubstituted pyridyl group, a substituted or unsubstituted pyrimidinyl group or a substituted or unsubstituted triazinyl group.

18. The compound according to claim 3, wherein $Ar_1$ is a substituted or unsubstituted phenyl group, a substituted or unsubstituted dibenzofuranyl group, a substituted or unsubstituted dibenzothiophenyl group, a substituted or unsubstituted carbazolyl group, a substituted or unsubstituted azadibenzofuranyl group, a substituted or unsubstituted azadibenzothiophenyl group, a substituted or unsubstituted azacarbazolyl group, a substituted or unsubstituted pyridyl group, a substituted or unsubstituted pyrimidinyl group or a substituted or unsubstituted triazinyl group.

19. The compound according to claim 1, wherein $Ar_2$ is a substituted or unsubstituted phenyl group, a substituted or unsubstituted dibenzofuranyl group, a substituted or unsubstituted dibenzothiophenyl group, a substituted or unsubstituted carbazolyl group, a substituted or unsubstituted azadibenzofuranyl group, a substituted or unsubstituted azadibenzothiophenyl group, a substituted or unsubstituted azacarbazolyl group, a substituted or unsubstituted pyridyl group, a substituted or unsubstituted pyrimidinyl group or a substituted or unsubstituted triazinyl group.

20. The compound according to claim 3, wherein $Ar_2$ is a substituted or unsubstituted phenyl group, a substituted or unsubstituted dibenzofuranyl group, a substituted or unsubstituted dibenzothiophenyl group, a substituted or unsubstituted carbazolyl group, a substituted or unsubstituted azadibenzofuranyl group, a substituted or unsubstituted azadibenzothiophenyl group, a substituted or unsubstituted azacarbazolyl group, a substituted or unsubstituted pyridyl group, a substituted or unsubstituted pyrimidinyl group or a substituted or unsubstituted triazinyl group.

21. The compound according to claim 1, wherein one of $X_5$ to $X_8$ is a carbon atom bonding to one of $X_9$ to $X_{12}$, and one of $X_5$ to $X_8$ that is adjacent to the carbon atom bonding to one of $X_9$ to $X_{12}$ is $CR_2$; and the remaining $X_5$ to $X_8$ are CH or N.

22. The compound according to claim 1, wherein the substituted or unsubstituted aryl group including 6 to 18 ring carbon atoms of $Ar_1$, $Ar_2$, $R_1$ and $R_2$ is a substituted or unsubstituted phenyl group, a substituted or unsubstituted triphenylenyl group, a substituted or unsubstituted fluorenyl group, a substituted or unsubstituted 9,9-dimethylfluorenyl group, a substituted or unsubstituted biphenyl group or a substituted or unsubstituted terphenyl group;

the substituted or unsubstituted heteroaryl group including 5 to 18 ring atoms of $Ar_1$, $Ar_2$, $R_1$ and $R_2$ is a substituted or unsubstituted pyrrolyl group, a substituted or unsubstituted pyrazinyl group, a substituted or unsubstituted pyridinyl group, a substituted or unsubstituted indolyl group, a substituted or unsubstituted isoindolyl group, a substituted or unsubstituted imidazolyl group, a substituted or unsubstituted furyl group, a substituted or unsubstituted benzofuranyl group, a substituted or unsubstituted isobenzofuranyl group, a substituted or unsubstituted dibenzofuranyl group, a substituted or unsubstituted dibenzothiophenyl group, a substituted or unsubstituted carbazolyl group, a substituted or unsubstituted phenylcarbazolyl group, a substituted or unsubstituted acridinyl group, a substituted or unsubstituted phenothiazinyl group, a substituted or unsubstituted phenoxazinyl group, a substituted or unsubstituted oxazolyl group, a substituted or unsubstituted oxadiazolyl group, a substituted or unsubstituted furazanyl group, a substituted or unsubstituted thienyl group, a substituted or unsubstituted benzothiophenyl group, a substituted or unsubstituted azacarbazolyl group, a substituted or unsubstituted azadibenzofuranyl group or a substituted or unsubstituted azadibenzothiophenyl group; and the substituted or unsubstituted alkyl group including 1 to 20 carbon atoms is a substituted or unsubstituted methyl group, a substituted or unsubstituted ethyl group, a substituted or unsubstituted propyl group, a substituted or unsubstituted isopropyl group, a substituted or unsubstituted n-butyl group, a substituted or unsubstituted isobutyl group, a substituted or unsubstituted sec-butyl group, a substituted or unsubstituted tert-butyl group, a substituted or unsubstituted n-pentyl group, a substituted or unsubstituted n-hexyl group, a substituted or unsubstituted n-heptyl group or a substituted or unsubstituted n-octyl group.

23. The compound according to claim 1, wherein the heteroaryl group of at least one of $Ar_1$ and $Ar_2$ comprises 5 to 13 ring atoms.

24. The compound according to claim 1, wherein
 $Ar_1$ is a substituted or unsubstituted phenyl group, a substituted or unsubstituted dibenzofuranyl group, a substituted or unsubstituted dibenzothiophenyl group, a substituted or unsubstituted carbazolyl group, a substituted or unsubstituted azadibenzofuranyl group, a substituted or unsubstituted azadibenzothiophenyl group, a substituted or unsubstituted azacarbazolyl group, a substituted or unsubstituted pyridyl group, a substituted or unsubstituted pyrimidinyl group or a substituted or unsubstituted triazinyl group;
 $Ar_2$ is a substituted or unsubstituted phenyl group, a substituted or unsubstituted dibenzofuranyl group, a substituted or unsubstituted dibenzothiophenyl group, a substituted or unsubstituted carbazolyl group, a substituted or unsubstituted azadibenzofuranyl group, a substituted or unsubstituted azadibenzothiophenyl group, a substituted or unsubstituted azacarbazolyl group, a substituted or unsubstituted pyridyl group, a substituted or unsubstituted pyrimidinyl group or a substituted or unsubstituted triazinyl group; and
 at least one of $Ar_1$ and $Ar_2$ is a substituted or unsubstituted heteroaryl group including 5 to 18 ring atoms.

25. The compound according to claim 1, wherein the heteroaryl group of at least one of $Ar_1$ and $Ar_2$ is a substituted or unsubstituted pyridyl group, a substituted or unsubstituted pyrimidinyl group or a substituted or unsubstituted triazinyl group.

26. The compound according to claim 1, wherein $Ar_1$ is a substituted or unsubstituted heteroaryl group including 5 to 18 ring atoms.

27. A compound represented by the following formula (1):

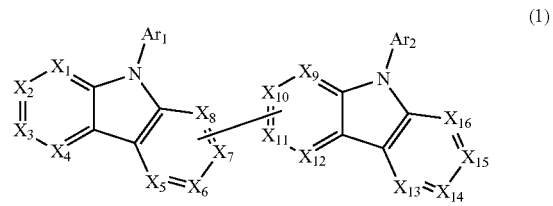

wherein in the formula (1),
 $Ar_1$ and $Ar_2$ are independently a substituted or unsubstituted aryl group including 6 to 18 ring carbon atoms, a substituted or unsubstituted heteroaryl group including 5 to 18 ring atoms, or a substituted or unsubstituted alkyl group including 1 to 20 carbon atoms;
 $X_1$ to $X_4$ and $X_{13}$ to $X_{16}$ are independently $CR_1$, CH or N;
 one of $X_5$ to $X_8$ is a carbon atom bonding to one of $X_9$ to $X_{12}$, and at least one of $X_5$ to $X_8$ that is adjacent to the carbon atom bonding to one of $X_9$ to $X_{12}$ is $CR_2$;
 one of $X_9$ to $X_{12}$ is a carbon atom bonding to one of $X_5$ to $X_8$, and $X_9$ to $X_{12}$ that is adjacent to the carbon atom bonding to one of $X_5$ to $X_8$ is CH or N;
 the remaining $X_5$ to $X_8$ and the remaining $X_9$ to $X_{12}$ are $CR_1$, CH or N;
 $R_1$ is a substituted or unsubstituted aryl group including 6 to 18 ring carbon atoms, or a substituted or unsubstituted heteroaryl group including 5 to 18 ring atoms; and
 $R_2$ is a substituted pyridyl group, a substituted pyrimidinyl group or a substituted triazinyl group.

28. The compound according to claim 27, wherein one of $X_5$ to $X_8$ is a carbon atom bonding to one of $X_9$ to $X_{12}$, and one of $X_5$ to $X_8$ that is adjacent to the carbon atom bonding to one of $X_9$ to $X_{12}$ is $CR_2$; and
 the remaining $X_5$ to $X_8$ are CH or N.

29. The compound according to claim 27, wherein the substituted or unsubstituted aryl group including 6 to 18 ring carbon atoms of $Ar_1$, $Ar_2$, and $R_1$ is a substituted or unsubstituted phenyl group, a substituted or unsubstituted triphenylenyl group, a substituted or unsubstituted fluorenyl group, a substituted or unsubstituted 9,9-dimethylfluorenyl group, a substituted or unsubstituted biphenyl group or a substituted or unsubstituted terphenyl group;
 the substituted or unsubstituted heteroaryl group including 5 to 18 ring atoms of $Ar_1$, $Ar_2$, and $R_1$ is a substituted or unsubstituted pyrrolyl group, a substituted or unsubstituted pyrazinyl group, a substituted or unsubstituted pyridinyl group, a substituted or unsubstituted indolyl group, a substituted or unsubstituted isoindolyl group, a substituted or unsubstituted imidazolyl group, a substituted or unsubstituted furyl group, a substituted or unsubstituted benzofuranyl group, a substituted or unsubstituted isobenzofuranyl group, a substituted or unsubstituted dibenzofuranyl group, a substituted or unsubstituted dibenzothiophenyl group, a substituted or unsubstituted carbazolyl group, a substituted or unsubstituted phenylcarbazolyl group, a substituted or unsubstituted acridinyl group, a substituted or unsubstituted phenothiazinyl group, a substituted or unsubstituted phenoxazinyl group, a substituted or unsubstituted oxazolyl group, a substituted or unsubstituted oxadiazolyl group, a substituted or unsubstituted furazanyl group, a substituted or unsubstituted thienyl group, a substituted or unsubstituted benzothiophenyl group, a substituted or unsubstituted azacarbazolyl group, a substituted or unsubstituted azadibenzofuranyl group or a substituted or unsubstituted azadibenzothiophenyl group; and the substituted or unsubstituted alkyl group including 1 to 20 carbon atoms is a substituted or unsubstituted methyl group, a substituted or unsubstituted ethyl group, a substituted or unsubstituted propyl group, a substituted or unsubstituted isopropyl group, a substituted or unsubstituted n-butyl group, a substituted or unsubstituted isobutyl group, a substituted or unsubstituted sec-butyl group, a substituted or unsubstituted tert-butyl group, a substituted or unsubstituted n-pentyl group, a substituted or unsubstituted n-hexyl group, a substituted or unsubstituted n-heptyl group or a substituted or unsubstituted n-octyl group.

30. A material for an organic electroluminescence device comprising the compound according to claim 27.

31. An organic electroluminescence device comprising one or more organic thin film layers including an emitting layer between a cathode and an anode, at least one layer of the organic thin film layers comprising the material for an organic electroluminescence device according to claim 30.

32. The compound according to claim 27, wherein $Ar_1$ and $Ar_2$ are independently a substituted or unsubstituted aryl group including 6 to 18 ring carbon atoms or a substituted or unsubstituted heteroaryl group including 5 to 18 ring atoms.

33. The compound according to claim 27, wherein $Ar_1$ and $Ar_2$ are independently a substituted or unsubstituted aryl group including 6 to 18 ring carbon atoms.

34. The compound according to claim 27, wherein $X_1$ to $X_4$ and $X_{13}$ to $X_{16}$ are independently $CR_1$ or CH;

one of $X_5$ to $X_8$ is a carbon atom bonding to one of $X_9$ to $X_{12}$, and at least one of $X_5$ to $X_8$ that is adjacent to the carbon atom bonding to one of $X_9$ to $X_{12}$ is $CR_2$;

one of $X_9$ to $X_{12}$ is a carbon atom bonding to one of $X_5$ to $X_8$, and $X_9$ to $X_{12}$ that is adjacent to the carbon atom bonding to one of $X_5$ to $X_8$ is CH;

the remaining $X_5$ to $X_8$ and the remaining $X_9$ to $X_{12}$ are $CR_1$ or CH.

35. The compound according to claim 27, wherein one of $X_5$ to $X_8$ is the carbon atom bonding to one of $X_9$ to $X_{12}$, and one of $X_5$ to $X_8$ that is adjacent to the carbon atom bonding to one of $X_9$ to $X_{12}$ is $CR_2$.

36. The compound according to claim 27, wherein the remaining $X_5$ to $X_8$ and the remaining $X_9$ to $X_{12}$ are CH or N.

37. The compound according to claim 27, wherein the remaining $X_5$ to $X_8$ and the remaining $X_9$ to $X_{12}$ are CH.

38. The compound according to claim 27, wherein $Ar_1$ and $Ar_2$ are independently the substituted or unsubstituted aryl group including 6 to 18 ring carbon atoms, or the substituted or unsubstituted heteroaryl group including 5 to 18 ring atoms;

one of $X_5$ to $X_8$ is the carbon atom bonding to one of $X_9$ to $X_{12}$, and one of $X_5$ to $X_8$ that is adjacent to the carbon atom bonding to one of $X_9$ to $X_{12}$ is $CR_2$; and the remaining $X_5$ to $X_8$ and the remaining $X_9$ to $X_{12}$ are CH.

39. The compound according to claim 27, wherein $Ar_1$ and $Ar_2$ are independently a substituted or unsubstituted aryl group including 6 to 18 ring carbon atoms;

one of $X_5$ to $X_8$ is the carbon atom bonding to one of $X_9$ to $X_{12}$, and one of $X_5$ to $X_8$ that is adjacent to the carbon atom bonding to one of $X_9$ to $X_{12}$ is $CR_2$; and the remaining $X_5$ to $X_8$ and the remaining $X_9$ to $X_{12}$ are CH.

40. The compound according to claim 38, wherein when $Ar_1$, $Ar_2$, or $R_1$ is the substituted aryl group including 6 to 18 ring carbon atoms, or the substituted heteroaryl group including 5 to 18 ring atoms, it is substituted with one or more selected from the group consisting of an alkyl group including 1 to 20 carbon atoms, an aryl group including 6 to 18 ring carbon atoms, a heteroaryl group including 5 to 18 ring atoms, a halogen atom, and a cyano group; and the substituted pyridyl group, the substituted pyrimidinyl group or the substituted triazinyl group of $R_2$ is substituted with one or more selected from the group consisting of an alkyl group including 1 to 20 carbon atoms, an aryl group including 6 to 18 ring carbon atoms, a heteroaryl group including 5 to 18 ring atoms, a halogen atom, and a cyano group.

41. The compound according to claim 39, wherein when $Ar_1$ or $Ar_2$ is the substituted aryl group including 6 to 18 ring carbon atoms, it is substituted with one or more selected from the group consisting of an alkyl group including 1 to 20 carbon atoms, an aryl group including 6 to 18 ring carbon atoms, a heteroaryl group including 5 to 18 ring atoms, a halogen atom, and a cyano group;

when $R_1$ is the substituted aryl group including 6 to 18 ring carbon atoms, or the substituted heteroaryl group including 5 to 18 ring atoms, it is substituted with one or more selected from the group consisting of an alkyl group including 1 to 20 carbon atoms, an aryl group including 6 to 18 ring carbon atoms, a heteroaryl group including 5 to 18 ring atoms, a halogen atom, and a cyano group; and the substituted pyridyl group, the substituted pyrimidinyl group or the substituted triazinyl group of $R_2$ is substituted with one or more selected from the group consisting of an alkyl group including 1 to 20 carbon atoms, an aryl group including 6 to 18 ring carbon atoms, a heteroaryl group including 5 to 18 ring atoms, a halogen atom, and a cyano group.

42. The compound according to claim 27, wherein $X_7$ is a carbon atom bonding to $X_{11}$, and at least one of $X_6$ and $X_8$ is $CR_2$;

$X_{11}$ is a carbon atom bonding to $X_7$, and $X_{10}$ and $X_{12}$ are CH or N; and the remaining $X_5$, $X_6$, $X_8$ and $X_9$ are $CR_1$, CH or N.

43. The compound according to claim 27, wherein $R_2$ is the substituted triazinyl group.

* * * * *

UNITED STATES PATENT AND TRADEMARK OFFICE
CERTIFICATE OF CORRECTION

PATENT NO. : 9,991,447 B2
APPLICATION NO. : 14/347937
DATED : June 5, 2018
INVENTOR(S) : Toshihiro Iwakuma and Kei Yoshida It is certified that error appears in the above-identified patent and that said Letters Patent is hereby corrected as shown below:

On the Title Page

Item (71), The Applicants:
Please delete:
"Toshihiro Iwakuma, Sodegaura (JP);
Kei Yoshida, Sodegaura (JP)"
Please replace with:
IDEMITSU KOSAN CO., LTD.

Item (73), The Assignee:
Please delete:
"IDEMITSU KOREA CO., LTD."
Please replace with:
IDEMITSU KOSAN CO., LTD Signed and Sealed this
Tenth Day of March, 2020

Andrei Iancu
*Director of the United States Patent and Trademark Office*